United States Patent
Watters et al.

(10) Patent No.: US 10,696,733 B2
(45) Date of Patent: *Jun. 30, 2020

(54) MICROBE-BINDING MOLECULES AND USES THEREOF

(71) Applicant: PRESIDENT AND FELLOWS OF HARVARD COLLEGE, Cambridge, MA (US)

(72) Inventors: Alexander Watters, North Andover, MA (US); Brendon Dusel, West Roxbury, MA (US); Michael Super, Lexington, MA (US); Mark Cartwright, West Newton, MA (US); Donald E. Ingber, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/553,635

(22) Filed: Aug. 28, 2019

(65) Prior Publication Data

US 2019/0389935 A1    Dec. 26, 2019

Related U.S. Application Data

(63) Continuation of application No. 15/750,788, filed as application No. PCT/US2016/045509 on Aug. 4, 2016, now Pat. No. 10,435,457.

(60) Provisional application No. 62/201,745, filed on Aug. 6, 2015.

(51) Int. Cl.
| | |
|---|---|
| *C07K 14/78* | (2006.01) |
| *G01N 33/569* | (2006.01) |
| *C07K 14/00* | (2006.01) |
| *C07K 14/47* | (2006.01) |
| *C07K 19/00* | (2006.01) |
| *A61K 38/00* | (2006.01) |

(52) U.S. Cl.
CPC ............. *C07K 14/78* (2013.01); *C07K 14/00* (2013.01); *C07K 14/4726* (2013.01); *C07K 19/00* (2013.01); *G01N 33/569* (2013.01); *A61K 38/00* (2013.01); *C07K 2319/30* (2013.01); *G01N 2333/78* (2013.01); *G01N 2400/00* (2013.01)

(58) Field of Classification Search
None
See application file for complete search history.

(56) References Cited

U.S. PATENT DOCUMENTS

| | | |
|---|---|---|
| 4,425,330 A | 1/1984 | Norcross et al. |
| 5,137,810 A | 8/1992 | Sizemore et al. |
| 5,270,199 A | 12/1993 | Ezekowitz |
| 5,273,884 A | 12/1993 | Gale et al. |
| 5,405,832 A | 4/1995 | Potempa |
| 5,474,904 A | 12/1995 | Potempa et al. |
| 5,545,820 A | 8/1996 | Gatehouse et al. |
| 5,585,349 A | 12/1996 | Potempa |
| 5,783,179 A | 7/1998 | Nestor, Jr. et al. |
| 5,874,238 A | 2/1999 | Potempa et al. |
| 5,951,976 A | 9/1999 | Segal |
| 6,057,295 A | 5/2000 | Caretto et al. |
| 6,117,977 A | 9/2000 | Lasky et al. |
| 6,225,046 B1 | 5/2001 | Vesey et al. |
| 6,376,473 B1 | 4/2002 | Audonnet et al. |
| 6,471,968 B1 | 10/2002 | Baker et al. |
| 6,503,761 B1 | 1/2003 | Koenig et al. |
| 6,528,618 B1 | 3/2003 | Fridkin et al. |
| 6,528,624 B1 | 3/2003 | Idusogie et al. |
| 6,562,784 B1 | 5/2003 | Thiel et al. |
| 6,703,219 B1 | 3/2004 | Potempa et al. |
| 6,733,753 B2 | 5/2004 | Boone et al. |
| 6,846,649 B1 | 1/2005 | Thiel et al. |
| 6,900,292 B2 | 5/2005 | Sun et al. |
| 7,182,945 B2 | 2/2007 | Fridkin et al. |
| 7,202,207 B2 | 4/2007 | Thiel et al. |

(Continued)

FOREIGN PATENT DOCUMENTS

| | | |
|---|---|---|
| EP | 0375736 B1 | 5/1998 |
| EP | 0861667 A2 | 8/2001 |

(Continued)

OTHER PUBLICATIONS

Michelow et al., "A Novel L-ficolin/Mannose-binding Lectin Chimeric Molecule with Enhanced Activity against Ebola Virus", The Journal of Biological Chemistry 285(32):24729-24739 (2010).

(Continued)

*Primary Examiner* — Brian Gangle
(74) *Attorney, Agent, or Firm* — Nixon Peabody LLP; David S. Resnick; Nicole D. Kling

(57) ABSTRACT

Described herein are engineered microbe-targeting molecules, microbe-targeting articles, kits comprising the same, and uses thereof. Such microbe-targeting molecules, microbe-targeting articles, or the kits comprising the same can not only bind or capture of a microbe or microbial matter thereof, but they also have improved capability (e.g., enhanced sensitivity or signal intensity) of detecting a microbe or microbial matter. Thus, the microbe-targeting molecules, microbe-targeting articles, and/or the kit described herein can be used in various applications, e.g., but not limited to assays for detection of a microbe or microbial matter, diagnostic and/or therapeutic agents for diagnosis and/or treatment of an infection caused by microbes in a subject or any environmental surface, and/or devices for removal of a microbe or microbial matter from a fluid.

18 Claims, 18 Drawing Sheets

Specification includes a Sequence Listing.

(56) References Cited

U.S. PATENT DOCUMENTS

| | | |
|---|---|---|
| 7,211,396 B2 | 5/2007 | Uttenthal |
| 7,226,429 B2 | 6/2007 | Tullis |
| 7,439,224 B2 | 10/2008 | Thiel et al. |
| 7,462,596 B2 | 12/2008 | Larsen et al. |
| 7,566,694 B2 | 7/2009 | Rider |
| 7,629,440 B2 | 12/2009 | Segal et al. |
| 7,695,937 B2 | 4/2010 | Baum |
| 7,763,436 B2 | 7/2010 | Das et al. |
| 8,013,120 B2 | 9/2011 | Du Clos et al. |
| 8,080,245 B2 | 12/2011 | Visintin et al. |
| 8,084,275 B2 | 12/2011 | Hirai et al. |
| 8,088,596 B2 | 1/2012 | Zeng et al. |
| 8,415,118 B2 | 4/2013 | Huang et al. |
| 8,598,324 B2 | 12/2013 | Rider |
| 9,150,631 B2 | 10/2015 | Super et al. |
| 9,644,021 B2 | 5/2017 | Wang et al. |
| 2003/0162248 A1 | 8/2003 | Wakamiya |
| 2003/0166878 A1 | 9/2003 | Nishiya et al. |
| 2003/0180814 A1 | 9/2003 | Hodges et al. |
| 2004/0018611 A1 | 1/2004 | Ward et al. |
| 2004/0229212 A1 | 11/2004 | Thiel et al. |
| 2005/0014932 A1 | 1/2005 | Imboden et al. |
| 2005/0037949 A1 | 2/2005 | O'Brien et al. |
| 2006/0040362 A1 | 2/2006 | Wakamiya |
| 2006/0104975 A1 | 5/2006 | Geijtenbeek et al. |
| 2006/0177879 A1 | 8/2006 | Mayes et al. |
| 2006/0188963 A1 | 8/2006 | Kongerslev et al. |
| 2006/0251580 A1 | 11/2006 | Keppler et al. |
| 2007/0031819 A1 | 2/2007 | Koschwanez et al. |
| 2007/0049532 A1 | 3/2007 | Feige et al. |
| 2007/0072247 A1 | 3/2007 | Wong et al. |
| 2007/0122850 A1 | 5/2007 | Teng |
| 2007/0184463 A1 | 8/2007 | Molho et al. |
| 2007/0224640 A1 | 9/2007 | Caldwell |
| 2007/0231833 A1 | 10/2007 | Arcidiacono et al. |
| 2007/0269818 A1 | 11/2007 | Savage |
| 2008/0014576 A1 | 1/2008 | Jovanovich et al. |
| 2008/0056949 A1 | 3/2008 | Lee et al. |
| 2008/0108120 A1 | 5/2008 | Cho et al. |
| 2008/0156736 A1 | 7/2008 | Hirai et al. |
| 2008/0182793 A1 | 7/2008 | Baum |
| 2008/0193965 A1 | 8/2008 | Zeng et al. |
| 2008/0260738 A1 | 10/2008 | Moore |
| 2008/0300188 A1 | 12/2008 | Yang et al. |
| 2009/0078614 A1 | 3/2009 | Varghese et al. |
| 2009/0175797 A1 | 7/2009 | Warren et al. |
| 2009/0181041 A1 | 7/2009 | Holgersson et al. |
| 2009/0220932 A1 | 9/2009 | Ingber et al. |
| 2009/0252729 A1 | 10/2009 | Farrington et al. |
| 2009/0269843 A1 | 10/2009 | Blume et al. |
| 2009/0297516 A1 | 12/2009 | Mayo et al. |
| 2010/0044232 A1 | 2/2010 | Lin et al. |
| 2010/0055675 A1 | 3/2010 | Kumamoto et al. |
| 2010/0266558 A1 | 10/2010 | Zipori |
| 2010/0323342 A1 | 12/2010 | Gomez et al. |
| 2010/0323429 A1 | 12/2010 | Hu et al. |
| 2010/0331240 A1 | 12/2010 | Michelow et al. |
| 2011/0027267 A1 | 2/2011 | Kyneb et al. |
| 2011/0053145 A1 | 3/2011 | Takakura et al. |
| 2011/0053250 A1 | 3/2011 | Takakura et al. |
| 2011/0065095 A1 | 3/2011 | Kida et al. |
| 2011/0159000 A1 | 6/2011 | Silverman |
| 2011/0183398 A1 | 7/2011 | Dasaratha et al. |
| 2011/0281792 A1 | 11/2011 | Zion et al. |
| 2012/0100140 A1 | 4/2012 | Reyes et al. |
| 2012/0164628 A1 | 6/2012 | Duffin et al. |
| 2013/0029428 A1 | 1/2013 | Kim et al. |
| 2013/0035283 A1 | 2/2013 | Super |
| 2013/0072445 A9 | 3/2013 | Du Clos et al. |
| 2014/0227723 A1 | 8/2014 | Ingber et al. |
| 2014/0249087 A1 | 9/2014 | Warren et al. |
| 2015/0173883 A1 | 6/2015 | Ingber et al. |

FOREIGN PATENT DOCUMENTS

| | | |
|---|---|---|
| EP | 0915970 B1 | 9/2004 |
| EP | 1862541 A1 | 12/2007 |
| EP | 1812459 B1 | 3/2011 |
| JP | S54-18198 A | 2/1979 |
| JP | 2006-517512 A | 7/2006 |
| JP | 2008515389 A | 5/2008 |
| JP | 2010122205 A | 6/2010 |
| JP | 2010268800 A | 12/2010 |
| WO | 2000/006603 A1 | 2/2000 |
| WO | 2001/003737 A1 | 1/2001 |
| WO | 02/32292 A2 | 4/2002 |
| WO | 03/014150 A2 | 2/2003 |
| WO | 2003/054164 A2 | 7/2003 |
| WO | 2004/018698 A2 | 3/2004 |
| WO | 2005092925 A2 | 10/2005 |
| WO | 2006/018428 A2 | 2/2006 |
| WO | 2006/044650 A2 | 4/2006 |
| WO | 2007/001332 A2 | 1/2007 |
| WO | 2007/044642 A2 | 4/2007 |
| WO | 2007/111496 A1 | 10/2007 |
| WO | 2008/130618 A1 | 10/2008 |
| WO | 2009/040048 A2 | 4/2009 |
| WO | 2009/062195 A2 | 5/2009 |
| WO | 2009/119722 A1 | 10/2009 |
| WO | 2009/126346 A2 | 10/2009 |
| WO | 2011/084749 A1 | 7/2011 |
| WO | 2011/090954 A2 | 7/2011 |
| WO | 2011/091037 A2 | 7/2011 |
| WO | 2011/103144 A1 | 8/2011 |
| WO | 2012/019178 A2 | 2/2012 |
| WO | 2012/050874 A2 | 4/2012 |
| WO | 2012/100099 A2 | 7/2012 |
| WO | 2012/135834 A2 | 10/2012 |
| WO | 2012142515 A2 | 10/2012 |
| WO | 2013/012924 A2 | 1/2013 |
| WO | 2013/130875 A1 | 9/2013 |
| WO | 2014/144325 A1 | 9/2014 |
| WO | 2014/190040 A1 | 11/2014 |
| WO | 2014/190229 A1 | 11/2014 |
| WO | 2015/009734 A2 | 1/2015 |
| WO | 2015/095604 A1 | 6/2015 |

OTHER PUBLICATIONS

Nadesalingam et al., "Mannose-Binding Lectin Recognizes Peptidoglycan via the N-acetyl Glucosamine Moiety, and Inhibits Ligand-Induced Proinflammatory Effect and Promotes Chemokine Production by Macrophages", The Journal of Immunology 175:1785-1794 (2005).

Nakamura et al., "Characterization of the interaction between serum mannan-binding protein and nucleic acid ligands", Journal of Leukocyte Biology 86:737-748 (2009).

Neth et al., "Enhancement of Complement Activation and Opsonophagocytosis by Complexes of Mannose-Binding Lectin with Mannose-Binding Lectin-Associated Serine Protease After Binding to *Staphylococcus aureus*", The Journal of Immunology 169:4430-4436 (2002).

Neth et al., "Mannose-Binding Lectin Binds to a Range of Clinically Relevant Microorganisms and Promotes Complement Deposition", Infection and Immunity 68(2):688-693 (2000).

Nisnevitch et al., "The solid phase in affinity chromatography: strategies for antibody attachment", Journal of Biochemical and Biophysical Methods 49:467-480 (2001).

Ogden et al., "C1q and Mannose Binding Lectin Engagement of Cell Surface Calreticulin and CD91 Initiates Macropinocytosis and Uptake of Apoptotic Cells", The Journal of Experimental Medicine 194(6):781-795 (2001).

Perham, "Domains, Motifs, and Linkers in 2-Oxo Acid Dehydrogenase Multienzyme Complexes: A Paradigm in the Design of a Multifunction Protein", Biochemistry 30(35):8501-8512 (1991).

Product Datasheet, "Human Mannan Binding Lectin peptide (237-248) (Carboxyterminal end) ab45655". Downloaded from the world

(56) References Cited

OTHER PUBLICATIONS wide web from abcam.com/Human-Mannan-Binding-Lectin-peptide-237-248-Carboxyterminal-end-ab45655.html on May 14, 2015.
Rouhandeh et al., "Surface membrane redistribution and stabilization of concanavalin A-specific receptors following Yaba tumor poxvirus infection." Biochimica et Biophysica Acta (BBA)-Biomembranes 600(2):301-312 (1980).
Rutishauser et al., "Amino Acid Sequence of the Fc Region of a Human γG Immunoglobulin", Biochemistry 61:1414-1421 (1968).
Safarik et al., "The application of magnetic separations in applied microbiology", Journal of Applied Bacteriology 78:575-585 (1995).
Schmidt, "Fusion proteins as biopharmaceuticals—Applications and challenges", Current Opinion in Drug Discovery & Development 12(2):284-295 (2009).
Sheriff et al., "Human mannose-binding protein carbohydrate recognition domain trimerizes through a triple alpha-helical coiled-coil", Nat Struct Biol 1(11) 789-794 (1994).
Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry 276 (9):6591-6604 (2001).
Shoulders et al., "Collagen structure and stability." Annual Review of Biochemistry 78(1):929-958 (2009).
Sibille et al., "Comparison of serological tests for the diagnosis of feline immunodeficiency virus infection of cats", Veterinary Microbiology 45:259-267 (1995).
Sprong et al., "Mannose-Binding Lectin Is a Critical Factor in Systemic Complement Activation during Meningococcal Septic Shock", Clinical Infectious Diseases 49:1380-1386 (2009).
Steentoft et al. "Precision mapping of the human O-GalNAc glycoproteome through SimpleCell technology," EMBO J. May 15;32(10)1478-88. (2013).
Steurer et al., "Ex Vivo Coating of Islet Cell Allografts with Murine CTLA4/Fc Promotes Graft Tolerance", The Journal of Immunology 155:1165-1174 (1995).
Stuart et al., "Mannose-Binding Lectin-Deficient Mice Display Defective Apoptotic Cell Clearance but No Autoimmune Phenotype", The Journal of Immunology 174:3220-3226 (2005).
Takahashi et al., "Mannose-binding lectin and its associated proteases (MASPs) mediate coagulation and its deficiency is a risk factor in developing complications from infection, including disseminated intravascular coagulation", Immunobiology 216(1-2):96-102 (2011).
Terai et al., "Relationship between gene polymorphisms of mannose-binding lectin (MBL) and two molecular forms of MBL", European Journal of Immunology 33:2755-2763 (2003).
Thiel et al., "A second serine protease associated with mannan-binding lectin that activates complement", Nature 386:506-510 (1997).
Vaccaro et al., "Engineering the Fc region of immunoglobulin G to modulate in vivo antibody levels", Nature Biotechnology 23(10):1283-1288 (2005).
Ward et al., "Characterization of Humanized Antibodies Secreted by Aspergillus niger", Applied and Environmental Microbiology 70(5):2567-2576 (2004).
Warwick et al., "Use of Quantitative 16S Ribosomal DNA Detection for Diagnosis of Central Vascular Catheter-Associated Bacterial Infection", Journal of Clinical Microbiology 42(4):1402-1408 (2004).
Witus et al., "Identification of Highly Reactive Sequences for PLP-Mediated Bioconjugation Using a Combinatorial Peptide Library", Journal of the American Chemical Society 132:16812-16817 (2010).
Wong et al., "Bioinspired self-repairing slippery surfaces with pressure-stable omniphobicity", Nature 477:443-447 (2011).
Wriggers et al., "Control of Protein Functional Dynamics by Peptide Linkers", Biopolymers (Peptide Science) 80:736-746 (2005).
Xia et al., "Combined microfluidic-micromagnetic separation of living cells in continuous flow", Biomed Microdevices 8:299-308 (2006).
Ye et al., "Surface display of a glucose binding protein", Journal of Molecular Catalysis B: Enzymatic 28:201-206 (2004).
Yung et al., "Micromagnetic-microfluidic blood cleansing device", Lab on a Chip 9:1171-1177 (2009).
Zettner et al., "Principles of competitive binding assays (saturation analyses). II. Sequential saturation", Clin Chem 20(1) 5-14 (1974).
Zettner et al., "Principles of competitive binding assays (saturation analysis). 1. Equilibrium techniques", Clin Chem 19(7) 699-705 (1973).
Agrawal et al., "C-reactive protein mutant that does not bind to phosphocholine and pneumococcal C-polysaccharide", J. Immunol. 169(6):3217-3222 (2002).
Barnum et al., "Comparative Studies on the Binding Specificities of C-Reactive Protein (CRP) and HOPC 8", Annals of the New York Academy of Sciences 389:431-434 (1982).
Culley et al., "C-reactive protein binds to phosphorylated carbohydrates", Glycobiology 10(1):59-65 (2000).
Dumont et al., "Monomeric Fc Fusions: Impact on Pharmacokinetic and Biological Activity of Protein Therapeutics", Biodrugs 20(3):151-160 (2006).
Hohenester, "Tackling the Legs of Mannan-Binding Lectin", Structure 19:1538-1540 (2011).
Huang et al., "Integrated microfluidic system for rapid screening of CRP aptamers utilizing systematic evolution of ligands by exponential enrichment (SELEX)", Biosensors and Bioelectronics 25:1761-1766 (2010).
Lee et al., "Carbohydrate-binding properties of human neo-CRP and its relationship to phosphorylcholine-binding site", Glycobiology 13(1):11-21 (2003).
Mold et al., "Binding of Human C-Reactive Protein to Bacteria", Infection and Immunity 38(1):392-395 (1982).
Presanis et al., "Biochemistry and genetics of mannan-binding lectin (MBL)", Biochemical Society Transactions 31 (4):748-752 (2003).
Szalai, "The biological functions of C-reactive protein", Vascular Pharmacology 39:105-107 (2002).
Ying et al., "Soluble Monomeric IgG1 Fc", The Journal of Biological Chemistry 287(23):19399-19408 (2012).
Zhavnerko et al., "Oriented Immobilization of C-Reactive Protein on Solid Surface for Biosensor Applications", Frontiers of Multifunctional Integrated Nanosystems 95-108 (2004).
Bossola et al., "Circulating Bacterial-Derived DNA Fragments and Markers of Inflammation in Chronic Hemodialysis Patients", Clinical Journal of the American Society of Nephrology 4:379-385 (2009).
Arakawa et al., "Elution of antibodies from a Protein-A column by aqueous arginine solutions", Protein Expression and Purification 36:244-248 (2004).
Armour et al., "Recombinant human IgG molecules lacking Fcγ receptor I binding and monocyte triggering activities", European Journal of Immunology 29:2613-2624 (1999).
Ashkenazi et al., "Immunoadhesins as research tools and therapeutic agents", Current Opinion in Immunology 9:195-200 (1997).
Azevedo et al., "Horseradish peroxidase: a valuable tool in biotechnology," Biotechnology Annual Review 9:199-247 (2003).
Bangs Laboratories, Inc., "Protein Coated Microspheres", Tech. Note #51 (1997). (4 pages).
Bayston et al., "Bacterial endotoxin and current concepts in the diagnosis and treatment of endotoxaemia", Journal of Medical Microbiology 31:73-83 (1990).
Brooks et al., "Expression and secretion of ficolin β by porcine neutrophils", Biochimica et Biophysica Acta 1624:36-45 (2003).
Brouwer et al., "Mannose-Binding Lectin (MBL) Facilitates Opsonophagocytosis of Yeasts but Not of Bacteria despite MBL Binding", The Journal of Immunology 180:4124-4132 (2008).
Casey et al., "The acute-phase reactant C-Reactive protein binds to phosphorylcholine-expressing Neisseria meningitidis and increased uptake by human phagocytes", Infection and Immunity 76(3): 1298-1304 (2008).
Castle et al., "The binding of 125I-labeled concanavalin A to the cell surface of rabbit peritoneal polymorphonuclear leucocytes." Biochemical Medicine 28(1):1-15 (1982).
Chamow et al., "Immunoadhesins: principles and applications", Trends Biotechnology 14:52-60 (1996).

(56) References Cited

OTHER PUBLICATIONS

Chang et al., "Crystallization and Preliminary X-ray Analysis of a Trimeric Form of Human Mannose Binding Protein", Journal of Molecular Biology 241:125-127 (1994).
Chen et al., "Fabrication of an Oriented Fc-Fused Lectin Microarray through Boronate Formation", Angewandte Chemie International Edition 47:8627-8630 (2008).
Choma et al. "Design of a Heme-Binding Four-Helix Bundle", J. Am. Chem. Soc. 116:856-865 (1994).
Chuang et al., "Computational prediction of N-linked glycosylation incorporating structural properties and patterns," Bioinformatics. Sep. 1; 28(17): 2249-2255 (2012).
Cooper, "A generic pathogen capture technology for sepsis diagnosis", retrieved from http://hdl.handle.net/1721.1/83966 (2013).
Czajkowsky et al., "Fc-fusion proteins: new developments and future perspectives", EMBO Mol Med., 4(10):1015-1028 (2012).
Feng et al., "Identification of carbohydrates on the surface membrane of pathogenic and nonpathogenic piscine haemoflagellates, *Cryptobia salmositica*, *C. bullocki* and *C. catostomi* (Kinetoplastida)." Diseases of Aquatic Organisms 32(3):201-209 (1998).
Foster, "Immune Evasion by *Staphylococci*", Nature 3:948-958 (2005).
Fox et al., "Single amino acid substitutions on the surface of *Escherichia coli* maltose-binding protein can have a profound impact on the solubility of fusion proteins", Protein Science 10:622-630 (2001).
Frakking et al., "Safety and phamacokinetics of plasma-derived mannose-binding lectin (MBL) substitution in children with chemotherapy-induced neutropaenia", European Journal of Cancer 45:505-512 (2009).
Furukawa et al. "Identification of a novel mechanism of action of bovine IgG antibodies specific for *Staphylococcus aureus*"Vet Res. 49: 22 (2018).
Garred et al., "Mannose-binding lectin and its genetic variants", Genes and Immunity 7:85-94 (2006).
Gouin et al., "Multimeric Lactoside "Click Clusters" as Tools to Investigate the Effect of Linker Length in Specific Interactions with Peanut Lectin, Galectin-1, and -3", ChemBioChem 11:1430-1442 (2010).
Grogl et al., "Leishmania braziliensis: Protein, Carbohydrate, and Antigen Differences between Log Phase and Stationary Phase Promastigotes in Vitro", Experimental Parasitology 63:352-359 (1987).
Hinton et al., "Engineered Human IgG Antibodies with Longer Serum Half-lives in Primates", The Journal of Biological Chemistry 279(8):6213-6216 (2004).
Holmskov et al., "Affinity and kinetic analysis of the bovine plasma C-type lectin collectin-43 (CL-43) interacting with mannan", FEBS Letters 393:314-316 (1996).
Huang et al., "Porcine DC-SIGN: Molecular cloning, gene structure, tissue distribution and binding characteristics", Developmental and Comparative Immunology 33:464-480 (2009).
Hwang et al., "The Pepper Mannose-Binding Lectin Gene CaMBL1 Is Required to Regulate Cell Death and Defense Responses to Microbial Pathogens", Plant Physiology 155:447-463 (2011).
Idusogie et al., "Engineered Antibodies with Increased Activity to Recruit Complement", The Journal of Immunology 166:2571-2575 (2001).
Ilyas et al., "High glucose disrupts oligosaccharide recognition function via competitive inhibition: a potential mechanism for immune dysregulation in diabetes mellitus", Immunobiology 216(1-2) 126-131 (2011).
INVIVO GEN INSIGHT, "IgG-Fc Engineering for Therapeutic Use", (2006). (4 pages).
Jack et al., "Mannose-binding lectin: targeting the microbial world for complement attack and opsonophagocytosis", Immunological Reviews 180:86-99 (2001).
Jarva et al., "*Streptococcus pneumoniae* Evades Complement Attack and Opsonophagocytosis by Expressing the pspC Locus-Encoded Hic Protein That Binds to Short Consensus Repeats 8-11 of Factor H", The Journal of Immunology 168:1886-1894 (2002).
Johnson et al. "Iron metabolism and the innate immune response to infection." Microbes and infection / Insitut Pasteur 14:207 (2012).
Jones et al. "Immunisation with ID83 fusion protein induces antigen-specific cell mediated and humoral immune responses in cattle." Vaccine. Oct. 25;31(45):5250-5. (2013).
Kang et al., "The human macrophage mannose receptor directs *Mycobacterium tuberculosis* lipoarabinomanan-mediated phagosome biogenesis", The Journal of Experimental Medicine 202(7):987-999 (2005).
Keen et al., "Interrelationship Between pH and Surface Growth of Nitrobacter", Soil Biology and Biochemistry 19(6):665-672 (1987).
Kehres, "A kinetic model for binding protein-mediated arabinose transport", Protein Science 1:1661-1665 (1992).
Kjaer et al., "M-ficolin binds selectively to the capsular polysaccharides of *Streptococcus pneumoniae* serotypes 19B and 19C and of a *Streptococcus mitis* strain", Infect Immun 81(2) 452-459 (2013).
Krarup et al., "Simultaneous Activation of Complement and Coagulation by MBL-Associated Serine Protease 2",PloS One 2(7):e623 (2007). (8 pages).
Li et al. "GlycoMine: a machine learning-based approach for predicting N-, C- and O-linked glycosylation in the human proteome," Bioinformatics, vol. 31, Issue 9,pp. 1411-1419 (2015).
Lin et al. "Synergistic inflammation is induced by blood degradation products with microbial Toll-like receptor agonists and is blocked by hemopexin." The Journal of Infectious Diseases 202:624 (2010).
Linehan et al., "Endogenous ligands of carbohydrate recognition domains of the mannose receptor in murine macrophages, endothelial cells and secretory cells; potential relevance to inflammation and immunity", European Journal of Immunology 31:1857-1866 (2001).
Lo et al., "High level expression and secretion of Fc-X fusion proteins in mammalian cells", Protein Engineering 11(6):495-500 (1998).
Loosdrecht et al., "Influence of Interfaces on Microbial Activity", Microbiological Reviews 54(1):75-87 (1990).
Mantuano et al., "The hemopexin domain of matrix metalloproteinase-9 activates cell signaling and promotes migration of schwann cells by binding to low-density lipoprotein receptor-related protein.", The Journal of Neuroscience 28(45):11571-11582 (2008).
Matsushita et al., "Activation of the Classical Complement Pathway by Mannose-binding Protein in Association with a Novel C1s-like Serine Protease", Journal of Experimental Medicine 176(6):1497-1502 (1992).
Mauk et al. "An alternative view of the proposed alternative activities of hemopexin." Protein Science. 20:791 (2011).

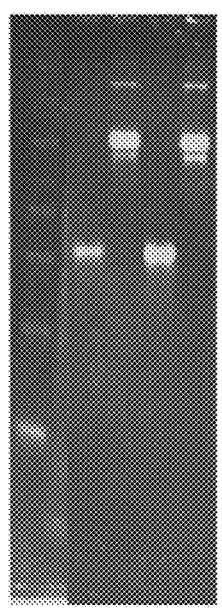
*FIG. 4*
Lane 1: MW marker
Lane 2: StemFcMBL_Ntrimmed
Lane 3: StemFcMBL_Ctrimmed
*FIG. 5A*
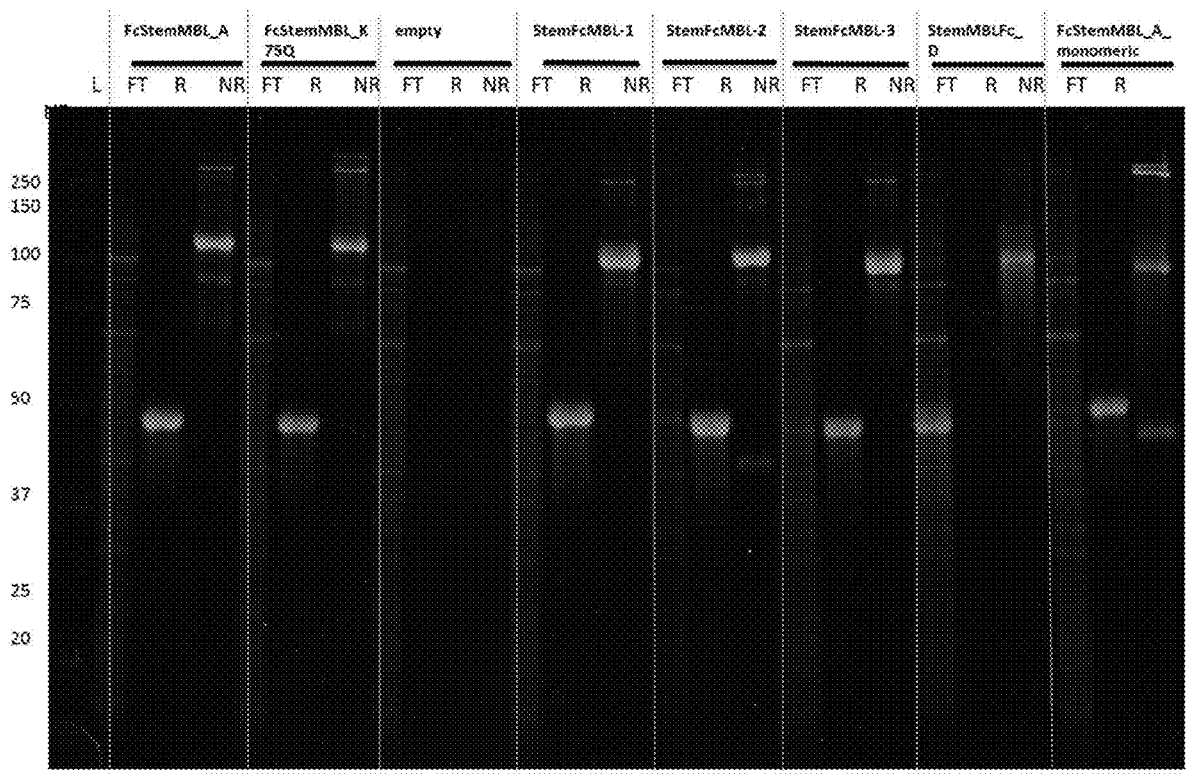

| Protein | Fc Hinge | Glycosylation | Protein Length | Protein Weight | Extinction Coefficient | Theoretical pI |
|---|---|---|---|---|---|---|
| StemFc MBL-2 | No hinge | None | 425aa | 46366.1 Da | 53900 | 6.31 |
| StemFc MBL-3 | Has hinge | None | 414aa | 45365 Da | 54025 | 6.24 |

*FIG. 11*

| # | Molecule | Full aa# MBL# | Short aa# MBL# | Hinge | C-term CRD | Stem | Kink? | Fc-Stem | Stem-Fc | mFc | Neck2? | MASP Site K75->? |
|---|---|---|---|---|---|---|---|---|---|---|---|---|
|   | 'FcMBL' | 101 | 81 |   |   | none | N | n/a | n/a |   |   |   |
| 1 | FcStemMBL_A | 42 | 22 |   |   | full |   | Y |   |   |   | wt |
| 2 | FcStemMBL_A_mono | 42 | 22 |   |   | full |   | Y |   |   |   | M |
| 3 | A-N | 42 | 22 |   |   | full |   | Y |   |   |   | N |
| 4 | FcStemMBL_K75Q | 42 | 22 |   |   | full |   | Y |   |   |   | Q |
| 5 | mA | 42 | 22 |   |   | full |   | Y |   | mFc |   | wt |
| 6 | mA-M | 42 | 22 |   |   | full |   | Y |   | mFc |   | M |
| 7 | mA-N | 42 | 22 |   |   | full |   | Y |   | mFc |   | N |
| 8 | mA-Q | 42 | 22 |   |   | full |   | Y |   | mFc |   | Q |
| 9 | B1 | 68 | 48 |   |   | short | N | Y |   |   |   |   |
| 10 | B2 | 68 | 48 |   |   | short | N | Y |   |   | Y |   |
| 11 | mB1 | 68 | 48 |   |   | short | N | Y |   | mFc |   |   |
| 12 | mB2 | 68 | 48 |   |   | short | N | Y |   | mFc | Y |   |
| 13 | StemFcMBL-1 | 42 | 22 |   |   | Full |   |   | Y |   |   |   |
| 14 | StemFcMBL-2 | 42 | 22 | N |   | Full |   |   | Y |   |   |   |
| 15 | StemFcMBL-3 | 68 | 48 |   |   | Short | N |   | Y |   |   |   |
| 16 | C4 | 68 | 48 | N |   | Short | N |   | Y |   |   |   |
| 17 | StemMBLFc_D | 68 | 48 |   | C-term Fc | Short | N | n/a | n/a |   |   |   |

*FIG. 12A*

| Name | Transient Expression YIELDS mg/L |
|---|---|
| FcStemMBL_A | 28.5 |
| FcStemMBL_K75Q | 38.25 |
| StemFcMBL-1 | 7.37 |
| StemFcMBL-2 | 41.5 |
| StemFcMBL-3 | 42 |
| StemMBLFc_D | 13.05 |
| FcStemMBL_A_monomeric | 5.68 |

| Name | sequence MW | hplc MW | dls MW | Multimer #: by HPLC | Multimer #: by dls |
|---|---|---|---|---|---|
| FcStemMBL_A | 47887.9 | 1045 | 1335 | 22 | 28 |
| FcStemMBL_K75Q | 47887.8 | 1150 | 1342 | 24 | 28 |
| StemFcMBL-1 | 47975 | 724 | 544 | 15 | 18 |
| StemFcMBL-2 | 46366.1 | 620 | 486 | 13 | 21 |
| StemFcMBL-3 | 45365.1 | 662 | 457 | 15 | 21 |
| StemMBLFc_D | 45278 | 510 | 346 | 11 | 30 |
| FcStemMBL_A_monomeric | 47865.8 | 603 | 426 | 13 | 20 |

FcStemMBL_K75Q

FcStemMBL_K75Q

StemMBLFc_D

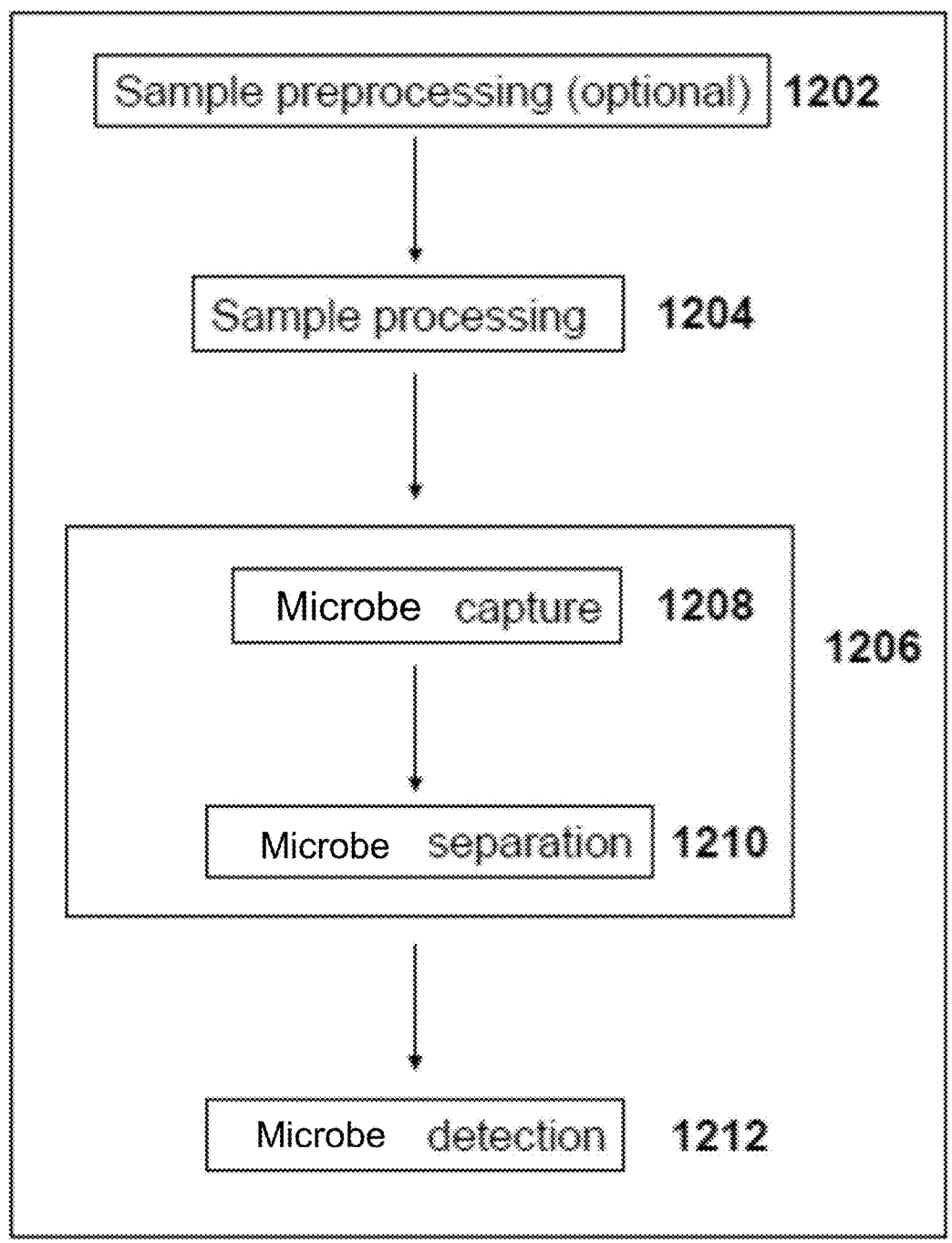

Microbe-binding molecule coupled to a detectable label, e.g., HRP (e.g., HRP-StemFcMBL) for detection of microbe. FcMBL magnetic bead can also be replaced with StemFcMBL-coated magnetic bead for capture of microbe

SEQUENCE LISTING

<160> NUMBER OF SEQ ID NOS: 45

<210> SEQ ID NO 1
<211> LENGTH: 223
<212> TYPE: PRT
<213> ORGANISM: Homo sapiens

<400> SEQUENCE: 1

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

```
Pro Glu Val Thr Cys Val Val Asp Val Ser His Glu Asp Pro Glu
         35                  40                  45

Val Gln Phe Asn Trp Tyr Val Asp Gly Met Glu Val His Asn Ala Lys
 50                  55                  60

Thr Lys Pro Arg Glu Glu Gln Phe Asn Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
                115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
                210                 215                 220

<210> SEQ ID NO 2
<211> LENGTH: 227
<212> TYPE: PRT
<213> ORGANISM: Homo sapiens

<400> SEQUENCE: 2

Asp Thr Pro Pro Cys Pro Arg Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
                 35                  40                  45

Glu Asp Pro Glu Val Gln Phe Lys Trp Tyr Val Asp Gly Val Glu Val
 50                  55                  60

His Asn Ala Lys Thr Lys Pro Arg Glu Glu Gln Tyr Asn Ser Thr Phe
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Thr Lys Gly Gln Pro Arg Glu Pro Gln Val
                115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
                180                 185                 190
```

Asp Lys Ser Arg Trp Gln Gln Gly Asn Ile Phe Ser Cys Ser Val Met
            195                 200                 205

His Glu Ala Leu His Asn Arg Phe Thr Gln Lys Ser Leu Ser Leu Ser
    210                 215                 220

Pro Gly Lys
225

<210> SEQ ID NO 3
<211> LENGTH: 224
<212> TYPE: PRT
<213> ORGANISM: Homo sapiens

<400> SEQUENCE: 3

Pro Pro Cys Pro Ser Cys Pro Ala Pro Glu Phe Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser Gln Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Gly Leu Pro Ser Ser Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Gln Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Arg Leu Thr Val Asp Lys Ser
            180                 185                 190

Arg Trp Gln Glu Gly Asn Val Phe Ser Cys Ser Val Met His Glu Ala
        195                 200                 205

Leu His Asn His Tyr Thr Gln Lys Ser Leu Ser Leu Ser Leu Gly Lys
    210                 215                 220

<210> SEQ ID NO 4
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

-continued

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asp Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Asn Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Asn
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Ala
225                 230

<210> SEQ ID NO 5
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Pro Lys Ser Ser Asp Lys Thr His Thr Cys Pro Pro Cys Pro Ala
 1                   5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asp Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr

```
                      165                 170                 175
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala
225                 230

<210> SEQ ID NO 6
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 7
<211> LENGTH: 58
<212> TYPE: PRT
<213> ORGANISM: Homo sapiens

<400> SEQUENCE: 7

Gly Ile Asn Gly Phe Pro Gly Lys Asp Gly Arg Asp Gly Thr Lys Gly
```

-continued

```
                1               5                  10                  15
Glu Lys Gly Glu Pro Gly Gln Gly Leu Arg Gly Leu Gln Gly Pro Pro
               20                  25                  30
Gly Lys Leu Gly Pro Pro Gly Asn Pro Gly Pro Ser Gly Ser Pro Gly
           35                  40                  45
Pro Lys Gly Gln Lys Gly Asp Pro Gly Lys
       50                  55
```

<210> SEQ ID NO 8
<211> LENGTH: 32
<212> TYPE: PRT
<213> ORGANISM: Homo sapiens

<400> SEQUENCE: 8

```
Gly Leu Gln Gly Pro Pro Gly Lys Leu Gly Pro Pro Gly Asn Pro Gly
1               5                  10                  15
Pro Ser Gly Ser Pro Gly Pro Lys Gly Gln Lys Gly Asp Pro Gly Lys
               20                  25                  30
```

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gly Leu Gln Gly Pro Pro Gly Ser Leu Gly Pro Pro Gly Asn Pro Gly
1               5                  10                  15
Pro Ser Gly Ser Pro Gly Pro Ser Gly Gln Ser Gly Asp Pro Gly Ser
               20                  25                  30
```

<210> SEQ ID NO 10
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gly Ile Asn Gly Phe Pro Gly Lys Asp Gly Arg Asp Gly Thr Lys Gly
1               5                  10                  15
Glu Lys Gly Glu Pro Gly Gln Gly Leu Arg Gly Leu Gln Gly Pro Pro
               20                  25                  30
Gly Gln Leu Gly Pro Pro Gly Asn Pro Gly Pro Ser Gly Ser Pro Gly
           35                  40                  45
Pro Lys Gly Gln Lys Gly Asp Pro Gly Lys
       50                  55
```

<210> SEQ ID NO 11
<211> LENGTH: 20
<212> TYPE: PRT
<213> ORGANISM: Homo sapiens

<400> SEQUENCE: 11

```
Gly Leu Gln Gly Pro Pro Gly Lys Leu Gly Pro Pro Gly Asn Pro Gly
1               5                  10                  15
Pro Ser Gly Ser
               20
```

<210> SEQ ID NO 12
<211> LENGTH: 20
<212> TYPE: PRT
<213> ORGANISM: Homo sapiens

<400> SEQUENCE: 12

Gly Asn Pro Gly Pro Ser Gly Ser Pro Gly Pro Lys Gly Gln Lys Gly
1               5                   10                  15

Asp Pro Gly Lys
            20

<210> SEQ ID NO 13
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ser Pro Gly Ile Pro Gly Thr Pro Gly Ser His Gly Leu Pro Gly
1               5                   10                  15

Arg Asp Gly Arg Asp Gly Val Lys Gly Asp Pro Gly Pro Pro Gly Pro
            20                  25                  30

Met Gly Pro Pro Gly Glu Thr Pro Cys Pro Pro Gly Asn Asn Gly Leu
        35                  40                  45

Pro Gly Ala Pro Gly Val Pro Gly Glu Arg Gly Glu Lys Gly Glu Ala
    50                  55                  60

Gly Glu Arg Gly Pro Pro Gly
65                  70

<210> SEQ ID NO 14
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Cys Pro Gly Leu Pro Gly Ala Pro Gly Pro Lys Gly Glu Ala Gly
1               5                   10                  15

Thr Asn Gly Lys Arg Gly Glu Arg Gly Pro Pro Gly Pro Pro Gly Lys
            20                  25                  30

Ala Gly Pro Pro Gly Pro Asn Gly Ala Pro
        35                  40

<210> SEQ ID NO 15
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Asp Ala Gly Glu Lys Gly Asp Lys Gly Ala Pro Gly Arg Pro Gly
1               5                   10                  15

Arg Val Gly Pro Thr Gly Glu Lys Gly Asp Met Gly Asp Lys Gly Gln
            20                  25                  30

Lys Gly Ser Val Gly Arg His Gly Lys Ile Gly Pro Ile Gly Ser Lys
        35                  40                  45

```
Gly Glu Lys Gly Asp Ser Gly Asp Ile Gly Pro Pro Gly Pro Asn
         50                  55                  60
```

<210> SEQ ID NO 16
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gly Pro Pro Gly Pro Ser Gly Ser Pro Gly Lys Asp Gly Pro Pro Gly
1               5                   10                  15

Pro Ala Gly Asn Thr Gly Ala Pro Gly Ser Pro Gly Val Ser Gly Pro
            20                  25                  30

Lys Gly Asp Ala Gly Gln Pro Gly Glu Lys Gly Ser Pro Gly Ala Gln
        35                  40                  45

Gly Pro Pro Gly
    50
```

<210> SEQ ID NO 17
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gly Ile Asn Gly Phe Pro Gly Lys Asp Gly Arg Asp Gly Thr Lys Gly
1               5                   10                  15

Glu Lys Gly Glu Pro Gly Gln Gly Leu Arg Gly Leu Gln Gly Pro Pro
            20                  25                  30

Gly Lys Leu Gly Pro Pro Gly Asn Pro Gly Pro Ser Gly Ser Pro Gly
        35                  40                  45

Pro Lys Gly Gln Lys Gly Asp Pro Gly Lys Ser Ala Pro Glu Leu Leu
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

His Glu Asp Pro Glu Val Lys Phe Asn Trp Tyr Val Asp Gly Val Glu
            100                 105                 110

Val His Asn Ala Lys Thr Lys Pro Arg Glu Glu Gln Tyr Asp Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Ala Leu Pro Ala Pro
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Arg Asp Glu Leu Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220
```

```
Pro Val Leu Asp Ser Asp Gly Ser Phe Phe Leu Tyr Ser Lys Leu Thr
225                 230                 235                 240

Val Asp Lys Ser Arg Trp Gln Gln Gly Asn Val Phe Ser Cys Ser Val
            245                 250                 255

Met His Glu Ala Leu His Asn His Tyr Thr Gln Lys Ser Leu Ser Leu
        260                 265                 270

Ser Pro Gly Ala Ser Pro Asp Gly Asp Ser Ser Leu Ala Ala Ser Glu
    275                 280                 285

Arg Lys Ala Leu Gln Thr Glu Met Ala Arg Ile Lys Lys Trp Leu Thr
290                 295                 300

Phe Ser Leu Gly Lys Gln Val Gly Asn Lys Phe Phe Leu Thr Asn Gly
305                 310                 315                 320

Glu Ile Met Thr Phe Glu Lys Val Lys Ala Leu Cys Val Lys Phe Gln
                325                 330                 335

Ala Ser Val Ala Thr Pro Arg Asn Ala Ala Glu Asn Gly Ala Ile Gln
            340                 345                 350

Asn Leu Ile Lys Glu Glu Ala Phe Leu Gly Ile Thr Asp Glu Lys Thr
        355                 360                 365

Glu Gly Gln Phe Val Asp Leu Thr Gly Asn Arg Leu Thr Tyr Thr Asn
    370                 375                 380

Trp Asn Glu Gly Glu Pro Asn Asn Ala Gly Ser Asp Glu Asp Cys Val
385                 390                 395                 400

Leu Leu Leu Lys Asn Gly Gln Trp Asn Asp Val Pro Cys Ser Thr Ser
                405                 410                 415

His Leu Ala Val Cys Glu Phe Pro Ile
            420                 425

<210> SEQ ID NO 18
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
```

```
                    145                 150                 155                 160
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Gly Ile Asn Gly Phe Pro Gly Lys
225                 230                 235                 240

Asp Gly Arg Asp Gly Thr Lys Gly Glu Lys Gly Glu Pro Gly Gln Gly
                245                 250                 255

Leu Arg Gly Leu Gln Gly Pro Pro Gly Lys Leu Gly Pro Pro Gly Asn
            260                 265                 270

Pro Gly Pro Ser Gly Ser Pro Gly Pro Lys Gly Gln Lys Gly Asp Pro
        275                 280                 285

Gly Lys Ser Pro Asp Gly Asp Ser Ser Leu Ala Ala Ser Glu Arg Lys
    290                 295                 300

Ala Leu Gln Thr Glu Met Ala Arg Ile Lys Lys Trp Leu Thr Phe Ser
305                 310                 315                 320

Leu Gly Lys Gln Val Gly Asn Lys Phe Phe Leu Thr Asn Gly Glu Ile
                325                 330                 335

Met Thr Phe Glu Lys Val Lys Ala Leu Cys Val Lys Phe Gln Ala Ser
            340                 345                 350

Val Ala Thr Pro Arg Asn Ala Ala Glu Asn Gly Ala Ile Gln Asn Leu
        355                 360                 365

Ile Lys Glu Glu Ala Phe Leu Gly Ile Thr Asp Glu Lys Thr Glu Gly
    370                 375                 380

Gln Phe Val Asp Leu Thr Gly Asn Arg Leu Thr Tyr Thr Asn Trp Asn
385                 390                 395                 400

Glu Gly Glu Pro Asn Asn Ala Gly Ser Asp Glu Asp Cys Val Leu Leu
                405                 410                 415

Leu Lys Asn Gly Gln Trp Asn Asp Val Pro Cys Ser Thr Ser His Leu
            420                 425                 430

Ala Val Cys Glu Phe Pro Ile
        435

<210> SEQ ID NO 19
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

```
Asp Gly Val Glu Val His Asn Ala Lys Thr Lys Pro Arg Glu Glu Gln
 65                  70                  75                  80

Tyr Asp Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Asn Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Asn
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Ala Gly Ile Asn Gly Phe Pro Gly Lys
225                 230                 235                 240

Asp Gly Arg Asp Gly Thr Lys Gly Glu Lys Gly Glu Pro Gly Gln Gly
                245                 250                 255

Leu Arg Gly Leu Gln Gly Pro Pro Gly Lys Leu Gly Pro Pro Gly Asn
            260                 265                 270

Pro Gly Pro Ser Gly Ser Pro Gly Pro Lys Gly Gln Lys Gly Asp Pro
        275                 280                 285

Gly Lys Ser Pro Asp Gly Asp Ser Ser Leu Ala Ala Ser Glu Arg Lys
290                 295                 300

Ala Leu Gln Thr Glu Met Ala Arg Ile Lys Lys Trp Leu Thr Phe Ser
305                 310                 315                 320

Leu Gly Lys Gln Val Gly Asn Lys Phe Phe Leu Thr Asn Gly Glu Ile
                325                 330                 335

Met Thr Phe Glu Lys Val Lys Ala Leu Cys Val Lys Phe Gln Ala Ser
            340                 345                 350

Val Ala Thr Pro Arg Asn Ala Ala Glu Asn Gly Ala Ile Gln Asn Leu
        355                 360                 365

Ile Lys Glu Glu Ala Phe Leu Gly Ile Thr Asp Glu Lys Thr Glu Gly
370                 375                 380

Gln Phe Val Asp Leu Thr Gly Asn Arg Leu Thr Tyr Thr Asn Trp Asn
385                 390                 395                 400

Glu Gly Glu Pro Asn Asn Ala Gly Ser Asp Glu Asp Cys Val Leu Leu
                405                 410                 415

Leu Lys Asn Gly Gln Trp Asn Asp Val Pro Cys Ser Thr Ser His Leu
            420                 425                 430

Ala Val Cys Glu Phe Pro Ile
            435
```

<210> SEQ ID NO 20
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Gly Ile Asn Gly Phe Pro Gly Lys Asp Gly Arg Asp Gly Thr Lys Gly
1               5                   10                  15

Glu Lys Gly Glu Pro Gly Gln Gly Leu Arg Gly Leu Gln Gly Pro Pro
            20                  25                  30

Gly Lys Leu Gly Pro Pro Gly Asn Pro Gly Pro Ser Gly Ser Pro Gly
        35                  40                  45

Pro Lys Gly Gln Lys Gly Asp Pro Gly Lys Ser Glu Pro Lys Ser Ser
    50                  55                  60

Asp Lys Thr His Thr Cys Pro Pro Cys Pro Ala Pro Glu Leu Leu Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser His
            100                 105                 110

Glu Asp Pro Glu Val Lys Phe Asn Trp Tyr Val Asp Gly Val Glu Val
        115                 120                 125

His Asn Ala Lys Thr Lys Pro Arg Glu Glu Gln Tyr Asp Ser Thr Tyr
    130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Ala Leu Pro Ala Pro Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Arg Asp Glu Leu Thr Lys Asn Gln Val Ser
        195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Lys Leu Thr Val
                245                 250                 255

Asp Lys Ser Arg Trp Gln Gln Gly Asn Val Phe Ser Cys Ser Val Met
            260                 265                 270

His Glu Ala Leu His Asn His Tyr Thr Gln Lys Ser Leu Ser Leu Ser
        275                 280                 285

Pro Gly Ala Ser Pro Asp Gly Asp Ser Ser Leu Ala Ala Ser Glu Arg
    290                 295                 300

Lys Ala Leu Gln Thr Glu Met Ala Arg Ile Lys Lys Trp Leu Thr Phe
305                 310                 315                 320

Ser Leu Gly Lys Gln Val Gly Asn Lys Phe Phe Leu Thr Asn Gly Glu
                325                 330                 335

Ile Met Thr Phe Glu Lys Val Lys Ala Leu Cys Val Lys Phe Gln Ala
            340                 345                 350

Ser Val Ala Thr Pro Arg Asn Ala Ala Glu Asn Gly Ala Ile Gln Asn
        355                 360                 365

Leu Ile Lys Glu Glu Ala Phe Leu Gly Ile Thr Asp Glu Lys Thr Glu
    370                 375                 380

Gly Gln Phe Val Asp Leu Thr Gly Asn Arg Leu Thr Tyr Thr Asn Trp
385                 390                 395                 400
```

```
Asn Glu Gly Glu Pro Asn Asn Ala Gly Ser Asp Glu Asp Cys Val Leu
            405                 410                 415

Leu Leu Lys Asn Gly Gln Trp Asn Asp Val Pro Cys Ser Thr Ser His
        420                 425                 430

Leu Ala Val Cys Glu Phe Pro Ile
    435                 440

<210> SEQ ID NO 21
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Leu Gln Gly Pro Pro Gly Lys Leu Gly Pro Pro Gly Asn Pro Gly
1               5                   10                  15

Pro Ser Gly Ser Pro Gly Pro Lys Gly Gln Lys Gly Asp Pro Gly Lys
            20                  25                  30

Ser Glu Pro Lys Ser Ser Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asp Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Ala Ser Pro Asp Gly Asp Ser Ser
            260                 265                 270

Leu Ala Ala Ser Glu Arg Lys Ala Leu Gln Thr Glu Met Ala Arg Ile
        275                 280                 285

Lys Lys Trp Leu Thr Phe Ser Leu Gly Lys Gln Val Gly Asn Lys Phe
    290                 295                 300

Phe Leu Thr Asn Gly Glu Ile Met Thr Phe Glu Lys Val Lys Ala Leu
305                 310                 315                 320
```

```
Cys Val Lys Phe Gln Ala Ser Val Ala Thr Pro Arg Asn Ala Ala Glu
                325                 330                 335

Asn Gly Ala Ile Gln Asn Leu Ile Lys Glu Glu Ala Phe Leu Gly Ile
            340                 345                 350

Thr Asp Glu Lys Thr Glu Gly Gln Phe Val Asp Leu Thr Gly Asn Arg
        355                 360                 365

Leu Thr Tyr Thr Asn Trp Asn Glu Gly Glu Pro Asn Asn Ala Gly Ser
    370                 375                 380

Asp Glu Asp Cys Val Leu Leu Lys Asn Gly Gln Trp Asn Asp Val
385                 390                 395                 400

Pro Cys Ser Thr Ser His Leu Ala Val Cys Glu Phe Pro Ile
                405                 410
```

<210> SEQ ID NO 22
<211> LENGTH: 413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gly Leu Gln Gly Pro Pro Gly Lys Leu Gly Pro Pro Gly Asn Pro Gly
1               5                   10                  15

Pro Ser Gly Ser Pro Gly Pro Lys Gly Gln Lys Gly Asp Pro Gly Lys
            20                  25                  30

Ser Pro Asp Gly Asp Ser Ser Leu Ala Ala Ser Glu Arg Lys Ala Leu
        35                  40                  45

Gln Thr Glu Met Ala Arg Ile Lys Lys Trp Leu Thr Phe Ser Leu Gly
    50                  55                  60

Lys Gln Val Gly Asn Lys Phe Phe Leu Thr Asn Gly Glu Ile Met Thr
65                  70                  75                  80

Phe Glu Lys Val Lys Ala Leu Cys Val Lys Phe Gln Ala Ser Val Ala
                85                  90                  95

Thr Pro Arg Asn Ala Ala Glu Asn Gly Ala Ile Gln Asn Leu Ile Lys
            100                 105                 110

Glu Glu Ala Phe Leu Gly Ile Thr Asp Glu Lys Thr Glu Gly Gln Phe
        115                 120                 125

Val Asp Leu Thr Gly Asn Arg Leu Thr Tyr Thr Asn Trp Asn Glu Gly
    130                 135                 140

Glu Pro Asn Asn Ala Gly Ser Asp Glu Asp Cys Val Leu Leu Leu Lys
145                 150                 155                 160

Asn Gly Gln Trp Asn Asp Val Pro Cys Ser Thr Ser His Leu Ala Val
                165                 170                 175

Cys Glu Phe Pro Ile Glu Pro Lys Ser Ser Asp Lys Thr His Thr Cys
            180                 185                 190

Pro Pro Cys Pro Ala Pro Glu Leu Leu Gly Gly Pro Ser Val Phe Leu
        195                 200                 205

Phe Pro Pro Lys Pro Lys Asp Thr Leu Met Ile Ser Arg Thr Pro Glu
    210                 215                 220

Val Thr Cys Val Val Val Asp Val Ser His Glu Asp Pro Glu Val Lys
225                 230                 235                 240

Phe Asn Trp Tyr Val Asp Gly Val Glu Val His Asn Ala Lys Thr Lys
                245                 250                 255

Pro Arg Glu Glu Gln Tyr Asp Ser Thr Tyr Arg Val Val Ser Val Leu
```

```
                 260                 265                 270
Thr Val Leu His Gln Asp Trp Leu Asn Gly Lys Glu Tyr Lys Cys Lys
            275                 280                 285

Val Ser Asn Lys Ala Leu Pro Ala Pro Ile Glu Lys Thr Ile Ser Lys
        290                 295                 300

Ala Lys Gly Gln Pro Arg Glu Pro Gln Val Tyr Thr Leu Pro Pro Ser
305                 310                 315                 320

Arg Asp Glu Leu Thr Lys Asn Gln Val Ser Leu Thr Cys Leu Val Lys
            325                 330                 335

Gly Phe Tyr Pro Ser Asp Ile Ala Val Glu Trp Glu Ser Asn Gly Gln
        340                 345                 350

Pro Glu Asn Asn Tyr Lys Thr Thr Pro Pro Val Leu Asp Ser Asp Gly
            355                 360                 365

Ser Phe Phe Leu Tyr Ser Lys Leu Thr Val Asp Lys Ser Arg Trp Gln
        370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Ala
            405                 410

<210> SEQ ID NO 23
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Leu Gln Gly Pro Pro Gly Ser Leu Gly Pro Pro Gly Asn Pro Gly
1               5                   10                  15

Pro Ser Gly Ser Pro Gly Pro Ser Gly Gln Ser Gly Asp Pro Gly Ser
            20                  25                  30

Ser Glu Pro Lys Ser Ser Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asp Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205
```

-continued

```
Tyr Lys Thr Thr Pro Pro Val Leu Asp Ser Asp Gly Ser Phe Phe Leu
210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Ala Ser Pro Asp Gly Asp Ser Ser
            260                 265                 270

Leu Ala Ala Ser Glu Arg Lys Ala Leu Gln Thr Glu Met Ala Arg Ile
                275                 280                 285

Lys Lys Trp Leu Thr Phe Ser Leu Gly Lys Gln Val Gly Asn Lys Phe
290                 295                 300

Phe Leu Thr Asn Gly Glu Ile Met Thr Phe Glu Lys Val Lys Ala Leu
305                 310                 315                 320

Cys Val Lys Phe Gln Ala Ser Val Ala Thr Pro Arg Asn Ala Ala Glu
                325                 330                 335

Asn Gly Ala Ile Gln Asn Leu Ile Lys Glu Glu Ala Phe Leu Gly Ile
                340                 345                 350

Thr Asp Glu Lys Thr Glu Gly Gln Phe Val Asp Leu Thr Gly Asn Arg
                355                 360                 365

Leu Thr Tyr Thr Asn Trp Asn Glu Gly Glu Pro Asn Asn Ala Gly Ser
370                 375                 380

Asp Glu Asp Cys Val Leu Leu Leu Lys Asn Gly Gln Trp Asn Asp Val
385                 390                 395                 400

Pro Cys Ser Thr Ser His Leu Ala Val Cys Glu Phe Pro Ile
                405                 410

<210> SEQ ID NO 24
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asp Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160
```

-continued

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
        180                 185                 190

Ser Lys Leu Thr Val Asp Lys Ser Arg Trp Gln Gln Gly Asn Val Phe
    195                 200                 205

Ser Cys Ser Val Met His Glu Ala Leu His Asn His Tyr Thr Gln Lys
210                 215                 220

Ser Leu Ser Leu Ser Pro Gly Ala Gly Ile Asn Gly Phe Pro Gly Lys
225                 230                 235                 240

Asp Gly Arg Asp Gly Thr Lys Gly Glu Lys Gly Glu Pro Gly Gln Gly
            245                 250                 255

Leu Arg Gly Leu Gln Gly Pro Pro Gly Gln Leu Gly Pro Pro Gly Asn
        260                 265                 270

Pro Gly Pro Ser Gly Ser Pro Gly Pro Lys Gly Gln Lys Gly Asp Pro
    275                 280                 285

Gly Lys Ser Pro Asp Gly Asp Ser Ser Leu Ala Ala Ser Glu Arg Lys
    290                 295                 300

Ala Leu Gln Thr Glu Met Ala Arg Ile Lys Lys Trp Leu Thr Phe Ser
305                 310                 315                 320

Leu Gly Lys Gln Val Gly Asn Lys Phe Phe Leu Thr Asn Gly Glu Ile
            325                 330                 335

Met Thr Phe Glu Lys Val Lys Ala Leu Cys Val Lys Phe Gln Ala Ser
        340                 345                 350

Val Ala Thr Pro Arg Asn Ala Ala Glu Asn Gly Ala Ile Gln Asn Leu
    355                 360                 365

Ile Lys Glu Glu Ala Phe Leu Gly Ile Thr Asp Glu Lys Thr Glu Gly
    370                 375                 380

Gln Phe Val Asp Leu Thr Gly Asn Arg Leu Thr Tyr Thr Asn Trp Asn
385                 390                 395                 400

Glu Gly Glu Pro Asn Asn Ala Gly Ser Asp Glu Asp Cys Val Leu Leu
            405                 410                 415

Leu Lys Asn Gly Gln Trp Asn Asp Val Pro Cys Ser Thr Ser His Leu
        420                 425                 430

Ala Val Cys Glu Phe Pro Ile
        435

<210> SEQ ID NO 25
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Leu Gln Gly Pro Pro Gly Lys Leu Gly Pro Pro Gly Asn Pro Gly
1               5                   10                  15

Pro Ser Gly Ser Ser Glu Pro Lys Ser Ser Asp Lys Thr His Thr Cys
            20                  25                  30

Pro Pro Cys Pro Ala Pro Glu Leu Leu Gly Gly Pro Ser Val Phe Leu
        35                  40                  45

Phe Pro Pro Lys Pro Lys Asp Thr Leu Met Ile Ser Arg Thr Pro Glu
    50                  55                  60

Val Thr Cys Val Val Val Asp Val Ser His Glu Asp Pro Glu Val Lys 65                  70                  75                  80
Phe Asn Trp Tyr Val Asp Gly Val Glu Val His Asn Ala Lys Thr Lys
                    85                  90                  95

Pro Arg Glu Glu Gln Tyr Asp Ser Thr Tyr Arg Val Val Ser Val Leu
                100                 105                 110

Thr Val Leu His Gln Asp Trp Leu Asn Gly Lys Glu Tyr Lys Cys Lys
            115                 120                 125

Val Ser Asn Lys Ala Leu Pro Ala Pro Ile Glu Lys Thr Ile Ser Lys
130                 135                 140

Ala Lys Gly Gln Pro Arg Glu Pro Gln Val Tyr Thr Leu Pro Pro Ser
145                 150                 155                 160

Arg Asp Glu Leu Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Ala Ser Pro Asp
                245                 250                 255

Gly Asp Ser Ser Leu Ala Ala Ser Glu Arg Lys Ala Leu Gln Thr Glu
            260                 265                 270

Met Ala Arg Ile Lys Lys Trp Leu Thr Phe Ser Leu Gly Lys Gln Val
        275                 280                 285

Gly Asn Lys Phe Phe Leu Thr Asn Gly Glu Ile Met Thr Phe Glu Lys
290                 295                 300

Val Lys Ala Leu Cys Val Lys Phe Gln Ala Ser Val Ala Thr Pro Arg
305                 310                 315                 320

Asn Ala Ala Glu Asn Gly Ala Ile Gln Asn Leu Ile Lys Glu Glu Ala
                325                 330                 335

Phe Leu Gly Ile Thr Asp Glu Lys Thr Glu Gly Gln Phe Val Asp Leu
            340                 345                 350

Thr Gly Asn Arg Leu Thr Tyr Thr Asn Trp Asn Glu Gly Glu Pro Asn
        355                 360                 365

Asn Ala Gly Ser Asp Glu Asp Cys Val Leu Leu Leu Lys Asn Gly Gln
370                 375                 380

Trp Asn Asp Val Pro Cys Ser Thr Ser His Leu Ala Val Cys Glu Phe
385                 390                 395                 400

Pro Ile

<210> SEQ ID NO 26
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Asn Pro Gly Pro Ser Gly Ser Pro Gly Pro Lys Gly Gln Lys Gly
1               5                   10                  15

Asp Pro Gly Lys Ser Glu Pro Lys Ser Ser Asp Lys Thr His Thr Cys

Pro Pro Cys Pro Ala Pro Glu Leu Leu Gly Gly Pro Ser Val Phe Leu
           20                  25                  30             35

Phe Pro Pro Lys Pro Lys Asp Thr Leu Met Ile Ser Arg Thr Pro Glu
 50                  55                  60

Val Thr Cys Val Val Val Asp Val Ser His Glu Asp Pro Glu Val Lys
 65                  70                  75                  80

Phe Asn Trp Tyr Val Asp Gly Val Glu Val His Asn Ala Lys Thr Lys
                     85                  90                  95

Pro Arg Glu Glu Gln Tyr Asp Ser Thr Tyr Arg Val Val Ser Val Leu
                100                 105                 110

Thr Val Leu His Gln Asp Trp Leu Asn Gly Lys Glu Tyr Lys Cys Lys
                115                 120                 125

Val Ser Asn Lys Ala Leu Pro Ala Pro Ile Glu Lys Thr Ile Ser Lys
                130                 135                 140

Ala Lys Gly Gln Pro Arg Glu Pro Gln Val Tyr Thr Leu Pro Pro Ser
145                 150                 155                 160

Arg Asp Glu Leu Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
                180                 185                 190

Pro Glu Asn Asn Tyr Lys Thr Thr Pro Pro Val Leu Asp Ser Asp Gly
                195                 200                 205

Ser Phe Phe Leu Tyr Ser Lys Leu Thr Val Asp Lys Ser Arg Trp Gln
210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Ala Ser Pro Asp
                245                 250                 255

Gly Asp Ser Ser Leu Ala Ala Ser Glu Arg Lys Ala Leu Gln Thr Glu
                260                 265                 270

Met Ala Arg Ile Lys Lys Trp Leu Thr Phe Ser Leu Gly Lys Gln Val
                275                 280                 285

Gly Asn Lys Phe Phe Leu Thr Asn Gly Glu Ile Met Thr Phe Glu Lys
290                 295                 300

Val Lys Ala Leu Cys Val Lys Phe Gln Ala Ser Val Ala Thr Pro Arg
305                 310                 315                 320

Asn Ala Ala Glu Asn Gly Ala Ile Gln Asn Leu Ile Lys Glu Glu Ala
                325                 330                 335

Phe Leu Gly Ile Thr Asp Glu Lys Thr Glu Gly Gln Phe Val Asp Leu
                340                 345                 350

Thr Gly Asn Arg Leu Thr Tyr Thr Asn Trp Asn Glu Gly Glu Pro Asn
                355                 360                 365

Asn Ala Gly Ser Asp Glu Asp Cys Val Leu Leu Leu Lys Asn Gly Gln
                370                 375                 380

Trp Asn Asp Val Pro Cys Ser Thr Ser His Leu Ala Val Cys Glu Phe
385                 390                 395                 400

Pro Ile

<210> SEQ ID NO 27
<211> LENGTH: 439
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 27

```
Gly Ser Pro Gly Ile Pro Gly Thr Pro Gly Ser His Gly Leu Pro Gly
1               5                   10                  15

Arg Asp Gly Arg Asp Gly Val Lys Gly Asp Pro Gly Pro Pro Gly Pro
            20                  25                  30

Met Gly Pro Pro Gly Glu Thr Pro Cys Pro Pro Gly Asn Asn Gly Leu
        35                  40                  45

Pro Gly Ala Pro Gly Val Pro Gly Glu Arg Gly Glu Lys Gly Glu Ala
    50                  55                  60

Gly Glu Arg Gly Pro Pro Gly Ser Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asp Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Asp Glu Leu Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285

Ala Lys Ser Pro Asp Gly Asp Ser Ser Leu Ala Ala Ser Glu Arg Lys
    290                 295                 300

Ala Leu Gln Thr Glu Met Ala Arg Ile Lys Lys Trp Leu Thr Phe Ser
305                 310                 315                 320

Leu Gly Lys Gln Val Gly Asn Lys Phe Phe Leu Thr Asn Gly Glu Ile
                325                 330                 335

Met Thr Phe Glu Lys Val Lys Ala Leu Cys Val Lys Phe Gln Ala Ser
            340                 345                 350

Val Ala Thr Pro Arg Asn Ala Ala Glu Asn Gly Ala Ile Gln Asn Leu
        355                 360                 365

Ile Lys Glu Glu Ala Phe Leu Gly Ile Thr Asp Glu Lys Thr Glu Gly
    370                 375                 380

Gln Phe Val Asp Leu Thr Gly Asn Arg Leu Thr Tyr Thr Asn Trp Asn
385                 390                 395                 400
```

```
Glu Gly Glu Pro Asn Asn Ala Gly Ser Asp Glu Asp Cys Val Leu Leu
                405                 410                 415
Leu Lys Asn Gly Gln Trp Asn Asp Val Pro Cys Ser Thr Ser His Leu
            420                 425                 430
Ala Val Cys Glu Phe Pro Ile
        435

<210> SEQ ID NO 28
<211> LENGTH: 248
<212> TYPE: PRT
<213> ORGANISM: Homo sapiens

<400> SEQUENCE: 28

Met Ser Leu Phe Pro Ser Leu Pro Leu Leu Leu Ser Met Val Ala
1               5                   10                  15
Ala Ser Tyr Ser Glu Thr Val Thr Cys Glu Asp Ala Gln Lys Thr Cys
            20                  25                  30
Pro Ala Val Ile Ala Cys Ser Ser Pro Gly Ile Asn Gly Phe Pro Gly
            35                  40                  45
Lys Asp Gly Arg Asp Gly Thr Lys Gly Glu Lys Gly Glu Pro Gly Gln
50                  55                  60
Gly Leu Arg Gly Leu Gln Gly Pro Pro Gly Lys Leu Gly Pro Pro Gly
65                  70                  75                  80
Asn Pro Gly Pro Ser Gly Ser Pro Gly Pro Lys Gly Gln Lys Gly Asp
                85                  90                  95
Pro Gly Lys Ser Pro Asp Gly Asp Ser Ser Leu Ala Ala Ser Glu Arg
            100                 105                 110
Lys Ala Leu Gln Thr Glu Met Ala Arg Ile Lys Lys Trp Leu Thr Phe
            115                 120                 125
Ser Leu Gly Lys Gln Val Gly Asn Lys Phe Phe Leu Thr Asn Gly Glu
130                 135                 140
Ile Met Thr Phe Glu Lys Val Lys Ala Leu Cys Val Lys Phe Gln Ala
145                 150                 155                 160
Ser Val Ala Thr Pro Arg Asn Ala Ala Glu Asn Gly Ala Ile Gln Asn
                165                 170                 175
Leu Ile Lys Glu Glu Ala Phe Leu Gly Ile Thr Asp Glu Lys Thr Glu
            180                 185                 190
Gly Gln Phe Val Asp Leu Thr Gly Asn Arg Leu Thr Tyr Thr Asn Trp
            195                 200                 205
Asn Glu Gly Glu Pro Asn Asn Ala Gly Ser Asp Glu Asp Cys Val Leu
        210                 215                 220
Leu Leu Lys Asn Gly Gln Trp Asn Asp Val Pro Cys Ser Thr Ser His
225                 230                 235                 240
Leu Ala Val Cys Glu Phe Pro Ile
                245

<210> SEQ ID NO 29
<211> LENGTH: 228
<212> TYPE: PRT
<213> ORGANISM: Homo sapiens

<400> SEQUENCE: 29

Glu Thr Val Thr Cys Glu Asp Ala Gln Lys Thr Cys Pro Ala Val Ile
1               5                   10                  15
Ala Cys Ser Ser Pro Gly Ile Asn Gly Phe Pro Gly Lys Asp Gly Arg
            20                  25                  30
```

```
Asp Gly Thr Lys Gly Glu Lys Gly Glu Pro Gly Gln Gly Leu Arg Gly
            35                  40                  45

Leu Gln Gly Pro Pro Gly Lys Leu Gly Pro Pro Gly Asn Pro Gly Pro
    50                  55                  60

Ser Gly Ser Pro Gly Pro Lys Gly Gln Lys Gly Asp Pro Gly Lys Ser
65                  70                  75                  80

Pro Asp Gly Asp Ser Ser Leu Ala Ala Ser Glu Arg Lys Ala Leu Gln
                85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
        115                 120                 125

Glu Lys Val Lys Ala Leu Cys Val Lys Phe Gln Ala Ser Val Ala Thr
    130                 135                 140

Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190

Pro Asn Asn Ala Gly Ser Asp Glu Asp Cys Val Leu Leu Leu Lys Asn
        195                 200                 205

Gly Gln Trp Asn Asp Val Pro Cys Ser Thr Ser His Leu Ala Val Cys
    210                 215                 220

Glu Phe Pro Ile
225

<210> SEQ ID NO 30
<211> LENGTH: 20
<212> TYPE: PRT
<213> ORGANISM: Homo sapiens

<400> SEQUENCE: 30

Met Ser Leu Phe Pro Ser Leu Pro Leu Leu Leu Leu Ser Met Val Ala
1               5                   10                  15

Ala Ser Tyr Ser
            20

<210> SEQ ID NO 31
<211> LENGTH: 141
<212> TYPE: PRT
<213> ORGANISM: Homo sapiens

<400> SEQUENCE: 31

Ala Ala Ser Glu Arg Lys Ala Leu Gln Thr Glu Met Ala Arg Ile Lys
1               5                   10                  15

Lys Trp Leu Thr Phe Ser Leu Gly Lys Gln Val Gly Asn Lys Phe Phe
            20                  25                  30

Leu Thr Asn Gly Glu Ile Met Thr Phe Glu Lys Val Lys Ala Leu Cys
        35                  40                  45

Val Lys Phe Gln Ala Ser Val Ala Thr Pro Arg Asn Ala Ala Glu Asn
    50                  55                  60

Gly Ala Ile Gln Asn Leu Ile Lys Glu Glu Ala Phe Leu Gly Ile Thr
65                  70                  75                  80

Asp Glu Lys Thr Glu Gly Gln Phe Val Asp Leu Thr Gly Asn Arg Leu
                85                  90                  95
```

Thr Tyr Thr Asn Trp Asn Glu Gly Glu Pro Asn Asn Ala Gly Ser Asp
                100                 105                 110

Glu Asp Cys Val Leu Leu Lys Asn Gly Gln Trp Asn Asp Val Pro
        115                 120                 125

Cys Ser Thr Ser His Leu Ala Val Cys Glu Phe Pro Ile
    130                 135                 140

<210> SEQ ID NO 32
<211> LENGTH: 115
<212> TYPE: PRT
<213> ORGANISM: Homo sapiens

<400> SEQUENCE: 32

Val Gly Asn Lys Phe Phe Leu Thr Asn Gly Glu Ile Met Thr Phe Glu
1               5                   10                  15

Lys Val Lys Ala Leu Cys Val Lys Phe Gln Ala Ser Val Ala Thr Pro
            20                  25                  30

Arg Asn Ala Ala Glu Asn Gly Ala Ile Gln Asn Leu Ile Lys Glu Glu
        35                  40                  45

Ala Phe Leu Gly Ile Thr Asp Glu Lys Thr Glu Gly Gln Phe Val Asp
50                  55                  60

Leu Thr Gly Asn Arg Leu Thr Tyr Thr Asn Trp Asn Glu Gly Glu Pro
65                  70                  75                  80

Asn Asn Ala Gly Ser Asp Glu Asp Cys Val Leu Leu Lys Asn Gly
                85                  90                  95

Gln Trp Asn Asp Val Pro Cys Ser Thr Ser His Leu Ala Val Cys Glu
            100                 105                 110

Phe Pro Ile
        115

<210> SEQ ID NO 33
<211> LENGTH: 148
<212> TYPE: PRT
<213> ORGANISM: Homo sapiens

<400> SEQUENCE: 33

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
        35                  40                  45

Glu Lys Val Lys Ala Leu Cys Val Lys Phe Gln Ala Ser Val Ala Thr
50                  55                  60

Pro Arg Asn Ala Ala Glu Asn Gly Ala Ile Gln Asn Leu Ile Lys Glu
65                  70                  75                  80

Glu Ala Phe Leu Gly Ile Thr Asp Glu Lys Thr Glu Gly Gln Phe Val
                85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Lys Asn
        115                 120                 125

Gly Gln Trp Asn Asp Val Pro Cys Ser Thr Ser His Leu Ala Val Cys
    130                 135                 140

Glu Phe Pro Ile
145

<210> SEQ ID NO 34
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

Thr Asn Gly Glu Ile Met Thr Phe Glu Lys Val Lys Ala Leu Cys Val
        275                 280                 285

Lys Phe Gln Ala Ser Val Ala Thr Pro Arg Asn Ala Ala Glu Asn Gly
290                 295                 300

Ala Ile Gln Asn Leu Ile Lys Glu Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Leu Lys Asn Gly Gln Trp Asn Asp Val Pro Cys
```

```
                355                 360                 365
Ser Thr Ser His Leu Ala Val Cys Glu Phe Pro Ile
        370                 375                 380

<210> SEQ ID NO 35
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
                245                 250                 255

Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
        275                 280                 285

Leu Cys Val Lys Phe Gln Ala Ser Val Ala Thr Pro Arg Asn Ala Ala
    290                 295                 300

Glu Asn Gly Ala Ile Gln Asn Leu Ile Lys Glu Glu Ala Phe Leu Gly
305                 310                 315                 320

Ile Thr Asp Glu Lys Thr Glu Gly Gln Phe Val Asp Leu Thr Gly Asn
                325                 330                 335
```

```
Arg Leu Thr Tyr Thr Asn Trp Asn Glu Gly Glu Pro Asn Asn Ala Gly
                340                 345                 350

Ser Asp Glu Asp Cys Val Leu Leu Lys Asn Gly Gln Trp Asn Asp
            355                 360                 365

Val Pro Cys Ser Thr Ser His Leu Ala Val Cys Glu Phe Pro Ile
    370                 375                 380

<210> SEQ ID NO 36
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Thr Ser Gln Val Gly Asn Lys
225                 230                 235                 240

Phe Phe Leu Thr Asn Gly Glu Ile Met Thr Phe Glu Lys Val Lys Ala
                245                 250                 255

Leu Cys Val Lys Phe Gln Ala Ser Val Ala Thr Pro Arg Asn Ala Ala
            260                 265                 270

Glu Asn Gly Ala Ile Gln Asn Leu Ile Lys Glu Glu Ala Phe Leu Gly
        275                 280                 285

Ile Thr Asp Glu Lys Thr Glu Gly Gln Phe Val Asp Leu Thr Gly Asn
    290                 295                 300

Arg Leu Thr Tyr Thr Asn Trp Asn Glu Gly Glu Pro Asn Asn Ala Gly
305                 310                 315                 320
```

```
Ser Asp Glu Asp Cys Val Leu Leu Lys Asn Gly Gln Trp Asn Asp
                325                 330                 335

Val Pro Cys Ser Thr Ser His Leu Ala Val Cys Glu Phe Pro Ile
            340                 345                 350

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Lys Gln Val Gly Asn Lys Phe Phe Leu Thr Asn Gly Glu Ile Met Thr
1               5                   10                  15

Phe Glu Lys Val Lys Ala Leu Cys Val Lys Phe Gln Ala Ser Val Ala
                20                  25                  30

Thr Pro Arg Asn Ala Ala Glu Asn Gly Ala Ile Gln Asn Leu Ile Lys
            35                  40                  45

Glu Glu Ala Phe Leu Gly Ile Thr Asp Glu Lys Thr Glu Gly Gln Phe
    50                  55                  60

Val Asp Leu Thr Gly Asn Arg Leu Thr Tyr Thr Asn Trp Asn Glu Gly
65                  70                  75                  80

Glu Pro Asn Asn Ala Gly Ser Asp Glu Asp Cys Val Leu Leu Lys
                85                  90                  95

Asn Gly Gln Trp Asn Asp Val Pro Cys Ser Thr Ser His Leu Ala Val
            100                 105                 110

Cys Glu Phe Pro Ile
        115

<210> SEQ ID NO 38
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Leu Thr Pro Thr Phe Tyr Asp Asn Ser Cys Pro Asn Val Ser Asn
1               5                   10                  15

Ile Val Arg Asp Thr Ile Val Asn Glu Leu Arg Ser Asp Pro Arg Ile
                20                  25                  30

Ala Ala Ser Ile Leu Arg Leu His Phe His Asp Cys Phe Val Asn Gly
            35                  40                  45

Cys Asp Ala Ser Ile Leu Leu Asp Asn Thr Thr Ser Phe Arg Thr Glu
    50                  55                  60

Lys Asp Ala Phe Gly Asn Ala Asn Ser Ala Arg Gly Phe Pro Val Ile
65                  70                  75                  80

Asp Arg Met Lys Ala Ala Val Glu Ser Ala Cys Pro Arg Thr Val Ser
                85                  90                  95

Cys Ala Asp Leu Leu Thr Ile Ala Ala Gln Gln Ser Val Thr Leu Ala
            100                 105                 110

Gly Gly Pro Ser Trp Arg Val Pro Leu Gly Arg Arg Asp Ser Leu Gln
        115                 120                 125

Ala Phe Leu Asp Leu Ala Asn Ala Asn Leu Pro Ala Pro Phe Phe Thr
    130                 135                 140
```

```
Leu Pro Gln Leu Lys Asp Ser Phe Arg Asn Val Gly Leu Asn Arg Ser
145                 150                 155                 160

Ser Asp Leu Val Ala Leu Ser Gly Gly His Thr Phe Gly Lys Asn Gln
            165                 170                 175

Cys Arg Phe Ile Met Asp Arg Leu Tyr Asn Phe Ser Asn Thr Gly Leu
        180                 185                 190

Pro Asp Pro Thr Leu Asn Thr Thr Tyr Leu Gln Thr Leu Arg Gly Leu
    195                 200                 205

Cys Pro Leu Asn Gly Asn Leu Ser Ala Leu Val Asp Phe Asp Leu Arg
    210                 215                 220

Thr Pro Thr Ile Phe Asp Asn Lys Tyr Tyr Val Asn Leu Glu Glu Gln
225                 230                 235                 240

Lys Gly Leu Ile Gln Ser Asp Gln Glu Leu Phe Ser Ser Pro Asn Ala
                245                 250                 255

Thr Asp Thr Ile Pro Leu Val Arg Ser Phe Ala Asn Ser Thr Gln Thr
            260                 265                 270

Phe Phe Asn Ala Phe Val Glu Ala Met Asp Arg Met Gly Asn Ile Thr
        275                 280                 285

Pro Leu Thr Gly Thr Gln Gly Gln Ile Arg Leu Asn Cys Arg Val Val
    290                 295                 300

Asn Ser Asn Ser
305

<210> SEQ ID NO 39
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
cagttaaccc ctacattcta cgacaatagc tgtcccaacg tgtccaacat cgttcgcgac        60
acaatcgtca acgagctcag atccgatccc aggatcgctg cttcaatatt acgtctgcac       120
ttccatgact gcttcgtgaa tggttgcgac gctagcatat tactgacaaa caccaccagt       180
ttccgcactg aaaaggatgc attcgggaac gctaacagcg ccaggggctt ccagtgatc        240 gatcgcatga aggctgccgt tgagtcagca tgcccacgaa cagtcagttg tgcagacctg       300
ctgactatag ctgcgcaaca gagcgtgact cttgcaggcg gaccgtcctg gagagtgccg       360
ctcggtcgac gtgactccct acaggcattc ctagatctgg ccaacgccaa cttgcctgct       420
ccattcttca ccctgcccca gctgaaggat agctttagaa acgtgggtct gaatcgctcg       480
agtgaccttg tggctctgtc cggaggacac acatttggaa agaaccagtg taggttcatc       540
atggataggc tctacaattt cagcaacact gggttacctg accccacgct gaacactacg       600
tatctccaga cactgagagg cttgtgccca ctgaatggca acctcagtgc actagtggac       660
tttgatctgc ggaccccaac catcttcgat aacaagtact atgtgaatct agaggagcag       720
aaaggcctga tacagagtga tcaagaactg tttagcagtc caaacgccac tgacaccatc       780
ccactggtga gaagttttgc taactctact caaaccttct ttaacgcctt cgtggaagcc       840
atggaccgta tgggtaacat taccectctg acgggtaccc aaggccagat cgtctgaac         900 tgcagagtgg tcaacagcaa ctcttaatga                                          930

<210> SEQ ID NO 40
```

<211> LENGTH: 33
<212> TYPE: PRT
<213> ORGANISM: Homo sapiens

<400> SEQUENCE: 40

```
Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln
```

<210> SEQ ID NO 41
<211> LENGTH: 21
<212> TYPE: PRT
<213> ORGANISM: Homo sapiens

<400> SEQUENCE: 41

```
Glu Thr Val Thr Cys Glu Asp Ala Gln Lys Thr Cys Pro Ala Val Ile
1               5                   10                  15

Ala Cys Ser Ser Pro
            20
```

<210> SEQ ID NO 42
<211> LENGTH: 747
<212> TYPE: DNA
<213> ORGANISM: Homo sapiens
<220> FEATURE:
<221> NAME/KEY: CDS
<222> LOCATION: (1)..(744)

<400> SEQUENCE: 42

| | |
|---|---:|
| atg tcc ctg ttt cca tca ctc cct ctc ctt ctc ctg agt atg gtg gca<br>Met Ser Leu Phe Pro Ser Leu Pro Leu Leu Leu Leu Ser Met Val Ala<br>1               5                   10                  15 | 48 |
| gcg tct tac tca gaa act gtg acc tgt gag gat gcc caa aag acc tgc<br>Ala Ser Tyr Ser Glu Thr Val Thr Cys Glu Asp Ala Gln Lys Thr Cys<br>            20                  25                  30 | 96 |
| cct gca gtg att gcc tgt agc tct cca ggc atc aac ggc ttc cca ggc<br>Pro Ala Val Ile Ala Cys Ser Ser Pro Gly Ile Asn Gly Phe Pro Gly<br>        35                  40                  45 | 144 |
| aaa gat ggg cgt gat ggc acc aag gga gaa aag ggg gaa cca ggc caa<br>Lys Asp Gly Arg Asp Gly Thr Lys Gly Glu Lys Gly Glu Pro Gly Gln<br>    50                  55                  60 | 192 |
| ggg ctc aga ggc tta cag ggc ccc cct gga aag ttg ggg cct cca gga<br>Gly Leu Arg Gly Leu Gln Gly Pro Pro Gly Lys Leu Gly Pro Pro Gly<br>65                  70                  75                  80 | 240 |
| aat cca ggg cct tct ggg tca cca gga cca aag ggc caa aaa gga gac<br>Asn Pro Gly Pro Ser Gly Ser Pro Gly Pro Lys Gly Gln Lys Gly Asp<br>                85                  90                  95 | 288 |
| cct gga aaa agt ccg gat ggt gat agt agc ctg gct gcc tca gaa aga<br>Pro Gly Lys Ser Pro Asp Gly Asp Ser Ser Leu Ala Ala Ser Glu Arg<br>            100                 105                 110 | 336 |
| aaa gct ctg caa aca gaa atg gca cgt atc aaa aag tgg ctc acc ttc<br>Lys Ala Leu Gln Thr Glu Met Ala Arg Ile Lys Lys Trp Leu Thr Phe<br>        115                 120                 125 | 384 |
| tct ctg ggc aaa caa gtt ggg aac aag ttc ttc ctg acc aat ggt gaa<br>Ser Leu Gly Lys Gln Val Gly Asn Lys Phe Phe Leu Thr Asn Gly Glu<br>    130                 135                 140 | 432 |
| ata atg acc ttt gaa aaa gtg aag gcc ttg tgt gtc aag ttc cag gcc<br>Ile Met Thr Phe Glu Lys Val Lys Ala Leu Cys Val Lys Phe Gln Ala<br>145                 150                 155                 160 | 480 |

| | | |
|---|---|---|
| tct gtg gcc acc ccc agg aat gct gca gag aat gga gcc att cag aat<br>Ser Val Ala Thr Pro Arg Asn Ala Ala Glu Asn Gly Ala Ile Gln Asn<br>                            165                    170                  175 | | 528 |
| ctc atc aag gag gaa gcc ttc ctg ggc atc act gat gag aag aca gaa<br>Leu Ile Lys Glu Glu Ala Phe Leu Gly Ile Thr Asp Glu Lys Thr Glu<br>   180                    185                    190 | | 576 |
| ggg cag ttt gtg gat ctg aca gga aat aga ctg acc tac aca aac tgg<br>Gly Gln Phe Val Asp Leu Thr Gly Asn Arg Leu Thr Tyr Thr Asn Trp<br>          195                    200                    205 | | 624 |
| aac gag ggt gaa ccc aac aat gct ggt tct gat gaa gat tgt gta ttg<br>Asn Glu Gly Glu Pro Asn Asn Ala Gly Ser Asp Glu Asp Cys Val Leu<br>   210                    215                    220 | | 672 |
| cta ctg aaa aat ggc cag tgg aat gac gtc ccc tgc tcc acc tcc cat<br>Leu Leu Lys Asn Gly Gln Trp Asn Asp Val Pro Cys Ser Thr Ser His<br>225                    230                    235                    240 | | 720 |
| ctg gcc gtc tgt gag ttc cct atc tga<br>Leu Ala Val Cys Glu Phe Pro Ile<br>          245 | | 747 |

```
<210> SEQ ID NO 43
<211> LENGTH: 687
<212> TYPE: DNA
<213> ORGANISM: Homo sapiens
<220> FEATURE:
<221> NAME/KEY: CDS
<222> LOCATION: (1)..(684)

<400> SEQUENCE: 43
```

| | | |
|---|---|---|
| gaa act gtg acc tgt gag gat gcc caa aag acc tgc cct gca gtg att<br>Glu Thr Val Thr Cys Glu Asp Ala Gln Lys Thr Cys Pro Ala Val Ile<br>1                 5                    10                    15 | | 48 |
| gcc tgt agc tct cca ggc atc aac ggc ttc cca ggc aaa gat ggg cgt<br>Ala Cys Ser Ser Pro Gly Ile Asn Gly Phe Pro Gly Lys Asp Gly Arg<br>                 20                    25                    30 | | 96 |
| gat ggc acc aag gga gaa aag ggg gaa cca ggc caa ggg ctc aga ggc<br>Asp Gly Thr Lys Gly Glu Lys Gly Glu Pro Gly Gln Gly Leu Arg Gly<br>          35                    40                    45 | | 144 |
| tta cag ggc ccc cct gga aag ttg ggg cct cca gga aat cca ggg cct<br>Leu Gln Gly Pro Pro Gly Lys Leu Gly Pro Pro Gly Asn Pro Gly Pro<br>50                    55                    60 | | 192 |
| tct ggg tca cca gga cca aag ggc caa aaa gga gac cct gga aaa agt<br>Ser Gly Ser Pro Gly Pro Lys Gly Gln Lys Gly Asp Pro Gly Lys Ser<br>65                    70                    75                    80 | | 240 |
| ccg gat ggt gat agt agc ctg gct gcc tca gaa aga aaa gct ctg caa<br>Pro Asp Gly Asp Ser Ser Leu Ala Ala Ser Glu Arg Lys Ala Leu Gln<br>                         85                    90                    95 | | 288 |
| aca gaa atg gca cgt atc aaa aag tgg ctc acc ttc tct ctg ggc aaa<br>Thr Glu Met Ala Arg Ile Lys Lys Trp Leu Thr Phe Ser Leu Gly Lys<br>                 100                    105                    110 | | 336 |
| caa gtt ggg aac aag ttc ttc ctg acc aat ggt gaa ata atg acc ttt<br>Gln Val Gly Asn Lys Phe Phe Leu Thr Asn Gly Glu Ile Met Thr Phe<br>          115                    120                    125 | | 384 |
| gaa aaa gtg aag gcc ttg tgt gtc aag ttc cag gcc tct gtg gcc acc<br>Glu Lys Val Lys Ala Leu Cys Val Lys Phe Gln Ala Ser Val Ala Thr<br>130                    135                    140 | | 432 |
| ccc agg aat gct gca gag aat gga gcc att cag aat ctc atc aag gag<br>Pro Arg Asn Ala Ala Glu Asn Gly Ala Ile Gln Asn Leu Ile Lys Glu<br>145                    150                    155                    160 | | 480 |
| gaa gcc ttc ctg ggc atc act gat gag aag aca gaa ggg cag ttt gtg<br>Glu Ala Phe Leu Gly Ile Thr Asp Glu Lys Thr Glu Gly Gln Phe Val<br>                 165                    170                    175 | | 528 |

```
gat ctg aca gga aat aga ctg acc tac aca aac tgg aac gag ggt gaa     576
Asp Leu Thr Gly Asn Arg Leu Thr Tyr Thr Asn Trp Asn Glu Gly Glu
            180                 185                 190 ccc aac aat gct ggt tct gat gaa gat tgt gta ttg cta ctg aaa aat     624
Pro Asn Asn Ala Gly Ser Asp Glu Asp Cys Val Leu Leu Leu Lys Asn
195                 200                 205 ggc cag tgg aat gac gtc ccc tgc tcc acc tcc cat ctg gcc gtc tgt     672
Gly Gln Trp Asn Asp Val Pro Cys Ser Thr Ser His Leu Ala Val Cys
        210                 215                 220 gag ttc cct atc tga                                                 687
Glu Phe Pro Ile
225

<210> SEQ ID NO 44
<211> LENGTH: 1275
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1275)

<400> SEQUENCE: 44 ggc atc aac ggc ttc cca ggc aaa gat ggg cgt gat ggc acc aag gga      48
Gly Ile Asn Gly Phe Pro Gly Lys Asp Gly Arg Asp Gly Thr Lys Gly
1               5                   10                  15 gaa aag ggg gaa cca ggc caa ggg ctc aga ggc tta cag ggc ccc cct      96
Glu Lys Gly Glu Pro Gly Gln Gly Leu Arg Gly Leu Gln Gly Pro Pro
                20                  25                  30 gga aag ttg ggg cct cca gga aat cca ggg cct tct ggg tca cca gga     144
Gly Lys Leu Gly Pro Pro Gly Asn Pro Gly Pro Ser Gly Ser Pro Gly
            35                  40                  45 cca aag ggc caa aaa gga gac cct gga aaa agt gca cca gag ctg ctg     192
Pro Lys Gly Gln Lys Gly Asp Pro Gly Lys Ser Ala Pro Glu Leu Leu
        50                  55                  60 ggc gga cca agc gtg ttc ctg ttt cca ccc aag ccc aaa gat act ctg     240
Gly Gly Pro Ser Val Phe Leu Phe Pro Pro Lys Pro Lys Asp Thr Leu
65                  70                  75                  80 atg att tct cga aca ccc gaa gtg act tgc gtg gtc gtg gac gtg agc     288
Met Ile Ser Arg Thr Pro Glu Val Thr Cys Val Val Val Asp Val Ser
                85                  90                  95 cac gag gat cct gaa gtg aag ttc aac tgg tac gtg gac ggc gtc gag     336
His Glu Asp Pro Glu Val Lys Phe Asn Trp Tyr Val Asp Gly Val Glu
                100                 105                 110 gtg cat aat gcc aag aca aaa ccc cgg gag gaa cag tac gac tct acc     384
Val His Asn Ala Lys Thr Lys Pro Arg Glu Glu Gln Tyr Asp Ser Thr
            115                 120                 125 tat cgc gtc gtg agt gtc ctg aca gtg ctg cat cag gat tgg ctg aac     432
Tyr Arg Val Val Ser Val Leu Thr Val Leu His Gln Asp Trp Leu Asn
        130                 135                 140 gga aag gag tat aag tgc aaa gtg tcc aat aag gca ctg cct gcc cca     480
Gly Lys Glu Tyr Lys Cys Lys Val Ser Asn Lys Ala Leu Pro Ala Pro
145                 150                 155                 160 atc gag aaa act att tct aag gct aaa ggc cag cct aga gaa cca cag     528
Ile Glu Lys Thr Ile Ser Lys Ala Lys Gly Gln Pro Arg Glu Pro Gln
                165                 170                 175 gtg tac acc ctg cct cca agc cgg gac gag ctg act aag aac cag gtg     576
Val Tyr Thr Leu Pro Pro Ser Arg Asp Glu Leu Thr Lys Asn Gln Val
            180                 185                 190 tcc ctg acc tgt ctg gtc aaa ggc ttc tac cct tcc gat atc gca gtg     624
Ser Leu Thr Cys Leu Val Lys Gly Phe Tyr Pro Ser Asp Ile Ala Val
```

```
Ser Leu Thr Cys Leu Val Lys Gly Phe Tyr Pro Ser Asp Ile Ala Val
        195                 200                 205 gag tgg gaa tct aat ggg cag cca gag aac aat tac aag acc aca ccc      672
Glu Trp Glu Ser Asn Gly Gln Pro Glu Asn Asn Tyr Lys Thr Thr Pro
210                 215                 220 cct gtg ctg gac tct gat ggc agt ttc ttt ctg tat tca aag ctg acc      720
Pro Val Leu Asp Ser Asp Gly Ser Phe Phe Leu Tyr Ser Lys Leu Thr
225                 230                 235                 240 gtg gat aaa agc cgg tgg cag cag gga aat gtc ttc agt tgt tca gtg      768
Val Asp Lys Ser Arg Trp Gln Gln Gly Asn Val Phe Ser Cys Ser Val
            245                 250                 255 atg cac gaa gca ctg cac aac cac tac act cag aaa agc ctg tcc ctg      816
Met His Glu Ala Leu His Asn His Tyr Thr Gln Lys Ser Leu Ser Leu
        260                 265                 270 tcc cct gga gca agt ccg gat ggt gat agt agc ctg gct gcc tca gaa      864
Ser Pro Gly Ala Ser Pro Asp Gly Asp Ser Ser Leu Ala Ala Ser Glu
    275                 280                 285 aga aaa gct ctg caa aca gaa atg gca cgt atc aaa aag tgg ctc acc      912
Arg Lys Ala Leu Gln Thr Glu Met Ala Arg Ile Lys Lys Trp Leu Thr
290                 295                 300 ttc tct ctg ggc aaa caa gtt ggg aac aag ttc ttc ctg acc aat ggt      960
Phe Ser Leu Gly Lys Gln Val Gly Asn Lys Phe Phe Leu Thr Asn Gly
305                 310                 315                 320 gaa ata atg acc ttt gaa aaa gtg aag gcc ttg tgt gtc aag ttc cag     1008
Glu Ile Met Thr Phe Glu Lys Val Lys Ala Leu Cys Val Lys Phe Gln
            325                 330                 335 gcc tct gtg gcc acc ccc agg aat gct gca gag aat gga gcc att cag     1056
Ala Ser Val Ala Thr Pro Arg Asn Ala Ala Glu Asn Gly Ala Ile Gln
        340                 345                 350 aat ctc atc aag gag gaa gcc ttc ctg ggc atc act gat gag aag aca     1104
Asn Leu Ile Lys Glu Glu Ala Phe Leu Gly Ile Thr Asp Glu Lys Thr
    355                 360                 365 gaa ggg cag ttt gtg gat ctg aca gga aat aga ctg acc tac aca aac     1152
Glu Gly Gln Phe Val Asp Leu Thr Gly Asn Arg Leu Thr Tyr Thr Asn
370                 375                 380 tgg aac gag ggt gaa ccc aac aat gct ggt tct gat gaa gat tgt gta     1200
Trp Asn Glu Gly Glu Pro Asn Asn Ala Gly Ser Asp Glu Asp Cys Val
385                 390                 395                 400 ttg cta ctg aaa aat ggc cag tgg aat gac gtc ccc tgc tcc acc tcc     1248
Leu Leu Leu Lys Asn Gly Gln Trp Asn Asp Val Pro Cys Ser Thr Ser
            405                 410                 415 cat ctg gcc gtc tgt gag ttc cct atc                                 1275
His Leu Ala Val Cys Glu Phe Pro Ile
        420                 425

<210> SEQ ID NO 45
<211> LENGTH: 1242
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1242)

<400> SEQUENCE: 45 ggc tta cag ggc ccc cct gga aag ttg ggg cct cca gga aat cca ggg       48
Gly Leu Gln Gly Pro Pro Gly Lys Leu Gly Pro Pro Gly Asn Pro Gly
1               5                   10                  15 cct tct ggg tca cca gga cca aag ggc caa aaa gga gac cct gga aaa       96
Pro Ser Gly Ser Pro Gly Pro Lys Gly Gln Lys Gly Asp Pro Gly Lys
```

```
                20              25              30
agt gaa ccc aag tct agt gac aaa act cac acc tgc cca cct tgt cca    144
Ser Glu Pro Lys Ser Ser Asp Lys Thr His Thr Cys Pro Pro Cys Pro
    35              40              45 gca cca gag ctg ctg ggc gga cca agc gtg ttc ctg ttt cca ccc aag    192
Ala Pro Glu Leu Leu Gly Gly Pro Ser Val Phe Leu Phe Pro Pro Lys
50              55              60 ccc aaa gat act ctg atg att tct cga aca ccc gaa gtg act tgc gtg    240
Pro Lys Asp Thr Leu Met Ile Ser Arg Thr Pro Glu Val Thr Cys Val
65              70              75              80 gtc gtg gac gtg agc cac gag gat cct gaa gtg aag ttc aac tgg tac    288
Val Val Asp Val Ser His Glu Asp Pro Glu Val Lys Phe Asn Trp Tyr
            85              90              95 gtg gac ggc gtc gag gtg cat aat gcc aag aca aaa ccc cgg gag gaa    336
Val Asp Gly Val Glu Val His Asn Ala Lys Thr Lys Pro Arg Glu Glu
        100             105             110 cag tac gac tct acc tat cgc gtc gtg agt gtc ctg aca gtg ctg cat    384
Gln Tyr Asp Ser Thr Tyr Arg Val Val Ser Val Leu Thr Val Leu His
    115             120             125 cag gat tgg ctg aac gga aag gag tat aag tgc aaa gtg tcc aat aag    432
Gln Asp Trp Leu Asn Gly Lys Glu Tyr Lys Cys Lys Val Ser Asn Lys
130             135             140 gca ctg cct gcc cca atc gag aaa act att tct aag gct aaa ggc cag    480
Ala Leu Pro Ala Pro Ile Glu Lys Thr Ile Ser Lys Ala Lys Gly Gln
145             150             155             160 cct aga gaa cca cag gtg tac acc ctg cct cca agc cgg gac gag ctg    528
Pro Arg Glu Pro Gln Val Tyr Thr Leu Pro Pro Ser Arg Asp Glu Leu
            165             170             175 act aag aac cag gtg tcc ctg acc tgt ctg gtc aaa ggc ttc tac cct    576
Thr Lys Asn Gln Val Ser Leu Thr Cys Leu Val Lys Gly Phe Tyr Pro
        180             185             190 tcc gat atc gca gtg gag tgg gaa tct aat ggg cag cca gag aac aat    624
Ser Asp Ile Ala Val Glu Trp Glu Ser Asn Gly Gln Pro Glu Asn Asn
    195             200             205 tac aag acc aca ccc cct gtg ctg gac tct gat ggc agt ttc ttt ctg    672
Tyr Lys Thr Thr Pro Pro Val Leu Asp Ser Asp Gly Ser Phe Phe Leu
210             215             220 tat tca aag ctg acc gtg gat aaa agc cgg tgg cag cag gga aat gtc    720
Tyr Ser Lys Leu Thr Val Asp Lys Ser Arg Trp Gln Gln Gly Asn Val
225             230             235             240 ttc agt tgt tca gtg atg cac gaa gca ctg cac aac cac tac act cag    768
Phe Ser Cys Ser Val Met His Glu Ala Leu His Asn His Tyr Thr Gln
            245             250             255 aaa agc ctg tcc ctg tcc cct gga gca agt ccg gat ggt gat agt agc    816
Lys Ser Leu Ser Leu Ser Pro Gly Ala Ser Pro Asp Gly Asp Ser Ser
        260             265             270 ctg gct gcc tca gaa aga aaa gct ctg caa aca gaa atg gca cgt atc    864
Leu Ala Ala Ser Glu Arg Lys Ala Leu Gln Thr Glu Met Ala Arg Ile
    275             280             285 aaa aag tgg ctc acc ttc tct ctg ggc aaa caa gtt ggg aac aag ttc    912
Lys Lys Trp Leu Thr Phe Ser Leu Gly Lys Gln Val Gly Asn Lys Phe
290             295             300 ttc ctg acc aat ggt gaa ata atg acc ttt gaa aaa gtg aag gcc ttg    960
Phe Leu Thr Asn Gly Glu Ile Met Thr Phe Glu Lys Val Lys Ala Leu
305             310             315             320 tgt gtc aag ttc cag gcc tct gtg gcc acc ccc agg aat gct gca gag   1008
Cys Val Lys Phe Gln Ala Ser Val Ala Thr Pro Arg Asn Ala Ala Glu
            325             330             335 aat gga gcc att cag aat ctc atc aag gag gaa gcc ttc ctg ggc atc   1056
```

-continued

| | | | | | | | | | | | | | | |
|---|---|---|---|---|---|---|---|---|---|---|---|---|---|---|
| Asn | Gly | Ala | Ile | Gln | Asn | Leu | Ile | Lys | Glu | Glu | Ala | Phe | Leu | Gly | Ile |
| | | | 340 | | | | | 345 | | | | | 350 | | |

| act | gat | gag | aag | aca | gaa | ggg | cag | ttt | gtg | gat | ctg | aca | gga | aat | aga | 1104 |
|---|---|---|---|---|---|---|---|---|---|---|---|---|---|---|---|---|
| Thr | Asp | Glu | Lys | Thr | Glu | Gly | Gln | Phe | Val | Asp | Leu | Thr | Gly | Asn | Arg | |
| | | 355 | | | | | 360 | | | | | 365 | | | | |

| ctg | acc | tac | aca | aac | tgg | aac | gag | ggt | gaa | ccc | aac | aat | gct | ggt | tct | 1152 |
|---|---|---|---|---|---|---|---|---|---|---|---|---|---|---|---|---|
| Leu | Thr | Tyr | Thr | Asn | Trp | Asn | Glu | Gly | Glu | Pro | Asn | Asn | Ala | Gly | Ser | |
| | 370 | | | | | 375 | | | | | 380 | | | | | |

| gat | gaa | gat | tgt | gta | ttg | cta | ctg | aaa | aat | ggc | cag | tgg | aat | gac | gtc | 1200 |
|---|---|---|---|---|---|---|---|---|---|---|---|---|---|---|---|---|
| Asp | Glu | Asp | Cys | Val | Leu | Leu | Leu | Lys | Asn | Gly | Gln | Trp | Asn | Asp | Val | |
| 385 | | | | 390 | | | | | 395 | | | | | 400 | | |

| ccc | tgc | tcc | acc | tcc | cat | ctg | gcc | gtc | tgt | gag | ttc | cct | atc | 1242 |
|---|---|---|---|---|---|---|---|---|---|---|---|---|---|---|
| Pro | Cys | Ser | Thr | Ser | His | Leu | Ala | Val | Cys | Glu | Phe | Pro | Ile | |
| | | | | 405 | | | | | 410 | | | | | |

MICROBE-BINDING MOLECULES AND USES THEREOF

CROSS-REFERENCE TO RELATED APPLICATIONS

This application is a continuation under 35 U.S.C. § 120 of co-pending U.S. application Ser. No. 15/750,788 filed on Feb. 6, 2018, which is a 371 National Phase Entry of International Patent Application No. PCT/US2016/045509 filed on Aug. 4, 2016, which claims benefit under 35 U.S.C. § 119(e) of U.S. Provisional Application No. 62/201,745 filed on Aug. 6, 2015, the contents of each of which are incorporated herein by reference in their entireties.

GOVERNMENT SUPPORT

This invention was made with government support under grant no. N66001-11-1-4180 awarded by Defense Advanced Research Projects Agency (DARPA). The government has certain rights in the invention.

SEQUENCE LISTING

The instant application contains a Sequence Listing which has been submitted electronically in ASCII format and is hereby incorporated by reference in its entirety. Said ASCII copy, created on Aug. 3, 2016, is named 002806-084581-PCT_SL.txt and is 102,798 bytes in size.

TECHNICAL FIELD

Described herein relates generally to molecules, products, kits and methods for detecting and/or removing microbes in a sample or a target area, including bodily fluids such as blood and tissues of a subject, food, water, and environmental surfaces.

BACKGROUND

Sepsis is a major cause of morbidity and mortality in humans and other animals. In the United States, sepsis is the second leading cause of death in intensive care units among patients with non-traumatic illnesses. It is also the leading cause of death in young livestock, affecting 7.5-29% of neonatal calves, and is a common medical problem in neonatal foals. Despite the major advances of the past several decades in the treatment of serious infections, the incidence and mortality due to sepsis continues to rise.

Sepsis results from the systemic invasion of microorganisms into blood and can present two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and, often times, death.

There are three major types of sepsis characterized by the type of infecting organism. For example, gram-negative sepsis is the most frequently isolated (with a case fatality rate of about 35%). The majority of these infections are caused by *Escherichia coli, Klebsiella pneumoniae* and *Pseudomonas aeruginosa*. Gram-positive pathogens such as the Staphylococci and Streptococci are the second major cause of sepsis. The third major group includes fungi, with fungal infections causing a relatively small percentage of sepsis cases, but with a high mortality rate; these types of infections also have a higher incidence in immuno-compromised patients.

Many patients with septicemia or suspected septicemia exhibit a rapid decline over a 24-48 hour period. It has been reported that patients with septic shock require adapted treatment in less than 6 hours in order to benefit from antimicrobial therapy. Thus, rapid, reliable and sensitive diagnostic and treatment methods are essential for effective patient care. In addition, the ability to rapidly detect with high sensitivity pathogens for non-medical applications, such as food, water, and/or environmental testing would also have great value, in addition to medical applications, e.g., for preventing infections and sepsis in the population. Hence, there remains a need for improved reagents and techniques that can not only provide high-affinity binding for capture of microbes (e.g., pathogens) and/or microbial matter, but can also provide high-sensitivity detection capability to detect the presence of microbes (e.g., pathogens) and/or microbial matter.

SUMMARY

Embodiments described herein are based on, at least in part, engineering a microbe-targeting molecule or a microbe-binding molecule that provides not only high-affinity binding to a microbe and/or microbial matter, but also high-sensitivity detection of a microbe and/or microbial matter. For example, the inventors have engineered improved variants of FcMBL that show greater sensitivity to detect microbes and/or microbial matter (e.g., microbial cell wall components, and endotoxins) in an ELISA assay, and are also easier to express the proteins than full-length MBL proteins, which is generally difficult to make. The engineered microbe-targeting molecules described herein provide a valuable building block for various applications including, but not limited to, diagnosis or treatment of diseases caused by microbes or pathogens, removal of microbes or pathogens from a sample, including bodily fluids and tissues of a subject, foods, water, or an environmental surface; and development of targeted drug delivery devices.

Generally, the microbe-binding molecule comprises (i) a collagen domain; (ii) an Fc domain; and (iii) a microbe-binding domain comprising a helical domain and a carbohydrate recognition domain (CRD). In some embodiments, the Fc domain can link the collagen domain to the microbe-surface binding domain. In some embodiments, the collagen domain can link the Fc domain to the microbe-surface binding domain, and there is no cysteine-rich crosslinking domain between the collagen domain and the Fc domain. In some embodiments, the microbe-surface binding domain can link the collagen domain to the Fc domain, and the collagen domain that is not linked to the microbe-binding domain does not comprise a cysteine-rich crosslinking domain.

Without wishing to be bound by theory, addition of the collagen domain to the microbe-binding molecules increases the sensitivity (e.g., providing a higher detectable signal) of using the microbe-binding molecules as detection agents, partly because the collagen domain can provide multimerization function, which enables formation of a larger multimer from a plurality of individual microbe-binding molecules described herein as monomers, and thus the multimer can generate a higher detectable signal, as compared to individual monomers. The multimerization of the microbe-binding molecules can also provide increased avidity of individual monomers to bind a microbe and/or microbial matter, thereby increasing the sensitivity of microbe detection. Alternatively or additionally, the collagen domain can be adapted to provide more binding sites for a detectable label, which enables generation of a higher detectable signal, without formation of a larger multimer. In some embodiments, the collagen domain can also be adapted to provide complement signaling capabilities, which can be useful as therapeutic agents that provide complement dependent cytotoxicity (CDC) capabilities. Accordingly, the addition of the collagen domain to the microbe-binding molecules can provide various design flexibility and confer various advantages to suit the need of different application.

Due to their enhanced sensitivity and design flexibility, the engineered microbe-binding molecules described herein can be used in various applications other than as detection agents for microbes and/or microbial matter. For example, the engineered microbe-binding molecules can also be used as capture agents for microbes and/or microbial matter. In some embodiments, the engineered microbe-binding molecules can be provided as soluble proteins, e.g., in therapeutic compositions, or be immobilized to a carrier scaffold for various applications ranging from diagnosis and/or treatment of a microbial infection or disease, to microbe-clearing compositions or devices, to drug delivery.

Other aspects also describe kits and assays for detecting the presence or absence of microbes, and/or differentiating between, different microbes or pathogens in a test sample or an environmental surface. Such kits can be used for analysis, e.g., by an enzyme-linked immunosorbent assay (ELISA), fluorescent linked immunosorbent assay (FLISA), immunofluorescent microscopy, fluorescence in situ hybridization (FISH), magnetic and/or electrochemical detection, or any other radiological, chemical, enzymatic or optical detection assays. In some embodiments, the kits and assays described herein can be adapted for antibiotic susceptibility tests, e.g., to determine susceptibility of a microbe in a test sample to one or more antibiotics, regardless of whether the identity of the microbe is known or not.

BRIEF DESCRIPTION OF THE DRAWINGS

FIGS. 1A-1B shows a schematic representation (FIG. 1A) and the corresponding amino acid and nucleotide sequence (FIG. 1B) of a construct for the microbe-binding molecule according to one embodiment described herein. The inset of FIG. 1A shows protein expression of the microbe-binding molecule under reducing and non-reducing conditions. The microbe-binding molecule comprises FcMBL81 (SEQ ID NO: 34) with the collagen portion of MBL (residues 22-79 of SEQ ID NO: 29 or equivalently, residues 42-99 of SEQ ID NO: 28) (also referred to as "MBLStem58" herein) replacing the hinge region of the Fc portion. Replacement of the hinge region of the Fc portion with the collagen portion can provide a more rigid conformation. FIG. 1B discloses SEQ ID NOS 44 and 17, respectively, in order of appearance.

FIGS. 2A-2B shows a schematic representation (FIG. 2A) and the corresponding amino acid and nucleotide sequence (FIG. 2B) of a construct for the microbe-binding molecule according to another embodiment described herein. The microbe-binding molecule comprises FcMBL81 (SEQ ID NO: 34) with the collagen portion of MBL (residues 48-79 of SEQ ID NO: 29, or equivalently, residues 68-99 of SEQ ID NO: 28) (also referred to as "MBLStem32" herein) fused to the N-terminus of the FcMBL81 molecule. In this embodiment, the kink and charged region of the MBL collagen portion was removed. Having the Fc portion to separate the collagen portion and carbohydrate recognition domain of MBL can increase accessibility to MASP (mannose-associated serine protease) and low more flexibility between the collagen domain and the carbohydrate recognition domain. FIG. 2B discloses SEQ ID NOS 45 and 21, respectively, in order of appearance.

FIG. 3A is a line graph showing detection of mannan in buffer. FIG. 3B is a line graph showing detection of mannan in human blood. In both figures, FcMBL (e.g., as described in the International Patent Publication Nos. WO 2013/012924 and WO 2011/090954, the contents of each of which are incorporated herein by reference in their entirety) was used as a capture agent, and rhMBL-HRP and indicated embodiments of microbe-binding molecules described herein were respectively used as a detection agent.

FIG. 4 is an image of SDS PAGE gel showing microbe-binding molecules according to some embodiments described herein under reducing and non-reducing conditions. The corresponding amino acid sequences of the microbe-binding molecules are defined by SEQ ID NO: 25 and SEQ ID NO: 26, respectively. The microbe-binding molecule monomers formed multimers, as evidenced by lower molecular weight proteins (corresponding to monomers) detected under a reducing condition. R=reducing condition; NR=non-reducing condition FIGS. 5A-5B are gel images showing microbe-binding molecules according to some embodiments described herein under reducing and non-reducing conditions. The corresponding amino acid sequences of the microbe-binding molecules are found in the Sequence Listing based on the indicated identifier, e.g., "FcStemMBL_A." The microbe-binding molecule monomers formed multimers, as evidenced by lower molecular weight proteins (corresponding to monomers) detected under a reducing condition. FIG. 5A is a SDS-PAGE gel image. Dimers and higher-order disulfide bonded structures-like structures were observed on the SDS-PAGE. FIG. 5B is a gel image of Western blot for Fc domain, showing Fc domain forming dimers under a non-reducing condition. R=reducing condition; NR=non-reducing condition

FIG. 11 is a table showing various microbe-binding molecules with different components and configuration.

FIGS. 12A-12B shows experimental data showing characteristics of various microbe-binding molecule construct as indicated. FIG. 12A is a table showing expression yields of various microbe-binding molecule constructs as indicated. FIG. 12B is a table showing multimerization analysis of various microbe-binding molecule constructs as indicated by HPLC and DLS.

FIGS. 13A-13D show schematic representations of constructs for various microbe-binding molecules according to some embodiments described herein. The inset of FIG. 13A shows protein expression of a microbe-binding molecule with monomeric Fc domain under reducing and non-reducing conditions. Some of the microbe-binding molecules retain as monomers (indicated by the arrow in the inset).

FIG. 14 is a schematic of an exemplary microbial capture and detection process or diagnosis process.

DETAILED DESCRIPTION OF THE INVENTION

Figure 1A:
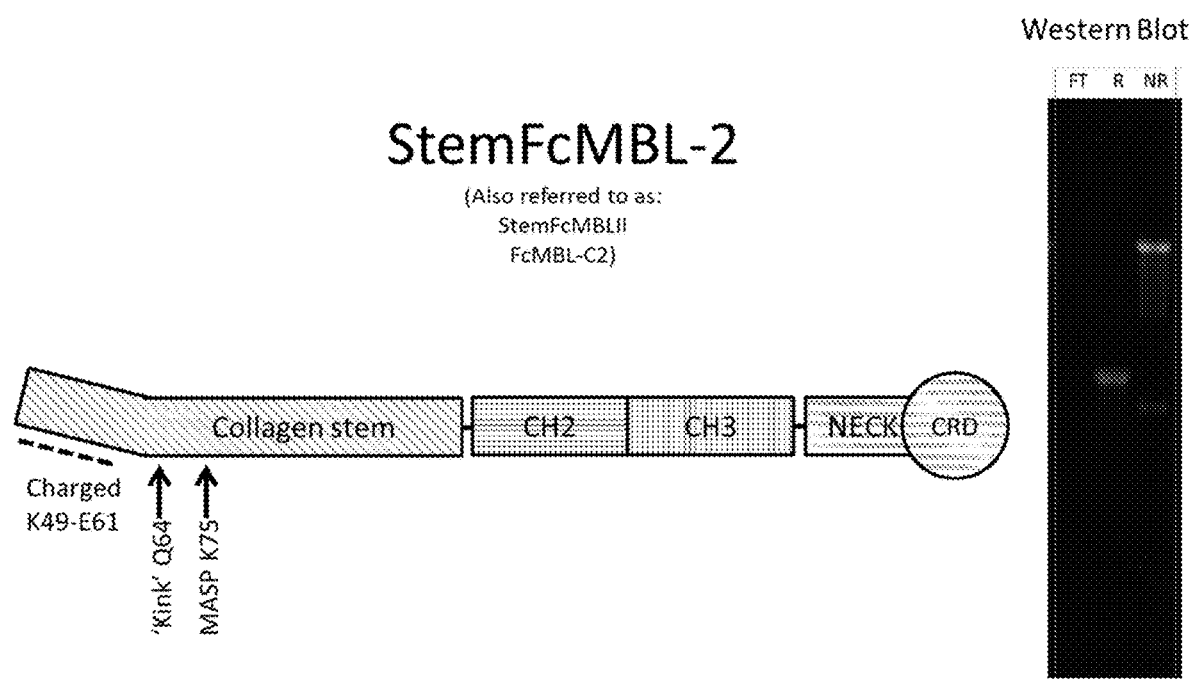

There is a need to develop a microbe-binding molecule with at least one or more of the following characteristics: (i) a combination of high binding affinity for microbes and high sensitivity for detecting microbes; (ii) an ability of lectin pathway activation; (iii) Fc recycling for serum half-life; and (iv) a combination of avidity, functionality/activation, and an ability to purify with high expression and retain in serum. Various aspects described herein are based on, at least in part, the inventors' creation of improved variants of FcMBL that show greater sensitivity to detect microbes and/or microbial matter (e.g., microbial cell wall components, and endotoxins) in an ELISA assay, and are also easier to express the proteins than full-length MBL proteins, which is generally difficult to make.

The original FcMBL molecule, unlike the improved variants of FcMBL, lacks a collagen domain and a cysteine-rich domain of MBL, both of which are responsible for the cage-like structure of native MBL, MASP binding or complement activation, and enhanced multimerization. The term "FcMBL" as used herein refers to a fusion molecule comprising an Fc domain and a carbohydrate recognition domain derived from MBL, but no collagen domain or cysteine-rich domain of MBL. Additional information of FcMBL molecules can be found, e.g., in the International Patent Publication Nos. WO 2013/012924 and WO 2011/090954, the contents of each of which are incorporated herein by reference in their entirety.

While the improved variants of FcMBL each comprises a collagen domain, the improved variants, however, are significantly different from the full-length MBL molecules, in part because the improved variants do not have the cysteine-rich domain of MBL, and/or the collagen domain of MBL present in the improved variants is truncated and/or separated from the carbohydrate recognition domain of MBL by an Fc domain. Accordingly, some aspects described herein relate to improvement of FcMBL while retaining the ability of FcMBL to be purified and retain in serum.

MBL is an example of collectin, which forms a family of collagenous $Ca^{2+}$-dependent lectins. Each member of the collectin family, like MBL, generally consists of four parts: a cysteine-rich domain at the N-terminus, a collagen domain, a helical domain (e.g., a coiled-coil neck domain), and a carbohydrate recognition domain. Accordingly, the design configurations and rules of the improved variants of FcMBL discovered by the inventors can be extended to other types of collectins, including, e.g., but not limited to surfactant protein A (SP-A), surfactant protein D (SP-D), collectin liver 1 (CL-L1), collectin placenta 1 (CL-P1), conglutinin collectin of 43 kDa (CL-43), collectin of 46 kDa (CL-46), collectin kidney 1 (CL-K1), and conglutinin. In addition, it has been contemplated that the structural design of the improved variants of FcMBL can be applied to modify non-collectin microbe-binding proteins, e.g., but not limited to DC-SIGN, macrophage mannose receptors and/or sugar binding lectins, to acquire the desired function(s) of the microbe-binding molecules described herein, e.g., multimerization of individual microbe-binding molecules to form a larger multimer for enhanced binding affinity as a capture agent and/or increased sensitivity as a detection agent. Accordingly, various aspects described herein relate to a microbe-targeting molecule or a microbe-binding molecule that provides not only high-affinity binding to a microbe and/or microbial matter, but also high-sensitivity detection of a microbe and/or microbial matter. In addition, the microbe-binding molecules described herein can be easily produced due to their high protein expression.

Due to their enhanced sensitivity and design flexibility, the engineered microbe-binding molecules described herein provide a valuable building block for various applications. In some embodiments, the engineered microbe-binding molecules described herein can be used as detection agents for microbes and/or microbial matter. In some embodiments, the engineered microbe-binding molecules can be also used as capture agents for removal of microbes or pathogens from a sample, including bodily fluids and tissues of a subject, foods, water, or an environmental surface. In some embodiments, the engineered microbe-binding molecules can be provided as soluble proteins, e.g., in therapeutic compositions, or be immobilized to a carrier scaffold for various applications ranging from diagnosis and/or treatment of a microbial infection or disease, to microbe-clearing compositions or devices, to drug delivery. A carrier scaffold comprising a microbe-targeting molecule conjugated therewith is also referred to as a microbe-targeting article herein. Accordingly, other aspects described herein relate to methods of using the microbe-binding molecules or compositions for various applications, as well as kits and assays for detecting the presence or absence of microbes, and/or differentiating between, different microbes or pathogens in a test sample or an environmental surface. Such kits can be used for analysis, e.g., by an enzyme-linked immunosorbent assay (ELISA), fluorescent linked immunosorbent assay (FLISA), immunofluorescent microscopy, fluorescence in situ hybridization (FISH), magnetic and/or electrochemical detection, or any other radiological, chemical, enzymatic or optical detection assays. In some embodiments, the kits and assays described herein can be adapted for antibiotic susceptibility tests, e.g., to determine susceptibility of a microbe in a test sample to one or more antibiotics, regardless of whether the identity of the microbe is known or not.

Some aspects described herein relate to microbe-binding molecules. The terms "microbe-binding" and "microbe-targeting" as used interchangeably herein refers to an ability of a molecule or composition to not only bind and/or capture a microbe and/or microbial matter, but also to provide high sensitivity in detecting the microbe and/or microbial matter when the molecule or composition is used as a detection agent. The term "microbe" as used herein refers to an intact or whole microbe or any matter or component that is derived, originated or secreted from a microbe. Any matter or component that is derived, originated or secreted from a microbe is also referred to as "microbial matter" herein. Thus, the microbe-binding molecules disclosed herein can bind/capture and also detect an intact or whole microbe or microbial matter derived, originated or secreted from the microbe. Exemplary microbial matter that can bind to the microbe-targeting molecule can include, but is not limited to, a cell wall component, an outer membrane, a plasma membrane, a ribosome, a microbial capsule, a pili or flagella, any fragments of the aforementioned microbial components, any nucleic acid (e.g., DNA, including 16S ribosomal DNA, and RNA) derived from a microbe, microbial endotoxin (e.g., lipopolysaccharide), and the like. In addition, microbial matter can encompass non-viable microbial matter that can cause an adverse effect (e.g., toxicity) to a host or an environment.

In some embodiments, the microbe-binding molecules or compositions described herein can exhibit a higher binding affinity and/or avidity for a microbe and/or microbial matter than a reference molecule by at least about 10% or more, including, e.g., at least about 20%, at least about 30%, at least about 40%, at least about 50%, at least about 60%, at least about 70%, at least about 80%, at least about 90%, at least about 95% or more. In some embodiments, the microbe-binding molecules or compositions described herein can exhibit a higher binding affinity and/or avidity for a microbe and/or microbial matter than a reference molecule by at least about 1.1-fold or higher, including, e.g., at least about 1.5-fold, at least about 2-fold, at least about 3-fold, at least about 5-fold, at least about 10-fold, at least about 100-fold, or higher. including, e.g., at least about 20%, at least about 30%, at least about 40%, at least about 50%, at least about 60%, at least about 70%, at least about 80%, at least about 90%, at least about 95% or more. In some embodiments where the carbohydrate recognition domain of the microbe-binding molecules described herein is derived from MBL, the reference molecule can be an FcMBL or a full-length MBL.

In some embodiments, the microbe-binding molecules or compositions described herein, when used as a detection agent, can show a higher sensitivity (e.g., providing a higher detectable signal for the same amount of target present) in detecting the microbe and/or microbial matter than a reference molecule by at least about 10% or more, including, e.g., at least about 20%, at least about 30%, at least about 40%, at least about 50%, at least about 60%, at least about 70%, at least about 80%, at least about 90%, at least about 95% or more. In some embodiments, the microbe-binding molecules or compositions described herein, when used as a detection agent, can show a higher sensitivity (e.g., providing a higher detectable signal for the same amount of target present) in detecting the microbe and/or microbial matter than a reference molecule by at least about 1.1-fold or higher, including, e.g., at least about 1.5-fold, at least about 2-fold, at least about 3-fold, at least about 5-fold, at least about 10-fold, at least about 100-fold, or higher. In some embodiments where the carbohydrate recognition domain of the microbe-binding molecules described herein is derived from MBL, the reference molecule can be an FcMBL or a full-length MBL. Methods to measure sensitivity of an agent as a detection agent are known in the art. Example 1 shows an exemplary method to compare sensitivities of different detection agents for detecting a microbial matter, e.g., mannan.

As used herein, the term "detection agent" refers to a molecule or composition comprising (i) a moiety or domain for specific binding of a target molecule to be detected; and (ii) a binding moiety or domain for at least one detectable label or for a sufficient amount of detectable labels to generate a detectable signal. Thus, a detection agent can bind to a target molecule (e.g., a microbe and/or microbial matter) and to at least one detectable label. For example, the microbe-binding molecules or compositions described herein can be used as detection agents, because they can bind to microbes and/or microbial matter, and also to at least one detectable label. Without wishing to be limited, the microbe-binding molecules or compositions described herein can also be used as capture agents. As used herein, the term "capture agent" refers to a molecule or composition comprising a moiety or domain for the specific binding of a target molecule to be detected, but not necessarily comprising a binding moiety or domain for at least one detectable label to generate a detectable signal.

Generally, the microbe-binding molecule described herein comprises (i) a collagen domain; (ii) an Fc domain; and (iii) a microbe-binding domain comprising a helical domain and a carbohydrate recognition domain (CRD). These three domains can be arranged in any configuration provided that the resulting microbe-binding molecule retains of the function of each domain.

In some embodiments, the Fc domain can link the collagen domain to the microbe-surface binding domain. Accordingly, in one aspect, described herein is a microbe-binding molecule comprising: (i) a collagen domain; (ii) an Fc domain; and (iii) a microbe-binding domain comprising a helical domain and a carbohydrate recognition domain (CRD); wherein the Fc domain links the collagen domain to the microbe-surface binding domain.

In some embodiments, the collagen domain can link the Fc domain to the microbe-surface binding domain, and there is no cysteine-rich crosslinking domain between the collagen domain and the Fc domain. Accordingly, in another aspect, described herein is a microbe-binding molecule comprising: (i) a collagen domain; (ii) an Fc domain; and (iii) a microbe-binding domain comprising a helical domain and a carbohydrate recognition domain (CRD), wherein the collagen domain links the Fc domain to the microbe-surface binding domain, and wherein no cysteine-rich crosslinking domain is present between the collagen domain and the Fc domain.

In some embodiments of this aspect and other aspects described herein, the carbohydrate recognition domain can form the C-terminus of the microbe-binding molecule.

In some embodiments, the microbe-surface binding domain can link the collagen domain to the Fc domain, and the collagen domain that is not linked to the microbe-binding domain does not comprise a cysteine-rich crosslinking domain. Accordingly, in another aspect, described herein is a microbe-binding molecule comprising: (i) a collagen domain; (ii) an Fc domain; and (iii) a microbe-binding domain comprising a helical domain and a carbohydrate recognition domain (CRD); wherein the microbe-surface binding domain links the collagen domain to the Fc domain, and wherein the collagen domain that is not linked to the microbe-binding domain does not comprise a cysteine-rich crosslinking domain.

In some embodiments of this aspect and other aspects described herein, the microbe-binding molecule can exclude a cysteine-rich domain. As used herein, the term "cysteine-rich domain" refers to a domain comprising cysteine residues that constitute at least 10% or higher of the domain, including, at least 15%, at least 20%, at least 30%, at least 40%, at least 50%, or higher of the domain. In one embodiment, the cysteine-rich domain can comprise cysteine residues that constitute about 10% to about 20% of the domain. For example, the cysteine-rich domain of MBL generally has an amino acid sequence of ETVTCEDAQKTCPAVI-ACSSP (SEQ ID NO: 41), in which there are three cysteine residues in the sequence of 24 amino acids. Thus, the cysteine-rich domain of MBL comprises 14% cysteine residues. Generally, a cysteine-rich domain enables formation of disulfide bond(s) with another cysteine-rich domain of another molecule, thus crosslinking at least two molecules to form a dimer or a higher-order multimer. In these embodiments, instead of having a plurality of microbe-binding molecules described herein present as monomers covalently linked at the cysteine-rich domain, via disulfide bonds, to form a multimer, the microbe-binding molecule monomers can interact with each other, e.g., at the collagen domain, through non-covalent interactions, e.g., hydrophobic and/or hydrogen bond interactions, to form a multimer.

Collagen Domain:

As used herein, the term "collagen domain" is a domain comprising a polypeptide chain that is capable of forming a helical structure with at least two or more polypeptide chains (e.g., collagen domains of other microbe-binding molecules). In some embodiments, the collagen domain is a domain comprising a polypeptide chain that is capable of forming a collagen-like triple helix. The term "collagen-like triple helix" refers to a helical structure formed by three polypeptide chains of collagen or collagen-like molecules. Modifications to the collagen domain, e.g., by conservative substitution, are also within the scope described herein.

In some embodiments, the collagen domain can comprise, essentially consist of, or consist of a plurality of (e.g., at least two or more) glycine (Gly)-$X_{aa1}$-$X_{aa2}$ triplets or $X_{aa1}$-$X_{aa2}$-Gly triplets, wherein $X_{aa1}$ and $X_{aa2}$ are each independently an animo acid residue. In some embodiments, the collagen domain can comprise, essentially consist of, or consist of at least 5 or more (including, e.g., at least 6, at least 7, at least 8, at least 9, at least 10, at least 11, at least 12, at least 13, at least 14, at least 15, at least 16, at least 17, at least 18, at least 19, at least 20 or more) Gly-$X_{aa1}$-$X_{aa2}$ triplets, wherein $X_{aa1}$ and $X_{aa2}$ are each independently an animo acid residue. In some embodiments, any two adjacent Gly-$X_{aa1}$-$X_{aa2}$ triplets or $X_{aa1}$-$X_{aa2}$-Gly triplets can be linked together by a linker as defined in detail below, including, e.g., but not limited to a chemical bond, an amino acid residue, and a group of amino acid residues.

In some embodiments, $X_{aa1}$ and $X_{aa2}$ can be independently an amino acid residue selected from the group consisting of alanine; arginine; asparagine; aspartic acid; cysteine; glutamic acid; glutamine; glycine; histidine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; γ-carboxyglutamate; hippuric acid; octahydroindole-2-carboxylic acid; statine; 1,2,3,4-tetrahydroisoquinoline-3-carboxylic acid; penicillamine (3-mercapto-D-valine); omithine (Om); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; gamma-aminobutyric acid; difluorophenylalanine; nipecotic acid; N-α-imidazole acetic acid (IMA); thienyl-alanine; t-butylglycine; desamino-Tyr; aminovaleric acid (Ava);

pyroglutaminic acid (<Glu); α-aminoisobutyric acid (αAib); γ-aminobutyric acid (γAbu); α-aminobutyric acid (αAbu); αγ-aminobutyric acid (αγAbu); 3-pyridylalanine (Pal); Isopropyl-α-N$^ε$lysine (ILys); Napthyalanine (Nal); α-napthyalanine (α-Nal); β-napthyalanine (D-Nal); Acetyl-β-napthyalanine (Ac-β-napthyalanine); α,β-napthyalanine; N$^ε$-picoloyl-lysine (PicLys); 4-halo-Phenyl; 4-pyrolidylalanine; isonipecotic carboxylic acid (inip); beta-amino acids; and isomers, analogs and derivatives thereof. One of skill in the art would know that this definition includes, D- and L-amino acids; alpha-, beta- and gamma-amino acids; chemically modified amino acids; naturally occurring non-proteogenic amino acids; rare amino acids; and chemically synthesized compounds that have properties known in the art to be characteristic of an amino acid. Additionally, each embodiment can include any combinations of the groups.

Furthermore, as used herein, the term "amino acid" includes a compound or molecule which departs from the structure of the naturally occurring amino acids, but which have substantially the structure of an amino acid, such that they can be used for substitution of the naturally-occurring amino acids within a peptide, after which the peptide's activity, e.g., activity of forming a helical structure, is still retained. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways.

In some embodiments, the $X_{aa1}$ residue of the Gly-$X_{aa1}$-$X_{aa2}$ triplets or $X_{aa1}$-$X_{aa2}$-Gly triplets can be proline and the corresponding $X_{aa2}$ residue can be hydroxyproline. The unique size and backbone angle of glycine and proline respectively enable the tight helical structure referred to as "collagen helix." The canonical triplet can be highly substituted but if the glycine spacing is absent or abbreviated a kink in the linear chain is introduced, as with "GQG" in MBL (aa43-45 of SEQ ID NO: 29).

The Gly-$X_{aa1}$-$X_{aa2}$ triplets or $X_{aa1}$-$X_{aa2}$-Gly triplets are not confined to collagens, and short stretches of the motif are also found in number of innate proteins of the immune system, e.g., but not limited to the macrophage scavenger receptor A, the complement protein C1q, and mannan-binding lectin (MBL). Accordingly, in some embodiments, the collagen domain can be derived from a collagen domain of a collagen-containing molecule or a fragment thereof. Examples of the collagen-containing molecule include, but are not limited to collectin (e.g., but not limited to mannose binding lectin, surfactant protein), ficolin, complement protein C1q, macrophage scavenger receptor A, a naturally-occurring collagen-like peptides (e.g., but not limited to, any of collagen types (e.g., Type I, II, III, IV, V, XI, etc.), a synthetic collagen-like peptide, variants thereof, and any combinations thereof. Variants of the collagen-containing molecules include, but are not limited to mutants that are modified, e.g., to remove MASP binding, to enhance complement dependent cytotoxicity (CDC) capability, and/or to provide additional binding sites for detectable labels. By way of example only, lysine at the amino acid residue 75 of MBL (SEQ ID NO: 28) (within the collagen domain) is important for MASP binding. One can mutate the amino acid residue from lysine to a different residue (e.g., glutamine (Q)) to remove the MASP binding function when MASP binding is not desirable for a target application.

In some embodiments, the collagen domain can comprise, essentially consist of, or consist of a collagen-like stem of mannose binding lectin, a fragment thereof, or a variant thereof.

As used herein, the term "fragment" generally refers to a molecule or a protein domain having an amino acid sequence that is about 20% or more (including about 30%, about 40%, about 50%, about 60%, about 70%, about 90%, up to less than 100%) identical or homology to a reference molecule or protein domain (e.g., wild-type or parent molecule), and is capable of retaining (e.g., at least 50% or more) the function of the reference molecule or protein domain. For example, when used in reference to a collagen domain of a collagen-containing molecule, the term "fragment" refers to a molecule or a protein domain having an amino acid sequence that is about 20% or more (including about 30%, about 40%, about 50%, about 60%, about 70%, about 90%, up to less than 100%) identical or homology to the collagen domain of a wild-type or parent collagen-containing molecule, and is capable of causing multimerization of the microbe-binding molecules (monomers) described herein. For example, in some embodiments, the collagen domain can comprise a collagen-like stem of mannose binding lectin without the charged region (K49-E61 of SEQ ID NO: 28 or equivalently, K29-E41 of SEQ ID NO: 29) and/or the kink at residue Q64 of SEQ ID NO: 28 or equivalently, Q44 of SEQ ID NO: 29.

Figure 5B:
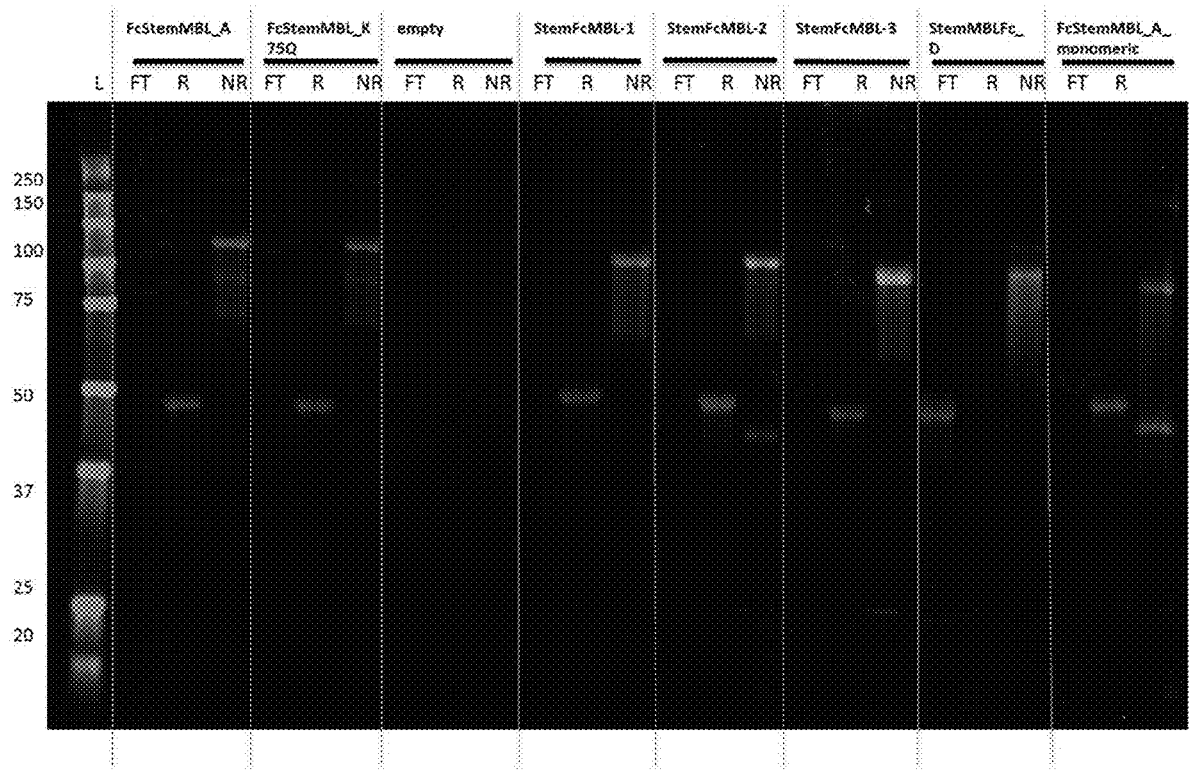
Figure 6:
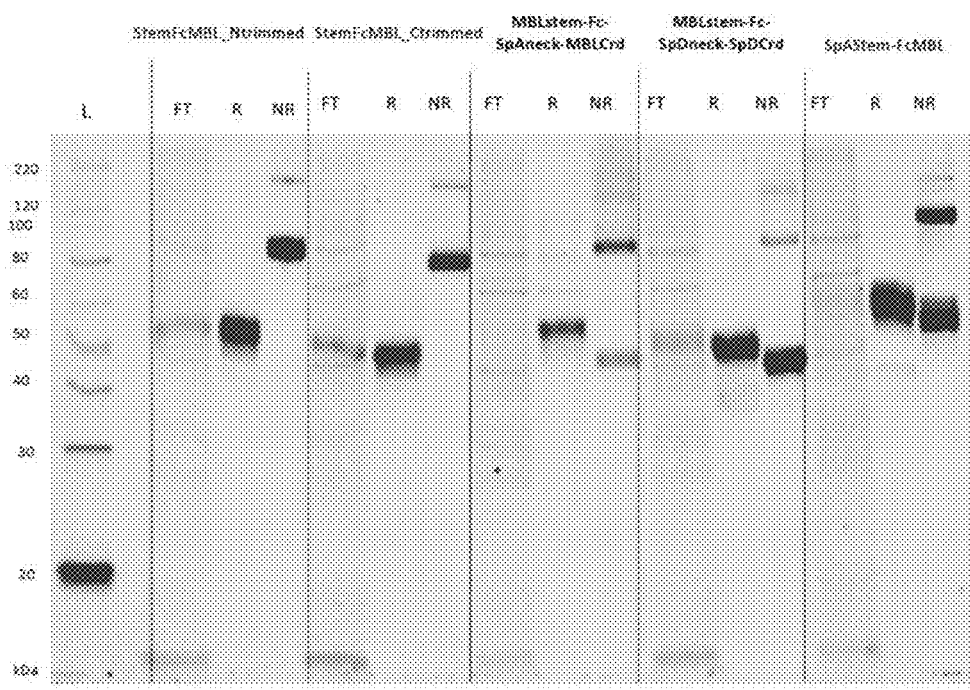
FIG. 6 is an image of SDS PAGE gel showing microbe-binding molecules according to some embodiments described herein under reducing and non-reducing conditions. The corresponding amino acid sequences of the microbe-binding molecules (labeled as "StemFcMBL_Ntrimmed" and "StemFcMBL_Ctrimmed") are defined by SEQ ID NO: 26 and SEQ ID NO: 25, respectively. The corresponding amino acid sequence of the microbe-binding molecule labeled as "SpAStem-FcMBL" is defined by SEQ ID NO: 27. The microbe-binding molecule labeled as "MBLstem-Fc-SpAneck-MBLCrd" corresponds to a molecule comprising, from N-terminus to C-terminus, (i) a collagen domain of MBL, (ii) an Fc domain, (iii) a neck or helical domain derived from surfactant protein A (SP-A), and (iv) a carbohydrate recognition domain of mannan-binding lectin (MBL). The microbe-binding molecule labeled as "MBLstem-Fc-SpDneck-SpDCrd" corresponds to a molecule comprising, from N-terminus to C-terminus, (i) a collagen domain of MBL, (ii) an Fc domain, (iii) a neck or helical domain derived from surfactant protein D (SP-D), and (iv) a carbohydrate recognition domain of SP-D. The figure shows that some of the microbe-binding molecule monomers more readily formed multimers, as evidenced by lower molecular weight proteins (corresponding to monomers) detected under a reducing condition. R=reducing condition; NR=non-reducing condition.

As used herein, the term "multimerization" refers to a combination of monomers (e.g., at least two monomers or more) holding together, e.g., by non-covalent interaction such as hydrophobic and/or hydrogen bond interactions, to form a larger aggregate, also known as a multimer. In some embodiments, the multimer can comprise at least about 10 or more (including, e.g., at least about 15, at least about 20 or more) monomers holding together, e.g., by non-covalent interaction. Methods to determine if multimerization occurs are known in the art, e.g., by crystallography, gel electrophoresis of proteins, column chromatography (e.g., high performance liquid chromatography), size exclusion chromatography (SEC), dynamic light scattering, and a combination of two or more thereof. For example, as shown in FIG. 5A, gel electrophoresis can be performed on a number of candidate microbe-binding molecules under a reducing (denaturing) condition and a non-reducing (native) condition. Under a reducing (denaturing) condition, a multimer will denature to a plurality of monomers that originally formed the multimer. Thus, by comparing the molecular weight of the protein bands detected under the reducing (denaturing) condition and the non-reducing (native condition), one can determine if the microbe-binding molecule forms a multimer. For example, under the native (non-reducing) condition, when there is a protein band on a gel corresponding to a molecular weight that is about twice or more the molecular weight of the protein band detected under the denaturing (reducing) condition, it indicates that the microbe-binding molecule is likely to form a dimer or a higher-order multimer. In contrast, if there is no significant difference between the reducing and non-reducing condition, it indicates that the microbe-binding molecule is likely to retain as monomers, rather than forming a multimer.

In some embodiments, the collagen domain can comprise, essentially consist of, or consist of an amino acid sequence selected from the group consisting of SEQ ID NOs: 7-16. In one embodiment, the collagen domain can comprise, essentially consist of, or consist of an amino acid sequence of SEQ ID NO: 7 or SEQ ID NO: 8. In some embodiments, the collagen domain can comprise, essentially consist of, or consist of an amino acid sequence from the group consisting of SEQ ID NOs: 7-10, and 13-16, with at least one or a group of amino acid residues (e.g., at least 2 amino acid residues, at least 3 amino acid residues, at least 4 amino acid residues, at least 5 amino acid residues, at least 10 amino acid residues, at least 15 amino acid residues, at least 20 amino acid residues, at least 25 amino acid residues, at least 30 amino acid residues or more) removed independently from the C-terminus and/or N-terminus of the selected sequence.

While the collagen domain can have any length provided that it does not significantly interfere with or impede binding of the microbe-binding molecule to a microbe or microbial matter, in some embodiments, the collagen domain can be at least about 15 amino acids or more in length. In some embodiments, the collagen domain can be at least about 20 amino acids or more in length, including, e.g., at least about 25 amino acids, at least about 30 amino acids, at least about 35 amino acids, at least about 40 amino acids, at least about 50 amino acids or more, in length. In some embodiments, the collagen domain can have a length of about 10 amino acids to about 80 amino acids. In some embodiments, the collagen domain can have a length of about 15 amino acids to 80 amino acids. In some embodiments, the collagen domain can have a length of about 20 amino acids to 60 amino acids.

Without wishing to be bound by theory, addition of a collagen domain can make the resulting microbe-binding molecule more elongated in structure, rather than forming a globular structure, which can increase the avidity of the microbe-binding molecule described herein. In addition, the addition of the collagen domain can increase the sensitivity (e.g., providing a higher detectable signal) of using the microbe-binding molecules as detection agents, partly because the collagen domain can provide multimerization function, which enables formation of a larger multimer from a plurality of individual microbe-binding molecules described herein as monomers, and thus the multimer can generate a higher detectable signal, as compared to individual monomers. The multimerization of the microbe-binding molecules can also provide increased avidity of individual monomers to bind a microbe and/or microbial matter, thereby increasing the sensitivity of microbe detection.

Alternatively or additionally, the collagen domain can be adapted to provide more binding sites for a detectable label, which enables generation of a higher detectable signal intensity, without formation of a larger multimer. For example, it is contemplated that the addition of the collagen domain can provide sterically-flavorable binding sites for horseradish peroxidase (HRP) that do not interfere with the protein's functional sites. In some embodiments of this aspect and other aspects described herein, the collagen domain can comprise a lysine-rich domain. As used herein, the term "lysine-rich domain" refers to a domain comprising lysine residues that constitute at least 10% or higher of the domain, including, at least 15%, at least 200%, at least 300%, at least 400%, at least 50%, or higher of the domain. In one embodiment, a lysine rich domain can comprise at least about 10% or greater lysine residues. Without wishing to be bound by theory, the lysine residues present in the collagen domain can provide binding sites for a detectable label, e.g., horseradish peroxidase, alkaline phosphatase (AP), luciferase, and/or beta-galactosidase. Lysines have primary amines that are available for amine-reactive coupling chemistry to permit coupling of a wide range of fluorophores, other labels, and/or labeling intermediates. Lysine residues present in the collagen domain can also allow for functionalization of surfaces with these proteins and/or microbe-binding molecules described herein.

In some embodiments, the collagen domain can also be adapted to provide complement signaling capabilities, which can be useful as therapeutic agents that provide complement dependent cytotoxicity (CDC) capabilities. In some circumstances, complement or coagulation activation can be undesirable depending on various applications, e.g., in vivo administration for treatment of sepsis. In such embodiments, the collagen domain can be adapted to remove complement signaling capabilities. By way of example, when the collagen domain is derived from mannose-binding lectin or a fragment thereof, at least about one amino acid residue (including, e.g., at least about two amino acid residues, at least about three amino acid residues, at least about four amino acid residues, at least about five amino acid residues, at least about six amino acid residues, at least about seven amino acid residues, at least about eight amino acid residues, at least about nine amino acid residues, at least about ten amino acid residues or more) around and including amino acid residue K75 or L76 of SEQ ID NO: 28 (or equivalently, amino acid residue K55 or L56 of SEQ ID NO: 29) can be mutated, removed or inserted. In some embodiments, the amino acid residue lysine (K) at residue 75 of SEQ ID NO: 28 (or equivalently, at amino acid residue 55 of SEQ ID NO: 29) can be mutated to glutamine (Q). Even without the mutation of the MASP binding site, it is contemplated that, in some embodiments, the collagen domain can lose the native capability of MASP binding because of the presence of the Fc domain that may interfere with the function. Accordingly, the addition of the collagen domain to the microbe-binding molecules can provide various design flexibility and confer various advantages to suit the need of different application.

Fc Domain:

As used herein, the term "Fc domain" is a domain comprising at least a portion of native fragment crystallization (Fc) region of an immunoglobulin or an Fc variant thereof. The term "native Fc" refers to a molecule or sequence comprising a sequence of a non-antigen-binding fragment derived from a whole antibody, whether in monomeric or multimeric form. Native Fc's are generally made up of monomeric polypeptides that can be linked into dimeric or multimeric forms by covalent (i.e., disulfide bonds) and non-covalent association. The number of intermolecular disulfide bonds between monomeric subunits of native Fc molecules can ranges from 1 to 4 depending on class (e.g., IgG, IgA, IgE) or subclass (e.g., IgG1, IgG2, IgG3, IgG4, IgA1, IgGA2). The term "native Fc" as used herein is generic to the monomeric, dimeric, and multimeric forms.

The term "Fc variant" refers to a molecule or sequence that is modified from a native Fc but still comprises at least a site for FcRn binding or protein A binding. Fc variants as described in the International applications WO 97/34631 and WO 96/32478, the contents of which are incorporated herein by reference, can be used included in the Fc domain. In some embodiments, an Fc variant can comprise a molecule or sequence that is humanized from a non-human native Fc. In some embodiments, an Fc variant can comprise a molecule or sequence with at least one or more modifications by conservative substitution. In some embodiments, an Fc variant can comprise a native Fc with at least one or more sites be removed for various purposes. For example, those sites to be removed from the native Fc provide structural features or biological activity that are not required for the microbe-binding molecules described herein. Accordingly, in some embodiments, an Fc variant can comprise a molecule or sequence that lacks one or more native Fc sites or residues that affect or are involved in, for example, (1) disulfide bond formation, (2) incompatibility with a selected host cell (3)N-terminal heterogeneity upon expression in a selected host cell, (4) glycosylation, (5) interaction with complement, (6) binding to an Fc receptor other than a salvage receptor, e.g., FcRn, (7) antibody-dependent cellular cytotoxicity (ADCC), or a combination of two or more thereof. Modifications to the native Fc domain, e.g., by conservative substitution, are also within the scope described herein.

The term "Fc domain" encompasses molecules in monomeric or multimeric form. The term "multimer" as applied to Fc domains or molecules comprising Fc domains refers to molecules having two or more polypeptide chains associated covalently, noncovalently, or by both covalent and non-covalent interactions. For example, Fc domain of IgG molecules can form dimers; IgM, pentamers; IgD, dimers; and IgA, monomers, dimers, trimers, or tetramers. The term "dimer" as applied to Fc domains or molecules comprising Fc domains refers to molecules having two polypeptide chains associated covalently or non-covalently.

By way of example only, IgG1 can be present in monomeric form (e.g., an Fc molecule is monomeric with respect to a microbe-binding domain coupled thereto) or dimeric form (e.g., an Fc molecule is dimeric with respect to a microbe-binding domain coupled thereto). Examples of amino acid sequences or information of monomeric IgG Fc can be found, e.g., in Ying et al. "Soluble Monomeric IgG1 Fc." Journal of Biological Chemistry (2012) 287: 19399-19408; and Dumont et al. "Monomeric Fc fusions: impact on pharmacokinetic and biological activity of protein therapeutics." BioDrugs (2006) 20(3): 151-60. In one embodiment, a monomeric Fc from IgG1 with an amino acid sequence of SEQ ID NO: 4 or a variant thereof can be included in the Fc domain. In this embodiment, the Fc domain does not form a multimer, and each monomeric Fc domain is coupled, directly or indirectly, to a microbe-binding domain described herein. In another embodiment, a dimeric Fc from IgG with an amino acid sequence of SEQ ID NO: 5 or a variant thereof can be included in the Fc domain. In this embodiment, the Fc domain forms a dimer and the dimeric Fc domain is coupled, indirectly or directly, to a microbe-binding domain described herein.

In some embodiments, the Fc domain can comprise at least one region selected from the group consisting of a hinge domain, a CH2 domain, a CH3 domain, and any combinations thereof. By way of example, in some embodiments, the Fc domain can comprise a hinge region, a CH2 domain and a CH3 domain. In some embodiments, a hinge domain can be excluded from the Fc domain.

The Fc domain can be derived from any immunoglobulin, including, e.g., but not limited to IgA, IgD, IgE, IgG and IgM including their subclasses (e.g., IgG1), or a modified molecule or recombinant thereof. In one embodiment, the Fc domain can be derived from IgG. In some embodiments, the Fc domain can be derived from any species. In one embodiment, the Fc domain can be derived from a mammalian origin (e.g., a human origin). In one embodiment, the IgG can be derived from a mammalian IgG (including, e.g., but not limited to IgG1, IgG2, IgG3, and IgG4), or a portion thereof.

In some embodiments, the Fc domain can comprise, essentially consist of, or consist of an amino acid sequence selected from the group consisting of SEQ ID NOs: 1-6, or a variant thereof.

In some embodiments, the Fc domain can be configured or used to facilitate and/or enhance expression and purification of the engineered microbe-binding molecules described herein. The N terminal Fc has been shown to improve expression levels, protein folding and secretion of the fusion partner. In addition, the Fc has a staphylococcal Protein A binding site, which can be used for one-step purification protein A affinity chromatography. See Lo K M et al. (1998) Protein Eng. 11: 495-500. Further, the Protein A binding site can be used to facilitate binding of Protein A-expressing or Protein G-expressing microbes in the absence of calcium ions. Such binding capability can be used to develop methods for distinguishing protein A-expressing microbes (e.g., S. aureus) from non-protein A-expressing or non-protein G-expressing microbes (e.g., E. coli) present in a test sample.

In some embodiments, the Fc domain can comprise at least one mutation relative to a native sequence, e.g., native Fc as defined herein, e.g., to modify the performance of the engineered microbe-binding molecules. For example, in some embodiments, the effector functions, such as cell-mediated complement-dependent cytotoxicity (CDC) and/or antibody-dependent cellular cytotoxicity (ADCC) of the Fc domain, and thus the microbe-binding molecules described herein can be reduced, e.g., by mutating an amino acid lysine (K) at the residue 107 of SEQ ID NO: 4, 5, or 6 to alanine (A). This mutation is also known as K322A using the numbering derived from human IgG1. In some embodiments, the glycosylation of the Fc domain can be removed, e.g., by aspartic acid (D) substitution at the residue 82 of SEQ ID NO: 4, 5, or 6 (where the wild-type residue 82 is asparagine (N)). This mutation is also known as N297D using the numbering derived from human IgG1. Other mutations, e.g., located at the interface between the CH2 and CH3 domains shown in Hinton et al (2004) J Biol Chem. 279:6213-6216 and Vaccaro C. et al. (2005) Nat Biotechnol. 23: 1283-1288, can be also used to increase the half-life of the IgG and thus the engineered microbe-binding molecules. In some embodiments, the mutation(s) in the Fc domain can be adapted to modify heavy chain and/or lower hinge-Cγ2 domain, to mutate CH2/CH3 junction, to modulate glycosylation, to optimize fusion partner, to increase valency, or a combination of two or more thereof. Additional information about examples of such modifications can be found, e.g., in Czajkowsky et al. "Fc-fusion proteins: new developments and future persepctives" (2012) EMBO Mol Med. 4(10): 1015-1028 (including supplemental information), the contents of each of which are incorporated by reference in their entirety. Various Fc modifications for desired applications are known in the art. For any known sequences of Fc, one of skill in the art can modify the Fc sequences to carry out or remove a function.

While the Fc domain is illustrated in different embodiments of the microbe-binding molecules described herein, it is contemplated that any other molecule (e.g., protein, peptide, peptidomimetic, nucleic acid, aptamer, and antibody) that can (i) facilitate expression and/or purification, and/or increase the half-life of the microbe-binding molecules described herein, and/or form a multimer (e.g., at least a dimer or a higher-order multimer) can also be used to replace the Fc domain. Examples of molecules that can be used to replace the Fc domain include, but are not limited to C1q, leucine zipper motif, toll-like receptor, interleukin, Collectin neck domains (including, e.g., ficolins, surfactant proteins A and D), IgM or other immunoglobulin, affinity tags (including, e.g., MYC, HA, His, and/or FLAG) and any combinations thereof.

The Fc domain can be provided in any length to suit the need of an application. In some embodiments, the Fc domain can have a length of about 15 amino acids to about 80 amino acids, or about 19 amino acids to about 60 amino acids, or about 30 amino acids to about 50 amino acids.

Microbe-Binding Domain Comprising a Helical Domain and a Carbohydrate Recognition Domain:

The term "microbe-binding domain" as used herein refers to any molecule or a fragment thereof that can specifically bind to the surface of a microbe or pathogen, e.g., any component present on a surface of a microbe or pathogen, or any matter or component/fragment that is derived, originated or secreted from a microbe or pathogen. Thus, it is not required that the entire microbe-binding domain is capable of specifically bind to a microbe or microbial matter. Molecules that can be used in the microbe-binding domain can include, for example, but are not limited to, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof. In some embodiments, the microbe-binding domain can comprise a peptidomimetic that mimics a molecule or a fragment thereof that can specifically bind to the surface of a microbe or pathogen, or microbial matter. For example, a microbe-binding domain can comprise a peptidomimetic that mimics a helical domain and a carbohydrate recognition domain, or fragments thereof, e.g., a helical domain and a carbohydrate recognition domain of MBL, or fragments thereof.

The microbe-binding domain of the microbe-binding molecules described herein comprises a helical domain and a carbohydrate recognition domain. As used herein, the term "helical domain" refers to a domain comprising a polypeptide chain that is capable of adopting a helical structure (e.g., a parallel trimer triple helical structure) in solution alone or in conjunction with the carbohydrate recognition domain described herein. In some embodiments, the helical domain can form a helical coiled-coil structure (e.g., an α-helical coiled-coil structure) with other helical peptides. The helical peptides can be coiled together. In some embodiments, at least two or more, including, e.g., at least three, at least four, at least five, at last six, at least seven or more, helical domains can be coiled together to form a coiled coil structure. Accordingly, the helical domain can promote multimerization of the microbe-binding domains. In some embodiments, the helical domain can also promote affinity binding of the carbohydrate-recognition domain to a microbe or microbial matter, for example, by at least about 30% or higher, including, e.g., at least about 40%, at least about 50%, at least about 60%, at least about 70%, at least about 80%, at least about 90%, at least about 95% or higher. In some embodiments, the helical domain can promote affinity binding of the carbohydrate-recognition domain to a microbe or microbial matter, for example, by at least about 1.1-fold or higher, including, e.g., at least about 1.5-fold, at least about 2-fold, at least about 3-fold, at least about 4-fold, at least about 5-fold, at least about 10-fold, at least about 100-fold or higher.

Proteins or peptides that can form coiled coils as well as methods to predict coiled coil structures from a protein sequence are known in the art. For example, Spiricoil database can be used to predict coiled coil presence for any sequenced organisms. CC+ is a relational database of coiled coils found in the Protein Data Bank (PDB). STRAP is an algorithm to predict coiled coils from amino acid sequences. One of skill in the art can use any art-recognized database and algorithms to design an amino acid sequence for the helical domain. To determine if the designed sequence for the helical domain affects multimerization of a plurality of microbe-binding domains, one can perform a gel electrophoresis of proteins under reducing and non-reducing conditions or other methods as discussed earlier with respect to identification of collagen domain that is capable of inducing formation of multimers. To determine if the designed sequence for the helical domain affects the affinity binding of the carbohydrate recognition domain, one can perform a function assay to determine the binding efficiency of microbes and/or microbial matter, as compared to a reference sequence.

In some embodiments, the helical domain can be derived from a helix-containing molecule selected from the group consisting of collectins (e.g., mannose binding lectin), mannose-binding proteins, surfactant protein lectins (e.g., surfactant protein D), ficolins, naturally-occurring or synthetic helical peptides, and any combinations thereof.

In one embodiment, the helical domain can comprise, essentially consist of, or consist of an amino acid sequence of PDGDSSLAASERKALQTEMARIKKWLTFSLGKQ (SEQ ID NO: 40) or a portion thereof, e.g., with a few amino acid residues (e.g., 1, 2, 3 amino acid residues) removed from either end or both ends. In one embodiment, the helical domain can comprise, essentially consist of, or consist of an amino acid sequence of PDGDSSLAASERKALQTEMARIKKWLTFSLGKQ (SEQ ID NO: 40) or a portion thereof, e.g., with a few amino acid residues (e.g., 1, 2, 3 amino acid residues) removed from the N-terminus of the sequence.

In some embodiments, the helical domain and the carbohydrate recognition domain can be both derived from the same microbe-binding molecule or carbohydrate-binding proteins described below. For example, in one embodiment, the microbe-binding domain can comprise a helical domain of MBL (also known as the neck region of MBL), e.g., having an amino acid sequence of SEQ ID NO: 40, and a carbohydrate recognition domain of MBL, e.g., having an amino acid sequence of SEQ ID NO: 32. In one embodiment, the microbe-binding domain can comprise, essentially consist of, or consist of an amino acid sequence of SEQ ID NO: 33. In some embodiments, the helical domain and the carbohydrate domain can each be derived from a different microbe-binding molecule and/or carbohydrate-binding proteins described below. By way of example only, the helical domain can be derived from a first microbe-binding molecule (e.g., surfactant protein A) while the carbohydrate recognition domain can be derived from a second microbe-binding molecule (e.g., a MBL) provided that the carbohydrate recognition domain retains at least 50% or more of the ability to bind a microbe or microbial matter, as compared to the carbohydrate recognition domain coupled to the helical domain derived from the same source.

The helical domain and the carbohydrate recognition domain can be linked together by a linker as defined in detail below, including, e.g., but not limited to a chemical bond, an amino acid residue, and a group of amino acid residues.

The term "carbohydrate recognition domain" or "CRD" as used interchangeably herein refers to a domain, at least a portion of which, can bind to carbohydrates on a surface of microbes or pathogens, or any matter or component/fragment that is derived, originated or secreted from a microbe or pathogen, e.g., microbial matter. In some embodiments, the carbohydrate recognition domain can comprise at least about 50% of the full length CRD, including at least about 60%, at least about 70%, at least about 80%, at least about 90% or higher, capable of binding to carbohydrates on a microbe surface and/or microbial matter. In some embodiments, 100% of the carbohydrate recognition domain can be used to bind to microbes or pathogens. In other embodiments, the carbohydrate recognition domain can comprise additional regions that are not capable of carbohydrate binding, but can have other characteristics or perform other functions, e.g., to provide flexibility to the carbohydrate recognition domain when interacting with microbes or pathogens.

Exemplary carbohydrate-binding proteins from which a CRD can be derived include, but are not limited to, lectin, collectin, surfactant protein (e.g., surfactant protein D), ficolin, mannose-binding lectin (MBL), maltose-binding protein, arabinose-binding protein, and glucose-binding protein. Additional carbohydrate-binding proteins from which a CRD can be derived can include, but are not limited to, lectins or agglutinins that are derived from a plant, e.g., *Galanthus nivalis* agglutinin (GNA) from the *Galanthus* (snowdrop) plant, and peanut lectin. In some embodiments, pentraxin family members (e.g., C-reactive protein) or a fragment thereof can also be used as in the CRD. Pentraxin family members can generally bind capsulated microbes. Without limitation, the carbohydrate-binding proteins can be wild-type, recombinant or a fusion protein. The respective carbohydrate recognition domains for such carbohydrate-binding proteins are known in the art, and can be modified for various embodiments of the engineered microbe-binding molecules described herein.

Any art-recognized recombinant carbohydrate-binding proteins or carbohydrate recognition domains can be used in the engineered microbe-binding molecules. For example, recombinant mannose-binding lectins, e.g., but not limited to, the ones disclosed in the U.S. Pat. Nos. 5,270,199; 6,846,649; U.S. Patent Application No. US 2004/0229212; and PCT Application No. WO 2011/090954, filed Jan. 19, 2011, the contents of all of which are incorporated herein by reference, can be used in constructing the microbe-targeting molecules described herein.

In some embodiments, the CRD is derived from an MBL, a member of the collectin family of proteins. A native MBL is a multimeric structure (e.g., about 650 kDa) composed of subunits, each of which contains three identical polypeptide chains. Each MBL polypeptide chain (containing 248 amino acid residues in length with a signal sequence: SEQ ID NO: 28) comprises a N-terminal cysteine rich region, a collagen-like region, a neck region, and a carbohydrate recognition domain (CRD). The sequence of each region has been identified and is well known in the art. SEQ ID NO: 29 is the full-length amino acid sequence of MBL without a signal sequence. In some embodiments, the signal sequence corresponds to amino acids 1-20 of SEQ ID NO: 28, i.e. SEQ ID NO: 30.

The full-length amino acid sequence of carbohydrate recognition domain (CRD) of MBL is shown in SEQ ID NO: 32. In some embodiments, the carbohydrate recognition domain of the engineered MBL molecule can comprise an amino acid sequence of SEQ ID NO: 32 or 37, or a fragment thereof, e.g., a truncated form of SEQ ID NO: 32 or 37 with about 1-3 amino acids independently removed from one or both of the C-terminal and N-terminal ends. In some embodiments, the carbohydrate recognition domain can comprise, essentially consist of, or consist of an amino acid sequence of SEQ ID NO: 32 or 37, with at least one or a group of amino acid residues (e.g., at least 2 amino acid residues, at least 3 amino acid residues, at least 4 amino acid residues, at least 5 amino acid residues, at least 10 amino acid residues, at least 15 amino acid residues, at least 20 amino acid residues, at least 25 amino acid residues, at least 30 amino acid residues or more) independently removed from, or added to, the C-terminus and/or N-terminus of the selected sequence. In some embodiments, the carbohydrate recognition domain can comprise, essentially consist of, or consist of an amino acid sequence of SEQ ID NO: 32 or 37, with at least one or a group of amino acid residues (e.g., at least 2 amino acid residues, at least 3 amino acid residues, at least 4 amino acid residues, at least 5 amino acid residues, at least 10 amino acid residues, at least 15 amino acid residues, at least 20 amino acid residues, at least 25 amino acid residues, at least 30 amino acid residues or more) removed from, or added to, the C-terminus of the selected sequence.

In some embodiments, the CRD of the microbe-binding molecules described herein can comprise "KQ" amino acid residues, e.g., at the N-terminus of the CRD domain. See, e.g., SEQ ID NO: 37.

In some embodiments, the microbe-binding domain can comprise a helical domain and a CRD coupled together by "KQ" amino acid residues.

In some embodiments, the carbohydrate recognition domain of MBL or a fragment thereof used in the engineered microbe-binding molecules described herein can be a wild-type molecule or a recombinant molecule. Modifications to the CRD fragments described herein, e.g., by conservative substitution, are also within the scope described herein.

In some embodiments, the CRD of the microbe-binding molecules described herein can be derived from a sugar-binding molecule selected from the group consisting of a sugar binding lectin (e.g., a mannose binding lectin, a collectin, a surfactant protein), DC-SIGN, macrophage mannose receptor, and any combinations thereof.

In some embodiments, the CRD of the microbe-binding molecules described herein can comprise a CRD of mannose binding lectin 2 (MBL2) or a fragment thereof.

In some embodiments, the microbe-binding domain can comprise, essentially consist of, or consist of an amino acid sequence selected from the group consisting of SEQ ID NOs: 28-29, 31, and 33-36.

Different domains described herein, e.g., the collagen domain, Fc domain, helical domain and/or carbohydrate recognition domain, are building blocks of the microbe-binding molecules described herein, and can be arranged in different orders provided that the resulting microbe-binding molecules retain the capability to bind and detect microbes and/or microbial matter. FIGS. 1A-2B and FIGS. 13A-13D show schematic representations of the microbe-binding molecules according to some embodiments described herein. Modifications to these embodiments within one of skill in the art are also within the scope described herein.

Figure 1B:
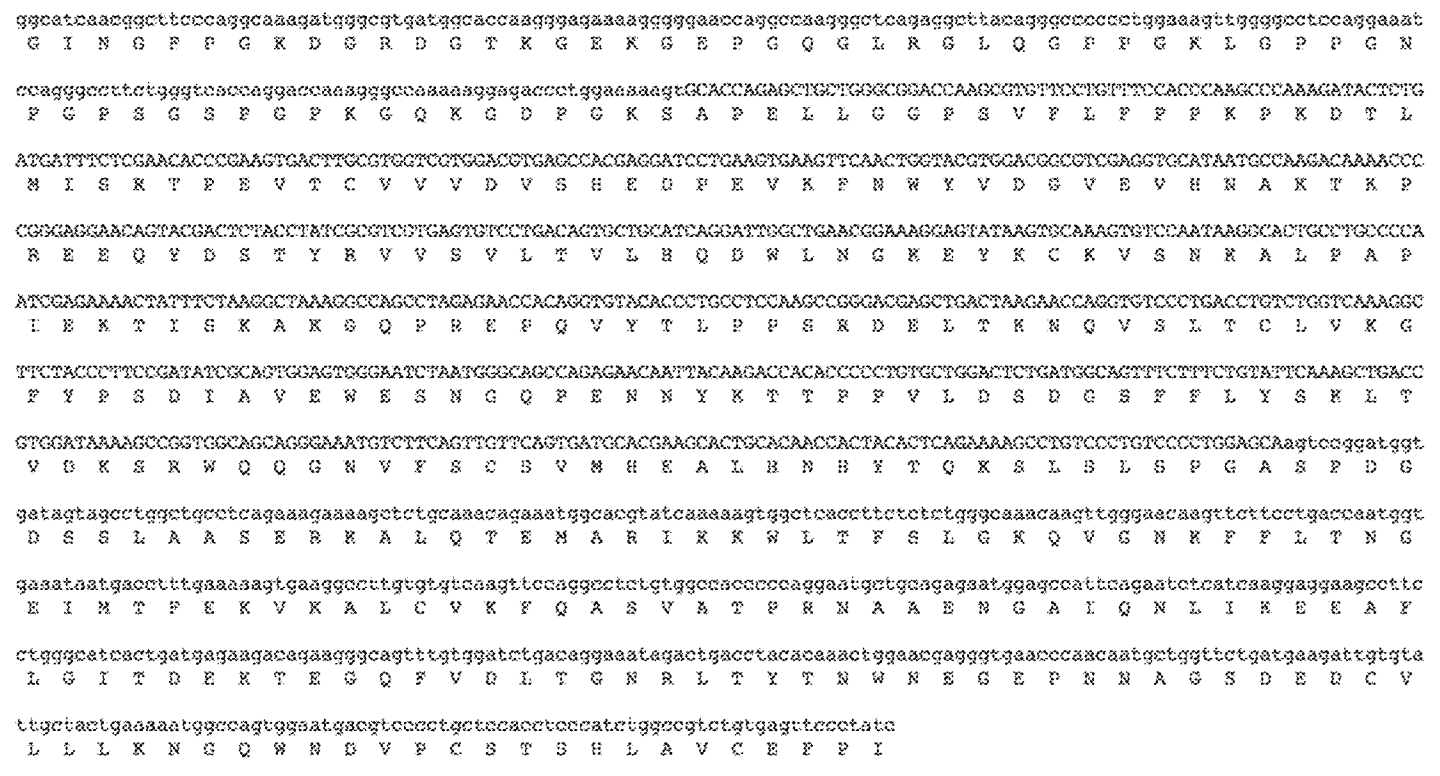
Figure 2A:
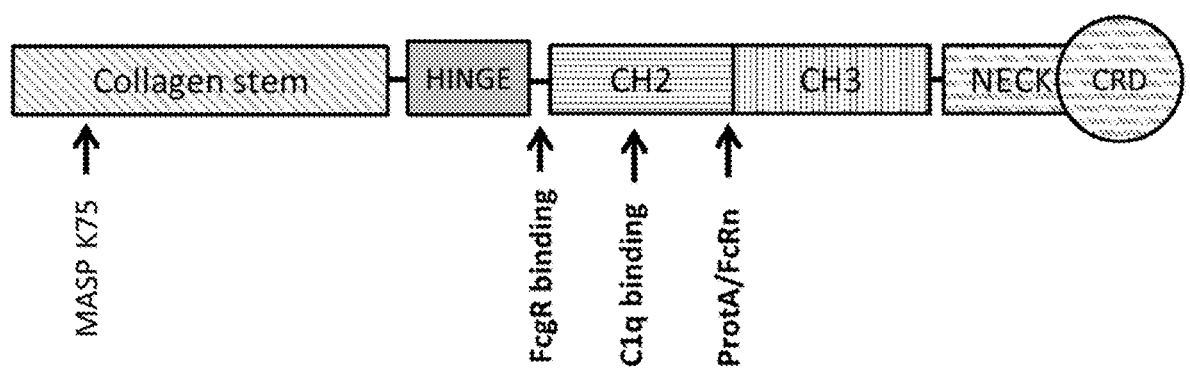
Figure 2B:
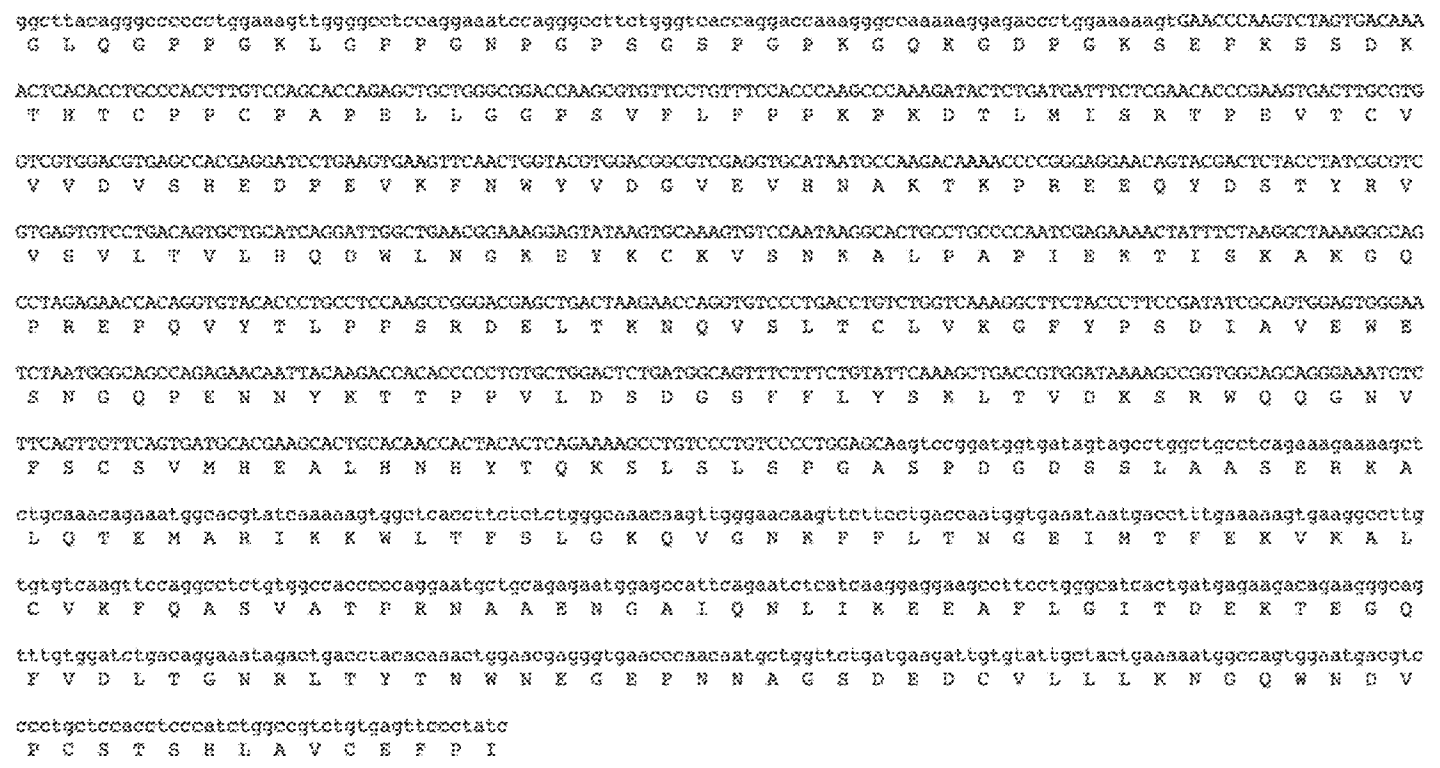

FIG. 1A shows a microbe-binding molecule comprising, from N-terminus to C-terminus, a collagen domain of MBL, an Fc domain, and a microbe-binding domain of MBL. The collagen domain does not contain cysteine-rich domain at the N-terminus. While FIGS. 1A-1B illustrate that the collagen domain comprises the charged region, the kink, and the MASP binding site, it is not construed to be limiting. In some embodiments, the charged region and the kink can be removed from the collagen domain, e.g., as shown in FIGS. 2A-2B. Further, the Fc domain in both FIGS. 1A-1B and FIGS. 2A-2B can be modified as discussed above, e.g., with or without a hinge domain and/or with a mutation in the Fc domain, e.g., to remove glycosylation.

Figures 12B, 13A:
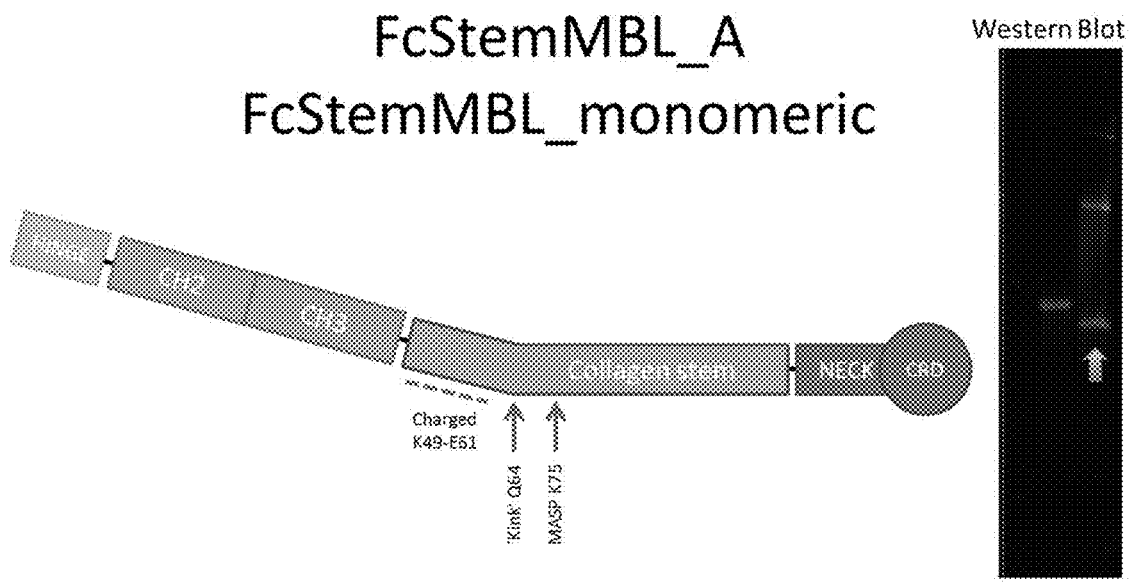

FIG. 13A shows a microbe-binding molecule comprising, from N-terminus to C-terminus, an Fc domain, a collagen domain of MBL and a microbe-binding domain (comprising a neck and CRD domain of MBL), wherein there is no cysteine-rich domain between the collagen domain and the Fc domain. The Q64 in the collagen domain of MBL is retained. In this embodiment, when the microbe-binding molecule forms a multimer, the Fc site at the apex of the multimer can be highly accessible when the microbe-surface-binding domain is bound to a target microbe or microbial matter. In some embodiments, the Fc domain can be a dimeric Fc. In some embodiments, the Fc domain can be a monomeric Fc domain. In some embodiments, the Fc domain can comprise a hinge. In some embodiments, the Fc domain can comprise no hinge.

Figure 13B:
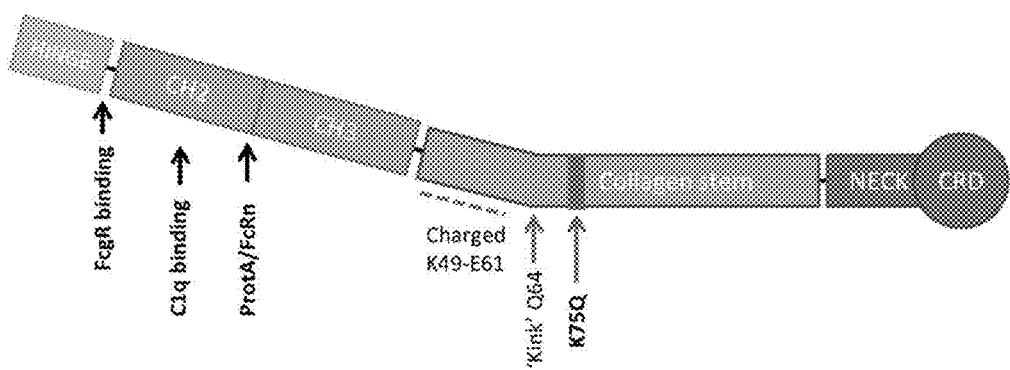

FIG. 13B shows a microbe-binding molecule comprising, from N-terminus to C-terminus, an Fc domain, a collagen domain of MBL and a microbe-binding domain (comprising a neck and CRD domain of MBL), wherein there is no cysteine-rich domain between the collagen domain and the Fc domain. In this embodiment, the domain responsible for binding MASP (e.g., K75Q) is mutated.

Figure 13C:
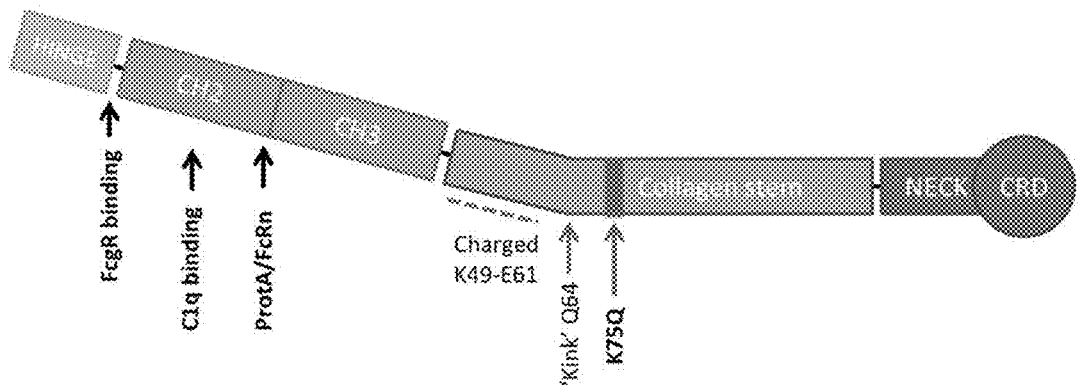

FIG. 13C shows a microbe-binding molecule comprising, from N-terminus to C-terminus, a collagen domain of MBL with the kink and charged regions, an Fc domain, and a microbe-binding domain (comprising a neck and CRD domain of MBL). In this embodiment, the microbe-binding molecule can allow enhanced expression while restoring MASP binding region.

Figure 13D:
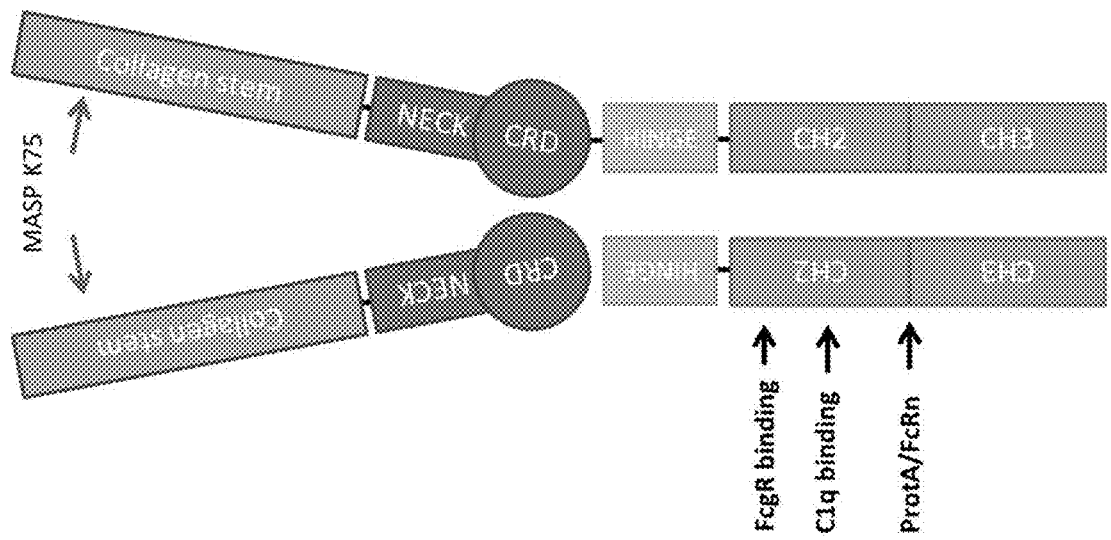

FIG. 13D shows a microbe-binding molecule comprising, from N-terminus to C-terminus, a collagen domain of MBL without the kink and charged regions, a microbe-binding domain (comprising a neck and CRD domain of MBL), and an Fc domain.

In some embodiments, the microbe-binding molecule can comprise, from N-terminus to C-terminus, an Fc domain, a collagen domain of MBL without the kink and charged regions, and a microbe-binding domain (comprising a neck and CRD domain of MBL), wherein there is no cysteine-rich domain between the collagen domain and the Fc domain. In one embodiment, the microbe-binding molecule can further comprise a second collagen domain that retains the minimum sequence required to bind MASP and activate the lectin pathway.

In some embodiments where the collagen domain comprises the charged region of the collagen stem of MBL, the Fc domain can exclude the hinge region.

In some embodiments where the Fc domain comprises a hinge, the collagen domain can exclude the charged region of the collagen stem of MBL.

In some embodiments, the microbe-binding molecule can comprise, essentially consist of, or consist of an amino acid sequence selected from the group consisting of SEQ ID NOs: 17-27.

Figure 15:
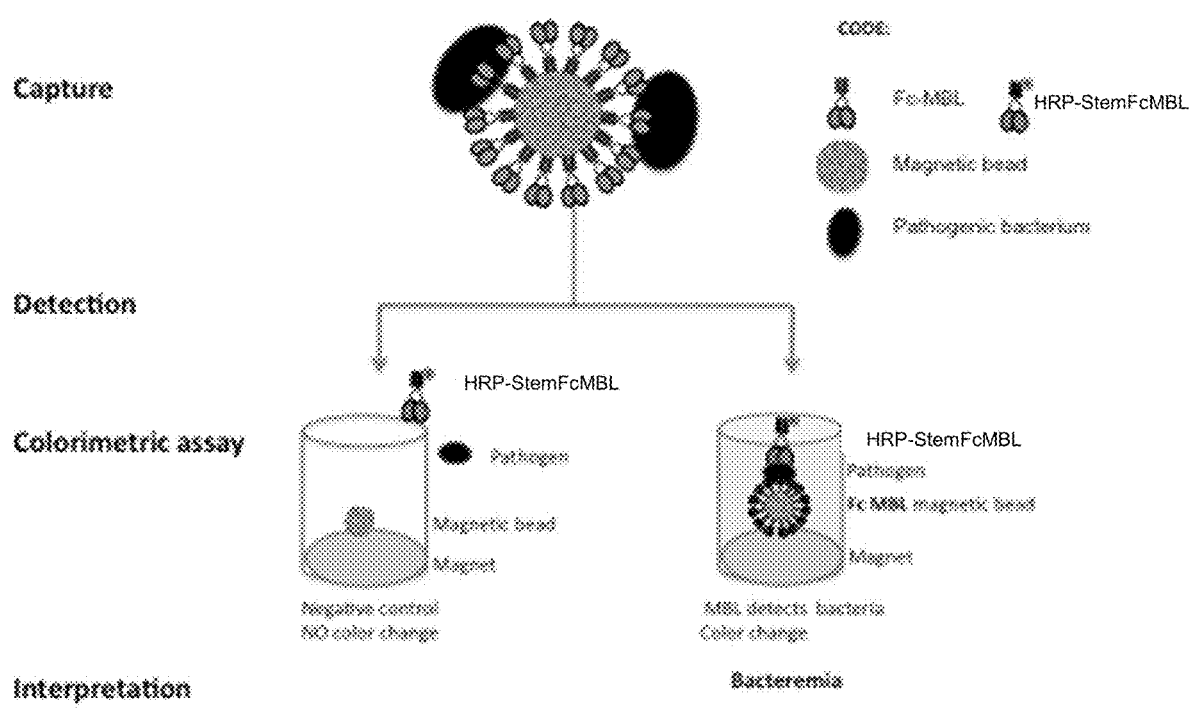
FIG. 15 is a schematic diagram of an exemplary ELISA assay comprising engineered microbe-binding molecules coupled to a detectable label (e.g., HRP) according to one or more embodiments described herein. The ELISA assay can be used for any diagnostic applications, e.g., for sepsis tests. While FcMBL is shown to capture microbes, the microbe-binding molecules according to one or more embodiments described herein can also be used to capture microbes or microbial matter.
Figure 16:
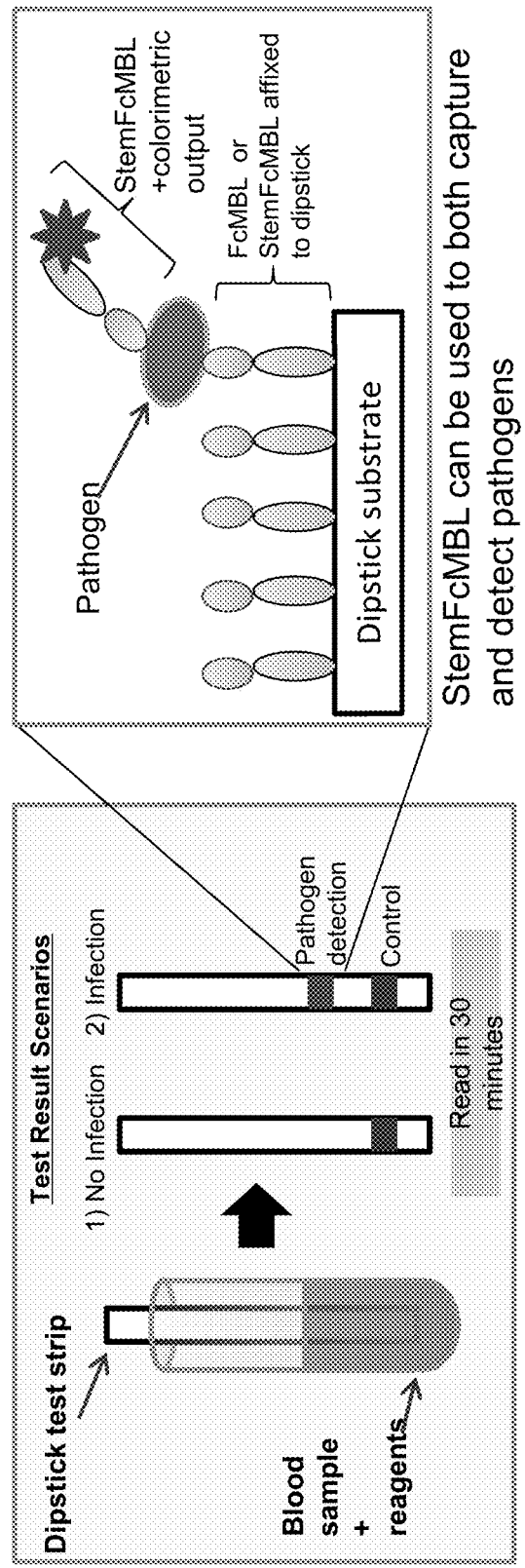
FIG. 16 is a schematic diagram showing one or more embodiments of a dipstick assay for microbial detection. The microbe-binding molecule according to one or more embodiments described herein and/or any art-recognized microbe-capture molecules can be attached to a membrane (for example Biodyne membrane). The membrane can be mixed with a test sample (e.g., blood sample), washed, incubated with a desirable detection agent (e.g., enzyme-linked microbe-binding molecule or specific antibody for certain microbes, e.g., bacteria or fungus), washed and added with a readout reagent for colorimetric development. The dipstick assay can be performed manually or modified for automation.
Figure 17:
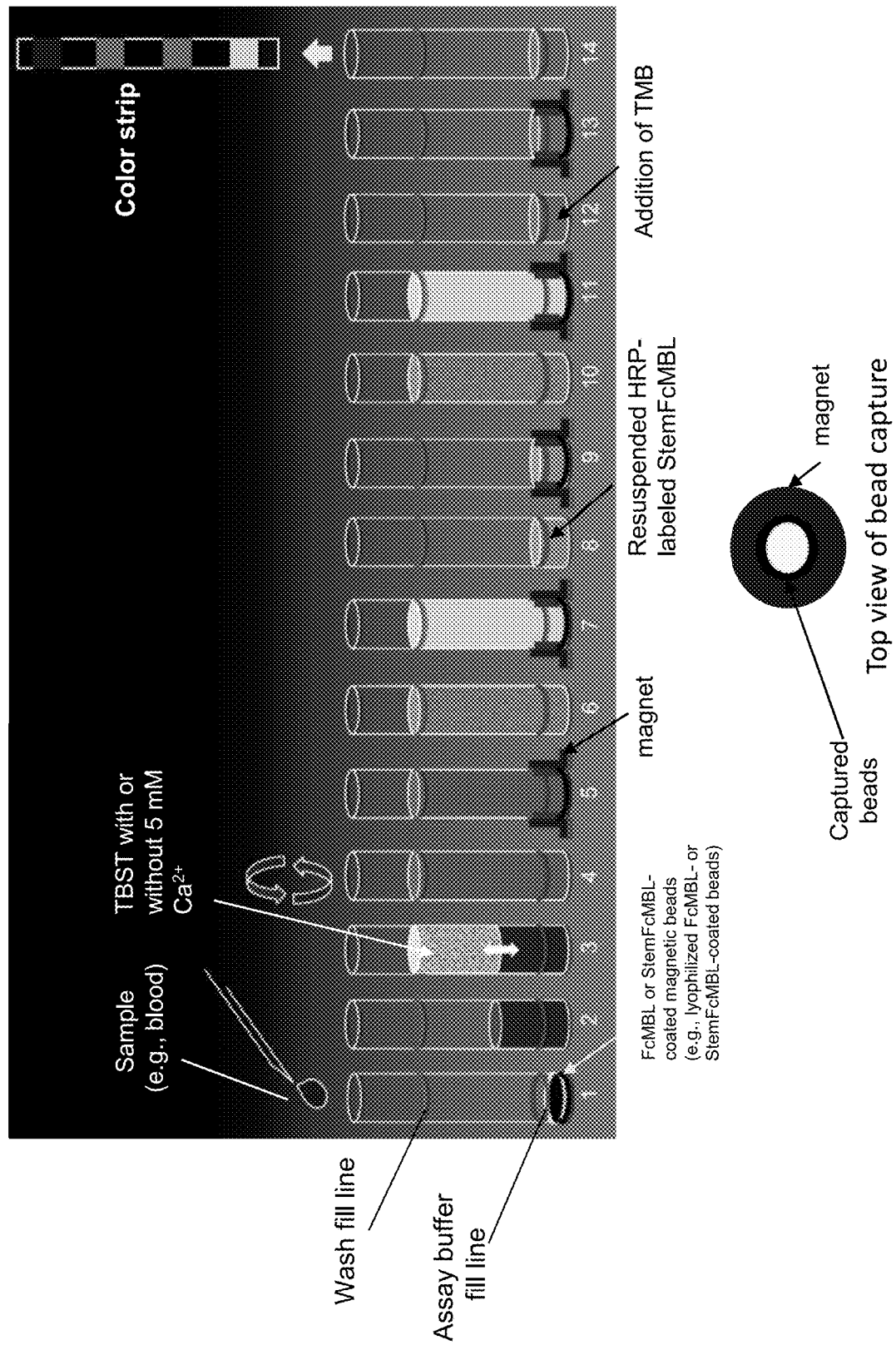
FIG. 17 is a schematic diagram showing one or more embodiments of an ELISA-based test for microbial detection. A test sample (e.g., blood sample) can be added into a single tube (e.g., a blood collection container such as EDTA VACUTAINER®) containing microbe-capture molecule-coated magnetic particles (e.g., art-recognized microbe-capture-molecule-coated magnetic particles such as FcMBL-coated magnetic particles, and/or magnetic particles coated with microbe-binding molecules according to one or more embodiments described herein). The ELISA-based test can be performed manually or modified for automation. In some embodiments, the single-tube based ELISA assay can be used to detect microbes or pathogens.

As the microbe-binding molecules described herein can be used as detection reagents, in any embodiments of the microbe-binding molecules described herein, the microbe-binding molecule can further comprise a detectable label coupled thereto. In some embodiments, the detectable label can be fused to the Fc domain and/or the collagen domain of the microbe-binding molecules described herein, thus forming recombinant fusion proteins. In some embodiments, the detectable label can bind to or interact with detectable label-binding sites available on the Fc domain and/or the collagen domain, via covalent or non-covalent interactions such as hydrophobic interactions and/or hydrogen bonds. For example, in one embodiment, the microbe-binding molecules described herein can be used as a secondary antibody, e.g., in an immunoassay such as ELISA, e.g., in FIG. 15.

As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include biotin, fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein.

In some embodiments, the detectable label can be an imaging agent or contrast agent. As used herein, the term "imaging agent" refers to an element or functional group in a molecule that allows for the detection, imaging, and/or monitoring of the presence and/or progression of a condition(s), pathological disorder(s), and/or disease(s). The imaging agent can be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like. In some embodiments, the detectable labels also encompass any imaging agent (e.g., but not limited to, a bubble, a liposome, a sphere, a contrast agent, or any detectable label described herein) that can facilitate imaging or visualization of a tissue or an organ in a subject, e.g., for diagnosis of an infection.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7;

APTS; Astrazon Brilliant Red 4G; Astrazon Orange R; Astrazon Red 6B; Astrazon Yellow 7 GLL; Atabrine; ATIO-TAGTH CBQCA; ATIO-TAGTH FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium CrimsonTH; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; *Lucifer* Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green 488-X; Oregon Green™ 488; Oregon Green™ 500; Oregon Green™514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; Tru-Red; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

In some embodiments, the fluorophore can be fused to the Fc domain and/or the collagen domain of the microbe-binding molecules described herein, thus forming recombinant fusion proteins. In some embodiments, the fluorophore can bind to or interact with detectable label-binding sites available on the Fc domain and/or the collagen domain, via covalent or non-covalent interactions such as hydrophobic interactions and/or hydrogen bonds.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane. Suitable non-metallic isotopes include, but are not limited to, 11C, 14C, 13N, 18F, 123I, 124I, and 125I. Suitable radioisotopes include, but are not limited to, 99mTc, 95Tc, 111In, 62Cu, 64Cu, Ga, 68Ga, and 153Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent or chelating agent-linker attached to the microbe-binding molecule. Suitable radionuclides for direct conjugation include, without limitation, 18F, 124I, 125I, 131I, and mixtures thereof. Suitable radionuclides for use with a chelating agent include, without limitation, 47Sc, 64Cu, 67Cu, 89Sr, 86Y, 87Y, 90Y, 105Rh, 111Ag, 111In, 117mSn, 149Pm, 153Sm, 166Ho, 177Lu, 186Re, 188Re, 211At, 212Bi, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to molecules such as the microbe-targeting molecules and carrier scaffolds disclosed herein.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label. Exemplary methods for in vivo detection or imaging of detectable labels include, but are not limited to, radiography, magnetic resonance imaging (MRI), Positron emission tomography (PET), Single-photon emission computed tomography (SPECT, or less commonly, SPET), Scintigraphy, ultrasound, CAT scan, photoacoustic imaging, thermography, linear tomography, poly tomography, zonography, orthopantomography (OPT or OPG), and computed Tomography (CT) or Computed Axial Tomography (CAT scan).

In some embodiments, the detectable label can include an enzyme. Exemplary enzymes for use as detectable labels include, but are not limited to, horseradish peroxidase (HRP), alkaline phosphastase (AP), luciferase, beta-galactosidase, and any combinations thereof. In some embodiments, the enzyme can be fused to the Fc domain and/or the collagen domain of the microbe-binding molecules described herein, thus forming recombinant fusion proteins. In these embodiments, the amino acid sequence for the enzyme can be optimized for a target species, e.g., a mammalian species. For example, the amino acid sequence of a mammalian-optimized HRP is defined by SEQ ID NO: 38, and the corresponding nucleotide sequence is defined by SEQ ID NO: 39. In some embodiments, the enzyme can bind to or interact with detectable label-binding sites available on the Fc domain and/or the collagen domain, via covalent or non-covalent interactions such as hydrophobic interactions and/or hydrogen bonds.

In some embodiments, the detectable label can include a microbial enzyme substrate conjugated to a detectable agent. For example, the detectable agent can be any moiety that, when cleaved from a microbial enzyme substrate by the enzyme possessed or secreted by the microbe, forms a detectable moiety but that is not detectable in its conjugated state. The microbial enzyme substrate is a substrate specific for one or more types of microbes to be detected, and it can be selected depending upon what enzymes the microbe possesses or secretes. See, e.g., International Patent Application: WO 2011/103144 for the use of such detectable label in detection of microbes, the content of which is incorporated herein by reference.

In some embodiments, the detectable label is a fluorophore or a quantum dot. Without wishing to be bound by a theory, using a fluorescent reagent can reduce signal-to-noise in the imaging/readout, thus maintaining sensitivity. Accordingly, in some embodiments, prior to detection, the microbes isolated from or remained bound on the microbe-binding substrate can be stained with at least one stain, e.g., at least one fluorescent staining reagent comprising a microbe-binding molecule, wherein the microbe-binding molecule comprises a fluorophore or a quantum dot. Examples of fluorescent stains include, but are not limited to, any microbe-binding molecules conjugated with a fluorophore or quantum dot, and any fluorescent stains used for detection as described herein.

In some embodiments, the detectable label can be used for detection and enhancement techniques. For example, microbes bound on microbe-binding molecules labeled with a detectable label can be isolated for enrichment of a sample with microbes in order to enhance signal detection. In some embodiments, the detectable label can comprise a metal particle. Examples of a metal particle can include particles of any metal, including, e.g., but not limited to e.g., gold particles and/or silver particles. In some embodiments, the detectable label can comprise a magnetic particle. In these embodiments, magnetic separation can be performed prior to detection of microbes.

In some embodiments, the detectable label can be configured to include a "smart label", which is undetectable when conjugated to the microbe-binding molecules, but produces a color change when released from the engineered molecules in the presence of a microbe enzyme. Thus, when a microbe binds to the engineered microbe-binding molecules, the microbe releases enzymes that release the detectable label from the engineered molecules. An observation of a color change indicates presence of the microbe in the sample.

In some embodiments, the detectable label can be a chromogenic or fluorogenic microbe enzyme substrate so that when a microbe binds to the engineered microbe-targeting molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-glucuronide, 2-methoxy-4-(2-nitrovinyl) phenyl-D-glu-copyranoside, 2-methoxy-4-(2-nitrovinyl) phenyl-D-cetamindo-2-deoxyglucopyranoside, and any other art-recognized microbe enzyme substrates. Such embodiments can act as an indicator for the presence of a microbe or pathogen.

As discussed earlier, the inventors have, in one aspect, developed microbe-binding molecules that can form a larger aggregate, or known as a multimer, which can not only promote avidity binding of individual microbe-binding molecules described herein to bind microbe(s) and/or microbial matter, but can also increase sensitivity limit of the microbe-binding molecules as detection agents. Accordingly, in one aspect, a microbe-binding multimeric molecule is provided herein. The microbe-binding multimeric molecule comprises a first microbe-binding molecule according to any embodiment described herein; and a second microbe-binding molecule according to any embodiment described herein, wherein the helical domain of the first microbe-binding molecule forms a coiled structure with the helical domain of the second microbe-binding molecule; and the collagen domain of the first microbe-binding molecule forms a helix structure with the collagen domain of the second microbe-binding molecule or the collagen domain of a third microbe-binding molecule described herein. In some embodiments, the collagen domain of the first microbe-binding molecule can form a triple helix structure with the collagen domain of the second microbe-binding molecule or the collagen domain of a third microbe-binding molecule described herein.

In some embodiments, the first, second, and third microbe-binding molecules can be of the same type. In some embodiments, at least two or all of the first, second, and third microbe-binding molecules can be of a different type.

The microbe-binding multimeric molecule can comprise any number of the microbe-binding molecules described herein present as monomers. For example, by arranging the microbe-binding domain, Fc domain and collagen domain in different configurations, the microbe-binding multimeric molecule can comprise at least 10 or higher, including, e.g., at least 11, at least 12, at least 13, at least 14, at least 15, at least 16, at least 17, at least 18, at least 19, at least 20, at least 21, at least 22, 23, at least 24 or higher, microbe-binding molecules as monomers.

In some embodiments, the microbe-binding molecule as monomers can exclude a cysteine-rich domain as defined herein. In these embodiments, instead of having a plurality of microbe-binding molecules described herein present as monomers covalently linked at the cysteine-rich domain, via disulfide bonds, to form a multimer, the microbe-binding molecule monomers can interact with each other, e.g., at the collagen domain, through non-covalent interactions, e.g., hydrophobic and/or hydrogen bond interactions, to form a multimer.

As the microbe-binding molecules described herein can also be used as a capture agent. The engineered microbe-binding molecules can be immobilized or conjugated on any substrate for various applications and/or purposes. For example, the engineered microbe-binding molecules can be immobilized on a solid substrate for easy handling during usage, e.g., for isolation, observation or microscopic imaging.

Accordingly, a further aspect provided herein is an article or product for targeting or binding microbes comprising at least one, including at least two, at least three, at least four, at least five, at least ten, at least 25, at least 50, at least 100, at least 250, at least 500, or more engineered microbe-binding molecules conjugated to a carrier scaffold or a surface thereof. The "carrier scaffold" is also referred to as a "carrier substrate" herein. In some embodiments, surface of the carrier scaffold can be coated with the microbe-binding molecule disclosed herein. As used herein, the term "article" refers to any distinct physical microscale or macroscale object. An article comprising a microbe-binding molecule conjugated to a carrier scaffold is also referred to as a "microbe-binding article" or a "microbe-binding article" herein.

Without limitations, the carrier scaffold can be selected from a wide variety of materials and in a variety of formats. For example, the carrier scaffold can be utilized in the form of beads or particles (including nanoparticles, microparticles, polymer microbeads, magnetic microbeads, and the like), filters, fibers, screens, mesh, tubes, hollow fibers, scaffolds, plates, channels, gold particles, magnetic materials, planar shapes (such as a rectangular strip or a circular disk, or a curved surface such as a stick), other substrates commonly utilized in assay formats, and any combinations thereof.

Examples of carrier scaffolds include, but are not limited to, nucleic acid scaffolds, protein scaffolds, lipid scaffolds, dendrimers, microparticles or microbeads, nanotubes, microtiter plates, medical apparatuses (e.g., needles or catheters) or implants, dipsticks or test strips, microchips, filtration devices or membranes, membranes, diagnostic strips, hollow-fiber reactors, microfluidic devices, living cells and biological tissues or organs, extracorporeal devices, mixing elements (e.g., spiral mixers), and the like. In some embodiments, the carrier scaffold can be in the form of a continuous roll on which the test area(s) and optionally reference area(s) are present in the form of continuous lines or a series of spots.

The carrier scaffold can be made of any material, including, but not limited to, metal, metal alloy, polymer, plastic, paper, glass, fabric, packaging material, biological material such as cells, tissues, hydrogels, proteins, peptides, nucleic acids, and any combinations thereof.

In some embodiments, the microbe-binding articles disclosed herein can be used to capture, detect, or remove microbe contaminants from any source or in any fluid, e.g., a biological fluid (e.g., blood sample), environmental fluid or surface (e.g., wastewater, building or machine surface), or an edible substance or fluid (e.g., food, water). In some embodiments where the fluid is blood, after removal of the microbe/pathogen from the blood collected from a subject with the microbe-binding magnetic microbeads, the blood can be circulated back to the same subject as a therapeutic intervention. In some embodiments, the microbe-binding articles disclosed herein can be used in diagnostics as a means of collecting potential pathogens for identification; not only in the diagnosis of disease, but in the identification of water- or food-borne pathogens, particulates or other contaminants. Alternatively, the carrier scaffold can comprise a hollow-fiber reactor or any other blood filtration membrane or flow device (e.g., a simple dialysis tube, spiral mixer or static mixer) or other resins, fibers, or sheets to selective bind and sequester the biological pathogens.

The microbe-binding articles disclosed herein also can be used as point-of-care diagnostic tools for microbe or pathogen detection. By way of example only, a microbe-binding article can be brought into contact with a test sample (e.g., a blood sample) from a patient or a subject, and incubated for a period of time, e.g., at least about 15 seconds, at least about 30 seconds, at least about 1 min, at least about 2 mins, at least about 5 mins, at least about 10 mins, at least about 15 mins, at least about 30 mins, at least about 1 hour or more. In some embodiments, the incubated dipstick or test strip can then be incubated in a blocking agent (e.g., BSA, normal serum, casesin, non-fat dry milk, and/or any commercially-available blocking agents to minimize non-specific binding). Depending on different embodiments of the engineered microbe-binding molecules, in some embodiments, the microbe-binding dipstick or test strip after contact with a test sample (e.g., a blood sample) can be further contacted with at least one additional agent to facilitate detection of pathogen, and/or to increase specificity of the pathogen detection. For example, some embodiments of the dipstick or test strip after contact with a test sample (e.g., a blood sample) can be further contacted with a detectable label that is conjugated to a molecule that binds to a microbe and/or microbial matter. Examples of such molecules can include, but are not limited to, one or more embodiments of the engineered microbe-binding molecule described herein, an antibody specific for the microbes or pathogens to be detected, a protein, a peptide, a carbohydrate or a nucleic acid that is recognized by the microbes or pathogens to be detected, and any combinations thereof.

In some embodiments, the readout of the microbe-binding article can be performed in a system or device, e.g., a portable device. The system or device can display a signal indicating the presence or the absence of a microbial infection in a test sample, and/or the extent of the microbial infection.

The particular format or material of the carrier scaffold depends on the particular use or application, for example, the separation/detection methods employed in an assay application. In some embodiments, the format or material of the carrier scaffold can be chosen or modified to maximize signal-to-noise ratios, e.g., to minimize background binding or for ease of separation of reagents and cost. For example, carrier scaffold can be treated or modified with surface chemistry to minimize chemical agglutination and non-specific binding. In some embodiments, at least a portion of the carrier scaffold surface that is in contact with a test sample can be treated to become less adhesive to any molecules (including microbes, if any) present in a test sample. By way of example only, the carrier scaffold surface in contact with a test sample can be silanized or coated with a polymer such that the surface is inert to the molecules present in the test sample, including but not limited to, cells or fragments thereof (including blood cells and blood components), proteins, nucleic acids, peptides, small molecules, therapeutic agents, microbes, microorganisms and any combinations thereof. In other embodiments, a carrier scaffold surface can be treated with an omniphobic layer, which can allow binding of a microbe by the engineered microbe-binding molecule without a subsequent hydrophobic binding between the microbe and the carrier scaffold surface. See, e.g., Wong T S et al., "Bioinspired self-repairing slippery surfaces with pressure-stable omniphobicity." (2011) *Nature* 477 (7365): 443-447, and International Application No.: PCT/US 12/21928, the content of which is incorporated herein by reference, for methods to produce a slippery carrier scaffold surface. Accordingly, non-specific binding of molecules from the test sample (including microbes and/or microbial matter) to a substrate surface can be reduced, thus increasing the sensitivity of the microbial detection.

In some embodiments, the carrier scaffold can be fabricated from or coated with a biocompatible material. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include, for example, derivatives and copolymers of polyimides, poly(ethylene glycol), polyvinyl alcohol, polyethyleneimine, and polyvinylamine, polyacrylates, polyamides, polyesters, polycarbonates, and polystyrenes. In some embodiments, biocompatible materials can include metals, such as titanium and stainless steel, or any biocompatible metal used in medical implants. In some embodiments, biocompatible materials can include paper substrate, e.g., as a carrier scaffold for a diagnostic strip. In some embodiments, biocompatible materials can include peptides or nucleic acid molecules, e.g., a nucleic acid scaffold such as a 2-D DNA sheet or 3-D DNA scaffold.

Additional material that can be used to fabricate or coat a carrier scaffold include, without limitations, polydimethylsiloxane, polyimide, polyethylene terephthalate, polymethylmethacrylate, polyurethane, polyvinylchloride, polystyrene, polysulfone, polycarbonate, polymethylpentene, polypropylene, polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

In some embodiments, the carrier scaffold can be fabricated from or coated with a biodegradable material. As used herein, the term "biodegradable" refers to the ability of a composition to erode or degrade in vivo to form smaller chemical fragments. Degradation can occur, for example, by enzymatic, chemical or physical processes. Non-limiting examples of biodegradable polymers that can be used in aspects provided herein include poly(lactide)s, poly(glycolide)s, poly(lactic acid)s, poly(glycolic acid)s, poly (lactide-co-glycolide), polyanhydrides, polyorthoesters, polycaprolactone, polyesteramides, polycarbonate, polycyanoacrylate, polyurethanes, polyacrylate, blends and copolymers thereof.

Other additional biodegradable polymers include biodegradable polyetherester copolymers. Generally speaking, the polyetherester copolymers are amphiphilic block copolymers that include hydrophilic (for example, a polyalkylene glycol, such as polyethylene glycol) and hydrophobic blocks (for example, polyethylene terephthalate). An exemplary block copolymer is, but is not limited to, poly(ethylene glycol)-based and poly(butylene terephthalate)-based blocks (PEG/PBT polymer). PEG/PBT polymers are commercially available from OctoPlus Inc, under the trade designation PolyActive™. Non-limiting examples of biodegradable copolymers or multiblock copolymers include the ones described in U.S. Pat. Nos. 5,980,948 and 5,252,701, the contents of which are incorporated herein by reference.

Other biodegradable polymer materials include biodegradable terephthalate copolymers that include a phosphorus-containing linkage. Polymers having phosphoester linkages, called poly(phosphates), poly(phosphonates) and poly (phosphites), are known in the art. See, for example, Penczek et al., *Handbook of Polymer Synthesis, Chapter 17*: "Phosphorus-Containing Polymers," 1077-1 132 (Hans R. Kricheldorf ed., 1992), as well as U.S. Pat. Nos. 6,153,212; 6,485,737; 6,322,797; 6,600,010; 6,419,709; 6,419,709; 6,485,737; 6,153,212; 6,322,797 and 6,600,010, the contents of which are incorporated herein by reference.

Biodegradable polyhydric alcohol esters can also be used as a material of a carrier scaffold (e.g., a microparticle) (See U.S. Pat. No. 6,592,895, which is incorporated herein by reference). In some embodiments, the biodegradable polymer can be a three-dimensional crosslinked polymer network containing hydrophobic and hydrophilic components which forms a hydrogel with a crosslinked polymer structure, such as the one described in U.S. Pat. No. 6,583,219. In yet further embodiments, the biodegradable polymer can comprise a polymer based upon α-amino acids (such as elastomeric copolyester amides or copolyester urethanes, as described in U.S. Pat. No. 6,503,538, which is incorporated herein by reference).

In some embodiments, the carrier scaffold can comprise a paper, nitrocellulose, glass, plastic, polymer, membrane material, nylon, and any combinations thereof. This is useful for using the article as a test strip of a dipstick.

As used herein, by the "coating" or "coated" is generally meant a layer of molecules or material formed on an outermost or exposed layer of a surface. With respect to a coating of engineered microbe-binding molecules on a carrier scaffold, the term "coating" or "coated" refers to a layer of engineered microbe-binding molecules formed on an outermost or exposed layer of a carrier scaffold surface. In some embodiments, the carrier scaffold surface can encompass an outer surface or an inner surface, e.g., with respect to a hollow structure. For example, the inner surface of a needle or catheter can be coated with the engineered microbe-binding molecules described herein. This can be useful for removing any potential microbe contaminants from a fluid before administering the fluid to a subject.

The amount of the engineered microbe-binding molecules conjugated to or coating on a carrier scaffold can vary with a number of factors such as a surface area, conjugation/coating density, types of engineered microbe-binding molecules, and/or binding performance. A skilled artisan can determine the optimum density of engineered microbe-binding molecules on a carrier scaffold using any methods known in the art. By way of example only, for magnetic microparticles as a carrier scaffold (as discussed in detail later), the amount of the engineered microbe-binding molecules used for conjugating to or coating magnetic microparticles can vary from about 1 wt % to about 30 wt %, or from about 5 wt % to about 20 wt %. In some embodiments, the amount of the engineered microbe-binding molecules used for conjugating to or coating magnetic microparticles can be higher or lower, depending on a specific need. However, it should be noted that if the amount of the engineered microbe-binding molecules used for conjugating to or coating the magnetic microparticles is too low, the magnetic microparticles can show a lower binding performance with a pathogen/microbe. On the contrary, if the amount of the engineered microbe-binding molecules used for conjugating to or coating the magnetic microparticles is too high, the dense layer of the engineered microbe-binding molecules can exert an adverse influence on the magnetic properties of the magnetic microbeads, which in turn can degrade the efficiency of separating the magnetic microbeads from a fluid utilizing the magnetic field gradient.

In some embodiments, the carrier scaffold can further comprise at least one area adapted for use as a reference area. By way of example only, the reference area can be adapted for use as a positive control, negative control, a reference, or any combination thereof. In some embodiments, the carrier scaffold can further comprise at least two areas, wherein one area is adapted for a positive control and the second area is adapted for a negative control.

In some embodiments, the carrier scaffold can further comprise at least one reference area or control area for comparison with a readout signal determined from the test area. The reference area generally excludes the engineered microbe-binding molecules, e.g., to account for any background signal. In some embodiments, the reference area can include one or more known amounts of the detectable label that the engineered microbe-binding molecules in the test area encompass. In such embodiments, the reference area can be used for calibration such that the amount of microbes in a test sample can be estimated or quantified.

In some embodiments, the carrier scaffold can further comprise a detectable label. The detectable label can be separate from the microbe-binding molecules conjugated with the carrier scaffold or linked to the microbe-binding molecules described herein conjugated with the carrier scaffold.

Microbe-Binding Microparticles:

In some embodiments, the carrier scaffold is a microparticle. Accordingly, some embodiments described herein provide a microbe-binding microparticle comprising at least one engineered microbe-binding molecule on its surface. The term "microparticle" as used herein refers to a particle having a particle size of about 0.001 µm to about 1000 µm, about 0.005 µm to about 50 µm, about 0.01 µm to about 25 µm, about 0.05 µm to about 10 µm, or about 0.05 µm to about 5 µm. In one embodiment, the microparticle has a particle size of about 0.05 µm to about 1 µm. In one embodiment, the microparticle is about 0.09 µm-about 0.2 µm in size.

In some embodiments, the microparticle can range in size from 1 nm to 1 mm, about 2.5 nm to about 500 µm, or about 5 nm to about 250 µm in size. In some embodiments, microparticle can be about 5 nm to about 100 pun in size. In some embodiments, microparticle can be about 0.01 µm to about 10 µm in size. In some embodiments, the microparticle can be about 0.05 µm to about 5 µm in size. In some embodiments, the microparticle can be about 0.08 µm to about 1 µm in size. In one embodiment, the microparticle can be about 10 nm to about 10 µm in size. In some embodiments, the microparticle can be about 1 nm to about 1000 nm, from about 10 nm to about 500 nm, from about 25 nm to about 300 nm, from about 40 nm to about 250 nm, or from about 50 nm to about 200 nm. In one embodiment, the microparticle can be about 50 nm to about 200 nm.

It will be understood by one of ordinary skill in the art that microparticles usually exhibit a distribution of particle sizes around the indicated "size." Unless otherwise stated, the term "size" as used herein refers to the mode of a size distribution of microparticles, i.e., the value that occurs most frequently in the size distribution. Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

Without limitations, the microparticle can be of any shape. Thus, the microparticle can be, but is not limited to, spherical, rod, elliptical, cylindrical, disc, and the like. In some embodiments, the term "microparticle" as used herein can encompass a microsphere. The term "microsphere" as used herein refers to a microparticle having a substantially spherical form. A substantially spherical microparticle is a microparticle with a difference between the smallest radii and the largest radii generally not greater than about 40% of the smaller radii, and more typically less than about 30%, or less than 20%.

In some embodiments, the microparticles having a substantially spherical shape and defined surface chemistry can be used to minimize chemical agglutination and non-specific binding.

In one embodiment, the term "microparticle" as used herein encompasses a microcapsule. The term "microcapsule" as used herein refers to a microscopic capsule that contains an active ingredient, e.g., a therapeutic agent or an imagining agent. Accordingly, in some embodiments, the microparticles comprising on their surface engineered microbe-binding molecules can encapsulate at least one active ingredient therein, e.g., a therapeutic agent to treat an infection, and be used as a cell-targeted drug delivery device. In such embodiments, the microparticles can comprise biocompatible polymers as described herein. In some embodiments, the microparticles can further comprise biodegradable polymers, e.g., for releasing the encapsulated drugs.

In general, any biocompatible material well known in the art for fabrication of microparticles can be used in embodiments of the microparticle described herein. Accordingly, a microparticle comprising a lipidic microparticle core is also within the scope described herein. An exemplary lipidic microparticle core is, but is not limited to, a liposome. A liposome is generally defined as a particle comprising one or more lipid bilayers enclosing an interior, e.g., an aqueous interior. In one embodiment, a liposome can be a vesicle formed by a bilayer lipid membrane. Methods for the preparation of liposomes are well described in the art, e.g., Szoka and Papahadjopoulos (1980) *Ann. Rev. Biophys. Bioeng.* 9: 467, Deamer and Uster (1983) Pp. 27-51 In: *Liposomes*, ed. M. J. Ostro, Marcel Dekker, New York.

Microbe-Binding Magnetic Microparticles:

In some embodiments, the microparticle is a magnetic microparticle. Thus, in some embodiments, provided herein is a "microbe-binding magnetic microparticle" wherein a magnetic microparticle comprising on its surface at least one engineered microbe-binding molecule. Without limitations, such microbe-binding magnetic microparticles can be used to separate microbes or pathogens from a test sample, e.g., but not limited to, any fluid, including a biological fluid such as blood. In some embodiments, the microbe-binding magnetic microparticle can be used to remove living microbes or pathogens. Using magnetic microparticles as a substrate can be advantageous because the microbe-bound magnetic microparticles can be easily separated from a sample fluid using a magnetic field gradient, be examined for the presence of the microbe, and/or be used to transfer the collected microbes to conventional pathogen culture and sensitivity testing assays. Thus, in some embodiments, the microbe-binding magnetic microparticles can be used to capture, detect, or remove microbe contaminants from any source or in any fluid, e.g., a biological fluid (e.g., blood sample), environmental fluid or surface (e.g., wastewater, building or machine surface), or an edible substance or fluid (e.g., food, water). In some embodiments where the fluid is blood, after removal of the microbe/pathogen from the blood collected from a subject with the microbe-binding magnetic microbeads, the blood can be circulated back to the same subject as a therapeutic intervention. In some embodiments, the microbe-binding magnetic microbeads can be used in diagnostics as a means of collecting potential pathogens for identification; not only in the diagnosis of disease, but in the identification of water- or food-borne pathogens, particulates or other contaminants. Alternatively, the solid substrate can comprise a hollow-fiber reactor or any other blood filtration membrane or flow device (e.g., a simple dialysis tube, spiral mixer or static mixer) or other resins, fibers, or sheets to selective bind and sequester the biological pathogens.

Magnetic microparticles can be manipulated using magnetic field or magnetic field gradient. Such particles commonly consist of magnetic elements such as iron, nickel and cobalt and their oxide compounds. Magnetic microparticles are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199, the contents of which are incorporated herein by reference.

Magnetic microparticles are also widely and commercially available, with or without functional groups capable of conjugation with the microbe-binding molecules disclosed herein. Magnetic microparticles functionalized with various functional groups, e.g., amino groups, carboxylic acid groups, epoxy groups, tosyl groups, or silica-like groups, are also widely and commercially available. Suitable magnetic microparticles are commercially available such as from AdemTech, Miltenyi, PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic microparticles that can be used herein can be any DYNABEADS® magnetic microbeads (Invitrogen Inc.), depending on the substrate surface chemistry.

Microbe-Binding Cells:

In some embodiments, the carrier scaffold to which the engineered microbe-binding molecule binds can be a living cell, or a biological tissue or organ. For example, the living cells can be associated with an immune response, and such cells include, but are not limited to, a phagocyte (macrophage, neutrophil, and dendritic cell), mast cell, eosinophil, basophil, and/or natural killer cell. Alternatively, the living cell can be the cell of biological tissues or organs of the immune system, such as spleen, lymph nodes, lymphatic vessels, tonsils, thymus, bone marrow, Peyer's patches, connective tissues, mucous membranes, the reticuloendothelial system, etc. In some embodiments, the surface to which the engineered microbe-binding molecules bind can also be the extracellular matrix of one or more of these tissues or organs.

Microbe-Binding Microtiter Plates:

In some embodiments, the bottom surface of microtiter wells can be coated with the engineered microbe-binding molecules described herein, e.g., for detecting and/or determining the amount of microbes in a sample. After microbes or pathogens in the sample binding to the engineered microbe-binding molecules bound to the microwell surface, the rest of the sample can be removed. Detectable molecules that can also bind to microbes or pathogens (e.g., an engineered microbe-binding molecule conjugated to a detectable molecule as described herein) can then be added to the microwells with microbes/pathogens for detection of microbes/pathogens. Various signal detection methods for determining the amount of proteins, e.g., using enzyme-linked immunosorbent assay (ELISA), with different detectable molecules have been well established in the art, and those signal detection methods can also be employed herein to facilitate detection of the signal induced by microbes/pathogens binding on the engineered microbe-binding molecules.

Microbe-Binding Dipsticks/Test Strips:

In some embodiments, the carrier scaffold having the microbe-binding molecule conjugated thereon can be in the form of a dipstick and/or a test strip for capture, detection, or clearance of microbes or pathogens. For example, a dipstick and/or a test strip can include at least one test area containing one or more engineered microbe-binding molecules described herein. The dipstick and/or a test strip can be in any shape and/or in any format, e.g., a planar shape such as a rectangular strip or a circular disk, or a curved surface such as a stick. Alternatively, a continuous roll can be utilized, rather than discrete test strips, on which the test area(s) and optionally reference area(s) are present in the form of continuous lines or a series of spots. In some embodiments, the microbe-binding dipsticks or test strips described herein can be used as point-of-care diagnostic tools for microbe or pathogen detection.

In some embodiments, the carrier scaffold in the form of a dipstick or a test strip can be made of any material, including, without limitations, paper, nitrocellulose, glass, plastic, polymer, membrane material, nylon, and any combinations thereof. In one embodiment, the carrier scaffold in the form of a dipstick or a test strip can include paper. In one embodiment, the carrier scaffold in the form of a dipstick or a test strip can include nylon.

In some embodiments, the dipstick or a test strip can further comprise at least one reference area or control area for comparison with a readout signal determined from the test area. The reference area generally excludes the engineered microbe-binding molecules, e.g., to account for any background signal. In some embodiments, the reference area can include one or more known amounts of the detectable label that the engineered microbe-binding molecules in the test area encompass. In such embodiments, the reference area can be used for calibration such that the amount of microbes in a test sample can be estimated or quantified.

In some embodiments, the dipstick/test strip can further comprise a detectable label as described herein. The detectable label can be linked to the microbe-binding molecule described herein conjugated with the dipstick/test strip or separate from the microbe-binding molecule conjugated with the dipstick/test strip.

In one embodiment, about 1 µg to about 100 µg microbe-binding molecules described herein can be coated on or attached to a dipstick or membrane surface. In another embodiment, about 3 µg to about 60 µg microbe-binding molecules can be coated on or attached to a dipstick or membrane surface. In some embodiments, about 0.1 mg/mL to about 50 mg/mL, about 0.5 mg/mL to about 40 mg/mL, about 1 mg/mL to about 30 mg/mL, about 5 mg/mL to about 20 mg/mL microbe-binding molecules can be coated on or attached to a dipstick or membrane surface. In one embodiment, about 11.5 mg/mL microbe-binding molecules can be coated on or attached to a dipstick or membrane surface.

In some embodiments, any two domains of the microbe-binding molecule (e.g., the collagen domain, the Fc domain, the helical domain, and the carbohydrate recognition domain) can be linked together by a linker. Further, the microbe-binding molecule can be conjugated to a carrier scaffold via linker. Accordingly, as used in this disclosure, the term "linker" means a moiety that connects two parts of a compound or molecule. Linkers typically comprise a direct bond or an atom such as oxygen or sulfur, a unit such as $NR^1$, C(O), C(O)O, OC(O)O, C(O)NH, NHC(O)O, NH, SS, SO, $SO_2$, $SO_3$, and $SO_2NH$, or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, $C(O)N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic. In some embodiments, the linker can be a non-covalent association (e.g., by non-covalent interactions) of the two parts of a molecule being conjugated together. Some exemplary non-covalent on ionic interactions, van der Waals interactions, dipole-dipole interactions, hydrogen bonds, electrostatic interactions, and/or shape recognition interactions. Some additional examples of linkers or functional groups for conjugation include, but are not limited to, an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, an urethane group, and any combinations thereof.

In some embodiments, the linker can comprise at least one cleavable linking group. A cleavable linking group is one which is sufficiently stable under one set of conditions, but which is cleaved under a different set of conditions to release the two parts the linker is holding together. In some embodiments, the cleavable linking group is cleaved at least 10 times or more, e.g., at least 100 times faster under a first reference condition (which can, e.g., be selected to mimic or represent a microbe-infected condition, such as a microbe-infected tissue or body fluid, or a microbial biofilm occurring in an environment) than under a second reference condition (which can, e.g., be selected to mimic or represent non-infected conditions, e.g., found in the non-infected blood or serum, or in an non-infected environment).

Cleavable linking groups are susceptible to cleavage agents, e.g., hydrolysis, pH, redox potential or the presence of degradative molecules. Generally, cleavage agents are more prevalent or found at higher levels or activities at a site of interest (e.g. a microbial infection) than in non-infected area. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell, organ, or tissue to be targeted. In some embodiments, cleavable linking group is cleaved at least 1.25, 1.5, 1.75, 2, 3, 4, 5, 10, 25, 50, or 100 times faster under a first reference condition (or under in vitro conditions selected to mimic a microbe-infected condition, such as a microbe-infected tissue or body fluid, or a microbial biofilm occurring in an environment or on a working surface) than under a second reference condition (or under in vitro conditions selected to mimic non-infected conditions, e.g., found in the non-infected blood or serum, or in an non-infected environment). In some embodiments, the cleavable linking group is cleaved by less than 90%, 80%, 70%, 60%, 50%, 40%, 30%, 20%, 10%, 5%, or 1% in the non-infected conditions, e.g., found in the non-infected blood or serum, or in an non-infected environment, as compared to a microbe-infected condition, such as a microbe-infected tissue or body fluid, or a microbial biofilm occurring in an environment or on a working surface.

Exemplary cleavable linking groups include, but are not limited to, hydrolyzable linkers, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease. In some embodiments, an acid cleavable linking group is cleavable in an acidic environment with a pH of about 6.5 or lower (e.g., about 6.5, 6.0, 5.5, 5.0, or lower), or by agents such as enzymes that can act as a general acid.

In some embodiments, the linker can be a peptide or a nucleic acid. In some embodiments, the peptide linker can vary from about 1 to about 1000 amino acids long, from about 10 to about 500 amino acids long, from about 30 to about 300 amino acids long, or from about 50 to about 150 amino acids long. In some embodiments, the peptidyl linker is from about 1 amino acid to about 20 amino acids long. In some embodiments, the nucleic acid linker can vary from about 1 to about 1000 nucleotides long, from about 10 to about 500 nucleotides long, from about 30 to about 300 nucleotides, or from about 50 to about 150 nucleotides. Longer or shorter linker sequences can be also used for the engineered microbe-binding molecules described herein.

The peptidyl linker can be configured to have a sequence comprising at least one of the amino acids selected from the group consisting of glycine (Gly), serine (Ser), asparagine (Asn), threonine (Thr), methionine (Met) or alanine (Ala). Such amino acids are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp). In alternative embodiments, polar amino acids can be added to modulate the flexibility of a linker. One of skill in the art can control flexibility of a linker by varying the types and numbers of residues in the linker. See, e.g., Perham, 30 *Biochem.* 8501 (1991); Wriggers et al., 80 *Biopolymers* 736 (2005).

In some embodiments, the peptidyl linker can comprise form 1 to about 25 amino acids, i.e., one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five amino acids.

In some embodiments, the linker is a bond.

In some embodiments, the linker conjugating a microbe-binding molecule to a carrier scaffold is a polyethylene glycol. Exemplary PEGs for use as linkers include, but are not limited to, PEG-2K, PEG-5K, PEG-10K, PEG-12K, PEG-15K, PEG-20K, PEG-40K, and the like.

In some embodiments, the linker can be albumin, transferrin or a fragment thereof. Without limitations, such linkers can be used to extend the plasma half-life of the engineered microbe-binding molecules. Thus, engineered microbe-binding molecules can be useful for in vivo administration. See Schmidt S R (2009) *Curr Opin Drug Discov Devel.* 12: 284. In some embodiments, the linker can be a physical substrate, e.g., microparticles or magnetic microbes.

The linkers can be of any shape. For example, the linker can be linear, folded, branched. In some embodiments, the linker can adopt the shape of a carrier scaffold. In some embodiments, the linkers can be linear. In some embodiments, the linkers can be folded. In some embodiments, the linkers can be branched. For branched linkers, each branch of a microbe-binding domain can comprise at least one microbe-binding domain. In other embodiments, the linker adopts the shape of the physical substrate.

In some embodiments, the linker can further comprise a detectable label. In some embodiments, the detectable label can be a chromogenic or fluorogenic microbe enzyme substrate so that when a microbe binds to the engineered microbe-binding molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-deoxyglucopyranoside, and any other art-recognized microbe enzyme substrates. Such embodiments can act as an indicator for the presence of a microbe or pathogen.

The aforementioned linkers for connecting any two of the domains of the microbe-binding molecules described herein can also be used to conjugate the microbe-binding molecules described herein to a carrier scaffold. Additionally or alternatively, the attachment of the engineered microbe-binding molecule disclosed herein to a surface of the carrier scaffold can be performed with multiple approaches, for example, by direct cross-linking the engineered microbe-binding molecule to the carrier scaffold surface; cross-linking the engineered microbe-binding molecule to the carrier scaffold surface via a nucleic acid matrix (e.g., DNA matrix or DNA/oligonucleotide origami structures) for orientation and concentration to increase detection sensitivity; cross-linking the microbe-binding molecule to the carrier scaffold surface via a dendrimer-like structure (e.g., PEG/Chitin-structure) to increase detection sensitivity; attracting microbe-binding molecule coated magnetic microbeads to the carrier scaffold surface with a focused magnetic field gradient applied to the carrier scaffold surface, attaching an engineered microbe-binding molecule to a carrier scaffold via biotin-avidin or biotin-avidin-like interaction, or any other art-recognized methods.

Without limitations, any conjugation chemistry known in the art for conjugating two molecules or different parts of a composition together can be used for conjugating at least one engineered microbe-binding molecule to a carrier scaffold. Exemplary coupling molecules and/or functional groups for conjugating at least one engineered microbe-binding molecule to a substrate include, but are not limited to, a polyethylene glycol (PEG, $NH_2$-$PEG_X$-COOH which can have a PEG spacer arm of various lengths X, where 1<X<100, e.g., PEG-2K, PEG-5K, PEG-10K, PEG-12K, PEG-15K, PEG-20K, PEG-40K, and the like), maleimide conjugation agent, PASylation, HESylation, Bis(sulfosuccinimidyl) suberate conjugation agent, DNA conjugation agent, peptide conjugation agent, silane conjugation agent, polysaccharide conjugation agent, hydrolyzable conjugation agent, and any combinations thereof.

For engineered microbe-binding molecules to be immobilized on or conjugated to a carrier scaffold, the microbe-binding molecules described herein can further comprise at least one (e.g., one, two, three, four, five, six, seven, eight, nine, ten, eleven, twelve, thirteen, fourteen, fifteen, sixteen, seventeen, eighteen, nineteen, twenty or more) domain adapted for orienting the microbe-binding molecule described herein away from the carrier scaffold surface. In some embodiments, the carrier scaffold surface can be functionalized with a coupling molecule to facilitate the conjugation of engineered microbe-binding molecule to the solid surface. A domain adapted for conjugating the microbe-binding molecule to a carrier scaffold is also referred to as a "conjugation domain" herein. As used herein, the term "conjugation domain" refers to any molecule or portion thereof that facilitates the conjugation of the engineered molecules described herein to a carrier scaffold.

In some embodiments, length of the conjugation domain can vary from 1 amino acid residue to about 10 amino acid residues, or about 2 amino acid residues to about 5 amino acid residues. Determination of an appropriate amino acid sequence of the conjugation domain for binding with different carrier scaffolds is well within one of skill in the art. For example, according to one or more embodiments, the conjugation domain can comprise an amino acid sequence of Alanine-Lysine-Threonine (A-K-T) (SEQ ID NO: 35), which provides a single biotinylation site for subsequent binding to streptavidin. Preferably the A-K-T is at the terminus or near the terminus (e.g., within less than 10 amino acids from the terminus) of the microbe-binding molecule. In some embodiments, the conjugation domain comprises a functional group for conjugating or linking the microbe-binding molecule to the carrier scaffold. Some exemplary functional groups for conjugation include, but are not limited to, an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, one partner of a binding pair, an amide group, an aryl group, an ester group, an ether group, a glycidyl group, a halo group, a hydride group, an isocyanate group, an urea group, an urethane group, and any combinations thereof.

Activation agents can be used to activate the components to be conjugated together. Without limitations, any process and/or reagent known in the art for conjugation activation can be used. Exemplary activation methods or reagents include, but are not limited to, 1-Ethyl-3-[3-dimethylaminopropyl]carbodiimide hydrochloride (EDC or EDAC), hydroxybenzotriazole (HOBT), N-Hydroxysuccinimide (NHS), 2-(1H-7-Azabenzotriazol-1-yl)-1,1,3,3-tetramethyl uronium hexafluorophosphate methanaminium (HATU), silanization, surface activation through plasma treatment, and the like.

In some embodiments, the conjugation domain can comprise at least one amino group that can be non-covalently or covalently coupled with functional groups on the carrier scaffold. For example, the primary amines of the amino acid residues (e.g., lysine or cysteine residues) can be used to conjugate the microbe-binding molecule with the carrier scaffold. In some embodiments, the amino group at the N-terminus of the microbe-binding molecule can be used for conjugating the microbe-binding molecule with the carrier scaffold.

Without limitations, the engineered microbe-binding molecule can be conjugated to the carrier-scaffold through covalent or non-covalent interactions or any combination of covalent and non-covalent interactions. Further, conjugation can be accomplished any of method known to those of skill in the art. For example, covalent immobilization can be accomplished through, for example, silane coupling. See, e.g., Weetall, 15 Adv. Mol. Cell Bio. 161 (2008); Weetall, 44 Meths. Enzymol. 134 (1976). The covalent interaction between the engineered microbe-binding molecule and/or coupling molecule and the surface can also be mediated by other art-recognized chemical reactions, such as NHS reaction or a conjugation agent. The non-covalent interaction between the engineered microbe-binding molecule and/or coupling molecule and the surface can be formed based on ionic interactions, van der Waals interactions, dipole-dipole interactions, hydrogen bonds, electrostatic interactions, and/or shape recognition interactions.

Without limitations, conjugation can include either a stable or a labile (e.g. cleavable) bond or conjugation agent. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, host-guest interactions, such as cyclodextrin/adamantly host guest interaction) and the like.

In some embodiments, the engineered microbe-binding molecule can be conjugated to the carrier scaffold by a coupling molecule pair. The terms "coupling molecule pair" and "coupling pair" as used interchangeably herein refer to the first and second molecules that specifically bind to each other. One member of the binding pair is conjugated with the carrier scaffold while the second member is conjugated with the microbe-binding molecule. As used herein, the phrase "first and second molecules that specifically bind to each other" refers to binding of the first member of the coupling pair to the second member of the coupling pair with greater affinity and specificity than to other molecules. Exemplary coupling molecule pairs include, without limitations, any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One example of using coupling pair conjugation is the biotin-avidin or biotin-streptavidin conjugation. In this approach, one of the members of molecules to be conjugated together (e.g., the engineered microbe-binding molecule or the carrier scaffold) is biotinylated and the other is conjugated with avidin or streptavidin. Many commercial kits are available for biotinylating molecules, such as proteins. For example, an aminooxy-biotin (AOB) can be used to covalently attach biotin to a molecule with an aldehyde or ketone group. In some embodiments, AOB is attached to the engineered microbe-binding molecule. Further, as described elsewhere herein, an AKT sequence on the N-terminal of the engineered microbe-binding molecule can allow the engineered microbe-binding molecule to be biotinylated at a single site and further conjugated to the streptavidin-coated solid surface. Moreover, the microbe-binding molecule can be coupled to a biotin acceptor peptide, for example, the AviTag or Acceptor Peptide (referred to as AP; Chen et al., 2 *Nat. Methods* 99 (2005)). The Acceptor Peptide sequence allows site-specific biotinylation by the *E. coli* enzyme biotin ligase (BirA; Id.). Thus, in some embodiments, the conjugation domain comprises an amino acid sequence of a biotin acceptor peptide.

Another non-limiting example of using conjugation with a coupling molecule pair is the biotin-sandwich method. See, e.g., Davis et al., 103 *PNAS* 8155 (2006). In this approach, the two molecules to be conjugated together are biotinylated and then conjugated together using tetravalent streptavidin. Another example for conjugation would be to use PLP-mediated bioconjugation. See, e.g., Witus et al., 132 *JACS* 16812 (2010). Still another example of using coupling pair conjugation is double-stranded nucleic acid conjugation.

In this approach, one of the members of molecules to be conjugated together is conjugated with a first strand of the double-stranded nucleic acid and the other is conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges.

The carrier scaffold can also be functionalized to include a functional group for conjugating with the microbe-binding molecule described herein. In some embodiments, the carrier scaffold can be functionalized to include a coupling molecule, or a functional fragment thereof, that is capable of selectively binding with an engineered microbe-binding molecule described herein. As used herein, the term "coupling molecule" refers to any molecule or any functional group that is capable of selectively binding with an engineered microbe-binding domain described herein. Representative examples of coupling molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule.

In some embodiments, the coupling molecule is an aptamer. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art. The aptamers can be of any length, e.g., from about 1 nucleotide to about 100 nucleotides, from about 5 nucleotides to about 50 nucleotides, or from about 10 nucleotides to about 25 nucleotides.

An exemplary process for detecting a microbe and/or microbial matter in a test sample is described herein. As shown in FIG. 14, the process 1200 comprises the optional step 1202 (preprocessing of the sample), step 1204 (processing of the sample), step 1206 comprising 1208 (microbe capture) and 1210 (microbe separation), and 1212 (microbe detection). While these are discussed as discrete processes, one or more of the preprocessing, processing, capture, microbe separation, and detection can be performed in a microfluidic device. Use of a microfluidic device can automate the analysis process and/or allow analysis of multiple samples at the same time. One of skill in the art is well aware of methods in the art for collecting, handling and processing biological fluids which can be used in the practice of the present disclosure. The process described herein can allow sample analysis at in short time periods. For example, the process can be completed in less than 6 hours, less than 5 hours, less than 4 hours, less than 3 hours, less than 2 hours, less than 1 hour, less than 30 minutes. In some embodiments, presence and identity of a microbe in the sample can be done within 10 minutes to 60 minutes of starting the process.

In some embodiments, the sample can be a biological fluid, e.g., blood, plasma, serum, lactation products, amniotic fluids, sputum, saliva, urine, semen, cerebrospinal fluid, bronchial aspirate, perspiration, mucus, liquefied stool sample, synovial fluid, lymphatic fluid, tears, tracheal aspirate, and any mixtures thereof. For example, the sample can be a whole blood sample obtained from a subject.

The process described herein can be utilized to detect the presence of a microbe in a sample of any given volume. In some embodiments, sample volume is about 0.25 ml to about 50 ml, about 0.5 ml to about 25 ml, about 1 ml to about 15 ml, about 2 ml to about 10 ml. In some embodiments, sample volume is about 5 ml. In one embodiment, sample volume is about 5 ml to about 10 ml.

1202 (Sample Preprocessing):

It can be necessary or desired that a test sample, such as whole blood, be preprocessed prior to microbe detection as described herein, e.g., with a preprocessing reagent. Even in cases where pretreatment is not necessary, preprocessing can be optionally done for mere convenience (e.g., as part of a regimen on a commercial platform). A preprocessing reagent can be any reagent appropriate for use with the assays or processes described herein.

The sample preprocessing step generally comprises adding one or more reagent to the sample. This preprocessing can serve a number of different purposes, including, but not limited to, hemolyzing blood cells, dilution of sample, etc. The preprocessing reagents can be present in the sample container before sample is added to the sample container or the preprocessing reagents can be added to a sample already present in the sample container. When the sample is a biological fluid, the sample container can be a VACUTAINER®, e.g., a heparinized VACUTAINER®.

The preprocessing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions. In some embodiments, a preprocessing reagent is a surfactant or a detergent. In one embodiment, the preprocessing reagent is Triton X100.

Amount of preprocessing reagent to be added can depend on a number of factors. Generally, the preprocessing reagent is added to a final concentration of about 0.1 mM to about 10 mM. If a liquid, the preprocessing reagent can be added so as to dilute the sample at least 5%, at least 10%, at least 20%, at least 30%, at least 40%, at least 50%, at least 60%, at least 60%, at least 80%, at least 90%, at least 1-fold, at least 2-fold, at least 3-fold, or at least 5-fold.

After addition of the preprocessing reagent, the reagent can be mixed into the sample. This can be simply accomplished by agitating the sample, e.g., shaking or vortexing the sample and/or moving the sample around, if it is in a microfluidic device.

After addition of the preprocessing reagent, the sample mixture can be incubated for a period of time. For example, the sample mixture can be incubated for at least one minute, at least two minutes, at least three minutes, at least four minutes, at least five minutes, at least ten minutes, at least fifteen minutes, at least thirty minutes, at least forty-five minutes, or at least one hour. In some embodiments, incubation is for about 5 seconds to about 60 seconds. In some embodiments, incubation is for about 10 to about 20 minutes. In one embodiment, incubation is for about 15 minutes. In some embodiments, there is no incubation and the sample mixture is used directly in the sample processing step.

Without limitations, incubation can be at any appropriate temperature. For example, the incubation can be at room temperature (about 16° C. to about 30° C.), a cold temperature (about 16° C. or lower, e.g., from about −4° C. to about 16° C.), or an elevated temperature (about 30° C. or higher, e.g., about 25° C. to about 95° C.). In some embodiments, the sample is incubated for about fifteen minutes at room temperature.

1204 (Sample Processing):

After the optional preprocessing step, the sample can be optionally processed by adding one or more processing reagents to the sample. These processing reagents can serve to lyse cells, degrade unwanted molecules present in the sample and/or dilute sample for further processing. These processing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions. Amount of the processing reagent to be added can depend on the particular sample to be analyzed, the time required for the sample analysis, identity of the microbe to be detected or the amount of microbe present in the sample to be analyzed.

It is not necessary, but if one or more reagents are to be added they can present in a mixture (e.g., in a solution, "processing buffer") in the appropriate concentrations. Amount of the various components of the processing buffer can vary depending upon the sample, microbe to be detected, concentration of the microbe in the sample, or time limitation for analysis.

Generally, addition of the processing buffer can increase the volume of the sample by 50%, 10%, 15%, 20%, 25%, 30%, 35%, 40%, 45%, 50%, or more. In some embodiments, about 50 µl to about 5000 µl of the processing buffer are added for each ml of the sample. In some embodiments, about 100 µl to about 250 µl of the processing buffer are added for each ml of the sample. In one embodiment, about 800 µl of the processing buffer are added for each 200 µl of the sample.

In some embodiments, a detergent or surfactant comprises about 5% to about 20% of the processing buffer volume. In some embodiment, a detergent or surfactant comprises about 5% to about 15% of the processing buffer volume. In one embodiment, a detergent or surfactant comprises about 10% of the processing buffer volume.

Exemplary surfactants and detergents include, but are not limited to, sulfates, such as, ammonium lauryl sulfate, sodium dodecyl sulfate (SDS), and sodium lauryl ether sulfate (SLES) sodium myreth sulfate; sulfonates, such as, dioctyl sodium sulfosuccinate (Docusates), perfluorooctanesulfonate (PFOS), perfluorobutanesulfonate, alkyl benzene sulfonates, and 3-[(3-Cholamidopropyl)dimethylammonio]-1-propanesulfonate (CHAPS); 3-[(3-cholamidopropyl)dimethylammonio]-2-hydroxy-1-propanesulfonate (CHAPSO); phosphates, such as alkyl aryl ether phosphate and alkyl ether phosphate; carboxylates, such as fatty acid salts, sodium stearate, sodium lauroyl sarcosinate, perfluorononanoate, and perfluorooctanoate (PFOA or PFO); octenidine dihydrochloride; alkyltrimethylammonium salts, such as cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; dioctadecyldimethylammonium bromide (DODAB); sultaines, such as cocamidopropyl hydroxysultaine; cetyl alcohol; stearyl alcohol; cetostearyl alcohol (consisting predominantly of cetyl and stearyl alcohols); oleyl alcohol; polyoxyethylene glycol alkyl ethers (Brij) such as, octaethylene glycol monododecyl ether and pentaethylene glycol monododecyl ether; polyoxypropylene glycol alkyl ethers; glucoside alkyl ethers, such as decyl glucoside, lauryl glucoside and octyl glucoside; polyoxyethylene glycol octylphenol ethers, such as Triton X-100; polyoxyethylene glycol alkylphenol ethers, such as Nonoxynol-9; glycerol alkyl esters, such as glyceryl laurate; polyoxyethylene glycol sorbitan alkyl esters, such as Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate); cocamide ME; cocamide DEA; dodecyldimethylamine oxide; poloxamers; DOC; nonyl phenoxypolyethoxylethanol NP-40 (Tergitol-type NP-40); octyl phenoxypolyethoxylethanol (Noidet P-40); cetyltrimethylammonium bromide; and any mixtures thereof.

In some embodiments, one ml of the processing buffer can comprise about 0.1 U to about 100U of a degradative enzyme. In some embodiments, one ml of the processing buffer comprises about 5U to about 50U of a degradative enzyme. In one embodiment, one ml of the processing buffer comprises about 10U of a degradative enzyme. Enzyme unit (U) is an art known term for the amount of a particular enzyme that catalyzes the conversion of 1 µmol of substrate per minute.

In some embodiments, one ml of the processing buffer can comprise about 1 µg to about 10 µg of an anti-coagulant. In some embodiment, one ml of the processing buffer can comprise about 1 µg to about 5 µg of an anti-coagulant. In one embodiment, one ml of the processing buffer comprises about 4.6 µg of an anti-coagulant.

In some embodiments, one ml of the processing buffer can comprise about 1 mg to about 10 mg of anti-coagulant. In some embodiment, one ml of the processing buffer can comprise about 1 mg to about 5 mg of anti-coagulant. In one embodiment, one ml of the processing buffer comprises about 4.6 mg of anti-coagulant.

Exemplary anti-coagulants include, but are not limited to, heparin, heparin substitutes, salicylic acid, D-phenylalanyl-L-prolyl-L-arginine chloromethyl ketone (PPACK), Hirudin, Ancrod (snake venom, Vipronax), tissue plasminogen activator (tPA), urokinase, streptokinase, plasmin, pro-thrombopenic anticoagulants, platelet phosphodiesterase inhibitors, dextrans, thrombin antagonists/inhibitors, ethylene diamine tetraacetic acid (EDTA), acid citrate dextrose (ACD), sodium citrate, citrate phosphate dextrose (CPD), sodium fluoride, sodium oxalate, potassium oxalate, lithium oxalate, sodium iodoacetate, lithium iodoacetate and mixtures thereof.

Suitable heparinic anticoagulants include heparins or active fragments and fractions thereof from natural, synthetic, or biosynthetic sources. Examples of heparin and heparin substitutes include, but are not limited to, heparin calcium, such as calciparin; heparin low-molecular weight, such as enoxaparin and lovenox; heparin sodium, such as heparin, lipo-hepin, liquaemin sodium, and panheprin; heparin sodium dihydroergotamine mesylate; lithium heparin; and ammonium heparin.

Suitable prothrombopenic anticoagulants include, but are not limited to, anisindione, dicumarol, warfarin sodium, and the like.

Examples of phosphodiesterase inhibitors suitable for use herein include, but are not limited to, anagrelide, dipyridamole, pentoxifyllin, and theophylline.

Suitable dextrans include, but are not limited to, dextran70, such as HYSKON™ (CooperSurgical, Inc., Shelton, Conn., U.S.A.) and MACRODEX™ (Pharmalink, Inc., Upplands Vasby, Sweden), and dextran 75, such as GENTRAN™ 75 (Baxter Healthcare Corporation).

Suitable thrombin antagonists include, but are not limited to, hirudin, bivalirudin, lepirudin, desirudin, argatroban, melagatran, ximelagatran and dabigatran.

As used herein, anticoagulants can also include factor Xa inhibitors, factor IIa inhibitors, and mixtures thereof. Various direct factor Xa inhibitors are known in the art including, those described in Hirsh and Weitz, *Lancet,* 93:203-241, (1999); Nagahara et al. *Drugs of the Future,* 20: 564-566, (1995); Pinto et al, 44: 566-578, (2001); Pruitt et al, *Biorg. Med. Chem. Lett.,* 10: 685-689, (2000); Quan et al, *J. Med. Chem.* 42: 2752-2759, (1999); Sato et al, *Eur. J. Pharmacol,* 347: 231-236, (1998); Wong et al, *J. Pharmacol. Exp. Therapy,* 292:351-357, (2000). Exemplary factor Xa inhibitors include, but are not limited to, DX-9065a, RPR-120844, BX-807834 and SEL series Xa inhibitors. DX-9065a is a synthetic, non-peptide, propanoic acid derivative, 571 D selective factor Xa inhibitor. It directly inhibits factor Xa in a competitive manner with an inhibition constant in the nanomolar range. See for example, Herbert et al, *J. Pharmacol. Exp. Ther.* 276:1030-1038 (1996) and Nagahara et al, *Eur. J. Med. Chem.* 30(suppl): 140s-143s (1995). As a non-peptide, synthetic factor Xa inhibitor, RPR-120844 (Rhone-Poulenc Rorer), is one of a series of novel inhibitors which incorporate 3-(S)-amino-2-pyrrolidinone as a central template. The SEL series of novel factor Xa inhibitors (SEL1915, SEL-2219, SEL-2489, SEL-2711: Selectide) are pentapeptides based on L-amino acids produced by combinatorial chemistry. They are highly selective for factor Xa and potency in the pM range.

Factor IIa inhibitors include DUP714, hirulog, hirudin, melgatran and combinations thereof. Melagatran, the active form of pro-drug ximelagatran as described in Hirsh and Weitz, *Lancet,* 93:203-241, (1999) and Fareed et al. *Current Opinion in Cardiovascular, pulmonary and renal investigational drugs,* 1:40-55, (1999).

Generally, salt concentration of the processing buffer can range from about 10 mM to about 100 mM. In some embodiments, the processing buffer comprises a salt at a concentration of about 25 mM to about 75 mM. In some embodiment, the processing buffer comprises a salt at a concentration of about 45 mM to about 55 mM. In one embodiment, the processing buffer comprises a salt at a concentration of about 43 mM to about 45 mM.

The processing buffer can be made in any suitable buffer solution known the skilled artisan. Such buffer solutions include, but are not limited to, TBS, PBS, BIS-TRIS, BIS-TRIS Propane, HEPES, HEPES Sodium Salt, MES, MES Sodium Salt, MOPS, MOPS Sodium Salt, Sodium Chloride, Ammonium acetate solution, Ammonium formate solution, Ammonium phosphate monobasic solution, Ammonium tartrate dibasic solution, BICINE buffer Solution, Bicarbonate buffer solution, Citrate Concentrated Solution, Formic acid solution, Imidazole buffer Solution, MES solution, Magnesium acetate solution, Magnesium formate solution, Potassium acetate solution, Potassium acetate solution, Potassium acetate solution, Potassium citrate tribasic solution, Potassium formate solution, Potassium phosphate dibasic solution, Potassium phosphate dibasic solution, Potassium sodium tartrate solution, Propionic acid solution, STE buffer solution, STET buffer solution, Sodium acetate solution, Sodium formate solution, Sodium phosphate dibasic solution, Sodium phosphate monobasic solution, Sodium tartrate dibasic solution, TNT buffer solution, TRIS Glycine buffer solution, TRIS acetate-EDTA buffer solution, Triethylammonium phosphate solution, Trimethylammonium acetate solution, Trimethylammonium phosphate solution, Tris-EDTA buffer solution, TRIZMA® Base, and TRIZMA® HCL. Alternatively, the processing buffer can be made in water.

In some embodiments, the processing buffer comprises a mixture of Trirton-X, DNAse I, human plasmin, $CaCl_2$ and Tween-20. In one embodiment, the processing buffer consists of a mixture of Trirton-X, DNAse I, human plasmin, $CaCl_2$ and Tween-20 in a TBS buffer.

In one embodiment, one ml of the processing buffer comprises 100 µl of Triton-X100, 10 µl of DNAse (1U/1 µl), 10 µl of human plasmin at 4.6 mg/ml and 870 µl of a mixture of TBS, 0.1% Tween-20 and 50 mM $CaCl_2$.

Reagents and treatments for processing blood before assaying are also well known in the art, e.g., as used for assays on Abbott TDx, AxSYM®, and ARCHITECT® analyzers (Abbott Laboratories), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, and U.S. Pat. App. Pub. No. 2008/0020401, content of all of which is incorporated herein by reference. It is to be understood that one or more of these known reagents and/or treatments can be used in addition to or alternatively to the sample treatment described herein.

In some embodiments, after addition of the processing buffer, the sample comprises 1% Triton-X, 10U of DNase, 4.6 mg/ml of plasmin, 5 mM Calcium, 0.01% of Tween 20, 2.5 mM of Tris, 150 mM of NaCl and 0.2 mM of KCl in addition to the components already present in the sample.

After addition of the processing buffer, the sample can undergo mixing. This can be simply accomplished by agitating the sample, e.g., shaking or vortexing the sample and/or moving the sample around, if it is in a microfluidic device. In some embodiments where the microbe-binding article is in the form of a dipstick or a membrane, the microbe-binding dipstick or membrane can be dipped in a volume of a test sample and gently agitated with a rocking motion.

After addition of the processing reagents, the sample can be incubated for a period of time, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature.

1206 (1208 (Microbe Capture) and 1210 (Microbe Separation)):

After processing of the sample, the sample can be subjected to a microbe capture process. During the microbe capture process, a microbe-binding article (either with art-recognized microbe-capture molecules or the microbe-binding molecules described herein) added into a test sample can capture one or more microbes present in the test sample. In some embodiments, the microbe capture process can be repeated and/or performed for a sufficient amount of time to allow for concentrating and/or cleaning up the test sample before microbe detection. Thus, microbe capture and separation process described herein can be used for concentrating and/or cleaning up a sample before analysis for a target component in the sample.

In some embodiments, the microbe capture process can comprise mixing a microbe-binding article (either with art-recognized microbe-capture molecules or the microbe-binding molecules described herein) with the test sample. In some embodiments, the microbe-binding article can be already present in the processing buffer. Amount of the microbe-binding article added to the sample can be dependent on a number of different factors, such as, number of microbe-binding molecules on each article, size of the article, shape of the article, binding affinity of the microbe-binding molecule to the microbe, and concentration of the microbe in the sample. Additionally, amount of the microbe-binding articles in the sample can be adjusted to optimize the capture of microbes. In some embodiments, amount of microbe-binding articles in the sample is such that one microbe-binding article binds with one microbe. However, each microbe can be bound to more than one microbe-binding article. This can reduce cross-linking of multiple microbes together which can lead to coagulation and/or precipitation of such cross-linked microbes from the sample.

In some embodiments where the microbe-binding molecules are used as capture agent in the article described herein, the total amount of the microbe-binding molecules contacted with the test sample can range from about 0.01 µg to about 1 mg, about 0.1 µg to about 500 µg, about 0.5 µg to about 250 µg, about 1 µg to about 100 µg, or about 3 µg to about 60 µg. In some embodiments, the total amount of the microbe-binding molecules contacted with the test sample can range from about 500 µg to about 1000 mg, about 1 mg to about 750 mg, about 5 mg to about 500 mg, about 10 mg to about 250 mg, or about 25 mg to about 100 mg.

In some embodiments, a plurality of microbe-binding articles (either with art-recognized microbe-capture molecules or the microbe-binding molecules described herein) can be contacted with a test sample. The plurality of microbe-binding articles can comprise at least two subsets (e.g., 2, 3, 4, 5, or more subsets), wherein each subset of microbe-binding articles have a pre-determined dimension. In some embodiments, the plurality of microbe-binding articles can comprise a first subset of the microbe-binding articles and a second subset of microbe-binding articles. In such embodiments, the first subset of the microbe-binding articles each has a first pre-determined dimension; and the second subset of the microbe-binding articles each has a second pre-determined dimension. Additionally, each subset of the microbe-binding articles can comprise on their surfaces substantially the same density or different densities of the microbe-binding molecules described herein.

Different subsets of the plurality of the microbe-binding articles (either with art-recognized microbe-capture molecules or the microbe-binding molecules described herein) can be brought into contact with a test sample in any manner. For example, in some embodiments, the plurality of the microbe-binding articles can be provided as a single mixture comprising at least two subsets of the microbe-binding articles to be added into a test sample. In some embodiments, in order to distinguish among different subsets of the microbe-binding articles, the microbe-binding articles in each subset can have a distinct detection label. For example, the microbe-binding articles in each subset can have a distinct-fluorescent label that can be sorted afterward, for example, by flow cytometry.

In other embodiments, the plurality of the microbe-binding articles (either with art-recognized microbe-capture molecules or the microbe-binding molecules described herein) can be brought into contact with a test sample in a sequential manner. For example, a test sample can be contacted with a first subset of the microbe-binding articles, followed by a contact with at least one more subsets of the microbe-binding articles. The previous subset of the microbe-binding articles can be removed from the test sample before addition of another subset of the microbe-binding articles into the test sample.

By way of example only, when the microbe-binding article is a microbe-binding molecule coated microparticle (also referred to as a coated-microparticle), generally, about 100 to about $10^9$ microparticles can be contacted with each ml of the sample. In some embodiments, about $10^4$ to about $5 \times 10^6$ coated-microparticles can be contacted with each ml of sample. In some embodiments, the microparticle can be coated with art-recognized microbe-capture molecules or the microbe-binding molecules described herein.

As discussed above, in some embodiments, a plurality of microbe-binding articles can be contacted with a test sample. Accordingly, in some embodiments, a plurality of coated-microparticles can be contacted with a test sample. The plurality of coated-microparticles can comprise at least two subsets (e.g., 2, 3, 4, 5, or more subsets), wherein each subset of coated-microparticles have a pre-determined dimension. In some embodiments, the plurality of coated-microparticles can comprise a first subset of the coated-microparticles and a second subset of the coated-microparticles. In such embodiments, the first subset of the coated-microparticles each has a first pre-determined dimension; and the second subset of the coated-microparticles each has a second pre-determined dimension. The pre-determined dimension of a coated-microparticle depends, in part, on the dimension of a microparticle described herein to which the engineered microbe-binding molecules are conjugated. For example, in some embodiments, the microparticle can have a size of about 10 nm to 10 µm, about 20 nm to about 5 n, about 40 nm to about 1 µm, about 50 nm to about 500 nm, or about 50 nm to about 200 nm. Additionally, each subset of the coated-microparticles can comprise on their surfaces substantially the same density or different densities of the microbe-binding molecules disclosed herein.

Different subsets of the plurality of the coated-microbeads can be brought into contact with a test sample in any manner. For example, in some embodiments, the plurality of the coated-microbeads can be provided as a single mixture comprising at least two subsets of the coated-microbeads to be added into a test sample. In some embodiments, in order to distinguish among different subsets of the coated-microbeads, the coated-microbeads in each subset can have a distinct detection label, e.g., a distinctly-fluorescent label that can be sorted afterward, for example, by flow cytometry.

In some embodiments, the coated-microparticles can be present in the processing buffer. In one embodiment, one ml of the processing buffer comprises 100 µl of Triton-X100, 10 µl of a solution comprising about 25 million coated-microparticles, 10 µl of DNAse (1U/1 µl), 10 µl of human plasmin at 4.6 mg/ml and 870 µl of a mixture of TBS, 0.1% Tween-20. In some embodiments, the processing buffer can include a calcium salt, e.g., $CaCl_2$ (e.g., ~50 mM $CaCl_2$). In some embodiments, the processing or capture buffer can include no calcium salt, e.g., $CaCl_2$.

After addition of the microbe-binding articles, the microbe-binding articles can be mixed in the sample to allow microbes to bind with the microbe-capture molecules (e.g., microbe-binding molecules described herein or art-recognized microbe-capture molecules). This can be simply accomplished by agitating the sample, e.g., shaking or vortexing the sample and/or moving the sample around in a microfluidic device. In some embodiments where the microbe-binding article is in a form of a dipstick or a membrane, the microbe-binding dipstick or membrane can be dipped in a volume of a test sample and gently agitated with a rocking motion.

The volume of the test sample required for contacting the microbe-binding article can vary with, e.g., the selection of the microbe-binding article (e.g., microbeads, fibers, filters, filters, fibers, screens, mesh, tubes, hollow fibers), the concentration of microbes present in the test sample, the platform used to carry out the assay (e.g., a microfluidic device, a blood collection tube, a microtiter plate, or like). For example, if the assay is performed in a microfluidic device, the test sample volume used to perform the assay can range from about 1 µL to about 500 µL, from about 5 µL to about 250 µL, or from about 10 µL to about 100 µL. In some embodiments, if the assay is performed in a test tube, the test sample volume can range from about 0.05 mL to about 50 mL, from about 0.25 ml to about 50 ml, about 0.5 ml to about 25 ml, about 1 ml to about 15 ml, or about 2 ml to about 10 ml. In some embodiments, the test sample volume used to perform the assay described herein can be about 1 mL to about 5 ml. In one embodiment, the test sample volume used to perform the assay described herein is about 5 ml to about 10 mL.

After contacting the test sample with the microbe-binding molecules described herein or art-recognized microbe-capture molecules (e.g., with a microbe-binding article), the sample mixture can be incubated for a period of time to allow the microbe of interest to bind onto the microbe-binding or micro-capture molecules on the microbe-binding article. Such incubation can be for any desired period of time to allow sufficient number of microbes to bind to the microbe-binding molecules and/or microbe-capture molecules. For example, the incubation can be for at least one minute, at least two minutes, at least three minutes, at least four minutes, at least five minutes, at least ten minutes, at least fifteen minutes, at least about twenty minutes, at least thirty minutes, at least forty-five minutes, or at least one hour. In one embodiment, the sample mixture can be incubated for a period of about 10-20 minutes. Further, such incubation can be performed at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the incubation can be performed at a temperature ranging from about room temperature to about 37° C. In some embodiments, the sample can be incubated for about 10 mins to about 20 mins at room temperature. In some embodiments, the sample is incubated for about fifteen minutes at room temperature.

To prevent or reduce agglutination (or non-specific binding) during separation of the microbes from the sample, additional reagents can be added to the sample mixture. Such reagents are also referred to as blocking reagents herein. For example, these blocking reagents can comprise a ligand of the affinity molecules on the coated-microbeads. Addition of such blocking reagents can reduce agglutination by binding with any empty ligand binding sites on the affinity molecules. Accordingly, when microbe-binding magnetic microbeads are used for capturing the microbes, the blocking reagent can be a carbohydrate, such as mannose. Amount of additional reagent can depend on the amount of microbeads added to the sample. Generally, about the reagent is added to a final concentration of about 0.1 mM to about 10 mM. The amount of the blocking agent required can vary, at least partly, with the amount and/or surface area of the microbe-binding substrate that is in contact with a test sample. In some embodiments, the blocking reagent can be added to a final concentration of about 0.1% (w/v) to about 10% (w/v), about 0.5% (w/v) to about 7.5% (w/v), or about 1% (w/v) to about 5% (w/v). In some embodiments, about 1% casein can be used as a blocking agent in the assay described herein.

After addition of the blocking reagent, the sample mixture can be incubated for a period of time to allow the blocking reagent to bind to with the microbe-binding molecules, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature. In some embodiments, incubation is for about 5 seconds to about 60 seconds. In some embodiments, the incubation can be performed at a temperature ranging from about room temperature to about 37° C. In some embodiments, the sample is incubated for about fifteen minutes at room temperature.

To prevent or reduce non-specific binding during the contact between a microbe-binding substrate and a test sample, in some embodiments, the microbe-binding article (e.g., coated-microparticles) or the test sample can be pretreated with a blocking agent that does not react with microbes, before contacting each other. Exemplary blocking agents include, but are not limited to, casein, normal serum, BSA, non-fat dry milk powder and any art-recognized block agent. Optionally, microbe-binding article after blocking can be washed with any art-recognized buffer to remove any leftover blocking agent. The number of wash steps can range from 1 to many, e.g., 1, 2, 3, 4, 5, 6, 7, 8, 9, 10 or more wash steps. In one embodiment, the microbe-binding substrate after blocking can be washed with a buffer, e.g., TBST, for about at least 1-3 times.

After incubation, the microbe-binding article (either with art-recognized microbe-capture molecules or the microbe-binding molecules described herein) can then be analyzed, as described below, for the presence or absence of a bound microbe.

Exemplary Optional Modifications to 1208 (Microbe Capture):

In accordance with one aspect described herein, the test sample can be contacted with a microbe-binding molecule in the presence of a chelating agent. Without wishing to be bound by theory, the addition of a chelating agent to a test sample and/or processing buffer can reduce the likelihood of any protein A- and protein G-negative microbe, but not protein A- or protein G-expressing microbe in the test sample, to bind with at least one microbe-binding molecule. Accordingly, detection of any microbes bound on the microbe-binding substrate described herein in the presence of a chelating agent can determine the presence or absence of a protein A- or protein G-expressing microbe in a test sample.

The chelating agent can be added into the processing buffer comprising the test sample. The amount of the chelating agent is sufficient to chelate free divalent ions (e.g., calcium ions) and thus prevent or reduce divalent ion-dependent (e.g., calcium ion-dependent) carbohydrate recognition domain binding (e.g., mannose-binding lectin) with a microbe. The amount of the chelating agent needed to prevent or reduce calcium-dependent carbohydrate recognition domain binding (e.g., mannose-binding lectin) with a microbe can depend on, e.g., the concentration of free divalent ions (e.g., calcium ions) present in a test sample and optionally a capture buffer, e.g., used to dilute a chelating agent and/or a test sample. Thus, in some embodiments, the concentration of the chelating agent can be higher than the total concentration of free divalent ions (e.g., calcium ions) present in the combined solution of a test sample and a capture buffer. For example, in some embodiments, the concentration of the chelating agent can be at least about 30% higher, including at least about 40%, at least about 50%, at least about 60%, at least about 70%, at least about 80%, at least about 90%, at least about 95%, at least about 98%, up to and including 100%, or any percent between about 30% and about 100%, higher than the total concentration of free calcium ions present in the combined solution of a test sample and a capture buffer. In other embodiments, the concentration of the chelating agent can be at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, at least about 50-fold, at least about 75-fold, at least about 100-fold or more, higher than the total concentration of free calcium ions present in the combined solution of a test sample and a capture buffer. In one embodiment, the concentration of the chelating agent can be at least about 5-fold to about 50-fold, or at least about 7-fold to about 25-fold, higher than the total concentration of free calcium ions present in the combined solution of a test sample and a capture buffer.

In some embodiments, the concentration of a chelating agent present in the test sample and optionally a processing or capture buffer, e.g., used to dilute the chelating agent or the test sample, can range from about 0.1 mM to about 1 M, about 10 mM to about 500 mM, about 20 mM to about 250 mM, or about 25 mM to about 125 mM. In one embodiment, the concentration of a chelating agent present in the test sample and optionally a capture buffer can be about 25 mM to about 125 mM.

In some embodiments, the concentration of a chelating agent present in the test sample containing the microbe-binding substrate can be sufficient to reduce the likelihood of a protein A- and protein G-negative microbe, if present in the test sample, to bind with at least one microbe-binding molecule. For example, the concentration of a chelating agent present in the test sample with the microbe-binding substrate can be sufficient to reduce the number of protein A- and protein G-negative microbes, if present in the test sample, to bind with at least one microbe-binding molecule, by at least about 30%, at least about 40%, at least about 50%, at least about 60%, at least about 70%, at least 80% or higher, as compared to the number of protein A- and protein G-negative microbes bound on the microbe binding molecules in the absence of the chelating agent. In some embodiments, the concentration of a chelating agent present in the test sample with the microbe-binding substrate can be sufficient to reduce the number of protein A- and protein G-negative microbes, if present in the test sample, to bind with at least one microbe-binding molecule, by at least about 85%, at least about 90%, at least about 95%, at least about 98%, at least about 99%, up to and including 100%, or any values between about 85% and about 100%, as compared to the number of protein A- and protein G-negative microbes bound on the microbe-binding molecules in the absence of the chelating agent.

The protein A-expressing and protein G-expressing microbes can generally bind to microbe-binding molecules via two independent (but additive) mechanisms: Fc-mediated binding and microbe-binding domain mediated binding. Without wishing to be bound by theory, while the protein A-expressing and protein G-expressing microbes can still be captured on the microbe-binding molecules in the presence of a chelating agent, the presence of free divalent ions (e.g., calcium ions) can further increase the number of protein A-expressing and protein G-expressing microbes bound to the microbe-binding molecules, because the overall binding in the presence of divalent ions (e.g., calcium ions) can be almost twice as strong as in the absence of calcium ions.

Accordingly, in some embodiments, the concentration of a chelating agent present in the test sample containing the microbe-binding articles can reduce the number of protein A-expressing microbes or protein G-expressing microbes bound onto the microbe-binding substrate, but such effect as compared to that on the protein A- and protein G-negative microbes is much smaller, e.g., at least about 30% smaller, at least about 40% smaller, at least about 50%, at least about 60% smaller, at least about 70% smaller, or at least about 80% smaller.

In some embodiments, the concentration of a chelating agent used in the assay described herein can be high enough to prevent at least about 80% or higher, including at least about 90%, at least about 95%, up to and including 100%, of the protein A- and protein G-negative microbes from binding to be microbe-binding substrate, but low enough to allow at least about 30% or higher, including at least about 40%, at least about 50%, at least about 60%, at least about 70% or higher, of the protein A-expressing microbes or protein G-expressing microbes to bind with the microbe-binding substrate. In one embodiment, the concentration of a chelating agent used in the assay described herein can be high enough to prevent at least about 90% or higher, of the protein A- and protein G-negative microbes, if any present in the test sample, from binding to be microbe-binding substrate, but low enough to allow at least about 50% of the protein A-expressing microbes or protein G-expressing microbes, if any present in the test sample, to bind with the microbe-binding substrate.

Examples of divalent ions (e.g., calcium ions)-chelating agents can include, but are not limited to, 1,2-bis(2-aminophenoxy)ethane-N,N,N',N'-tetraacetic acid, ethylenediaminetetraacetic acid (EDTA); ethylene glycol-bis(2-aminoethylether)-N,N,N',N'-tetraacetic acid; ethylene glycol-bis((-aminoethyl ether)-N,N,N',N'-tetraacetic acid (EGTA), 1,2-bis(o-aminophenoxy)ethane-N,N,N',N'-tetraacetic acid (BAPTA), a buffer containing citrate, N,N-Bis(2-(bis-(carboxymethyl)amino)ethyl)-glycine (DTPA), nitrilo-2,2',2"-triacetic acid (NTA), a buffer that precipitates a calcium ion from the test sample, including, e.g., a phosphate buffer, a carbonate buffer and a bicarbonate buffer, a low pH buffer (e.g., a pH buffer less than pH 7 or less than pH 6), citric acids and its salts, gluconic acid and its salts, alkali metal pyrophosphates, alkali metal polyphosphates, sodium hexametaphosphate, triethylene tetramine, diethylene triamine, o-phenanthroline, oxalic acid and any combinations thereof.

The chelating agent can be directly added to the test sample or prepared in a processing or capture buffer, which is then added to the test sample in contact with the microbe-binding substrate. The processing or capture buffer can be any buffered solutions, e.g., with a pH ranging from about 6 to about 10. In some embodiments, the processing or capture buffer can include, but is not limited to, a tris-buffered saline, a phosphate buffered saline or a combination thereof. In some embodiments, the processing or capture buffer can include a surfactant, e.g., to prevent non-specific binding of a microbe to a microbe-surface-binding domain of the microbe-binding substrate, and/or to saturate non-specific binding sites, if any, present in the microbe-binding substrate. A surfactant or detergent, e.g., as described earlier, can be dissolved in a buffered solution in any amount, e.g., ranging from about 0.001% (v/v) to about 5% (v/v), from about 0.01% (v/v) to about 2.5% (v/v), or from about 0.05% (v/v) to about 1% (v/v). In some embodiments, the surfactant added to the processing or capture buffer can include Tween 80 or polysorbate 80 at a concentration of about 0.01% to about 0.1%. In one embodiment, the surfactant added to the processing or capture buffer can include Tween 80 or polysorbates 80 at a concentration of about 0.05%.

After incubation, the microbe-binding article (either with art-recognized microbe-capture molecules and/or microbe-binding molecules described herein) can then be analyzed, as described below, for the presence or absence of a bound microbe. In the absence of a microbe-binding article-bound microbe, in some embodiments, the previous volume of the test sample or a new fresh volume of the test sample can be contacted with a fresh microbe-binding substrate in the presence of free divalent ions (e.g., calcium ions), e.g., to determine the presence or absence of protein A- and protein G-negative microbes. In some embodiments, the free divalent ions (e.g., calcium ions) can be produced adding a sufficient amount of divalent ion salts (e.g., calcium salts) in the test sample. If there has been a chelating agent present in the test sample, a higher amount of divalent ion salt (e.g., calcium salts) is generally needed in order to obtain free calcium ions.

As used herein, the term "free calcium ions" refers to calcium ions that are not complexed with any molecule or compound, e.g., a chelating agent, which can hinder its reaction with other molecules or ions to mediate binding of carbohydrate patterns on a microbial cell surface to a microbe-binding domain (e.g., MBL) of the engineered microbe-binding molecule. Accordingly, in some embodiments, free calcium ions can be present in the absence of chelating agent. In some embodiments, free calcium ions can be present in a solution comprising a chelating agent and calcium ions. In some embodiments, the amount of calcium ions present in the solution is at least about 30% more than an amount sufficient to interact with substantially all the chelating agent molecules present in the solution to form chelate complexes. For example, in some embodiments, in order to obtain free calcium ions, the amount of calcium ions present in the solution can be at least about 30%, including at least about 40%, at least about 50%, at least about 60%, at least about 70%, at least about 80%, at least about 90%, at least about 95%, at least about 98%, up to and including 100% and any percent between 30% and 100%, more than an amount sufficient to interact with substantially all the chelating agent molecules present in the solution to form chelate complexes. In some embodiments, in order to obtain free calcium ions, the amount of calcium ions present in the solution can be at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 100-fold, at least about 500-fold, at least about 1000-fold, more than an amount sufficient to interact with substantially all the chelating agent molecules present in the solution to form chelate complexes. In some embodiments, free calcium ions can be present in a solution when the concentration of calcium ions in the solution is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20-fold, or higher than the concentration of a chelating agent present in the same solution.

In some embodiments, calcium ions can be obtained from a water-soluble calcium salt. By the term "water-soluble calcium salt" is meant a calcium salt which has significant solubility in water at room temperature, for example at least 1 gram per 100 ml water, at least 10 grams per 100 ml water, or at least 25 grams per 100 ml water or higher. Examples of calcium salts include, without limitations, calcium chloride, calcium fluoride, calcium bromide, calcium iodide, calcium nitrate, calcium citrate, calcium formate, calcium acetate, calcium gluconate, calcium ascorbate, calcium lactate, calcium glycinate and mixtures thereof. In some embodiments, calcium chloride can be used as a source of calcium ions.

Free calcium ions can be present at a concentration or an amount sufficient to mediate binding of calcium-dependent carbohydrate recognition domain with a microbe surface. In some embodiments, free calcium ions can be present at a concentration of at least about 1 µM, at least about 10 µM, at least about 25 µM, at least about 50 µM, at least about 100 µM, at least about 250 µM, at least about 500 µM, or at least about 1 mM or higher. In some embodiments, the free calcium ions can be present at a concentration of at least about 1 mM, at least about 2.5 mM, at least about 5 mM, at least about 10 mM, at least about 25 mM, at least about 50 mM, at least about 75 mM, at least about 100 mM or higher. In other embodiments, the free calcium ions can be present at a concentration of at least about 100 mM, at least about 150 mM, at least about 200 mM, at least about 300 mM, at least about 400 mM, at least about 500 mM, at least about 600 mM, at least about 700 mM, at least about 800 mM, at least about 900 mM, at least about 1 M or higher. In one embodiment, the free calcium ions can be present at a concentration of about 1 mM to about 10 mM. In one embodiment, the free calcium ions can be present at a concentration of at least about 5 mM.

While a chelating agent can be added during an initial capture of a microbe on a microbe-binding substrate, the chelating agent can also be first excluded to allow the initial capture of any microbe, including protein A- and protein G-negative microbes, on a microbe-binding substrate in the presence of free calcium ions, but added after the capture to remove any captured protein A- or protein G-negative microbes from the microbe-binding substrate.

Accordingly, in some embodiments, the microbe capture can comprise (i) contacting at least a first volume of a test sample with a microbe-binding substrate described herein in the presence of free calcium ions, and (ii) contacting the microbe-binding molecule of the microbe-binding substrate described herein, upon the contact with the test sample, with a solution comprising a chelating agent.

When the microbe-binding substrate is contacted with a test sample in the presence of free calcium ions as described herein, microbes that primarily depend on calcium-dependent MBL-mediated binding such as protein A- and protein G-negative microbes, e.g., *E. coli* can bind to the microbe-target substrate, in addition to microbes associated with Fc-mediated binding such as protein A-expressing microbes (e.g., *S. aureus*), and protein G-expressing microbes.

To elute off or remove from the microbe-binding substrate the captured microbes that primarily depend on calcium-dependent MBL-mediated binding such as protein A- and protein G-negative microbes, e.g., *E. coli*, the microbe-binding molecules on the microbe-binding substrates can be contacted with a solution comprising a sufficient amount of a chelating agent as described herein. The solution comprising the chelating agent can be same as a capture buffer described above. In such embodiments, the microbe-binding substrate can be incubated with the solution comprising a chelating agent for a period of time to allow microbes that primarily bind to microbe-binding molecules via calcium-dependent MBL-mediated binding to elute off the microbe-binding substrate, e.g., incubation for at least one minute, at least two minutes, at least three minutes, at least four minutes, at least five minutes, at least ten minutes, at least fifteen minutes, at least thirty minutes, at least forty-five minutes, or at least one hour. Such incubation can be performed at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the microbe-binding substrate can be incubated with the solution comprising a chelating agent for at least about 5 mins to about 15 mins at room temperature.

In these embodiments, the concentration of a chelating agent used in the assay described herein is sufficient to elute off or remove from the microbe-binding substrate at least about 30% of the bound protein A- and protein G-negative microbes (e.g., *E. coli*). For example, the concentration of a chelating agent used in the assay described herein is suffi- cient to elute off or remove from the microbe-binding substrate at least about 30% of the bound protein A- and protein G-negative microbes (e.g., *E. coli*), including at least about 40%, at least about 50%, at least about 60%, at least about 70%, at least 80% or higher, of the bound protein A- and protein G-negative microbes (e.g., *E. coli*). In some embodiments, the concentration of a chelating agent used in the assay described herein is sufficient to elute off or remove from the microbe-binding substrate at least about 85% of the bound protein A- and protein G-negative microbes (e.g., *E. coli*), including at least about 85%, at least about 90%, at least about 95%, at least about 98%, up to and including 100%, or any values between about 85% and about 100%, of the bound protein A- and protein G-negative microbes (e.g., *E. coli*).

As noted above, the protein A-expressing and protein G-expressing microbes can bind to microbe-binding molecules via Fc-mediated and calcium ion-dependent MBL-mediated binding. Without wishing to be bound by theory, the concentration of a chelating agent used in the assay described herein can also elute off or remove at least a portion of the protein A-expressing and/or protein G-expressing microbes from the microbe-binding substrate. For example, the concentration of a chelating agent used to elute off or remove protein A- and protein G-negative microbes from the microbe-binding substrate can be sufficient to elute off or remove no more than 60%, no more than 50%, no more than 40%, no more than 30%, no more than 20%, no more than 10% or lower, of the bound protein A-expressing or protein G-expressing microbes. In some embodiments, the concentration of a chelating agent used to elute off or remove from the microbe-binding substrate at least about 80% or more, including at least about 90% or more, of the bound protein A- and protein G-negative microbes can be sufficient to elute off or remove no more than 50%, or more than 40% of the bound protein A-expressing and/or protein G-expressing microbes.

As a person having ordinary skill in the art can appreciate, the assay described herein can further comprise isolating the microbe-binding substrate from the test sample, e.g., as described below, before contacting microbe-binding molecules on its substrate surface with the solution comprising the chelating agent described herein.

1210 (Microbe Separation from Sample):

The sample mixture can be then subjected to a microbe separation process. In some embodiments, because microbes are bound with one or more magnetic microparticles, a magnet can be employed to separate the bound microbes from the test sample. The skilled artisan is well aware of methods for carrying out magnetic separations. Generally, a magnetic field gradient can be applied to direct the capture of magnetic microbeads. Optionally, the bound microbe can be washed with a buffer to remove any leftover sample and unbound components. Number of wash steps can range from 1 to many, e.g., 1, 2, 3, 4, 5, 6, 7, 8, 9, 10 or more wash steps. Without wishing to be bound by a theory, capture and separation of the bound microbes from the sample can concentrate the microbes and also remove components, which can interfere with the assay or process, from the test sample.

The magnetic field source can be any magnet device positioned to generate the magnetic field gradient that is used to pull the captured microbe out from the sample. An electromagnetic controller can be used to control and adjust the magnetic field and gradients thereof, and to control the migration, separation and orientation of the magnetically bound microbes. The magnetic field gradient can be generated by a permanent magnet or by an electromagnetic signal generator. The electromagnetic signal generator can include an electromagnet or electrically-polarizable element, or at least one permanent magnet. The magnetic field gradient can be produced at least in part according to a pre-programmed pattern. The magnetic field gradient can have a defined magnetic field strength and/or spatial orientation. In some embodiments, the magnetic field gradient has a defined magnetic field strength. The term "magnetic field gradient" as used herein refers to a variation in the magnetic field with respect to position. By way of example only, a one-dimensional magnetic field gradient is a variation in the magnetic field with respect to one direction, while a two-dimensional magnetic field gradient is a variation in the magnetic field with respect to two directions.

As used herein, the term "magnetic field" refers to magnetic influences which create a local magnetic flux that flows through a composition and can refer to field amplitude, squared-amplitude, or time-averaged squared-amplitude. It is to be understood that magnetic field can be a direct-current (DC) magnetic field or alternating-current (AC) magnetic field. The magnetic field strength can range from about 0.00001 Tesla per meter (T/m) to about 10 T/m. In some embodiments, the magnetic field strength can range from about 0.0001 T/m to about $10^4$ T/m. In some other embodiments, the magnetic field strength can range from about 0.001 T/m to about $10^3$ T/m.

In some embodiments, microbe capture and/or microbe-binding substrate separation can be performed by a rapid microbe diagnostic assay or device as described in Int. Pat. App. No. WO 2011/091037, filed Jan. 19, 2011, the content of which is incorporated herein by reference. A rapid microbe diagnostic device as described in Int. Pat. App. No. WO 2011/091037, filed Jan. 19, 2011, can be modified to replace the capture chamber or capture and visualization chamber with an s-shaped flow path. A magnet can then be used to capture bound microbe against the flow path wall; separating the bound microbe from rest of the sample.

In some embodiments, microbe capture and/or separation is by a device or method as described in U.S. Pat. App. Pub. No. 2009/0220932, No. 2009/007861, No. 2010/0044232, No. 2007/0184463, No. 2004/0018611, No. 2008/0056949, No. 2008/0014576, No. 2007/0031819, No. 2008/0108120, and No. 2010/0323342, the contents of which are all incorporated herein by reference.

In some embodiments, microbe capture, separation, or detection is by a device or method as described in PCT Application No. PCT/US2013/028409, filed Feb. 28, 2013, No. PCT/US2012/031864, filed Feb. 4, 2012, and No. PCT/US2011/021718 filed Jan. 19, 2011; U.S. patent application Ser. No. 13/918,193 filed Jun. 14, 2013; and US Prov. App. No. 61/788,570 filed Mar. 15, 2013, No. 61/772,436 filed Mar. 4, 2013, No. 61/772,360 filed Mar. 4, 2013, and No. 61/673,071 filed Jul. 18, 2013, the contents of which are all incorporated herein by reference.

Without limitations, if a microbe-binding substrate does not possess a magnetic property, isolation of a microbe-binding substrate (e.g., particles, posts, fibers, dipsticks, membrane, filters, capillary tubes, etc.) from the test sample can be carried out by non-magnetic means, e.g., centrifugation, and filtration. In some embodiments where the microbe-binding substrate is in a form a dipstick or membrane, the microbe-binding dipstick or membrane can be simply removed from the test sample, where microbes, if any, in the test sample, remained bound to the engineered microbe-binding molecules conjugated to the dipstick or membrane substrate.

Optionally, the microbe-binding substrate after isolated from the test sample or processing buffer can be washed with a buffer (e.g., TBST) to remove any residues of test sample, solution comprising the chelating agent or any unbound microbes. The number of wash steps can range from 1 to many, e.g., 1, 2, 3, 4, 5, 6, 7, 8, 9, 10 or more wash steps. In one embodiments, the microbe-binding substrate after isolated from the solution comprising the chelating agent and/or the test sample can be washed with a buffer (e.g., TBST) for about at least 1-3 times.

1212 (Microbe Detection/Analysis):

A detection component, device or system can be used to detect and/or analyze the presence of the separated microbe, for example, by spectroscopy, electrochemical detection, polynucleotide detection, fluorescence anisotropy, fluorescence resonance energy transfer, electron transfer, enzyme assay, magnetism, electrical conductivity, isoelectric focusing, chromatography, immunoprecipitation, immunoseparation, aptamer binding, filtration, electrophoresis, use of a CCD camera, immunoassay, ELISA, Gram staining, immunostaining, microscopy, immunofluorescence, western blot, polymerase chain reaction (PCR), RT-PCR, fluorescence in situ hybridization, sequencing, mass spectroscopy, or substantially any combination thereof. The separated microbe can remain bound on the microbe-binding substrate during detection and/or analysis, or be isolated form the microbe-binding substrate prior to detection and/or analysis.

As described herein, the microbe-binding molecules can be used as detection agents. Thus, in some embodiments, the microbe-binding molecule described herein coupled to at least one detectable label can be used to detect microbes captured microbe and/or microbial matter. In some embodiments, other art-recognized microbe-capture molecules including, e.g., but not limited to wheat germ agglutinin, lectins, antibodies (e.g., gram-negative antibodies or gram-positive antibodies, antibiotics to specific microbial strains or species), antigen binding fragments of antibodies, aptamers, ligands (agonists or antagonists) of cell-surface receptors and the like, can be used in the detection of microbes. The detection agent can also be a non-specific labeling molecule that non-specifically stains all viable cells in a sample.

Any method known in the art for detecting the particular label can be used for detection. Exemplary methods include, but are not limited to, spectrometry, fluorometry, microscopy imaging, immunoassay, and the like. While the microbe capture step can specifically capture microbes, it can be beneficial to use a labeling molecule that can enhance this specificity. If imaging, e.g., microscopic imaging, is to be used for detecting the label, the staining can be done either prior to or after the microbes have been laid out for microscopic imaging. Additionally, imaging analysis can be performed via automated image acquisition and analysis.

For optical detection, including fluorescent detection, more than one stain or dye can be used to enhance the detection or identification of the microbe. For example, a first dye or stain can be used that can bind with a genus of microbes, and a second dye or strain can be used that can bind with a specific microbe. Colocalization of the two dyes then provides enhanced detection or identification of the microbe by reducing false positive detection of microbes.

In some embodiments, microscopic imaging can be used to detect signals from label on the detection agent. Generally, the microbes in the subsample are stained with a staining reagent and one or more images taken from which an artisan can easily count the number of cells present in a field of view.

In particular embodiments, microbe can be detected through use of one or more enzyme assays, e.g., enzyme-linked assay (ELISA). Numerous enzyme assays can be used to provide for detection. Examples of such enzyme assays include, but are not limited to, beta-galactosidase assays, peroxidase assays, catalase assays, alkaline phosphatase assays, and the like. In some embodiments, enzyme assays can be configured such that an enzyme will catalyze a reaction involving an enzyme substrate that produces a fluorescent product. Enzymes and fluorescent enzyme substrates are known and are commercially available (e.g., Sigma-Aldrich, St. Louis, Mo.). In some embodiments, enzyme assays can be configured as binding assays that provide for detection of microbe. For example, in some embodiments, a microbe-binding molecule described herein can be conjugated with an enzyme for use in the enzyme assay. An enzyme substrate can then be introduced to the one or more immobilized enzymes such that the enzymes are able to catalyze a reaction involving the enzyme substrate to produce a detectable signal. Similarly, a variety of enzymes can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like. In some embodiments, the enzyme is a horseradish peroxidase (HRP), an alkaline peroxidase (AP), luciferase, and/or beta-galactosidase.

In some embodiments, an enzyme-linked assay (ELISA) can be used to detect signals from the microbe-binding molecule described herein used as a detection agent. In ELISA, the microbe-binding molecule can comprise an enzyme as the detectable label. Each microbe-binding molecule can comprise one or more (e.g., 1, 2, 3, 4, 5, 6, 7, 8, 9, 10 or more) enzymes. Additionally, each microbe-binding molecule can comprise one or more (e.g., 1, 2, 3, 4, 5, 6, 7, 8, 9, 10 or more) sites for binding with a microbe. Without wishing to be bound by a theory, the presence of multimeric molecules formed by a plurality of (e.g., at least 10 or more) microbe-binding molecules described herein can enhance ELISA signal.

A microbe-binding molecule described herein and the detectable label can be linked to each other by a linker. In some embodiments, the linker between the microbe-binding molecule and the detectable label an amide bond. In some embodiments, the linker between the microbe-binding molecule and the detectable label is a disulfide (S—S) bond. When the microbe-binding molecule is a peptide, polypeptide or a protein, the detectable label can be linked at the N-terminus, the C-terminus, or at an internal position of the microbe-binding molecule. Similarly, when the detectable label is an enzyme, the enzyme can be linked by its N-terminus, C-terminus, or an internal position.

In some embodiments, the microbes isolated from or remained bound on the microbe-binding substrate can be incubated with the enzyme labeled microbe-binding molecules for a period of time, e.g., at least about 5 mins, at least about 10 mins, at least about 15 mins, at least about 20 mins, at least about 25 mins, at least about 30 mins. The typical concentrations of enzyme-labeled molecules used in the ELISA assay can range from about 1:500 to about 1:20,000 dilutions. In one embodiment, the concentration of enzyme-labeled microbe-binding molecules can be about 1:1000 to about 1:10000 dilutions.

Following incubation with the ELISA probe molecules, the sample can be washed with a wash buffer one or more (e.g., 1, 2, 3, 4, 5 or more) times to remove any unbound probes. An appropriate substrate for the enzyme (e.g., HRP or AP) can be added to develop the assay. Chromogenic substrates for the enzymes (e.g., HRP or AP) are known to one of skill in the art. A skilled artisan can select appropriate chromogenic substrates for the enzyme, e.g., TMB substrate for the HRP enzyme, or BCIP/NBT for the AP enzyme. In some embodiments, the wash buffer used after incubation with an ELISA probe molecule can contain calcium ions at a concentration of about at least about 0.01 mM, at least about 0.05 mM, at least about 0.1 mM, at least about 0.5 mM, at least about 1 mM, at least about 2.5 mM, at least about 5 mM, at least about 10 mM, at least about 20 mM, at least about 30 mM, at least about 40 mM, at least about 50 mM or more. In alternative embodiments, the wash buffer used after incubation with an ELISA probe molecule can contain no calcium ions. In some embodiments, the wash buffer used after incubation with an ELISA probe molecule can contain a chelating agent. A wash buffer can be any art-recognized buffer used for washing between incubations with antibodies and/or labeling molecules. An exemplary wash buffer can include, but is not limited to, TBST.

In some embodiments, without wishing to be bound by theory, it can be desirable to use a wash buffer without a surfactant or a detergent for the last wash before addition of a chromogenic substrate, because a surfactant or detergent may have adverse effect to the enzymatic reaction with a chromogenic substrate.

One advantage of the ELISA-based approach is that the microbe-binding article does not need to be dispersed or dissociated from the microbe before binding the secondary reagents. This is in contrast to microscopic techniques, in which excess residual solid substrate may obscure the microbe during imaging. Furthermore, the optical readout components for ELISA are likely cheaper than in the microscopy case, and there is no need for focusing or for demanding that the sample be on the same focal plane. A further advantage of the ELISA-based approach is that it can take advantage of commercially available laboratory equipment. In particular, when the solid substrate is magnetic, magnetic separation can be automated using the KINGFISHER® system, the brief culture can be performed using an airlift fermenter, and the colorimetric/fluorescent readout can be attained using a standard plate reader.

In some embodiments, microbe can be detected through use of immunoassay. Numerous types of detection methods may be used in combination with immunoassay based methods.

In some embodiments, detection of microbes in a sample can also be carried out using light microscopy with phase contrast imaging based on the characteristic size (5 um diameter), shape (spherical to elliptical) and refractile characteristics of target components such as microbes that are distinct from all normal blood cells. Greater specificity can be obtained using optical imaging with fluorescent or cytochemical stains that are specific for all microbes or specific subclasses (e.g. calcofluor (1 μM to 100 μM) for chitin in fungi, fluorescent antibodies directed against fungal surface molecules, gram stains, acid-fast stains, fluorescent microbe-binding molecules, etc. . . . . .

Microbe detection can also be carried out using an epifluorescent microscope to identify the characteristic size (5 um diameter), shape (spherical to elliptical) and staining characteristics of microbes. For example, fungi stain differently from all normal blood cells, strongly binding calcofluor (1 μM to 100 μM) and having a rigid ellipsoid shape not found in any other normal blood cells.

In some embodiments, a microbe can be detected through use of spectroscopy. Numerous types of spectroscopic methods can be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., *Clinical Chemistry*, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, a microbe can be detected through use of fluorescence anisotropy. Fluorescence anisotropy is based on measuring the steady state polarization of sample fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel-Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy can be coupled to numerous fluorescent labels as have been described herein and as have been described in the art.

In some embodiments, microbe can be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect captured microbe. For example, in some embodiments, a first labeling molecule can be labeled with a fluorescent donor and second labeling molecule can be labeled with a fluorescent acceptor. Accordingly, such labeled first and second labeling molecules can be used within competition assays to detect the presence and/or concentration of microbe in a sample. Numerous combinations of fluorescent donors and fluorescent acceptors can be used for detection.

In some embodiments, a microbe can be detected through use of polynucleotide analysis. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described, for example, in U.S. Pat. Nos. 7,118,910 and 6,960,437; herein incorporated by reference). Such methods can be adapted to provide for detection of one or more microbe nucleic acids. In some embodiments, fluorescence quenching, molecular beacons, electron transfer, electrical conductivity, and the like can be used to analyze polynucleotide interaction. Such methods are known and have been described, for example, in Jarvius, *DNA Tools and Microfluidic Systems for Molecular Analysis*, Digital Comprehensive Summaries of Uppsala Dissertations from the Faculty of Medicine 161, ACTA UNIVERSITATIS UPSALIENSIS UPPSALA 2006, ISBN: 91-554-6616-8; Singh-Zocchi et al, *Proc. Natl. Acad. Sci,* 100:7605-7610 (2003); Wang et al. *Anal. Chem,* 75:3941-3945 (2003); and Fan et al, *Proc. Natl. Acad. Sci,* 100:9134-9137 (2003) and in U.S. Pat. Nos. 6,958,216; 5,093,268; and 6,090,545, the content of all of which is incorporated herein by reference. In some embodiments, the polynucleotide analysis is by polymerase chain reaction (PCR). The fundamentals of PCR are well-known to the skilled artisan, see, e.g. McPherson, et al., *PCR A Practical Approach, IRL Press, Oxford, Eng*. (1991), hereby incorporated by reference.

In some embodiments, a metabolic assay is used to determine the relative number of microbes in a sample compared to a control. As will be apparent to one of ordinary skill in the art any metabolic indicator that can be associated with cells can be used, such as but not limited to, turbidity, fluorescent dyes, and redox indicators such as, but not limited to, Alamar Blue, MTT, XTT, MTS, and WST. Metabolic indicators can be components inherent to the cells or components added to the environment of the cells. In some embodiments, changes in or the state of the metabolic indicator can result in alteration of ability of the media containing the sample to absorb or reflect particular wavelengths of radiation.

Exemplary metabolic assays include, but are not limited to, ATP Luminescence, reactive oxygen species (ROS) assays, Resazurin assays, Luminol, MTT-metabolic assays, and the like. Further, as one of skill in the art is well aware, kits and methods for carrying out metabolic assays are commercially available. For example, 2-(N-(7-Nitrobenz-2-oxa-1,3-diazol-4-yl)Amino)-2-Deoxyglucose (2-NBDG), ATP Determination Kit, AMPLEX® Red GalactoseGalactose Oxidase Assay Kit, AMPLEX® Red GlucoseGlucose Oxidase Assay Kit, AMPLEX® Red Glutamic Acid/Glutamate Oxidase Assay Kit, AMPLEX® Red Hydrogen PeroxidePeroxidase Assay Kit, AMPLEX® Red Monoamine Oxidase Assay Kit, AMPLEX® Red Neuraminidase (Sialidase) Assay Kit, AMPLEX® Red Phosphatidylcholine-Specific Phospholipase C Assay Kit, AMPLEX® Red Sphingomyelinase Assay kit, AMPLEX® Red Uric Acid/Uricase Assay Kit, AMPLEX® Red Xanthine/Xanthine Oxidase Assay Kit, THIOLTRACKER™ Violet (Glutathione Detection Reagent), THIOLTRACKERH Violet (Glutathione Detection Reagent), and VYBRANT® Cell Metabolic Assay Kit from Invitrogen; Adenosine 5'-triphospahte (ATP) Luminescence Assay Kit (ENLITEN® from Promega; ATPLITE™ from PerkinElmer Life Sciences; ATP Bioluminescence Assay kit HS II from Boehringer Mannheim, Germany; Adenosine 5'-triphosphate (ATP) Luminescence Assay Kit from EMD Millipore; Reactive Oxygen Species (ROS) Assays from Cell BioLabs, Inc.; Cellular Reactive Oxygen Species Detection Assay Kit from ABCAM®; hROS Detection Kit from Cell Technology, Inc.; and ABTS Antioxidant Assay Kit, ORAC Antioxidant Assay Kit, OxiSelect HORAC Activity Assay Kit, OxiSelect In vitro ROS/RNS Assay Kit (Green Fluorescence), OxiSelect Intracellular ROS Assay Kit (Green Fluorescence), OxiSelect ORAC Activity Assay Kit, OxiSelect Total Antioxidant Capacity (TAC) Assay Kit, and Total Antioxidant Capacity Assay Kit from BioCat.

In some embodiments, microbes isolated from or remained bound on microbe-binding article can be labeled with nucleic acid barcodes for subsequent detection and/or multiplexing detection. Nucleic acid barcoding methods for detection of one or more analytes in a sample are well known in the art.

In other embodiments, the captured microbe can be analyzed and/or detected in the capture chamber or capture and visualization chamber of a rapid microbe diagnostic device described in the Int. Pat. App. No. Int. Pat. App. No. WO 2011/091037, filed Jan. 19, 2011. Alternatively, the captured microbe can be recovered (i.e., removed) and analyzed and/or detected.

In some embodiments, the captured microbe is recovered and analyzed and/or detected using a particle on membrane assay as described in U.S. Pat. No. 7,781,226, content of which is incorporated herein by reference. A particle on membrane assay as described in U.S. Pat. No. 7,781,226 can be operably linked with a rapid microbe diagnostic device of the Int. Pat. App. No. Int. Pat. App. No. WO 2011/091037 to reduce the number of sample handling steps, automate the process and/or integrate the capture, separation and analysis/detection steps into a microfluidic device.

In some embodiments, microbe capture, separation and analysis can be done using a hybrid microfluidic SPR and molecular imagining device as described in U.S. Pat. App. Pub. No. US 2011/0039280.

In some embodiments, the microbe capture, separation and analysis using the microbe-binding molecules disclosed herein can be done by an assay or device described, for example, in PCT Application No. PCT/US2011/021603 filed Jan. 19, 2011, No. PCT/US2012/047201 filed Jul. 18, 2012, and No. PCT/US2013/028409 filed Feb. 28, 2013, and U.S. Provisional Application No. 61/788,570 filed Mar. 15, 2013, No. 61/772,436 filed Mar. 4, 2013, No. 61/673,071 filed Jul. 18, 2013, and No. 61/772,360 filed Mar. 4, 2013, contents of all of which are incorporated herein by reference.

In some embodiments, the processes or assays described herein can detect the presence or absence of a microbe and/or identify a microbe in a test sample in less than 24 hours, less than 12 hours, less than 10 hours, less than 8 hours, less than 6 hours, less than 4 hours, less than 3 hours, less than 2 hours, less than 1 hour, or lower. In some embodiments, the processes or assays described herein can detect the presence or absence of a microbe and/or identify a microbe in a test sample in less than 6 hours, less than 4 hours, less than 3 hours, less than 2 hours, less than 1 hour, or lower.

Optional Additional Analyses or Treatment—Culturing:

In some embodiments of any aspects described herein, the assay or process can further comprise culturing any microbe bound on the microbe-binding article (e.g., microbe-binding microparticles) for a period of time. In such embodiments, the microbe bound on the microbe-binding article can expand in population by at least about 10% after culturing for a period of time.

In some embodiments, the microbe bound on the microbe-binding article (e.g., microbe-binding microparticle) can be cultured for a period of time, e.g., at least about 15 mins, at least about 30 mins, at least about 1 hour, at least about 2 hours, at least about 3 hours, at least about 6 hours, at least about 9 hours, at least about 12 hours, at least about 18 hours, at least about 24 hours or longer. In some embodiments, the microbe bound on the microbe-binding article can be cultured for at least about 30 mins to at least about 3 hours.

In some embodiments, the number of microbes bound on the microbe-binding article after culturing for a certain period of time can be increased or expanded by at least about 30%, at least about 40%, at least about 50%, at least about 60%, at least about 70%, at least about 80%, at least about 90%, at least about 100%, as compared to the number of the microbes originally bound on the microbe-binding article. In some embodiments, the number of microbes bound on the microbe-binding article after culturing for a certain period of time can be increased or expanded by at least about 1.5-fold, at least about 2-fold, at least about 3-fold, at least about 4-fold, at least about 5-fold, at least about 10-fold, at least about 50-fold, at least about 100-fold, at least about 500-fold, at least about 1000-fold, at least about 10000-fold, at least about 100000-fold, as compared to the number of the microbes originally bound on the microbe-binding article.

In some embodiments, the microbes bound on the microbe-binding articles can be cultured on a microbe-compatible culture medium, e.g., plated on an agar plate or cultured in LB broth. One of skill in the art will readily recognize microbial culture techniques, including, but not limited to, the use of incubators and/or equipment used to provide a gentle agitation, e.g., rotator platforms, and shakers, if necessary, e.g., to prevent the cells from aggregation without subjecting them to a significant shear stress and provide aerial agitation.

The microbes can remain bound on the microbe-article during detection or additional analyses described herein or they can be detached, eluted off or removed from a microbe-binding article prior to detection or additional analyses described herein. In some embodiments where the bound microbes are desired to be detached, eluted off or removed from a microbe-binding article, the microbe-binding molecules of the microbe-binding article can be further contacted with a low pH buffer, e.g., a pH buffer less than 6, less than 5, less than 4, less than 3, less than 2, less than 1 or lower. In some embodiments, a low pH buffer that does not cause precipitation of a chelating agent, if present, can be used. In one embodiment, a low pH buffer can be arginine. In another embodiment, a low pH buffer can be pyrophosphate.

In some embodiments of any aspects described herein, the microbe-binding molecules of the microbe-binding article can be further contacted with a low pH buffer and a chelating agent. In some embodiments, the contact of the microbe-binding molecules of the microbe-binding article with the low pH buffer and the chelating agent can be concurrent or sequentially. In one embodiment, the microbe-binding molecules of the microbe-binding substrate can be further contacted with arginine (e.g., 2 M) with EDTA or EGTA at pH 4.4.

The isolated microbes can then be used for analyses described earlier or additional treatment, e.g., expansion in culture, antibiotic sensitivity testing, sequencing and/or DNA or RNA analysis.

Optional Additional Analyses or Treatment—Antibiotic Sensitivity or Susceptibility Testing:

In some embodiments of any aspects described herein, the process or assay described herein can further comprise subjecting the microbes bound on the microbe-binding article or the expanded cultures of microbes isolated from the microbe-binding article to one or more antibiotics. The response of the microbe to an antibiotic can then be evaluated with any known methods in the art, e.g., by measuring the viability of microbes. Thus, an appropriate antibiotic can be identified for treatment of an infection caused by a microbe, even though the specific species of the microbe bound onto the microbe-binding substrate is initially unknown. Additional details for use of engineered microbe-binding molecules described herein in antibiotic sensitivity testings can be found, e.g., in U.S. Prov. App. Nos. 61/604,878 filed Feb. 29, 2012 and 61/647,860 filed May 16, 2012, and PCT Application No. PCT/US2013/028409 filed Feb. 28, 2013, content of all of which is incorporated herein by reference in their entireties.

Any processes or steps described herein can be performed by a module or device. While these are discussed as discrete processes, one or more of the processes or steps described herein can be combined into one system for carrying out the assays of any aspects described herein.

In general, embodiments of the assays or processes of any aspects described herein can be used to detect the presence or absence of a microbe or microbial matter in a test sample or in situ (e.g., where the microbe actually resides, e.g., in a water reservoir or on a working surface). For example, in some embodiments, a test sample, e.g., obtained from a subject or an environmental source, or an environmental surface can be contacted with engineered microbe-binding molecules or engineered microbe-binding articles described herein, such that any microbes, if present, in the test sample or environmental surface can be captured by the engineered microbe-binding molecules or engineered microbe-binding articles e.g., using any embodiments of the exemplary process described above. In some embodiments, the captured microbes bound on the engineered microbe-binding molecules or microbe-binding articles can then be subjected to different analyses as described above, e.g., for identifying a microbe genus or species such as by immunoassay (e.g., using antibodies to a specific microbe), mass spectrometry, PCR, etc. In alternative embodiments where the engineered microbe-binding molecules comprise an imaging agent (e.g., a bubble, a liposome, a sphere, a diagnostic contrast agent or a detectable label described herein), the binding of the microbes to the engineered microbe-binding molecules can be detected in situ for identification of localized microbial infection or contamination, and also allow localized treatment of the infection or contamination.

In some embodiments, the assays or processes described herein can be used to diagnose or locate a microbial infection in situ in a subject. For example, engineered microbe-binding microbeads comprising an imaging agent (e.g., the engineered microbe-binding microbeads can be linked to an imaging agent, e.g., a bubble, a liposome, a sphere, a diagnostic contrast agent or a detectable label described herein) can be administered to a subject, either systemically (e.g., by injection), or locally. In such embodiments, the engineered microbe-binding microbeads comprising an imaging agent can be used to identify and/or localize pockets of localized microbial infection (e.g., in a tissue) in the subject and optionally allow localized treatment of the microbial infection, which is described in the section "Exemplary Compositions and Methods for Treating and/or Preventing a Microbial Infection" below.

In some embodiments, the method can further comprise administering or prescribing to the subject an antimicrobial agent when the subject is detected with an infection. Some exemplary antimicrobial agents include, but are not limited to, penicillin, methicillin, nafcillin, oxacillin, cloxacillin, dicloxacillin, flucloxacillin, vancomycin, and any combinations thereof.

Without wishing to be bound by theory, some embodiments of the engineered microbe-binding molecules can be used to opsonize a microbe, which is then cleared out by an innate immune response. In some embodiments, the microbe-binding molecules can be a more potent opsonin of a microbe. Accordingly, in some embodiments, when the subject is diagnosed with a microbial infection using the methods described herein, the subject can be administered or prescribed with a composition comprising at least one engineered microbe-binding molecule described herein. Without limitations, the methods of any aspects described herein can be used to diagnose a microbe that is resistant to at least one, at least two, at least three, at least four or more antibiotics.

In some embodiment, the assay disclosed herein can be performed using a "dipstick" format. By way of example only, a microbe-binding dipstick or test strip can be brought into contact with a test sample (e.g., a blood sample) from a patient or a subject, and incubated for a period of time, e.g., at least about 15 seconds, at least about 30 seconds, at least about 1 min, at least about 2 mins, at least about 5 mins, at least about 10 mins, at least about 15 mins, at least about 30 mins, at least about 1 hour or more. In some embodiments, the incubated dipstick or test strip can then be incubated in a blocking agent (e.g., BSA, normal serum, casesin, non-fat dry milk, and/or any commercially-available blocking agents to minimize non-specific binding). Depending on different embodiments of the engineered microbe-binding molecules, in some embodiments, the microbe-binding dipstick or test strip after contact with a test sample (e.g., a blood sample) can be further contacted with at least one additional agent to facilitate detection of pathogen, and/or to increase specificity of the pathogen detection. For example, some embodiments of the dipstick or test strip after contact with a test sample (e.g., a blood sample) can be further contacted with a detectable label that is conjugated to a molecule that binds to a microbe and/or microbial matter. Examples of such molecules can include, but are not limited to, one or more embodiments of the engineered microbe-binding molecule described herein, an antibody specific for the microbes or pathogens to be detected, a protein, a peptide, a carbohydrate or a nucleic acid that is recognized by the microbes or pathogens to be detected, and any combinations thereof.

In some embodiments, the readout of the microbe-binding dipsticks and/or test strips can be performed in a system or device, e.g., a portable device. The system or device can display a signal indicating the presence or the absence of a microbial infection in a test sample, and/or the extent of the microbial infection.

In one embodiment, the assay can be used for detecting or imaging a nidus of infection in vivo. For example, a subject can be administered a microbe-binding molecule disclosed herein, wherein the microbe-binding molecule comprises a detectable label; and scanning the subject using diagnostic imaging. Without limitations, the diagnostic imaging is selected from the group consisting of radiography, magnetic resonance imaging (MRI), Positron emission tomography (PET), Single-photon emission computed tomography (SPECT, or less commonly, SPET), Scintigraphy, ultrasound, CAT scan, photoacoustic imaging, thermography, linear tomography, poly tomography, zonography, orthopantomography (OPT or OPG), computed Tomography (CT) or Computed Axial Tomography (CAT scan), and any combinations thereof.

Due to the enhanced sensitivity of the microbe-binding molecules described herein, a lower dose (e.g., by at least 10% or more, including, e.g., at least 20%, at least 30%, at least 40%, at least 50%, at least 60%, at least 70%, or higher) of the microbe-binding molecules described can be used for the same therapeutic effect in a treatment, as compared to a reference molecule. In some embodiments, the reference molecule can be a molecule described in the International Patent Publication Nos. WO 2013/012924 and WO 2011/090954, the contents of each of which are incorporated herein by reference in their entirety. In some embodiments, the reference molecule can be an FcMBL as described herein when the microbe-binding molecules described herein comprise a carbohydrate recognition domain derived from MBL.

The binding of microbes to engineered microbe-binding molecules can facilitate isolation and removal of microbes and/or microbial matter from an infected area. Accordingly, another aspect provided herein relate to compositions for treating and/or preventing a microbial infection or microbial contamination comprising one or more engineered microbe-binding molecules or microbe-binding substrates (e.g., microbe-binding magnetic microbeads) described herein.

In some embodiments, the composition can be formulated for treating and/or preventing a microbial infection or a microbial contamination present in an environmental surface. The term "environmental surface" as used herein refers to any surface and/or body of an environment or an object. The environmental object can be a non-living object or a living object, e.g., a botanical plant. Examples of an environmental surface can include, but is not limited to, a medical device, an implantable device, a surface in a hospital or clinic (e.g., an operating room or an intensive-care unit), a machine or working surface for manufacturing or processing food or pharmaceutical products (e.g., drugs, therapeutic agents or imaging agents), a cell culture, a water treatment plant, a water reservoir and a botanical plant.

In some embodiments, the composition can be formulated for treating and/or preventing microbial infection in a body fluid of a subject, e.g., blood. While in some embodiments, the engineered microbe-binding molecules of the composition described herein can capture microbes and/or microbial matter in a circulating body fluid, e.g., blood, in other embodiments, the engineered microbe-binding molecules can opsonize a microbe and/or microbial matter such that the microbe and/or microbial matter can be recognized by an innate immune system for clearance.

Alternatively, the engineered microbe-binding molecules can localize a microbe and can thus prevent it from spreading, e.g., deeper into a wound. In some embodiments, the engineered microbe-binding molecules can be used to localize a microbe load, which can then be easily removed from an infected area. In some embodiments, the microbead can be labeled for specific imaging of infected sites. For SPECT imaging the tracer radioisotopes typically used such as iodine-123, technetium-99m, xenon-133, thallium-201, and fluorine-18 can be used. Technetium 99m can be used for scintigraphic assay. Iodine-derived or other radioopaque contrast agents can also be incorporated in the beads for radiographic or CT-scan imaging. The use of paramagnetic or superparamagnetic microbeads can be used for magnetic resonance imaging as contrast agents to alter the relaxation times of atoms within a nidus of infection. In another embodiment, the microspheres can be fluorescently dyed and applied to a surgical wound to determine the extension of an infectious process. This can be useful for assisting the surgeon in distinguishing between infected and healthy tissues during debridment surgeries for osteomyelitis, cellulitis or fascitis.

Accordingly, another aspect provided herein related to compositions for treating and/or preventing a microbial infection in a tissue of a subject. In some embodiments, the composition comprises at least one engineered microbe-binding molecule as described herein. In some embodiments, the amount of the engineered microbe-binding molecules and/or microbe-binding substrates present in the composition is sufficient to reduce the growth and/or spread of the microbe in the tissue of the subject. The phrase "reducing the growth and/or spread of the microbe in the tissue" as used herein refers to reducing the number of colonies of the microbe and/or movement of the microbe in the tissue. In some embodiments, the engineered microbe-binding molecule can capture and localize a microbe present in a tissue such that the number of colonies of the microbe in the tissue can be reduced by at least about 30%, at least about 40%, at least about 50%, at least about 60%, at least about 70%, at least about 80%, at least about 90%, at least about 95%, at least about 98%, up to and including 100%, as compared to in the absence of the engineered microbe-binding molecule. In some embodiments, the engineered microbe-binding molecule can capture and localize a microbe present in a tissue such that the number of colonies of the microbe in the tissue can be reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more, as compared to in the absence of the engineered microbe-binding molecules. In one embodiment, the binding of the engineered microbe-binding molecules with a microbe (e.g., S. aureus) reduces the number of colonies by at least about 4-fold to at least about 6-fold (e.g., at least about 5-fold), as compared to in the absence of the engineered microbe-binding molecules, after a period of at least about 12 hours, at least about 16 hours or at least about 24 hours.

In other embodiments, the engineered microbe-binding molecule can capture and localize a microbe present in a tissue such that the movement of the microbe within the tissue (e.g., in terms of a distance traveled deeper into the tissue and/or area of spread from the infected site) can be reduced by at least about 30%, at least about 40%, at least about 50%, at least about 60%, at least about 70%, at least about 80%, at least about 90%, at least about 95%, at least about 98%, up to and including 100%, as compared to in the absence of the engineered microbe-binding molecule. In some embodiments, the engineered microbe-binding molecule can capture and localize a microbe present in a tissue such that the movement of the microbe within the tissue (e.g., in terms of a distance traveled deeper into the tissue and/or area of spread from the infected site) can be reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold or more, as compared to in the absence of the engineered microbe-binding molecule.

In some embodiments, the composition can further comprise at least one of an antimicrobial agent and a drug delivery vehicle. For example, in some embodiments, the composition can further comprise at least 1, at least 2, at least 3, at least 4, at least 5 or more antimicrobial agents. In some embodiments, the composition can further comprise one or a plurality of (e.g., 2, 3, 4, 5, 6, 7, 8, 9, 10, 20, 30, 40, 50, 60, 70, 80, 90, 100, 500, 1000 or more) delivery vehicles. In some embodiments, the composition can further comprise a combination of at least one (including at least 2, at least 3, at least 4, at least 5 or more) antimicrobial agent and at least one (including 1, 2, 3, 4, 5, 6, 7, 8, 9, 10, 20, 30, 40, 50, 60, 70, 80, 90, 100, 500, 1000 or more) drug delivery vehicle. As used herein, the term "drug delivery vehicle" generally refers to any material that can be used to carry an active agent to a target site. Examples of drug delivery vehicles includes, but are not limited to, a cell, a peptide particle, a polymeric particle, a dendrimer, a vesicle, a liposome, a hydrogel, a nucleic acid scaffold, an aptamer, and any combinations thereof, In some embodiments where a drug delivery vehicle is included, an engineered microbe-binding molecule and/or an antimicrobial agent can be dispersed within (e.g., encapsulated or embedded in) a drug delivery vehicle and/or coated on a surface of the drug delivery vehicle.

In some embodiments where the composition includes at least one antimicrobial agent, the antimicrobial agent can be present as a separate entity from the engineered microbe-binding molecule and/or it can be fused with at least one engineered microbe-binding molecule, e.g., by genetic modification and/or chemical conjugation.

The term "antimicrobial agent" as used herein refers to any entity with antimicrobial activity, i.e. the ability to inhibit or reduce the growth and/or kill a microbe, e.g., by at least about 30%, at least about 40%, at least about 50%, at least about 75%, at least about 90% or more, as compared to in the absence of an antimicrobial agent. An antimicrobial agent can be, for example, but not limited to, a silver nanoparticle, a small molecule, a peptide, a peptidomimetics, an antibody or a fragment thereof, a nucleic acid, an enzyme (e.g., an antimicrobial metalloendopeptidase such as lysostaphin), an aptamer, a drug, an antibiotic, a chemical or any entity that can inhibit the growth and/or kill a microbe. Examples of an antimicrobial peptide that can be included in the composition described herein, include, but are not limited to, mefloquine, venturicidin A, antimycin, myxothiazol, stigmatellin, diuron, iodoacetamide, potassium tellurite hydrate, aDL-vinylglycine, N-ethylmaleimide, L-allyglycine, diaryquinoline, betaine aldehyde chloride, acivcin, psicofuraine, buthionine sulfoximine, diaminopemelic acid, 4-phospho-D-erythronhydroxamic acid, motexafin gadolinium and/or xycitrin or modified versions or analogues thereof.

In some embodiments, an antimicrobial agent included in the composition can be an antibiotic. As used herein, the term "antibiotic" is art recognized and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Substances of similar structure and mode of action can be synthesized chemically, or natural compounds can be modified to produce semi-synthetic antibiotics. Exemplary classes of antibiotics include, but are not limited to, (1) β-lactams, including the penicillins, cephalosporins monobactams, methicillin, and carbapenems; (2) aminoglycosides, e.g., gentamicin, kanamycin, neomycin, tobramycin, netilmycin, paromomycin, and amikacin; (3) tetracyclines, e.g., doxycycline, minocycline, oxytetracycline, tetracycline, and demeclocycline; (4) sulfonamides (e.g., mafenide, sulfacetamide, sulfadiazine and sulfasalazine) and trimethoprim; (5) quinolones, e.g., ciprofloxacin, norfloxacin, and ofloxacin; (6) glycopeptides (e.g., vancomycin, telavancin, teicoplanin); (7) macrolides, which include for example, erythromycin, azithromycin, and clarithromycin; (8) carbapenems (e.g., ertapenem, doripenem, meropenem, and imipenem); (9) cephalosporins (e.g., cefadroxil, cefepime, and ceftobiprole); (10) lincosamides (e.g., clindamycin, and lincomycin); (11) monobactams (e.g., aztreonam); (12) nitrofurans (e.g., furazolidone, and nitrofurantoin); (13) Penicillins (e.g., amoxicillin, and Penicillin G); (14) polypeptides (e.g., bacitracin, colistin, and polymyxin B); and (15) other antibiotics, e.g., ansamycins, polymycins, carbacephem, chloramphenicol, lipopeptide, and drugs against mycobacteria (e.g., the ones causing diseases in mammals, including tuberculosis (*Mycobacterium tuberculosis*) and leprosy (*Mycobacterium leprae*), and any combinations thereof.

Additional exemplary antimicrobial agent can include, but are not limited to, antibacterial agents, antifungal agents, antiprotozoal agents, antiviral agents, and any mixtures thereof.

Exemplary antibacterial agents include, but are not limited to, Acrosoxacin, Amifloxacin, Amoxycillin, Ampicillin, Aspoxicillin, Azidocillin, Azithromycin, Aztreonam, Balofloxacin, lc Benzylpenicillin, Biapenem, Brodimoprim, Cefaclor, Cefadroxil, Cefatrizine, Cefcapene, Cefdinir, Cefetamet, Cefmetazole, Cefprozil, Cefroxadine, Ceftibuten, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafloxacin, Tetracycline, Tetroxoprim, Tinidazole, Tosufloxacin, Trimethoprim, and phramceutically acceptable salts or esters thereof.

Exemplary antifungal agents include, but are not limited to, Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid, and pharmaceutically acceptable salts or esters thereof.

Exemplary antiprotozoal agents include, but are not limited to, Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole, and pharmaceutically acceptable salts or esters thereof.

Exemplary antiviral agents include, but are not limited to, Acyclovir, Brivudine, Cidofovir, Curcumin, Desciclovir, 1-Docosanol, Edoxudine, gQ Fameyclovir, Fiacitabine, Ibacitabine, Imiquimod, Lamivudine, Penciclovir, Valacyclovir, Valganciclovir, and pharmaceutically acceptable salts or esters thereof.

In some embodiments, the antimicrobial agent can include silver present in any form, e.g., a nanoparticle, a colloid, a suspension, powder, and any combinations thereof.

In some embodiments, the composition can be used to treat and/or prevent an infection caused by any microbe described herein. In one embodiment, the composition can be used to treat and/or prevent an infection caused by *S. aureus*.

In some embodiments, the composition can be used to treat and/or prevent an infection caused by a microbe that is resistant to at least one, at least two, at least three, at least four or more antimicrobial agents described herein. In one embodiment, the composition can be used to treat and/or prevent an infection caused by a microbe that is resistant to at least one, at least two, at least three, at least four or more antibiotics described herein. For example, in one embodiment, the composition can be used to treat and/or prevent an infection caused by methicillin-resistant *S. aureus*. In another embodiment, the composition can be used to treat and/or prevent an infection caused by vancomycin-resistant *S. aureus*.

Exemplary Antimicrobial Applications and/or Products:

The compositions described herein can be formulated or configured for different applications and/or products such antimicrobial products. In some embodiments, the composition described herein can be formulated as pharmaceutical compositions as described below, e.g., for therapeutic treatment as an antibiotic or antiseptic.

Wound Dressings:

In some embodiments, the composition described herein can be formulated for topical application, e.g., in wounds, lesions or abscesses. By way of example only, in some embodiments, a plurality of engineered microbe-binding molecules can be blended with, attached to or coated on a wound dressing, for example, but not limited to, a bandage, an adhesive, a gauze, a film, a gel, foam, hydrocolloid, alginate, hydrogel, paste (e.g., polysaccharide paste), a spray, a granule and a bead.

In some embodiments, the wound dressing can include an additional antimicrobial agent described herein and/or an antiseptic chemical, e.g., boracic lint and/or medicinal castor oil.

In one embodiment, a plurality of engineered microbe-binding molecules (e.g., microbe-binding microparticles or microbe-binding magnetic microbeads) can be attached or coated onto a wound dressing such as a bandage or an adhesive. When such wound dressing is applied to a wound or a lesion, any microbe (e.g., *S. aureus*) and/or microbial matter present in the wound or lesion can bind and localized to the wound dressing. Thus, regular replacement of the wound dressing can remove the microbe from the wound or lesion and thus prevent the microbe from moving deeper into the wound or lesion for further infection.

In one embodiment, a plurality of engineered microbe-binding molecules (e.g., microbe-binding microparticles or microbe-binding magnetic microbeads) can be formulated into a wound dressing spray, which can be handy and used anywhere, e.g., during a transportation on an emergency vehicle. When the wound dressing spray containing the microbe-binding magnetic microbeads, the microbe-binding magnetic microbeads with bound microbes (e.g., *S. aureus*) can be removed from the wound with a magnetic field gradient before re-application of the spray.

Debridement Fluids or Sprays:

In some embodiments, the composition described herein can be formulated as part of a debridement fluid (optionally with suspended particulates that are abrasive to a lesion area). In some embodiments, the composition described herein can be formulated as part of a debridement spray. As used herein, the term "debridement" generally refers to complete or partial removal of a subject's dead, damaged, and/or infected tissue to improve the healing potential of the remaining healthy and/or non-infected tissue. By way of example only, a plurality of engineered microbe-binding molecules (e.g., microbe-binding microparticles or magnetic microbeads) can be suspended in a debridement fluid or spray, e.g., for use in an orthopedic procedure. The debridement fluid or spray containing the engineered microbe-binding molecules can be applied to a lesion, an abscess or a wound, where the engineered microbe-binding microparticles or magnetic microbeads can capture a microbe (e.g., *S. aureus*) and/or microbial matter from the lesion, abscess or wound. The debridement fluid or spray can then be removed from the applied site by vacuum, or suction. In some embodiments, the debridement fluid or spray containing the engineered microbe-binding magnetic microbeads can be also removed from the applied site by exposing the applied site to a magnetic field gradient, which can pull or attract the applied microbe-binding magnetic microbeads out from the applied site.

Medical Device Coating:

In some embodiments, the composition described herein can be coated on a surface of a medical device, e.g., a fluid delivery device such as hollow fibers, tubing or a spiral mixer in an extracorporeal device, or an implantable device such as an indwelling catheter, chip or scaffold. By way of example only, a plurality of engineered microbe-binding molecules can be coated or conjugated to a surface of a fluid delivery device such that when a fluid (e.g., blood) flows through the fluid delivery device coated with engineered microbe-binding molecules, any microbe (e.g., *S. aureus*) and/or microbial matter present in the fluid (e.g., blood) can be extracted therefrom, thus reducing the chance of a microbial infection. In another embodiment, a plurality of engineered microbe-binding molecules coated on a medical device can comprise a detectable label, e.g., a "smart label" described herein, which can provide a detectable signal when any microbe (e.g., *S. aureus*) binds to a surface of the medical device, indicating that the medical device has been contaminated and/or infected, and thus is not appropriate for use or implantation.

The disclosure further provides methods for removing a microbe and/or microbial matter from a target area comprising contacting the target area with at least one composition described herein. As removal of a microbe and/or microbial matter from an infected area can treat and/or prevent a microbial infection or microbial contamination, provided herein also include methods for treating and/or preventing a microbial infection or microbial contamination in a target area. An exemplary method comprises contacting the target area with a composition comprising the engineered microbe-binding molecule disclosed herein. The target area can be anywhere, e.g., an environmental surface or in a body of a subject (e.g., body fluid, and/or tissue). In some embodiments, the method comprises contacting the tissue of the subject with any embodiments of the composition described herein. In some embodiments, the tissue can have an open wound, a lesion or an abscess.

In one embodiment, the composition can be formulated for use as a wound dressing described herein.

As the engineered microbe-binding molecules can localize a microbe (e.g., *S. aureus*) for easier removal of the microbe from the tissue, in some embodiments, the method can further comprise replacing the previously-applied composition in contact with the tissue with a fresh composition after a period of time. For example, depending on the condition of the microbial infection and/or specific compositions, the previously-applied composition can be replaced every 1 hour, every 2 hours, every 3 hours, every 4 hours, every 5 hours, every 6 hours, every 8 hours, every 10 hours, every 12 hours, every 16 hours, every 24 hours or longer.

In some embodiments, the method can further comprise administering an additional treatment to the tissue. Exemplary additional treatments can include, but are not limited to, a negative-pressure treatment, a vacuum-assisted debridement, administration of an antimicrobial agent, or any combinations thereof.

Without limitations, the compositions and/or methods of any aspects described herein can be used to treat and/or prevent a microbial infection or contamination in vitro, in situ or in vivo. In some embodiments, the compositions and/or methods of any aspects described herein can be used to treat and/or prevent a microbial infection or contamination in a fluid or on any surface, including, but not limited to, a tissue surface, a solid substrate surface, e.g., a medical device surface, an environmental surface, or food.

Additionally, in some embodiments where the composition comprises at least one engineered microbe-binding molecule conjugated to a detectable label described herein or an imaging agent, can be used to image an infection in situ. e.g., in a subject or on an environmental surface.

The disclosure also provides a method for delivering or concentrating an anti-microbial agent at a nidus of infection. Generally, the nidus is contacted with a composition of comprising at least one microbe-binding molecule disclosed herein and an anti-microbial agent. The microbial agent can be covalently or non-covalently linked with the microbe-binding molecule. In some embodiments, the anti-microbial agent can be encompassed in a particle covalently or non-covalently lined with the microbe-binding molecule.

Some embodiments of the engineered microbe-binding molecules can be used for therapeutic purposes. For administration to a subject in need thereof, engineered microbe-binding molecules described herein can be provided in pharmaceutically acceptable compositions. Accordingly, in yet another aspect, provided herein is a pharmaceutical composition comprising at least one engineered microbe-binding molecule described herein, and a pharmaceutically acceptable carrier.

When the engineered microbe-binding molecules are used as therapeutics in vivo, the collagen domain and/or the Fc domain can be further modified to modulate the effector function such as antibody-dependent cellular cytotoxicity (ADCC) and complement-dependent cytotoxicity (CDC). By way of example only, the Fc domain can mediate ADCC and CDC. In ADCC, the Fc domain can generally bind to Fc receptors on the surface of immune effector cells such as natural killers and macrophages, leading to the phagocytosis or lysis of a targeted cell. In CDC, the Fc domain can generally trigger the complement cascade at the cell surface to kill the targeted cell. Accordingly, modulating effector functions can be achieved by engineering the Fc domain to either increase or decrease their binding to the Fc receptors on the surface of the immune effector cells or the complement factors. For example, numerous mutations within a Fc region for modulating ADCC and CDC are well known to a skilled artisan, e.g., see Armour K L. et al. (1999) *Eur J Immmunol* 29: 2613-2624; Shields R L. et al. (2001) *J Biol Chem.* 276: 6591-6604; Idusogie E E. et al. (2001) *J Immunol.* 166: 2571-2575; Idusogie E E. et al. (2000) *J Immunol.* 155: 1165-1174; and Steurer W. et al. (1995) *J Immunol.* 155: 1165-1674. In one embodiment, the Fc domain can be modified to remove the glycosylation of Fc and thus, in turn, reduce ADCC and CDC functions. For example, the amino acid asparagine (N) at the residue 82 of the SEQ ID NO: 5 can be mutated to aspartic acid (D). In one embodiment, the Fc domain can comprise, essentially consist of, or consist of an amino acid sequence of SEQ ID NO: 6 or a fragment thereof or a variant thereof.

Depending on the selected administration route, the compositions or preparations can be in any form, e.g., a tablet, a lozenge, a suspension, a free-flowing powder, an aerosol, and a capsule. The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a pharmaceutically-acceptable material, composition or vehicle for administration of an active agent described herein. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) C2-C12 alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation. For compositions or preparations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a preparation described herein, depending on the administration route and formulation. The compositions and preparations described herein can be delivered via any administration mode known to a skilled practitioner. For example, the compositions and preparations described herein can be delivered in a systemic manner, via administration routes such as, but not limited to, oral, and parenteral including intravenous, intramuscular, intraperitoneal, intradermal, and subcutaneous. In some embodiments, the compositions and preparations described herein are in a form that is suitable for injection. In other embodiments, the compositions and preparations described herein are formulated for oral administration.

When administering parenterally, a composition and preparation described herein can be generally formulated in a unit dosage injectable form (solution, suspension, emulsion). The compositions and preparations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

An oral composition can be prepared in any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Liquid preparations for oral administration can also be prepared in the form of a dry powder to be reconstituted with a suitable solvent prior to use.

The compositions can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions described herein, however, any vehicle, diluent, or additive used should have to be biocompatible with the active agents described herein. Those skilled in the art will recognize that the components of the compositions should be selected to be biocompatible with respect to the active agent. This will present no problem to those skilled in chemical and pharmaceutical principles, or problems can be readily avoided by reference to standard texts or by simple experiments (not involving undue experimentation).

In some embodiments, the compositions and preparations described herein can be formulated in an emulsion or a gel. Such gel compositions and preparations can be implanted locally to a diseased tissue region of a subject.

For in vivo administration, the compositions or preparations described herein can be administered with a delivery device, e.g., a syringe. Accordingly, an additional aspect described herein provides for delivery devices comprising at least one chamber with an outlet, wherein the at least one chamber comprises a pre-determined amount of any composition described herein and the outlet provides an exit for the composition enclosed inside the chamber. In some embodiments, a delivery device described herein can further comprise an actuator to control release of the composition through the outlet. Such delivery device can be any device to facilitate the administration of any composition described herein to a subject, e.g., a syringe, a dry powder injector, a nasal spray, a nebulizer, or an implant such as a microchip, e.g., for sustained-release or controlled release of any composition described herein.

In some embodiments of the products described herein, the microbe-binding microparticles described herein itself can be modified to control its degradation and thus the release of active agents. In some embodiments, the engineered microbe-binding molecules, microbe-binding microparticles and/or microbe-binding cells described herein can be combined with other types of delivery systems available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations thereof. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neukal fats such as mono-, di- and triglycerides; hydrogel release systems; liposome-based systems; phospholipid based-systems; silastic systems; peptide based systems; or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and—29 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system can be used to deliver one or more embodiments of the compositions or preparations described herein. Use of a long-term sustained release formulations or implants can be particularly suitable for treatment of some infections. Long-term release, as used herein, means that a formulation or an implant is made and arranged to deliver compositions or preparations described herein at a therapeutic level for at least 30 days, or at least 60 days. In some embodiments, the long-term release refers to a formulation or an implant being configured to deliver an active agent at a therapeutic level over several months.

Kits for capturing and detecting and/or determining the presence or absence of a microbe and/or microbial matter in a sample are also provided herein. In some embodiments, the kit can comprise: (a) one or more containers containing a population of the microbe-binding molecules described herein; and (b) at least one reagent. In some embodiments, the microbe-binding molecules described herein can each comprise a detectable label coupled thereto. Thus, the microbe-binding molecules are provided as a ready-for-use detection agent. In other embodiments, the microbe-binding molecules can be provided with no detectable label fused thereto. Instead, users can couple their own choice of detectable labels to the microbe-binding molecules described herein. In some embodiments, the kit can further comprise one or more containers containing at least one detectable label.

Depending on the choice of detection methods, each distinct subset of the microbe-binding molecules can comprise a unique detection label or the same detection label. For example, if each distinct subset of the microbe-binding molecules is used in a different sampling well, the same detection label can be used on the microbe-binding molecules. However, if it is desirable to use multiple different microbe-binding molecules in the same well, it is preferably to have each distinct subset of microbe-binding molecules comprising a distinct detection label (e.g., a unique fluorescent molecule).

Detectable labels suitable for use in any kits provided herein include any composition detectable by spectroscopic, photochemical, biochemical, immunochemical, electrical, optical or chemical means. Any art-recognized detectable labels or the ones described herein can be included in the kits described herein.

Means of detecting such labels are well known to those of skill in the art and exemplary detection methods are described herein. For example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments, the kit can further comprise a microbe-capture device or microbe-binding article. As used interchangeably herein, the terms "microbe-capture device" and "microbe-binding article" refers to a device or an article that is capable of capturing microbe(s) and/or microbial matter. Examples of a microbe-capture device include, but are not limited to a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a spiral mixer, and a hollow-fiber reactor. In some embodiments, the microbe-capture device can comprise a solid surface and microbe-capture molecules coupled thereto. In some embodiments, the microbe-capture molecules can comprise any embodiments of the molecules described in the International Patent Publication Nos. WO 2013/012924 and WO 2011/090954, the contents of each of which are incorporated herein by reference in their entirety. In some embodiments, the microbe-capture molecules can be the microbe-binding molecules described herein. The microbe-binding molecules described herein can be used as a detection agent as well as a capture agent.

In these embodiments, a user can generate their own microbe-binding article by conjugating the microbe-capture molecules to their desired substrate or article, e.g., using any art-recognized conjugation chemistry and/or methods described herein. In such embodiments, the reagent can include, but is not limited to, a coupling agent for conjugation of microbe-capture molecules to a substrate. In some embodiments, the kit can further comprise one or more substrates (e.g., microbeads such as magnetic microbeads) to which the microbe-capture molecules are conjugated. In such embodiments, a user can further modify the surface chemistry of the provided substrate prior to conjugation of the microbe-capture molecules to the substrate.

In other embodiments, the kit can provide microbe-binding substrates that are ready for use. In some embodiments, the microbe-binding substrate can include one or more microbe-binding dipsticks, e.g., as described herein. In other embodiments, the microbe-binding substrate can include a population of microbe-binding microbeads (including, but not limited to, polymeric microbeads and magnetic microbeads). In some embodiments, the microbe-binding substrate can include a population of microbe-binding magnetic microbeads. The microbe-binding microbeads or microbe-binding magnetic microbeads can be provided in one or more separate containers, if desired. In some embodiments, the population of the microbe-binding microbeads or magnetic microbeads contained in one or more containers can be lyophilized.

In some embodiments of any aspects of the kits described herein, the population of the microbeads or microbe-binding microbeads can comprise at least one distinct subset of the microbeads or microbe-binding microbeads, respectively. For example, each distinct subset of the microbeads or microbe-binding microbeads can be provided in a separate container. In some embodiments, the distinct subset of the microbeads or microbe-binding microbeads can have a size. In some embodiments, the distinct subset of microbe-binding microbeads can comprise on their surfaces a different density of microbe-capture molecules from the rest of the population. In these embodiments, two or more subsets of the microbe-capture molecules having different sizes and/or different coating density of the microbe-capture molecules can be used to detect and differentiate microbes of different classes and/or sizes, e.g., employing the methods described herein. In some embodiments, the distinct subset of microbe-binding substrates, e.g., microbe-binding microbeads, can comprise a different carbohydrate recognition domain from the others.

In one embodiment, the microbe-binding article provided in the kit can include a dipstick or test strip or membrane containing one or more microbe-capture molecules, e.g., microbe-binding dipstick or membrane described herein. In this embodiment, the kit can comprise 1, 2, 3, 4, 5, 6, 7, 8, 9, 10, 15, 20, 25, 50, 75, 100, 150, 200 or more microbe-binding dipsticks or test strips described herein. These kits comprising the microbe-binding dipsticks or test strips can be used as a diagnostic or probe for a microbe anywhere, e.g., at home, in clinics or hospitals, on emergency vehicles, in outdoor environments, in food processing plants, and anywhere in need of microbe capture and/or detection.

In some embodiments, each microbe-binding article described herein, e.g., each microbe-binding dipstick or membrane, can be individually packaged to maintain their sterility. In some embodiments, two or more products (e.g., 2, 3, 4, 5, 6, 7, 8, 9, 10, 15, 20, 25, 50, or more products such as microbe-binding dipsticks or membranes) can be packaged into one single unit. In such embodiments, users may sterilize any unused products after opening, e.g., with UV radiation, high temperature, gamma-radiation, ethylene oxide sterilization or any other known methods that would not significantly affect the activity of the engineered microbe-binding molecules for microbe detection.

In other embodiments, the microbe-binding article provided in the kit can include a population of microbe-binding microparticles. In some embodiments, the microbe-binding microparticles can be lyophilized.

In some embodiments, the kit can further comprise at least one blood collection container or any equivalent sample container or chamber, including at least 1, at least 2, at least 3, at least 4, at least 5, at least 6, at least 7, at least 8, at least 9, at least 10, at least 15, at least 20 blood collection containers or equivalent sample containers or chambers. In some embodiments, the population of the microbe-binding microbeads or magnetic microbeads can be pre-loaded in at least one blood collection container. In some embodiments, the blood collection container can further comprise an anti-coagulant agent described herein. In some embodiments, a blood sample can be directly added to such blood collection container containing a population of the microbe-binding articles for carrying out a microbe detection assay, e.g., as described herein. An ordinary artisan will readily appreciate that some embodiments of the microbe-binding articles (without magnetic properties) described herein can also be applicable for the assay. For example, instead of using a magnet to collect the microbe-binding magnetic microparticles after contact with a test sample (e.g., a blood sample), the microbe-binding article (without magnetic properties) can also be collected, e.g., by filtration, centrifugation or any other methods known in the art.

In some embodiments where the kits comprise microbe-binding magnetic microbeads, the kits can further comprise a magnet adapted for use with the assay for isolation of the microbe-binding magnetic microbeads from a test sample. For example, if the assay is carried out in a blood collection tube, the magnet can be adapted for use with the blood collection tube, e.g., a magnet can be designed to be a magnet collar surrounding the blood collection tube to immobilize or isolate the microbe-binding magnetic microbeads from a test sample or an assay buffer.

In any aspects of the kits provided herein, the kits can further comprise a portable readout machine or device, e.g., to determine and display the signal produced from the assay performed with the kit. For example, the readout machine or device can detect a colorimetric signal and/or a fluorescent signal produced from the assay of pathogen detection performed with the kits described herein.

In any aspects of the kits described herein, the kits can further include a reference for comparison with a readout determined from a test sample. An exemplary reference can be a strip or a chart showing different colors corresponding to various extents or degrees of a microbial infection.

Depending on different embodiments of the engineered microbe-binding molecules and/or products provided in the kits, some embodiments of any aspects of the kits described herein can further comprise an additional agent. For example, in some embodiments where the engineered microbe-binding molecules present on the substrate are unlabeled, the kit can further comprise one or more containers containing a population of detectable labels described earlier, each of which is conjugated to a targeting agent specific for a microbe, e.g., without limitations, one or more embodiments of an engineered microbe-binding molecule or a fragment thereof, an antibody specific for at least one microbe (e.g., antibodies specific for Gram-positive microbes such as anti-LTA antibodies, antibodies specific for Gram-negative microbes such as anti-LPS antibodies, or antibodies specific for fungus, and any combinations thereof), or an enzyme that induces a color change in the presence of an appropriate enzyme substrate (e.g., HRP or AP).

In any aspects of the kits provided herein, when the detection label includes an enzyme (e.g., horseradish peroxidase, alkaline phosphatase and any others commonly used for colorimetric detection), the kits can further comprise one or more containers containing an enzyme substrate that produces a color change in the presence of the enzyme. One of skill in the art can readily recognize an appropriate enzyme substrate for any art-recognized enzymes used for colorimetric detection. By way of example only, an exemplary substrate for alkaline phosphatase can include BCIP/NBT or PNPP (p-Nitrophenyl Phosphate, Disodium Salt); an exemplary substrate for horseradish peroxidase can include TMB.

In any aspects of the kits provided herein, the at least one reagent can be a wash buffer, a dilution buffer, a stop buffer, e.g., to stop the color development, a buffer solution containing a chelating agent described herein, or any combinations thereof. In one embodiment, at least one of the reagents provided in the kit can include at least one buffered solution containing a chelating agent. The chelating agent can be used to chelate any ions (e.g., divalent ions) present in the test samples or assay buffer, e.g., for inhibiting calcium-dependent binding of certain microbes, but not others, to some embodiments of the microbe-binding molecules described herein. Accordingly, such kit can be used to distinguish one microbe (e.g., S. aureus) from another (e.g., E. coli) in a test sample, e.g. employing some embodiments of the method described herein.

In any aspects of the kits provided herein, the kits can further comprise at least one microtiter plate, e.g., for performing the reaction and the detection.

In addition to the above mentioned components, any embodiments of the kits described herein can include informational material. The informational material can be descriptive, instructional, marketing or other material that relates to the methods described herein and/or the use of the aggregates for the methods described herein. For example, the informational material can describe methods for using the kits provided herein to perform an assay for pathogen or microbe capture and/or detection. The kit can also include an empty container and/or a delivery device, e.g., which can be used to deliver a test sample to a test container.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments, the kit can contain separate containers, dividers or compartments for each component and informational material. For example, each different component can be contained in a bottle, vial, or syringe, and the informational material can be contained in a plastic sleeve or packet. In other embodiments, the separate elements of the kit are contained within a single, undivided container. For example, a collection of the magnetic microbeads is contained in a bottle, vial or syringe that has attached thereto the informational material in the form of a label.

In general, the kits described herein can be used to separate, remove, and/or detect a microbe present in a test sample. In some embodiments, the kits can be used to differentiate between different microbe species, classes, and/or sizes, by employing the methods and/or assays described herein. By way of example only, some embodiments of the kits can be used to detect the presence or absence of a gram-positive microbe in a test sample. Accordingly, some embodiments of the kits described herein can be used to detect or determine the presence or absence of at least one gram-positive microbe in a test sample.

In some embodiments, the kits described herein can be used to screen a pharmaceutical product (e.g., a drug, a therapeutic agent, or an imaging agent), or a medical device (including, but not limited to, implantable devices) for the presence or absence of microbial matter (including, but not limited to, endotoxins secreted by a microbe).

In accordance with some aspects described herein, a test sample or sample, including any fluid or specimen (processed or unprocessed), that is suspected of comprising a microbe and/or microbial matter can be subjected to an assay or method, kit and system described herein. The test sample or fluid can be liquid, supercritical fluid, solutions, suspensions, gases, gels, slurries, and combinations thereof. The test sample or fluid can be aqueous or non-aqueous.

In some embodiments, the test sample can be an aqueous fluid. As used herein, the term "aqueous fluid" refers to any flowable water-containing material that is suspected of comprising a microbe and/or microbial matter.

In some embodiments, the test sample can include a biological fluid obtained from a subject. Exemplary biological fluids obtained from a subject can include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In some embodiments, a biological fluid can include a homogenate of a tissue specimen (e.g., biopsy) from a subject.

In some embodiments, the biological fluid sample obtained from a subject, e.g., a mammalian subject such as a human subject or a domestic pet such as a cat or dog, can contain cells from the subject. In other embodiments, the biological fluid sample can contain non-cellular biological material, such as non-cellular fractions of blood, saliva, or urine, which can be used to measure plasma/serum biomarker expression levels.

The biological fluid sample can be freshly collected from a subject or a previously collected sample. In some embodiments, the biological fluid sample used in the assays and/or methods described herein can be collected from a subject no more than 24 hours, no more than 12 hours, no more than 6 hours, no more than 3 hours, no more than 2 hours, no more than 1 hour, no more than 30 mins or shorter.

In some embodiments, the biological fluid sample or any fluid sample described herein can be treated with a chemical and/or biological reagent described herein prior to use with the assays and/or methods described herein. In some embodiments, at least one of the chemical and/or biological reagents can be present in the sample container before a fluid sample is added to the sample container. For example, blood can be collected into a blood collection tube such as VACU-TAINER®, which has already contained heparin. Examples of the chemical and/or biological reagents can include, without limitations, surfactants and detergents, salts, cell lysing reagents, anticoagulants, degradative enzymes (e.g., proteases, lipases, nucleases, collagenases, cellulases, amylases), and solvents such as buffer solutions.

In some embodiments, the test sample can include a fluid or specimen obtained from an environmental source, e.g., but not limited to, water supplies (including wastewater), ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the test sample can include a fluid (e.g., culture medium) from a biological culture. Examples of a fluid (e.g., culture medium) obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the test sample can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

As used herein, the term "reagent" refers to any solution used in a laboratory or clinical setting for biomedical and molecular biology applications. Reagents include, but are not limited to, saline solutions, PBS solutions, buffered solutions, such as phosphate buffers, EDTA, Tris solutions, and any combinations thereof. Reagent solutions can be used to create other reagent solutions. For example, Tris solutions and EDTA solutions are combined in specific ratios to create "TE" reagents for use in molecular biology applications.

In some embodiments, the test sample can be a non-biological fluid. As used herein, the term "non-biological fluid" refers to any fluid that is not a biological fluid as the term is defined herein. Exemplary non-biological fluids include, but are not limited to, water, salt water, brine, buffered solutions, saline solutions, sugar solutions, carbohydrate solutions, lipid solutions, nucleic acid solutions, hydrocarbons (e.g. liquid hydrocarbons), acids, gasoline, petroleum, liquefied samples (e.g., liquefied samples), and mixtures thereof.

As used herein, the term "microbes" or "microbe" generally refers to microorganism(s), including bacteria, fungi, protozoan, archaea, protists, e.g., algae, and a combination thereof, as well as microbial matter. The term "microbes" encompasses both live and dead microbes. The term "microbes" also includes pathogenic microbes or pathogens, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis. In some embodiments, the microbe is a gram-positive microbe.

Microbe-induced diseases: In some other embodiments, the engineered microbe-binding molecules or articles, assays, products and kits described herein can be used to detect or bind to gram-positive microbe or associated microbial matter. Some exemplary gram-positive microbes include, but are not limited to, the genera *Aerococcus, Bacillus, Bifdobacterium, Carcina, Clostridium, Corprococcus, Corynebacterium, Deinobacter, Deinococcus, Enterococcus, Erysipelothrix, Eubacterium, Gemella, Lactobacillus, Lactococcus, Leuconostoc, Listeria, Marinococcus, Micrococcus, Pediococcus, Peptococcus, Peptostreptococcus, Planococcus, Propionibacterium, Ruminococcus, Saccharococcus, Salinococcus, Staphylococcus, Staphylococcus, Stomatococcus, Streptococcus. Streptomyces, Trichococcus,* and *Vagococcus*. Some specific gram-positive microbe species include, but are not limited to, *Actinomyces* spp., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus,*

*Bacillus licheniformis, Bacillus megaterium, Bacillus pumilus, Bacillus stearothennophilus, Bacillus subtilis, Bacillus thuringiensis, Bifidobacterium* spp., *Clostridium clostridiiforme, Clostridium difficile, Clostridium innocuum, Clostridium perfringens, Clostridium ramosum, Corynebacterium jeikeium, E. lentum, Enterococcus faecalis, Enterococcus faecium, Enterococcus gallinarum, Eubacterium aerofaciens, L. casei, L. plantarum, Lactobacillus acidophilus, Lactococcus lactis, Lactococcus* spp., *Leuconostoc* spp., *Listeria monocytogenes, Moraxella* spp. (including *M. catarrhalis*), *Mycobacterium leprae, Mycobacterium tuberculosis, P. asaccarolyticus, P. magnus, P. micros, P. prevotii, P. productus, Pediococcus, Peptostreptococcus anaerobius, Propionibacterium acnes, Staphylococcus aureus, Staphylococcus aureus* (MRSA), *Staphylococcus epidermidis, Staphylococcus haemolyticus, Staphylococcus hominis, Staphylococcus lugdunensis, Staphylococcus saprophytics, Streptococcus agalactiae, Streptococcus avium, Streptococcus bovis, Streptococcus lactis, Streptococcus mitis, Streptococcus pneumoniae, Streptococcus pyogenes, Streptococcus sangius, Streptococcus viridans*, and *Streptomyces lividans*.

In some embodiments, the engineered microbe-binding molecules or articles, products, and kits described herein can be described herein can be used to differentiate a gram-positive microbe from a gram-negative microbe by employing the methods or assays described herein.

One skilled in the art can understand that the engineered microbe-binding molecules or substrates, products and kits described herein can be used to target any microorganism with a microbe-binding domain described herein modified for each microorganism of interest. A skilled artisan can determine the cell-surface proteins or carbohydrates for each microorganism of interest using any microbiology techniques known in the art.

Biofilm:

Accordingly, in some embodiments, the microbe-binding molecules or substrates, products and kits herein can be used to detect microbes and/or associated microbial matter present in a biofilm or to treat equipment surfaces to prevent or inhibit formation of a biofilm. For example, *Listeria monocytogenes* can form biofilms on a variety of materials used in food processing equipment and other food and non-food contact surfaces (Blackman, J Food Prot 1996; 59:827-31; Frank, J Food Prot 1990; 53:550-4; Krysinski, J Food Prot 1992; 55:246-51; Ronner, J Food Prot 1993; 56:750-8). Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et al., Annu Rev Microbiol 1995; 49:711-45). In some embodiments, the engineered microbe-binding microparticles, e.g., encapsulating a drug or a chemical for treatment of a biofilm, can be sprayed on contaminated equipment surfaces. The bacteria present in the biofilm bind to the microbe-binding microparticles, which release the drug to treat the bacteria for targeted drug delivery.

In addition, *L. monocytogenes* attached to surfaces such as stainless steel and rubber, materials commonly used in food processing environments, can survive for prolonged periods (Helke and Wong, J Food Prot 1994; 57:963-8). This would partially explain their ability to persist in the processing plant. Common sources of *L. monocytogenes* in processing facilities include equipment, conveyors, product contact surfaces, hand tools, cleaning utensils, floors, drains, walls, and condensate (Tomkin et al., Dairy, Food Environ Sanit 1999; 19:551-62; Welboum and Williams, Dairy Food Environ Sanit 1999; 19:399-401). In some embodiments, the engineered microbe-binding molecules can be configured to include a "smart label", which is undetectable when conjugated to the engineered microbe-binding molecules, but produces a color change when released from the engineered molecules in the presence of a microbe enzyme. Thus, when a microbe binds to the engineered microbe-binding molecules, the microbe releases enzymes that release the detectable label from the engineered molecules. An observation of a color change indicates a risk for bacteria contamination on a particular surface, and thus some embodiments of the engineered microbe-binding molecules and products can be used for early detection of biofilm formation.

Plant Microbes:

In still further embodiments, the engineered microbe-binding molecules or substrates and products described herein can be used to target plant microbes and/or associated microbial matter. Plant fungi have caused major epidemics with huge societal impacts. Examples of plant fungi include, but are not limited to, *Phytophthora infestans, Crinipellis perniciosa*, frosty pod (*Moniliophthora roreri*), oomycete *Phytophthora capsici, Mycosphaerella fijiensis, Fusarium Ganoderma* spp fungi and *Phytophthora*. An exemplary plant bacterium includes *Burkholderia cepacia*. Exemplary plant viruses include, but are not limited to, soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

Military and Bioterrorism Applications:

In yet other embodiments, the engineered microbe-binding molecules and product comprising thereof can be used to detect or combat bioterror agents (e.g., *B. Anthracis*, and smallpox).

In accordance with some embodiments described herein, an engineered microbe-binding molecule or microbe-binding substrate can be modified to bind to any of the microbes, e.g., the ones described herein, including the associated microbial matter (e.g., but not limited to, fragments of cell wall, microbial nucleic acid and endotoxin).

General methods of preparing any embodiments of the engineered microbe-binding molecules are known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60).

While the exemplary sequences provided herein are derived from a human species, amino acid sequences for same or functionally equivalent domains from other species such as mice, rats, porcine, bovine, feline, and canine are known in the art and within the scope described herein. Further, a skill artisan can readily modify the identified sequences to modulate their orientation or binding performance, e.g., by theoretical modeling or in vitro binding experiments. In addition, based on the crystal structure of the native sequences, peptidomimetics that can effectively mimic at least a fragment of a given domain can be also used as a first or second domain of the engineered microbe-binding molecule described herein. One of skill in the art can readily determine such peptidomimetic structure without undue experimentations, using any methods known in the art and the known crystal structure.

In another strategy of directed evolution, the protein of interest is subjected to random mutagenesis and the resulting proteins are screened for desired qualities. This is a particularly useful technology for affinity maturation of phage display antibodies, where the antibody complementary determining regions (CDRs) are mutated by saturation mutagenesis and successful variants of the six CDRs are shuffled together to form the highest affinity antibodies.

The directed evolution paradigm can be applied to any domain described herein to select variants with a desired property, such as specific binding to, e.g., but not limited to, yeast, gram-positive bacteria, gram-negative, coagulase negative, and aerobic bacteria. For this to work, however, the pattern and nature of the target sugars or related surface features on these target microorganisms can differ between the classes or species.

Derivatives with a particular specificity can be isolated, e.g., by the following approach, which is a standard phage display strategy: First, express a set of variants from a phagemid vector; then bind this library to a target of interest and perform one or two rounds of selection; and then perform a round of negative selection against a related target, taking those phagemids that fail to bind. These cycles of positive and negative selection are then repeated until a population of phages that generally bind to the target and do not bind to the non-target is generated. This method can be applied to any pair of microbial strains against which differential binding is desired, such as bacteria that are resistant and sensitive to a given antibiotic. This positive/negative enrichment strategy can also be used with an antibody-phage display library, which is an even more standard way to isolate such specific binders.

The constructs for the microbe-binding molecules described herein can be inserted into a vector. As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, *Molecular Cloning: A Laboratory Manual.* 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., J-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any embodiment of the microbe-binding molecule described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*. Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

A nucleic acid molecule that encodes any embodiment of the microbe-binding molecule described herein can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

Another aspect described herein related to a method, which comprises recombinantly expressing in a cell one or more constructs encoding the microbe-binding molecule according to one or more embodiments disclosed herein. Some aspects provided herein are directed to cell culture medium or supernatant collected from culturing a cell expressing one or more nucleic acids described herein. Other aspects provided herein are directed to a method, comprising culturing in cell culture medium a cell expressing one or more nucleic acids described herein.

The engineered microbe-binding molecules can contain sequences from the same species or from different species. For example, an interspecies hybrid microbe-binding molecule can have one of the disclosed domains (e.g., collagen domain, Fc domain, helical domain, and carbohydrate recognition domain) from a murine species and the other from a human. The engineered microbe-binding molecules described herein can also include those that are made entirely from murine-derived sequences or fully human.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "StemFcMBL" refers to a microbe-binding molecule according to one or more embodiments described herein. In general, the microbe-binding molecule comprises a collagen domain, an Fc domain, a microbe-binding domain comprising a helical domain and a carbohydrate-recognition domain. In some embodiments, the Fc domain can link the collagen domain to the microbe-binding domain. In some embodiments, the collagen domain can link the Fc domain to the microbe-binding domain and there is no cysteine-rich domain between the Fc domain and the collagen domain. In some embodiments, the microbe-binding molecule can be coupled to a detectable label.

As used herein, the term "avidity" is a characteristic that describes the overall strength of binding between a molecule (e.g., a microbe-binding molecule) and its target (e.g., microbe(s) and/or microbial matter), taking into account their interactions with one another at multiple sites. In some instances, the overall strength of binding between a molecule (e.g., a microbe-binding molecule) and its target (e.g., microbe(s) and/or microbial matter) is greater than the sum of the individual bond affinities. To illustrate, for a molecule (e.g., a microbe-binding molecule) having multiple target binding sites (e.g., for microbes and/or microbial matter) that simultaneously interact with a single target, each individual binding interaction on its own can be readily broken. However, when a molecule (e.g., a microbe-binding molecule) and its target (e.g., microbe(s) and/or microbial matter) are bound at multiple sites, the overall effect is synergistic because binding of such a molecule (e.g., a microbe-binding molecule) to its target (e.g., microbe(s) and/or microbial matter) can be reinforced by the presence of other binding interactions when there is transient separation of a single binding site on the molecule from the target.

The term "antibody" as used herein refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, humanized antibodies, human antibodies, and single chain antibodies (scFvs).

The term "peptide" refers to a polymer of amino acids, or amino acid analogs, regardless of its size or function. In some embodiments, the term "peptide" refers to small polypeptides, e.g., a polymer of about 15-25 amino acids.

The term "oligonucleotide" as used herein refers to a short nucleic acid polymer, typically with twenty or fewer bases.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein.

In some embodiments, the subject is a mammal. The mammal can be a human, non-human primate, mouse, rat, dog, cat, horse, or cow, but are not limited to these examples. Mammals other than humans can be advantageously used as subjects that represent animal models of disorders.

A subject can be one who has been previously diagnosed with or identified as suffering from or having a disease or disorder caused by any microbes or pathogens described herein. By way of example only, a subject can be diagnosed with sepsis, inflammatory diseases, or infections.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

As used herein, the term "peptidomimetic" means a peptide-like molecule that has the activity of the peptide on which it is structurally based. Such peptidomimetics include chemically modified peptides, peptide-like molecules containing non-naturally occurring amino acids, and peptoids, and have an activity such as the microbe-binding specificity of the peptide upon which the peptidomimetic is derived (see, for example, Goodman and Ro, Peptidomimetics for Drug Design, in "Burger's Medicinal Chemistry and Drug Discovery", Vol. 1 (ed. M. E. Wolff; John Wiley & Sons 1995), pages 803-861).

A variety of peptidomimetics are known in the art and can be encompassed within embodiments described herein including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an Nα-Cαcyclized amino acid; an Nα-methylated amino acid; α- or γ-amino cycloalkane carboxylic acid; an α,β-unsaturated amino acid; a β,β-dimethyl or β-methyl amino acid; αβ-substituted-2,3-methano amino acid; an N-Cδ or Cα-Cδ cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; transolefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide described herein, as well as potential geometrical and chemical complementarity to a cognate receptor. Where no crystal structure of a peptide described herein is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide described herein, for example, having specificity for the microbes.

The terms "homology" as used herein refers to sequence similarity between two peptides or between two nucleic acid molecules. Homology can be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology refers to a function of the number of identical or similar amino acids at positions shared by the compared sequences. A sequence which is "unrelated" or "non-homologous" shares less than 40% identity. Determination of homologs of the genes or peptides described herein may be easily ascertained by the skilled artisan.

The term "conservative substitution," when describing a polypeptide, refers to a change in the amino acid composition of the polypeptide that does not substantially alter the polypeptide's activity, fore examples, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions." Insertions or deletions are typically in the range of about 1 to 5 amino acids.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, "operably linked" refers to juxtaposition such that the normal function of the components can be performed. Thus, a coding sequence "operably linked" to control sequences refers to a configuration wherein the coding sequences can be expressed under the control of these sequences. Such control may be direct, that is, a single gene associated with a single promoter, or indirect, as in the case where a polycistronic transcript is expressed from a single promoter. See, for example, U.S. Pat. Nos. 4,980,285; 5,631,150; 5,707,828; 5,759,828; 5,888,783 and, 5,919,670, and Sambrook et al., *Molecular Cloning: A Laboratory Manual.* 2nd Ed., Cold Spring Harbor Press (1989).

As used herein, "expression" refers to gene expression. Genes and gene products can be expressed. Such gene products include RNAs, and proteins.

As used herein, the term "promoter" has its art-recognized meaning, denoting a portion of a gene containing DNA sequences that provide for the binding of RNA polymerase and initiation of transcription. Promoter sequences are commonly, but not always, found in the 5' non-coding regions of genes. Sequence elements within promoters that function in the initiation of transcription are often characterized by consensus nucleotide sequences. Useful promoters include constitutive and inducible promoters. Many such promoter sequences are known in the art. See, for example, U.S. Pat. Nos. 4,980,285; 5,631,150; 5,707,828; 5,759,828; 5,888, 783; 5,919,670, and, Sambrook et al, *Molecular Cloning: A Laboratory Manual.* 2nd Ed., Cold Spring Harbor Press (1989). Other useful promoters include promoters which are neither constitutive nor responsive to a specific (or known) inducer molecule. Such promoters may include those that respond to developmental cues (such as growth phase of the culture or stage of cell differentiation), or environmental cues (such as pH, osmoticum, heat, or cell density). A heterologous promoter is a promoter which is not naturally linked to the gene. Heterologous promoters may be from the same or different species. For example, a heterologous promoter may be a promoter from the same organism as the gene but naturally found linked to a different gene.

As used herein, the term "transgene" when used in reference to polynucleotide sequences, refers to polynucleotide sequences not naturally present in a cell. Thus the term "transgene" includes, for example, the promoter of gene A operably joined to structural gene B, when A and B genes are from the same organism, as well as the case in which a polynucleotide sequence of one species is transferred to a cell of a different species (or strain). The term "transgene" also includes clones of transgenes which have been so modified. See, U.S. Pat. Nos. 4,980,285; 5,631,150; 5,707,828; 5,759,828; 5,888,783 and, 5,919,670.

As used herein, the terms "culture media," and "cell culture media," refers to media that are suitable to support the growth of cells in vitro (i.e., cell cultures). It is not intended that the term be limited to any particular cell culture medium. For example, it is intended that the definition encompass outgrowth as well as maintenance media. Indeed, it is intended that the term encompass any culture medium suitable for the growth of the cell cultures of interest.

As used herein, the term "cell type," refers to any cell, regardless of its source or characteristics.

As used herein, the term "isolated" means altered "by the hand of man" from the natural state. An "isolated" composition or substance is one that has been changed or removed from its original environment, or both. For example, a polynucleotide or a polypeptide naturally present in a cell or living animal is not "isolated," but the same polynucleotide or polypeptide separated from the coexisting materials of its natural state is "isolated," as the term is employed herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A microbe-binding molecule comprising:
   (i) a collagen domain;
   (ii) an Fc domain; and
   (iii) a microbe-binding domain comprising a helical domain and a carbohydrate recognition domain (CRD), wherein the Fc domain links the collagen domain to the microbe-surface binding domain.
2. The microbe-binding molecule of paragraph 1, wherein the microbe-binding molecule excludes a cysteine-rich domain.
3. A microbe-binding molecule comprising:
   (i) a collagen domain;
   (ii) an Fc domain; and
   (iii) a microbe-binding domain comprising a helical domain and a carbohydrate recognition domain (CRD), wherein the collagen domain links the Fc domain to the microbe-surface binding domain, and wherein the microbe-binding molecule excludes a cysteine-rich crosslinking domain.
4. The microbe-binding molecule of any of paragraphs 1-3, wherein the carbohydrate recognition domain forms the C-terminus of the microbe-binding molecule.
5. A microbe-binding molecule comprising:
   (i) a collagen domain;
   (ii) an Fc domain; and
   (iii) a microbe-binding domain comprising a helical domain and a carbohydrate recognition domain (CRD), wherein the microbe-surface binding domain links the collagen domain to the Fc domain, and wherein the microbe-binding molecule excludes a cysteine-rich crosslinking domain.
6. The microbe-binding molecule of any of paragraphs 1-5, wherein the collagen domain is at least about 15 amino acids or at least about 20 amino acids in length.
7. The microbe-binding molecule of any of paragraphs 1-6, wherein the collagen domain is from 15 to 60 amino acids in length.
8. The microbe-binding molecule of any of paragraphs 1-7, wherein the collagen domain forms a collagen-like triple helix with a second collagen domain of a second microbe-binding molecule.
9. The microbe-binding molecule of any of paragraph 1-8, wherein the collagen domain comprise a plurality of Gly-$Xaa_1$-$Xaa_2$ triplets, wherein $Xaa_1$ and $Xaa_2$ are each independently an animo acid residue.
10. The microbe-binding molecule of any of paragraphs 1-9, wherein the collagen domain is derived from a collagen-containing molecule selected from the group consisting of collectin (e.g., mannose binding lectin, surfactant protein), ficolin, a naturally-occurring or synthetic collagen-like peptide, and any combination thereof.
11. The microbe-binding molecule of paragraph 1-9, wherein the collagen domain comprises a collagen domain of mannose binding lectin or a fragment thereof.
12. The microbe-binding molecule of paragraph 11, wherein the collagen domain essentially consists of an amino acid sequence selected from a group consisting of SEQ ID NOs: 7-16.
13. The microbe-binding molecule of any of paragraphs 1-12, wherein the Fc domain comprises an IgG CH2 domain and an IgG CH3 domain and optionally comprises the hinge domain of an IgG microbe-binding molecule.
14. The microbe-binding molecule of paragraph 13, wherein the IgG is a mammalian IgG (e.g., IgG1, IgG2, IgG3, and IgG4) or a fragment thereof.
15. The microbe-binding molecule of any of paragraphs 1-12, wherein the Fc domain comprises a CH2 domain and a CH3 domain and optionally comprises the hinge domain of a mammalian IgA, IgD, IgE or IgM microbe-binding molecule.
16. The microbe-binding molecule of any of paragraphs 1-15, wherein the Fc domain comprises a mutation relative to a native sequence.
17. The microbe-binding molecule of paragraph 16, wherein the mutation is selected to: (i) increase biological half-life of the recombinant microbe-binding molecule; (ii) modulate anti-body dependent cell-mediated cytotoxicity; and/or (iii) modulate complement dependent cytotoxicity; and/or (iv) remove glycosylation of the Fc domain (e.g., N297D).
18. The microbe-binding molecule of any of paragraphs 1-17, wherein the helical domain is derived from a helix-containing molecule selected from the group consisting of collectin (e.g., mannose binding lectin, surfactant protein), ficolin, a synthetic helical peptide, and any combination thereof.
19. The microbe-binding molecule of any of paragraphs 1-18, wherein the CRD is derived from a sugar-binding molecule selected from the group consisting of: a sugar binding lectin (e.g., a mannose binding lectin; a collectin, a surfactant protein), DC-SIGN, macrophage mannose receptor, and any combinations thereof.
20. The microbe-binding molecule of paragraph 19, wherein the CRD comprises a CRD of mannose binding lectin 2 (MBL2) or a fragment thereof.
21. The microbe-binding molecule of any of paragraphs 1-20, wherein the microbe-binding molecule has an amino acid sequence selected from a group consisting of: SEQ ID NOs: 17-27, or an amino acid sequence having at least 90% homology to the selected amino acid sequence.
22. The microbe-binding molecule of any of paragraphs 1-21, further comprising a detectable label coupled thereto.
23. The microbe-binding molecule of paragraph 22, wherein the detectable label is selected from the group consisting of: biotin, fluorophore, luminescent or bioluminescent marker, a radiolabel, an enzyme, an enzyme substrate, a quantum dot, an imaging agent, a metal particle (e.g., a gold particle and/or silver particle), a magnetic particle, and any combinations thereof.
24. The microbe-binding molecule of paragraph 23, wherein the enzyme is selected from the group consisting of: horseradish peroxidase (HRP), alkaline phosphatase (AP), luciferase and beta-galactosidase.
25. The microbe-binding molecule of any of paragraphs 1-21, further comprising a detectable molecule fused to the Fc domain or the collagen domain.
26. The microbe-binding molecule of paragraph 25, wherein the detectable molecule comprises HRP, AP, luciferase, beta-galactosidase, or a fluorophore.
27. A microbe-binding multimeric molecule comprising:
(i) a first microbe-binding molecule of any of paragraphs 1-26;
(ii) a second microbe-binding molecule of any of paragraphs 1-26, wherein:
the helical domain of the first microbe-binding molecule forms a coiled structure with the helical domain of the second microbe-binding molecule; and
the collagen domain of the first microbe-binding molecule forms a triple helix structure with the collagen domain of the second microbe-binding molecule or the collagen domain of a third microbe-binding molecule of any of paragraphs 1-26.
28. The microbe-binding multimeric molecule of paragraph 27, comprising at least 10 microbe-binding molecule of any of paragraphs 1-26.
29. A kit for detection of microbial matter comprising:
(i) a container containing one or more microbe-binding molecules of any of paragraphs 22-28, wherein the microbe-binding molecules each comprises a detectable label; and
(ii) at least one reagent.
30. The kit of paragraph 29, further comprising a microbe-capture device, the microbe-capture device comprising a solid surface and microbe-capture molecules coupled thereto.
31. The kit of paragraph 30, wherein the microbe-capture device is selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a spiral mixer, and a hollow-fiber reactor.
32. The kit of any of paragraphs 29-31, wherein the detectable label is an enzyme and the kit further comprises a container containing an enzyme substrate that changes color in the presence of the enzyme.
33. The kit of any of paragraphs 29-31, wherein the detectable label comprises a fluorescent molecule.
34. The kit of any of paragraphs 29-33, wherein the at least one reagent is a wash buffer, a dilution buffer, a stop buffer, a buffered solution containing a chelating agent, or any combinations thereof.
35. A microbe-binding article comprising a solid surface, and at least one microbe-binding molecule of any of paragraphs 1-26 coupled to the solid surface.
36. The microbe-binding article of paragraph 35, wherein the solid surface is a surface of a solid substrate selected from the group consisting of a nucleic acid scaffold, a protein scaffold, a lipid scaffold, a dendrimer, microparticle or a microbead, a nanotube, a microtiter plate, a medical apparatus or implant, a microchip, a filtration device, a membrane, a diagnostic strip, a dipstick, an extracorporeal device, a spiral mixer, and a hollow fiber.
37. A pharmaceutical composition comprising at least one microbe-binding molecule of any of paragraphs 1-26 and a pharmaceutically acceptable carrier.
38. The pharmaceutical composition of paragraph 37, wherein the collagen domain, the Fc domain and the microbe-surface binding domain is derived from a human amino acid sequence.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Detection of a Microbe or Microbial Matter Using One or More Embodiments of the Microbe-Binding Molecules Described Herein as a Detection Agent The detection and capture of microbes (e.g., pathogens) and/or microbial matter in a microbial ELISA detection assay can be based on an FcMBL capture agent and a recombinant human full-length MBL detection reagent. For detailed information about FcMBL, please refer to the International Patent Publication Nos. WO 2013/012924 and WO 2011/090954, the contents of each of which are incorporated herein by reference in their entirety. While human full-length MBL is a great reagent, it is a non-renewable source and it is difficult to make. While FcMBL can be used as a detection agent, there is a need to engineer an improved microbe-binding molecule that shows greater sensitivity to recognize microbes and/or microbial matter (e.g., microbial cell wall components) in the detection ELISA. The inventors have, among other things, engineered at least two novel microbe-binding proteins (referred to as "StemFcMBL-2" and "StemFcMBL-3" herein) that both show higher sensitivity as a detection reagent than FcMBL and both are easier to produce than full-length MBL. The amino acid sequence and nucleotide sequence of StemFcMBL-2 are shown in FIG. 1B. The amino acid sequence and nucleotide sequence of StemFcMBL-3 are shown in FIG. 2B.

An exemplary detection assay using the microbe-binding molecules according to some embodiments described herein (e.g., StemFcMBL-2 or StemFcMBL-3) is described as follows:

1. Microbe-binding bead: FcMBL is coupled to superparamagnetic beads (example: FcMBL is biotinylated and coupled to streptavidin coated 1 µM MyONE beads). Alternatively, the microbe-binding molecule described herein can also be used as a microbe-capture agent and be coupled to superparamagnetic beads.
2. Capture: Microbe-binding beads are added to a test sample (for example, infected blood), mixed (capture step), removed, and washed for assaying.
3. Detection: Bead/microbe complex is detected by contacting the bead/microbe complex with one or more embodiments of the microbe-binding molecule described herein. In some embodiments, the microbe-binding molecule described herein can be coupled to a detectable label, e.g., a fluorophore or a horseradish peroxidase.

Figure 3A:
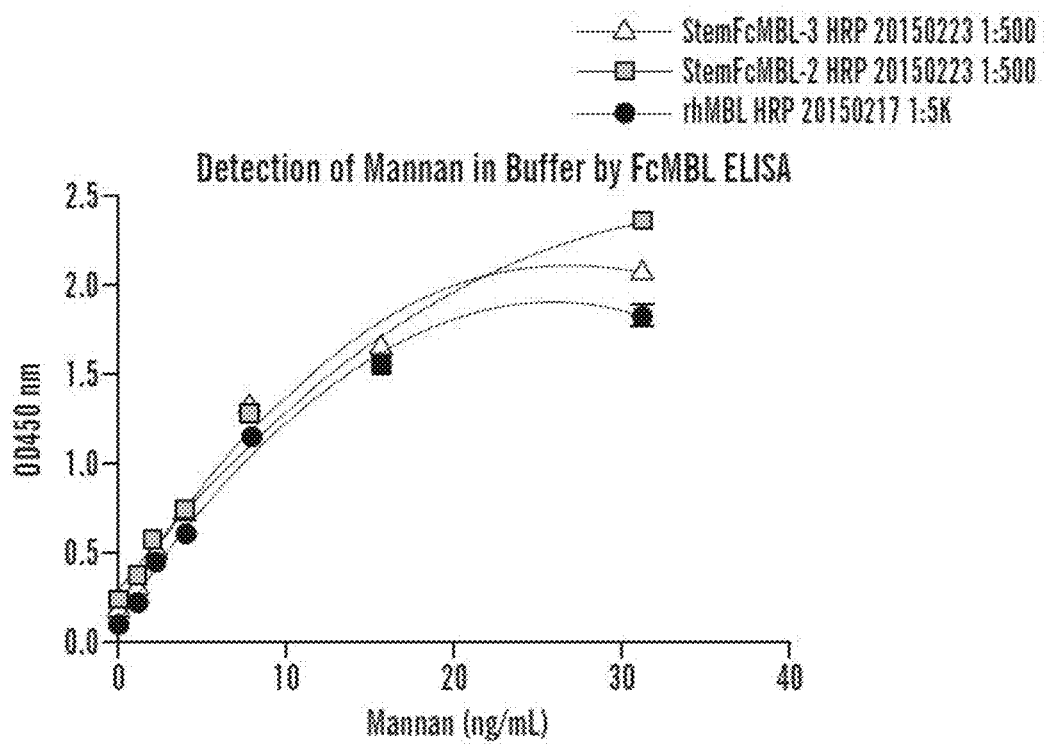
FIGS. 3A-3B show an example of mannan detection ELISA using rhMBL and different embodiments of microbe-binding molecules described herein as detection reagents.
Figure 3B:
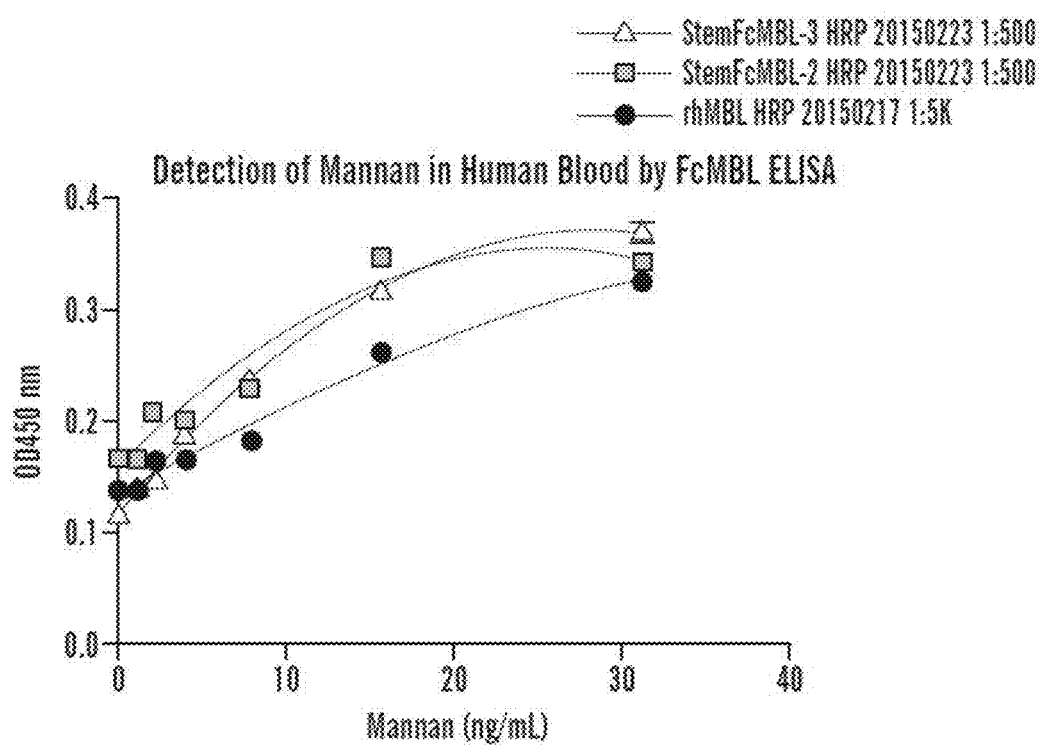

FIGS. 3A-3B show an example of mannan detection ELISA using rhMBL (full-length MBL), StemFcMBL-2, and StemFcMBL-3 as detection reagents. StemFcMBL-2 and StemFcMBL-3 were labeled with horseradish peroxidase (HRP) and used as detection agents in the mannan detection ELISA. FcMBL 1 µM beads were used to capture mannan, washed, mixed with the indicated detection agent. The sensitivity of each detection agent to detect microbial components was determined. FIG. 3B shows that StemFcMBL-2 and StemFcMBL-3 showed higher sensitivity in detecting mannan in a complex fluid, e.g., a blood sample, than the recombinant full-length MBL, and thus are better detection reagents.

Example 2: Synthesis and Expression of One or More Embodiments of the Microbe-Binding Molecules Described Herein Various construct for the microbe-binding molecules described herein were cloned into a mammalian expression vector downstream of a retroviral promoter. The vector was transfected into host cells, e.g., HEK 293F cells. Supernatant from the transfected cells was harvested to collect the microbe-binding protein molecules. For example, the supernatant from the transfected cells were run through a purification column, where the microbe-binding protein molecules were bound thereto in the presence of calcium and eluted using an EDTA containing buffer. In some embodiments, the methods used to purify FcMBL can be used for StemFcMBL-2 and/or StemFcMBL-3 purification.

Figures 7, 8:
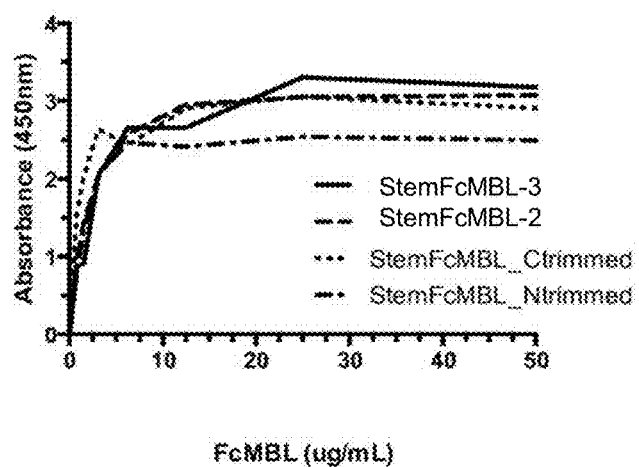
FIG. 7 is a graph showing detection of mannan with varying amounts of microbe-binding molecules according to some embodiments described herein.
FIG. 8 is a table showing the protein characteristics of some microbe-binding molecules according to two embodiments described herein.
Figure 9:
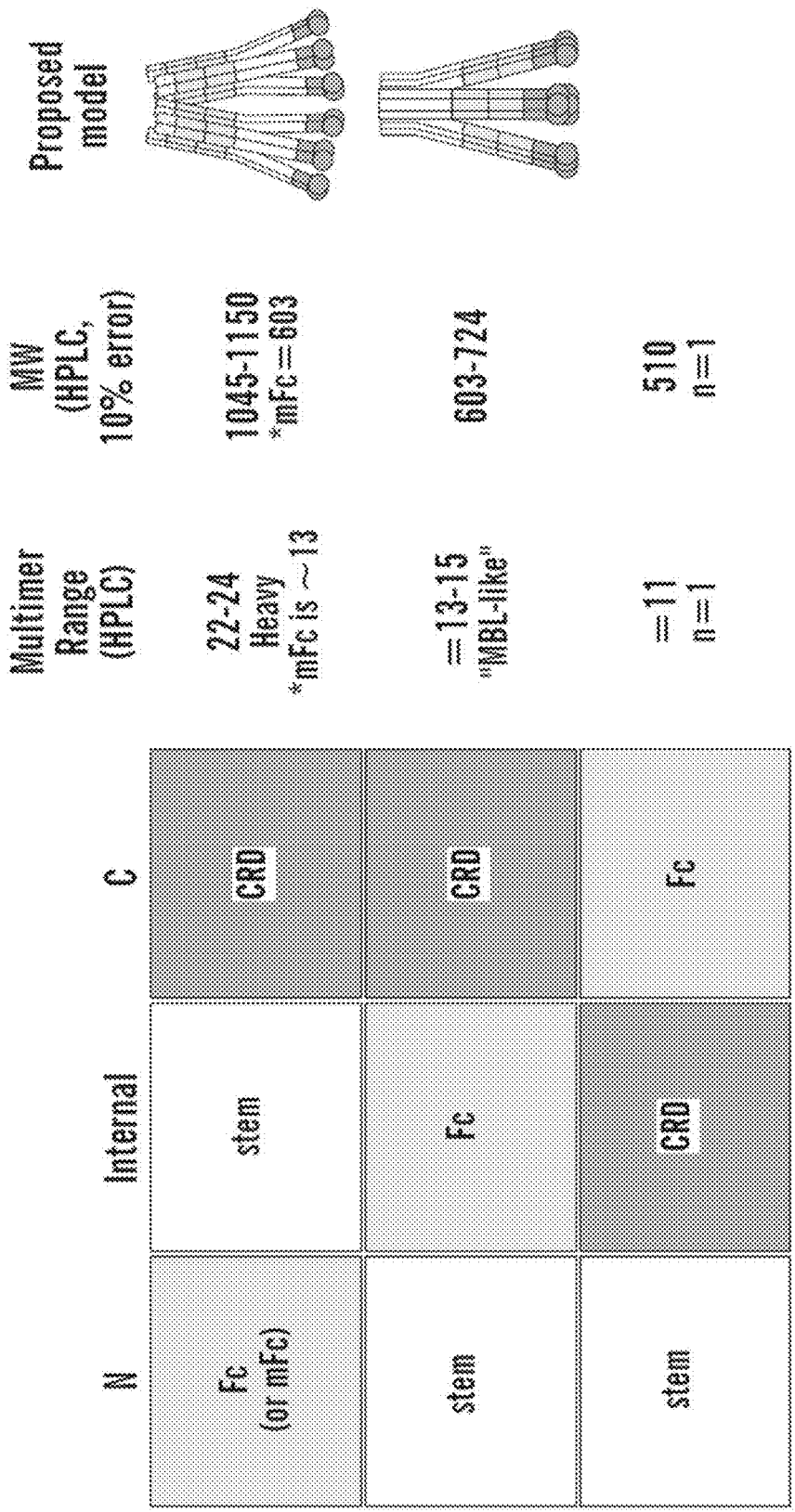
FIG. 9 shows exemplary microbe-binding molecules in different configurations and associated characteristics. For example, in some embodiments, the microbe-binding molecule can have its N-terminal domain comprising an Fc domain, its C-terminal domain comprising a carbohydrate recognition domain, and a collagen domain between the N-terminal domain and the C-terminal domain. In some embodiments, the microbe-binding molecule can have its N-terminal domain comprising a collagen domain, its C-terminal domain comprising a carbohydrate recognition domain, and an Fc domain between the N-terminal domain and the C-terminal domain. In some embodiments, the microbe-binding molecule can have its N-terminal domain comprising a collagen domain, its C-terminal domain comprising an Fc domain, and a carbohydrate recognition domain between the N-terminal domain and the C-terminal domain. Depending on the configuration of the microbe-binding molecule, the size of multimers formed from the microbe-binding molecule monomers can vary.

Example 3: Characterization of Binding Strength of One or More of the Microbe-Binding Molecules Described Herein Mannan ELISA can be be performed to assess the binding strength of the microbe-binding molecules described herein. For example, mannan was adsorbed onto a 96-well microtiter plate, which was subsequently blocked. The plate was then incubated with an indicated amount of StemFcMBL, washed with TBS-T, and assayed using HRP-conjugated anti-human IgG-Fc antibody & TMB substrate. As shown in FIG. 7, the higher the absorbance, the greater the retention of StemFcMBL and the better its binding strength.

Figure 10:
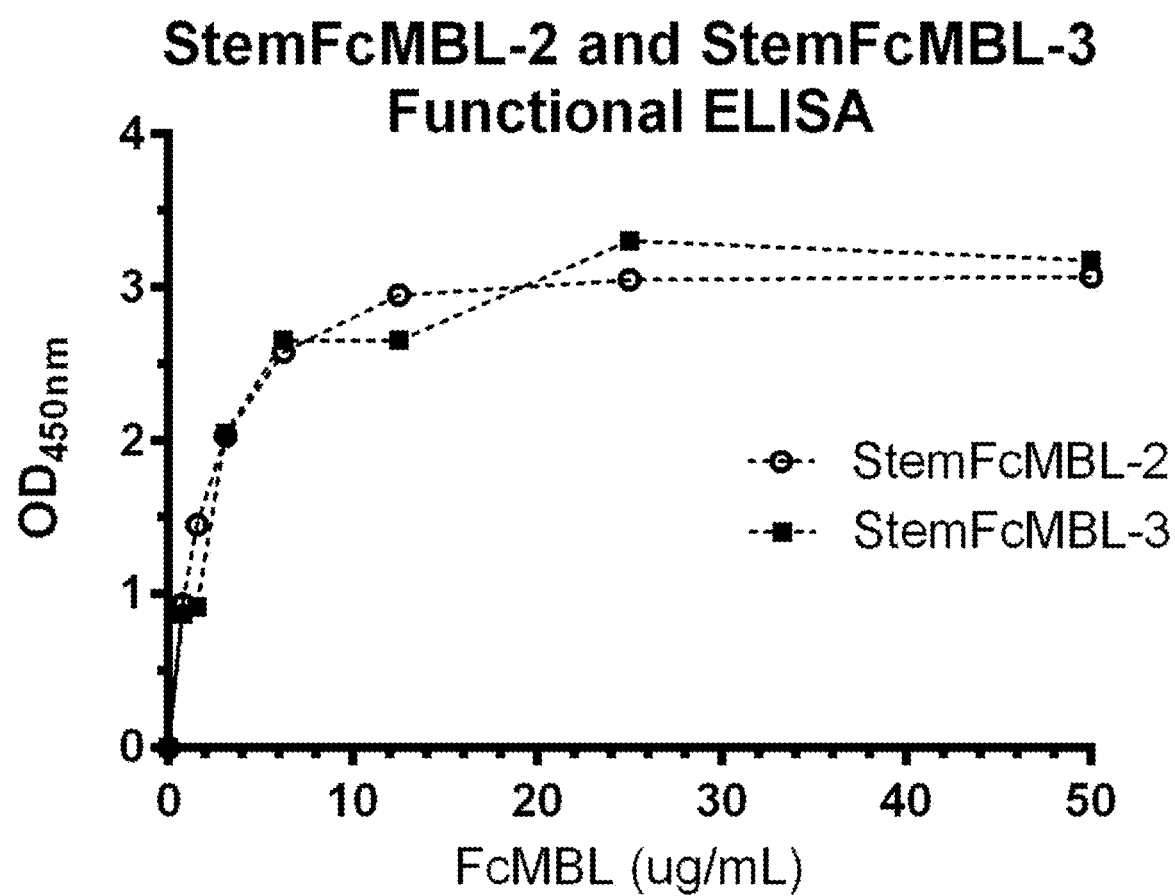
FIG. 10 is a line graph showing ELISA detection of mannan using large multimers of the microbe-binding molecules described herein.

Example 4: Characterization of Binding Strength of One or More of the Multimeric Microbe-Binding Molecules Described Herein Mannan ELISA can be performed to assess the binding strength of the multimeric microbe-binding molecules described herein. For example, mannan was adsorbed onto a 96-well microtiter plate, which was subsequently blocked. The plate was then incubated with an indicated amount of FcMBL monomers or multimers of various sizes (e.g., hexamers vs. about 13-15-mer), washed with TBS-T, and assayed using HRP-conjugated anti-human IgG-Fc antibody & TMB substrate. As shown in FIG. 10, the higher the absorbance, the greater the retention of the larger multimers and the better their binding strength.

Examples of Fc Sequences

```
Human IgG2 Fc
                                               (SEQ ID NO: 1)
VECPPCPAPPVAGPSVFLFPPKPKDTLMISRTPEVTCVVVDVSHEDPEVQ

FNWYVDGMEVHNAKTKPREEQFNSTFRVVSVLTVVHQDWLNGKEYKCKVS

NKGLPAPIEKTISKTKGQPREPQVYTLPPSREEMTKNQVSLTCLVKGFYP

SDIAVEWESNGQPENNYKTTPPMLDSDGSFFLYSKLTVDKSRWQQGNVFS

CSVMHEALHNHYTQKSLSLSPGK

Human IgG3 Fc
                                               (SEQ ID NO: 2)
DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQG

NIFSCSVMHEALHNRFTQKSLSLSPGK

Human IgG4 Fc
                                               (SEQ ID NO: 3)
PPCPSCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVF

SCSVMHEALHNHYTQKSLSLSLGK
```

Monomeric Fc from IgG1

(SEQ ID NO: 4)
EPKSSDKTHTCPPCPAPELLGGPSVFLFPPKPKDTLMISRTPEVTCVVVD
VSHEDPEVKFNWYVDGVEVHNAKTKPREEQYDSTYRVVSVLTVLHQDWLN
GKEYKCKVSNKALPAPIEKTISKAKGQPREPQVYTLPPSRDELTKNQVNL
TCLVKGFYPSDIAVEWESNGQPENNYKTTPPVLDSDGSFFLNSKLTVDKS
RWQQGNVFSCSVMHEALHNHYTQKSLSLSPGA

Dimeric Fc from IgG1 Human IgG-Fc domain including hinge region (underlined)

(SEQ ID NO: 5)
<u>EPKSSDKTHTCPPC</u>PAPELLGGPSVFLFPPKPKDTLMISRTPEVTCVVVD
VSHEDPEVKFNWYVDGVEVHNAKTKPREEQYDSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGA

An example Fc Sequence with Asn82Asp (N82D) modification. The modification is also commonly referred to as N297D (the numbering derived from human IgG)

(SEQ ID NO: 6)
EPKSSDKTHTCPPCPAPELLGGPSVFLFPPKPKDTLMISRTPEVTCVVVD
VSHEDPEVKFNWYVDGVEVHNAKTKPREEQYDSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPG

Exemplary Sequences for the Collagen Domain

MBLStem58: MBL residues 42-99:

(SEQ ID NO: 7)
GINGFPGKDGRDGTKGEKGEPGQGLRGLQGPPGKLGPPGNPGPSGSPGPK
GQKGDPGK

MBLStem32: MBL residues 68-99:

(SEQ ID NO: 8)
GLQGPPGKLGPPGNPGPSGSPGPKGQKGDPGK

MBLStem32(K_to_S): MBL residues 68-99, lysines replaced with serines:

(SEQ ID NO: 9)
GLQGPPGSLGPPGNPGPSGSPGPSGQSGDPGS

StemA_K75Q: MBL residues 42-99. K75Q mutation:

(SEQ ID NO: 10)
GINGFPGKDGRDGTKGEKGEPGQGLRGLQGPPGQLGPPGNPGPSGSPGPK
GQKGDPGK

MBLStem20_Ctrim: MBL residues 68-87:

(SEQ ID NO: 11)
GLQGPPGKLGPPGNPGPSGS

MBLStem20_Ntrim: MBL residues 80-99:

(SEQ ID NO: 12)
GNPGPSGSPGPKGQKGDPGK

SpA_Stem: Serum Protein A residues 28-98:

(SEQ ID NO: 13)
GSPGIPGTPGSHGLPGRDGRDGVKGDPGPPGPMGPPGETPCPPGNNGLPG
APGVPGERGEKGEAGERGPPG

Ficolin-L or Ficolin-2 residues 51-92:

(SEQ ID NO: 14)
GCPGLPGAPGPKGEAGTNGKRGERGPPGPPGKAGPPGPNGAP

Collectin-11 residues 44-107:

(SEQ ID NO: 15)
GDAGEKGDKGAPGRPGRVGPTGEKGDMGDKGQKGSVGRHGKIGPIGSKGE
KGDSGDIGPPGPN

Collagen type III (residues 891-942):

(SEQ ID NO: 16)
GPPGPSGSPGKDGPPGPAGNTGAPGSPGVSGPKGDAGQPGEKGSPGAQGP
PG

Exemplary Microbe-Binding Molecules with MBLStem58 as the Collagen Domain

StemFcMBL-2: -has hinge region, not glycosylated.

(SEQ ID NO: 17)
GINGFPGKDGRDGTKGEKGEPGQGLRGLQGPPGKLGPPGNPGPSGSPGPK
GQKGDPGKSAPELLGGPSVFLFPPKPKDTLMISRTPEVTCVVVDVSHEDP
EVKFNWYVDGVEVHNAKTKPREEQYDSTYRVVSVLTVLHQDWLNGKEYKC
KVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGN
VFSCSVMHEALHNHYTQKSLSLSPGASPDGDSSLAASERKALQTEMARIK
KWLTFSLGKQVGNKFFLTNGEIMTFEKVKALCVKFQASVATPRNAAENGA
IQNLIKEEAFLGITDEKTEGQFVDLTGNRLTYTNWNEGEPNNAGSDEDCV
LLLKNGQWNDVPCSTSHLAVCEFPI

FcStemMBL_A: - No Cys-rich domain of MBL (SEQ ID NO: 18)
EPKSSDKTHTCPPCPAPELLGGPSVFLFPPKPKDTLMISRTPEVTCVVVD
VSHEDPEVKFNWYVDGVEVHNAKTKPREEQYDSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGAGINGFPGKDGRDGTKGEK
GEPGQGLRGLQGPPGKLGPPGNPGPSGSPGPKGQKGDPGKSPDGDSSLAA
SERKALQTEMARIKKWLTFSLGKQVGNKFFLTNGEIMTFEKVKALCVKFQ
ASVATPRNAAENGAIQNLIKEEAFLGITDEKTEGQFVDLTGNRLTYTNWN
EGEPNNAGSDEDCVLLLKNGQWNDVPCSTSHLAVCEFPI FcStemMBL_A_monomeric: - No Cys-rich domain of MBL (SEQ ID NO: 19)
EPKSSDKTHTCPPCPAPELLGGPSVFLFPPKPKDTLMISRTPEVTCVVVD
VSHEDPEVKFNWYVDGVEVHNAKTKPREEQYDSTYRVVSVLTVLHQDWLN
GKEYKCKVSNKALPAPIEKTISKAKGQPREPQVYTLPPSRDELTKNQVNL
TCLVKGFYPSDIAVEWESNGQPENNYKTTPPVLDSDGSFFLNSKLTVDKS
RWQQGNVFSCSVMHEALHNHYTQKSLSLSPGAGINGFPGKDGRDGTKGEK
GEPGQGLRGLQGPPGKLGPPGNPGPSGSPGPKGQKGDPGKSPDGDSSLAA
SERKALQTEMARIKKWLTFSLGKQVGNKFFLTNGEIMTFEKVKALCVKFQ
ASVATPRNAAENGAIQNLIKEEAFLGITDEKTEGQFVDLTGNRLTYTNWN
EGEPNNAGSDEDCVLLLKNGQWNDVPCSTSHLAVCEFPI StemFcMBL-1:
(SEQ ID NO: 20)
GINGFPGKDGRDGTKGEKGEPGQGLRGLQGPPGKLGPPGNPGPSGSPGPK
GQKGDPGKSEPKSSDKTHTCPPCPAPELLGGPSVFLFPPKPKDTLMISRT
PEVTCVVVDVSHEDPEVKFNWYVDGVEVHNAKTKPREEQYDSTYRVVSVL
TVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFL
YSKLTVDKSRWQQGNVFSCSVMHEALHNHYTQKSLSLSPGASPDGDSSLA
ASERKALQTEMARIKKWLTFSLGKQVGNKFFLTNGEIMTFEKVKALCVKF
QASVATPRNAAENGAIQNLIKEEAFLGITDEKTEGQFVDLTGNRLTYTNW
NEGEPNNAGSDEDCVLLLKNGQWNDVPCSTSHLAVCEFPI Exemplary Microbe-Binding Molecules with MBLStem 32 as the Collagen Domain StemFcMBL-3: -has hinge region, not glycosylated.
(SEQ ID NO: 21)
GLQGPPGKLGPPGNPGPSGSPGPKGQKGDPGKSEPKSSDKTHTCPPCPAP
ELLGGPSVFLFPPKPKDTLMISRTPEVTCVVVDVSHEDPEVKFNWYVDGV
EVHNAKTKPREEQYDSTYRVVSVLTVLHQDWLNGKEYKCKVSNKALPAPI
EKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEAL
HNHYTQKSLSLSPGASPDGDSSLAASERKALQTEMARIKKWLTFSLGKQV
GNKFFLTNGEIMTFEKVKALCVKFQASVATPRNAAENGAIQNLIKEEAFL
GITDEKTEGQFVDLTGNRLTYTNWNEGEPNNAGSDEDCVLLLKNGQWNDV
PCSTSHLAVCEFPI StemMBLFc_D:
(SEQ ID NO: 22)
GLQGPPGKLGPPGNPGPSGSPGPKGQKGDPGKSPDGDSSLAASERKALQT
EMARIKKWLTFSLGKQVGNKFFLTNGEIMTFEKVKALCVKFQASVATPRN
AAENGAIQNLIKEEAFLGITDEKTEGQFVDLTGNRLTYTNWNEGEPNNAG
SDEDCVLLLKNGQWNDVPCSTSHLAVCEFPIEPKSSDKTHTCPPCPAPEL
LGGPSVFLFPPKPKDTLMISRTPEVTCVVVDVSHEDPEVKFNWYVDGVEV
HNAKTKPREEQYDSTYRVVSVLTVLHQDWLNGKEYKCKVSNKALPAPIEK
TISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHN
HYTQKSLSLSPGA Exemplary Microbe-Binding Molecule with MBLStem32(K to S) as the Collagen Domain StemFcMBL-3(S):
(SEQ ID NO: 23)
GLQGPPGSLGPPGNPGSGSPGPSGQSGDPGSSEPKSSDKTHTCPPCPA
PELLGGPSVFLFPPKPKDTLMISRTPEVTCVVVDVSHEDPEVKFNWYVD
GVEVHNAKTKPREEQYDSTYRVVSVLTVLHQDWLNGKEYKCKVSNKALP
APIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSV
MHEALHNHYTQKSLSLSPGASPDGDSSLAASERKALQTEMARIKKWLTF
SLGKQVGNKFFLTNGEIMTFEKVKALCVKFQASVATPRNAAENGAIQNL
IKEEAFLGITDEKTEGQFVDLTGNRLTYTNWNEGEPNNAGSDEDCVLLL
KNGQWNDVPCSTSHLAVCEFPI Exemplary Microbe-Binding Molecule with StemnA_K75Q as the Collagen Domain FcStemMBL_K75Q:
(SEQ ID NO: 24)
EPKSSDKTHTCPPCPAPELLGGPSVFLFPPKPKDTLMISRTPEVTCVVVDV
SHEDPEVKFNWYVDGVEVHNAKTKPREEQYDSTYRVVSVLTVLHQDWLNGK
EYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQ
GNVFSCSVMHEALHNHYTQKSLSLSPGAGINGFPGKDGRDGTKGEKGEPGQ
GLRGLQGPPGQLGPPGNPGPSGSPGPKGQKGDPGKSPDGDSSLAASERKAL
QTEMARIKKWLTFSLGKQVGNKFFLTNGEIMTFEKVKALCVKFQASVATPR
NAAENGAIQNLIKEEAFLGITDEKTEGQFVDLTGNRLTYTNWNEGEPNNAG
SDEDCVLLLKNGQWNDVPCSTSHLAVCEFPI Exemplary Microbe-Binding Molecule with MBLStem20_Ctrim as the Collagen Domain StemFcMBL_Ctrimmed:
(SEQ ID NO: 25)
GLQGPPGKLGPPGNPGPSGSSEPKSSDKTHTCPPCPAPELLGGPSVFLFPP
KPKDTLMISRTPEVTCVVVDVSHEDPEVKFNWYVDGVEVHNAKTKPREEQY
DSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGASP
DGDSSLAASERKALQTEMARIKKWLTFSLGKQVGNKFFLTNGEIMTFEKVK
ALCVKFQASVATPRNAAENGAIQNLIKEEAFLGITDEKTEGQFVDLTGNRL
TYTNWNEGEPNNAGSDEDCVLLLKNGQWNDVPCSTSHLAVCEFPI Exemplary Microbe-Binding Molecule with MBLStem20_Ntrim as the Collagen Domain StemFcMBL_Ntrimmed:
(SEQ ID NO: 26)
GNPGPSGSPGPKGQKGDPGKSEPKSSDKTHTCPPCPAPELLGGPSVFLFP
PKPKDTLMISRTPEVTCVVVDVSHEDPEVKFNWYVDGVEVHNAKTKPREE
QYDSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLS
PGASPDGDSSLAASERKALQTEMARIKKWLTFSLGKQVGNKFFLTNGEIM
TFEKVKALCVKFQASVATPRNAAENGAIQNLIKEEAFLGITDEKTEGQFV
DLTGNRLTYINWNEGEPNNAGSDEDCVLLLKNGQWNDVPCSTSHLAVCEF
PI Exemplary Microbe-Binding Molecule with SpA Stem as the Collagen Domain SpAStem-FcMBL:
(SEQ ID NO: 27)
GSPGIPGTPGSHGLPGRDGRDGVKGDPGPPGPMGPPGETPCPPGNNGLPG
APGVPGERGEKGEAGERGPPGSAPELLGGPSVFLFPPKPKDTLMISRTPE
VTCVVVDVSHEDPEVKFNWYVDGVEVHNAKTKPREEQYDSTYRVVSVLTV
LHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYS
KLTVDKSRWQQGNVFSCSVMHEALHNHYTQKSLSLSPGAKSPDGDSSLAA
SERKALQTEMARIKKWLTFSLGKQVGNKFFLTNGEIMTFEKVKALCVKFQ
ASVATPRNAAENGAIQNLIKEEAFLGITDEKTEGQFVDLTGNRLTYTNWN
EGEPNNAGSDEDCVLLLKNGQWNDVPCSTSHLAVCEFPI Other Sequences MBL full length with the signal sequence (SEQ ID NO: 28);
DNA sequence disclosed as SEQ ID NO: 42:
```
       atgtccctgtttccatcactccctctccttctcctgagtatggtggcagcgtcttactca
  1    M  S  L  F  P  S  L  P  L  L  L  L  S  M  V  A  A  S  Y  S gaaactgtgacctgtgaggatgcccaaaagacctgccctgcagtgattgcctgtagctct
 21    E  T  V  T  C  E  D  A  Q  K  T  C  P  A  V  I  A  C  S  S ccaggcatcaacggcttcccaggcaaagatgggcgtgatggcaccaagggagaaaagggg
 41    P  G  I  N  G  F  P  G  K  D  G  R  D  G  T  K  G  E  K  G gaaccaggccaagggctcagaggcttacagggccccctggaaagttggggcctccagga
 61    E  P  G  Q  G  L  R  G  L  Q  G  P  P  G  K  L  G  P  P  G aatccagggccttctgggtcaccaggaccaaagggccaaaaaggagaccctggaaaagt
 81    N  P  G  P  S  G  S  P  G  P  K  G  Q  K  G  D  P  G  K  S ccggatggtgatagtagcctggctgcctcagaaagaaaagctctgcaaacagaaatgga
101    P  D  G  D  S  S  L  A  A  S  E  R  K  A  L  Q  T  E  M  A cgtatcaaaaagtggctcaccttctctctgggcaaacaagttgggaacaagttcttcctg
121    R  I  K  K  W  L  T  F  S  L  G  K  Q  V  G  N  K  F  F  L accaatggtgaaataatgacctttgaaaaagtgaaggccttgtgtgtcaagttccaggcc
141    T  N  G  E  I  M  T  F  E  K  V  K  A  L  C  V  K  F  Q  A tctgtggccacccccaggaatgctgcagagaatggagccattcagaatctcatcaaggag
161    S  V  A  T  P  R  N  A  A  E  N  G  A  I  Q  N  L  I  K  E gaagccttcctgggcatcactgatgagaagacagaagggcagtttgtggatctgacagga
181    E  A  F  L  G  I  T  D  E  K  T  E  G  Q  F  V  D  L  T  G aatagactgacctacacaaactggaacgagggtgaacccaacaatgctggttctgatgaa
201    N  R  L  T  Y  T  N  W  N  E  G  E  P  N  N  A  G  S  D  E gattgtgtattgctactgaaaaatggccagtggaatgacgtcccctgctccacctcccat
221    D  C  V  L  L  L  K  N  G  Q  W  N  D  V  P  C  S  T  S  H ctggccgtctgtgagttccctatctga
241    L  A  V  C  E  F  P  I  *
```

MBL without the signal sequence (SEQ ID NO: 29); DNA sequence disclosed as SEQ ID NO: 43:
```
       gaaactgtgacctgtgaggatgcccaaaagacctgccctgcagtgattgcctgtagctct
  1    E  T  V  T  C  E  D  A  Q  K  T  C  P  A  V  I  A  C  S  S ccaggcatcaacggcttcccaggcaaagatgggcgtgatggcaccaagggagaaaagggg
 21    P  G  I  N  G  F  P  G  K  D  G  R  D  G  T  K  G  E  K  G gaaccaggccaagggctcagaggcttacagggccccctggaaagttggggcctccagga
 41    E  P  G  Q  G  L  R  G  L  Q  G  P  P  G  K  L  G  P  P  G aatccagggccttctgggtcaccaggaccaaagggccaaaaaggagaccctggaaaagt
 61    N  P  G  P  S  G  S  P  G  P  K  G  Q  K  G  D  P  G  K  S ccggatggtgatagtagcctggctgcctcagaaagaaaagctctgcaaacagaaatgga
 81    P  D  G  D  S  S  L  A  A  S  E  R  K  A  L  Q  T  E  M  A cgtatcaaaaagtggctcaccttctctctgggcaaacaagttgggaacaagttcttcctg
101    R  I  K  K  W  L  T  F  S  L  G  K  Q  V  G  N  K  F  F  L accaatggtgaaataatgacctttgaaaaagtgaaggccttgtgtgtcaagttccaggcc
121    T  N  G  E  I  M  T  F  E  K  V  K  A  L  C  V  K  F  Q  A tctgtggccacccccaggaatgctgcagagaatggagccattcagaatctcatcaaggag
141    S  V  A  T  P  R  N  A  A  E  N  G  A  I  Q  N  L  I  K  E
```

```
       gaagccttcctgggcatcactgatgagaagacagaagggcagtttgtggatctgacagga
161    E  A  F  L  G  I  T  D  E  K  T  E  G  Q  F  V  D  L  T  G aatagactgacctacacaaactggaacgagggtgaacccaacaatgctggttctgatgaa
181    N  R  L  T  Y  T  N  W  N  E  G  E  P  N  N  A  G  S  D  E gattgtgtattgctactgaaaaatggccagtggaatgacgtccctgctccacctcccat
201    D  C  V  L  L  L  K  N  G  Q  W  N  D  V  P  C  S  T  S  H ctggccgtctgtgagttccctatctga
221    L  A  V  C  E  F  P  I  *
```

MBL signal sequence (SEQ ID NO: 30)

MSLFPSLPLLLLSMVAASYS

Truncated MBL (SEQ ID NO: 31)

AASERKALQTEMARIKKWLTFSLGKQVGNKFFLTNGEIMTFEKVKALCVKFQASVATPRNA

AENGAIQNLIKEEAFLGITDEKTEGQFVDLTGNRLTYTNWNEGEPNNAGSDEDCVLLLKNGQ

WNDVPCSTSHLAVCEFPI

Carbohydrate recognition domain (CRD) of MBL (SEQ ID NO: 32)

VGNKFFLTNGEIMTFEKVKALCVKFQASVATPRNAAENGAIQNLIKEEAFLGITDEKTEGQFV

DLTGNRLTYTNWNEGEPNNAGSDEDCVLLLKNGQWNDVPCSTSHLAVCEFPI

Neck + Carbohydrate recognition domain of MBL (SEQ ID NO: 33)

PDGDSSLAASERKALQTEMARIKKWLTFSLGKQVGNKFFLTNGEIMTFEKVKALCVKFQASV

ATPRNAAENGAIQNLIKEEAFLGITDEKTEGQFVDLTGNRLTYTNWNEGEPNNAGSDEDCVL

LLKNGQWNDVPCSTSHLAVCEFPI

FcMBL.81

(SEQ ID NO: 34)

EPKSSDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGAPDGDSSLAASERKAL

QTEMARIKKWLTFSLGKQVGNKFFLTNGEIMTFEKVKALCVKFQASVATPRNAAENGAIQN

LIKEEAFLGITDEKTEGQFVDLTGNRLTYTNWNEGEPNNAGSDEDCVLLLKNGQWNDVPCS

TSHLAVCEFPI

AKT-FcMBL (SEQ ID NO: 35)

AKTEPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGAPDGDSSLAASERK

ALQTEMARIKKWLTFSLGKQVGNKFFLTNGEIMTFEKVKALCVKFQASVATPRNAAENGAI

QNLIKEEAFLGITDEKTEGQFVDLTGNRLTYTNWNEGEPNNAGSDEDCVLLLKNGQWNDVP

CSTSHLAVCEFPI

FcMBL.111

(SEQ ID NO: 36)

EPKSSDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGATSKQVGNKFFLTNGEI

```
MTFEKVKALCVKFQASVATPRNAAENGAIQNLIKEEAFLGITDEKTEGQFVDLTGNRLTYTN

WNEGEPNNAGSDEDCVLLLKNGQWNDVPCSTSHLAVCEFPI
```

A variant of a CRD sequence
(SEQ ID NO: 37)

```
KQVGNKFFLTNGEIMTFEKVKALCVKFQASVATPRNAAENGAIQNLIKEEAFLGITDEKTEG

QFVDLTGNRLTYTNWNEGEPNNAGSDEDCVLLLKNGQWNDVPCSTSHLAVCEFPI
```

Protein sequence of a mammalian-optimized HRP
(SEQ ID NO: 38)

```
QLTPTFYDNSCPNVSNIVRDTIVNELRSDPRIAASILRLHFHDCFVNGCDASILLDNTTSFRTEK

DAFGNANSARGFPVIDRMKAAVESACPRTVSCADLLTIAAQQSVTLAGGPSWRVPLGRRDSL

QAFLDLANANLPAPFFTLPQLKDSFRNVGLNRSSDLVALSGGHTFGKNQCRFIMDRLYNFSN

TGLPDPTLNTTYLQTLRGLCPLNGNLSALVDFDLRTPTIFDNKYYVNLEEQKGLIQSDQELFSS

PNATDTIPLVRSFANSTQTFFNAFVEAMDRMGNITPLTGTQGQIRLNCRVVNSNS
```

Nucleotide sequence of a mammalian-optimzed HRP
(SEQ ID NO: 39)

```
CAGTTAACCCCTACATTCTACGACAATAGCTGTCCCAACGTGTCCAACATCGTTCGCGAC

ACAATCGTCAACGAGCTCAGATCCGATCCCAGGATCGCTGCTTCAATATTACGTCTGCAC

TTCCATGACTGCTTCGTGAATGGTTGCGACGCTAGCATATTACTGGACAACACCACCAGT

TTCCGCACTGAAAAGGATGCATTCGGGAACGCTAACAGCGCCAGGGGCTTTCCAGTGAT

CGATCGCATGAAGGCTGCCGTTGAGTCAGCATGCCCACGAACAGTCAGTTGTGCAGACC

TGCTGACTATAGCTGCGCAACAGAGCGTGACTCTTGCAGGCGGACCGTCCTGGAGAGTG

CCGCTCGGTCGACGTGACTCCCTACAGGCATTCCTAGATCTGGCCAACGCCAACTTGCCT

GCTCCATTCTTCACCCTGCCCCAGCTGAAGGATAGCTTTAGAAACGTGGGTCTGAATCGC

TCGAGTGACCTTGTGGCTCTGTCCGGAGGACACACATTTGGAAAGAACCAGTGTAGGTTC

ATCATGGATAGGCTCTACAATTTCAGCAACACTGGGTTACCTGACCCCACGCTGAACACT

ACGTATCTCCAGACACTGAGAGGCTTGTGCCCACTGAATGGCAACCTCAGTGCACTAGTG

GACTTTGATCTGCGGACCCCAACCATCTTCGATAACAAGTACTATGTGAATCTAGAGGAG

CAGAAAGGCCTGATACAGAGTGATCAAGAACTGTTTAGCAGTCCAAACGCCACTGACAC

CATCCCACTGGTGAGAAGTTTTGCTAACTCTACTCAAACCTTCTTTAACGCCTTCGTGGAA

GCCATGGACCGTATGGGTAACATTACCCCTCTGACGGGTACCCAAGGCCAGATTCGTCTG

AACTGCAGAGTGGTCAACAGCAACTCTTAATGA
```

Neck sequence of MBL
(SEQ ID NO: 40)

```
PDGDSSLAASERKALQTEMARIKKWLTFSLGKQ
```

---

What is claimed is:

1. An assay for diagnosing an infection, the assay comprising:
   A. a substrate bearing at least one first microbe-binding molecule, the first microbe-binding molecule comprising:
   a carbohydrate recognition domain of a lectin;
   an Fc domain of an antibody; and
   at least a portion of a collagen domain;
   wherein the first microbe-binding molecule does not include a cysteine-rich domain of the lectin; and
   B. an antibody comprising a detectable label or a second microbe-binding molecule comprising:
   a carbohydrate recognition domain of a lectin;
   an Fc domain of an antibody; and
   at least a portion of a collagen domain;
   and a detectable label;
   wherein the second microbe-binding molecule does not include a cysteine-rich domain of the lectin.

2. The assay of claim 1, wherein the Fc domain links the collagen domain to the carbohydrate recognition domain.

3. The assay of claim 1, wherein the lectin comprises a calcium-dependent lectin.

4. The assay of claim 1, wherein the lectin comprises mannose binding lectin.

5. The assay of claim 1, wherein the substrate comprises a dipstick or test strip.

6. The assay of claim 1, wherein the substrate comprises magnetic microbeads.

7. The assay of claim 1, wherein the assay comprises an antibody comprising a detectable label.

8. The assay of claim 1, wherein the second microbe binding molecule comprises a carbohydrate recognition domain of the same lectin as the first microbe binding molecule or a carbohydrate recognition domain from a second lectin.

9. The assay of claim 1, wherein the detectable label comprises an enzyme.

10. The assay of claim 1, wherein the substrate comprises a surface of a microtiter well.

11. The assay of claim 1, wherein the assay is a point-of-care diagnostic tool for microbe or pathogen detection.

12. A treatment device for treating an infection, the device comprising:
   an extracorporeal filtering device comprising a substrate having linked thereto at least one microbe-binding molecule, the microbe-binding molecule comprising:
   a carbohydrate recognition domain of a lectin;
   an Fc domain of an antibody; and
   at least a portion of a collagen domain, wherein the microbe-binding molecule does not include a cysteine-rich domain of the lectin.

13. The treatment device of claim 12, wherein the lectin comprises a calcium-dependent lectin.

14. The treatment device of claim 12, wherein the lectin comprises mannose binding lectin.

15. The treatment device of claim 12, wherein the Fc domain links the collagen domain to the carbohydrate recognition domain.

16. The treatment device of claim 12, wherein the extracorporeal filtering device comprises a device selected from the group consisting of: a hollow fiber; hollow tubing; and a spiral mixer.

17. The treatment device of claim 12, wherein the extracorporeal filtering device comprises a plurality of the microbe-binding molecule coated or conjugated to a surface thereof such that when blood flows through the treatment device, microbes and/or microbial matter present are extracted therefrom.

18. The treatment device of claim 12, wherein when microbe-infected blood is passed through the filtering device, the microbe-binding molecule binds and removes microbes and/or microbial matter therefrom.

* * * * *